US009074213B2

(12) United States Patent
Kreutzer et al.

(10) Patent No.: US 9,074,213 B2
(45) **Date of Patent: *Jul. 7, 2015**

(54) COMPOSITIONS AND METHODS FOR INHIBITING EXPRESSION OF A TARGET GENE

(71) Applicant: Alnylam Pharmaceuticals, Inc., Cambridge, MA (US)

(72) Inventors: Roland Kreutzer, Weidenberg (DE); Stefan Limmer, Kulmbach (DE); Sylvia Limmer, Kulmbach (DE); Philipp Hadwiger, Bayreuth (DE)

(73) Assignee: Alnylam Pharmacuticals, Inc., Cambridge, MA (US)

( * ) Notice: Subject to any disclaimer, the term of this patent is extended or adjusted under 35 U.S.C. 154(b) by 59 days.

This patent is subject to a terminal disclaimer.

(21) Appl. No.: 14/012,994

(22) Filed: Aug. 28, 2013

(65) Prior Publication Data

US 2014/0106450 A1 Apr. 17, 2014

Related U.S. Application Data

(63) Continuation of application No. 12/894,018, filed on Sep. 29, 2010, now Pat. No. 8,546,143, which is a continuation of application No. 10/384,339, filed on Mar. 7, 2003, now Pat. No. 7,829,693, which is a continuation-in-part of application No. PCT/EP02/00152, filed on Jan. 9, 2001.

(30) Foreign Application Priority Data

Jan. 9, 2001 (DE) .................................. 10100586
Oct. 26, 2001 (DE) .................................. 10155280
Nov. 29, 2001 (DE) .................................. 10158411
Dec. 7, 2001 (DE) .................................. 10160151

(51) Int. Cl.
*C12N 15/113* (2010.01)
*C12N 15/11* (2006.01)
*A61K 38/00* (2006.01)

(52) U.S. Cl.
CPC ............. *C12N 15/1138* (2013.01); *A61K 38/00* (2013.01); *C12N 15/111* (2013.01); *C12N 15/1131* (2013.01); *C12N 2310/14* (2013.01); *C12N 2310/53* (2013.01); *C12N 2320/50* (2013.01)

(58) Field of Classification Search
USPC ............ 435/6.1, 91.1, 91.31, 455, 6.11, 375; 514/44; 536/23.1, 24.5, 24.3
See application file for complete search history.

(56) References Cited

U.S. PATENT DOCUMENTS 4,309,492 A 1/1982 Bernard
5,112,734 A 5/1992 Kramer et al.
5,225,347 A 7/1993 Goldberg et al.
5,246,921 A 9/1993 Reddy et al.
5,340,318 A 8/1994 Kunihiro
5,472,802 A 12/1995 Holland et al.
5,496,698 A 3/1996 Draper et al.
5,525,468 A 6/1996 McSwiggen
5,574,142 A 11/1996 Meyer, Jr. et al.
5,616,459 A 4/1997 Kramer et al.
5,635,385 A 6/1997 Leopold et al.
5,639,655 A 6/1997 Thompson et al.
5,712,257 A 1/1998 Carter
5,811,275 A 9/1998 Wong-Staal et al.
5,811,300 A 9/1998 Sullivan et al.
5,814,500 A 9/1998 Dietz
5,824,519 A 10/1998 Norris et al.
5,837,510 A 11/1998 Goldsmith et al.
5,854,067 A 12/1998 Newgard et al.
5,864,028 A 1/1999 Sioud
5,866,701 A 2/1999 Hampel et al.
5,891,717 A 4/1999 Newgard et al.
5,898,031 A 4/1999 Crooke (Continued)

FOREIGN PATENT DOCUMENTS

CA 2334951 12/1999
DE 19618797 11/1997

(Continued)

OTHER PUBLICATIONS

Agrawal et al., "Self-Stabilized Oligonucleotides as Novel Antisense Agents," *Delivery Strategies for Antisense Oligonucleotide Therapeutics,* Edited by Saghir Akhtar, CRC Press, pp. 105-121 (1995).

(Continued)

*Primary Examiner* — Jane Zara
(74) *Attorney, Agent, or Firm* — Fenwick & West LLP

(57) ABSTRACT

The present invention relates to a double-stranded ribonucleic acid (dsRNA) having a nucleotide sequence which is substantially identical to at least a part of a target gene and which is no more than 49, preferably less than 25, nucleotides in length, and which comprises a complementary (antisense) RNA strand having a 1 to 4 nucleotide overhang at the 3'-end and a blunt 5'-end. The invention further relates to a pharmaceutical composition comprising the dsRNA and a pharmaceutically acceptable carrier. The pharmaceutical compositions are useful for inhibiting the expression of a target gene, as well as for treating diseases caused by expression of the target gene, at low dosages (i.e., less than 5 milligrams, preferably less than 25 micrograms, per kg body weight per day). The invention also relates to methods for inhibiting the expression of a target gene, as well as methods for treating diseases caused by the expression of the gene.

15 Claims, 20 Drawing Sheets

(56) References Cited

U.S. PATENT DOCUMENTS

| | | | |
|---|---|---|---|
| 5,908,779 | A | 6/1999 | Carmichael et al. |
| 5,939,262 | A | 8/1999 | Pasloske et al. |
| 5,968,737 | A | 10/1999 | Ali-Osman et al. |
| 5,985,620 | A | 11/1999 | Sioud |
| 6,057,156 | A | 5/2000 | Akhtar et al. |
| 6,071,890 | A | 6/2000 | Scheule et al. |
| 6,077,705 | A | 6/2000 | Duan et al. |
| 6,080,851 | A | 6/2000 | Pachuk et al. |
| 6,087,164 | A | 7/2000 | Hochberg et al. |
| 6,087,172 | A | 7/2000 | Veerapaneni et al. |
| 6,099,823 | A | 8/2000 | Falb |
| 6,100,087 | A | 8/2000 | Rossi et al. |
| 6,100,444 | A | 8/2000 | Frelinger et al. |
| 6,107,094 | A | 8/2000 | Crooke |
| 6,183,959 | B1 | 2/2001 | Thompson |
| 6,187,585 | B1 | 2/2001 | Bennett et al. |
| 6,224,868 | B1 | 5/2001 | Wong et al. |
| 6,225,291 | B1 | 5/2001 | Lewin et al. |
| 6,245,560 | B1 | 6/2001 | Lisziewicz |
| 6,245,748 | B1 | 6/2001 | Wellstein et al. |
| 6,255,071 | B1 | 7/2001 | Beach et al. |
| 6,346,398 | B1 | 2/2002 | Pavco et al. |
| 6,355,415 | B1 | 3/2002 | Wagner et al. |
| 6,410,176 | B1 | 6/2002 | Genc et al. |
| 6,423,489 | B1 | 7/2002 | Anderson et al. |
| 6,482,803 | B1 | 11/2002 | Roth et al. |
| 6,486,299 | B1 | 11/2002 | Shimkets |
| 6,506,559 | B1 | 1/2003 | Fire |
| 6,573,046 | B1 | 6/2003 | Kmiec et al. |
| 7,105,656 | B2 | 9/2006 | Colgan |
| 7,427,605 | B2 | 9/2008 | Davis et al. |
| 7,718,629 | B2 | 5/2010 | Bumcrot et al. |
| 7,829,693 | B2 * | 11/2010 | Kreutzer et al. ............ 536/24.5 |
| 8,546,143 | B2 * | 10/2013 | Kreutzer et al. .............. 435/455 |
| 2002/0086356 | A1 | 7/2002 | Tuschl et al. |
| 2002/0114784 | A1 | 8/2002 | Li et al. |
| 2002/0123034 | A1 | 9/2002 | Canaani et al. |
| 2002/0132346 | A1 | 9/2002 | Cibelli |
| 2002/0162126 | A1 | 10/2002 | Beach et al. |
| 2002/0173478 | A1 | 11/2002 | Gewirtz |
| 2003/0027783 | A1 | 2/2003 | Zernicka-Goetz et al. |
| 2003/0108923 | A1 | 6/2003 | Tuschl et al. |
| 2003/0125281 | A1 | 7/2003 | Lewis et al. |
| 2003/0143732 | A1 | 7/2003 | Fosnaugh et al. |
| 2003/0148341 | A1 | 8/2003 | Sin et al. |
| 2003/0157030 | A1 | 8/2003 | Davis et al. |
| 2003/0170891 | A1 | 9/2003 | McSwiggen |
| 2003/0176671 | A1 | 9/2003 | Reed et al. |
| 2003/0180756 | A1 | 9/2003 | Shi et al. |
| 2003/0190635 | A1 | 10/2003 | McSwiggen |
| 2003/0198627 | A1 | 10/2003 | Arts et al. |
| 2004/0102408 | A1 * | 5/2004 | Kreutzer et al. ................ 514/44 |

FOREIGN PATENT DOCUMENTS

| | | | |
|---|---|---|---|
| DE | 19631919 | | 7/1998 |
| DE | 19956568 | A1 | 8/2000 |
| DE | 10155280 | | 10/2001 |
| DE | 10158411 | | 11/2001 |
| DE | 10100586 | | 1/2002 |
| DE | 10100586 | C1 | 4/2002 |
| DE | 10100588 | A1 | 7/2002 |
| DE | 10100587 | C1 | 11/2002 |
| DE | 10163098 | | 4/2003 |
| DE | 10160151 | | 6/2003 |
| DE | 20023125 | A1 | 6/2003 |
| DE | 10230997 | A1 | 7/2003 |
| DE | 10230966 | A1 | 1/2004 |
| EP | 0126325 | | 11/1991 |
| EP | 1001666 | A2 | 5/2000 |
| EP | 1107340 | A2 | 6/2001 |
| EP | 1214945 | A2 | 6/2002 |
| WO | WO 92/19732 | | 11/1992 |
| WO | WO 94/01550 | | 1/1994 |
| WO | WO 98/05770 | | 2/1998 |
| WO | WO 98/53083 | | 11/1998 |
| WO | WO 99/15682 | | 4/1999 |
| WO | WO 99/32619 | A1 | 7/1999 |
| WO | WO 99/49029 | | 9/1999 |
| WO | WO 99/53050 | A1 | 10/1999 |
| WO | WO 99/61631 | A1 | 12/1999 |
| WO | WO 00/01846 | A1 | 1/2000 |
| WO | WO 00/44895 | A1 | 8/2000 |
| WO | WO 00/44914 | A1 | 8/2000 |
| WO | WO 00/63364 | A1 | 10/2000 |
| WO | WO 00/68374 | A2 | 11/2000 |
| WO | WO 01/18197 | A1 | 3/2001 |
| WO | WO 01/29058 | A1 | 4/2001 |
| WO | WO 01/36646 | A1 | 5/2001 |
| WO | WO 01/42443 | A1 | 6/2001 |
| WO | WO 01/48183 | A2 | 7/2001 |
| WO | WO 01/68836 | A2 | 9/2001 |
| WO | WO 01/70949 | A1 | 9/2001 |
| WO | WO 01/75164 | A2 | 10/2001 |
| WO | WO 01/92513 | A1 | 12/2001 |
| WO | WO 02/16620 | A1 | 2/2002 |
| WO | WO 02/26780 | A2 | 4/2002 |
| WO | WO 02/44321 | A2 | 6/2002 |
| WO | WO 02/055692 | A2 | 7/2002 |
| WO | WO 02/055693 | A2 | 7/2002 |
| WO | WO 02/061034 | A1 | 8/2002 |
| WO | WO 02/068635 | A2 | 9/2002 |
| WO | WO 02/068637 | A2 | 9/2002 |
| WO | WO 03/006477 | A1 | 1/2003 |
| WO | WO 03/012052 | A2 | 2/2003 |
| WO | WO 03/012082 | A1 | 2/2003 |
| WO | WO 03/016572 | A1 | 2/2003 |
| WO | WO 03/033700 | A1 | 4/2003 |
| WO | WO 03/035082 | A1 | 5/2003 |
| WO | WO 03/035083 | A1 | 5/2003 |
| WO | WO 03/035868 | A1 | 5/2003 |
| WO | WO 03/035869 | A1 | 5/2003 |
| WO | WO 03/035870 | A1 | 5/2003 |
| WO | WO 03/035876 | A1 | 5/2003 |
| WO | WO 03/070283 | A2 | 8/2003 |
| WO | WO 03/070750 | A2 | 8/2003 |
| WO | WO 03/070969 | A2 | 8/2003 |
| WO | WO 03/070972 | A2 | 8/2003 |
| WO | WO 03/074654 | A2 | 9/2003 |
| WO | WO 03/080794 | A2 | 10/2003 |
| WO | WO 03/080807 | A2 | 10/2003 |

OTHER PUBLICATIONS

Alfonzo et al., "The mechanism of U insertion-deletion RNA editing in kinetoplastid mitochondria" Nucleic Acids Res. 25:3751-3759 (1997).

Anderson et al., "Human gene therapy" Nature 392:25-30 (1998).

Asanuma et al., "Photoregulation of the Formation and Dissociation of a DNA Duplex by Using the cis-trans Isomerization of Azobenzene" Angew. Chem. Int. Ed. 38:2393-2395 (1999).

Azhayeva et al., "Inhibitory properties of double helix forming circular oligonucleotides" Nucleic Acids Res. 25:4954-4961 (1997).

Bahramian et al., "Transcriptional and Posttranscriptional Silencing of Rodent 1(I) Collagen by a Homologous Transcriptionally Self-Silenced Transgene" Mol. Cell. Biol. 19:274-283 (1999).

Barawkar et al., "Synthesis, biophysical properties, and nuclease resistance properties of mixed backbone oligodeoxynucleotides containing cationic internucleoside guanidinium linkages: Deoxynucleic guanidine-DNA chimeras" Proc. Natl. Acad. Sci. USA 95:11047-11052 (1998).

Bhan et al., "2',5'-Linked oligo-3'-deoxyribonucleoside phosphorothioate chimeras: thermal stability and antisense inhibition of gene expression" Nucleic Acids Res. 25:3310-3317 (1997).

Billy et al., "Specific interference with gene expression induced by long, double-stranded RNA in mouse embryonal teratocarcinoma cell lines" Proc. Natl. Acad. Sci. USA 98:14428-14433 (2001).

Borecky et al., "Therapeutic use of double-stranded RNAs in man" Tex. Rep. Biol. Med. 41:575-581 (19811982) (Abstract only).

Braich et al., "Regiospecific Solid-Phase Synthesis of Branched Oligonucleotides. Effect of Vicinal 2',5'- (or 2',3'-) and 3',5'-

(56) References Cited

OTHER PUBLICATIONS

Phosphodiester Linkages on the Formation of Hairpin DNA" Bioconjug. Chem. 8:370-377 (1997).
Castelli et al., "The 2-5A system in viral infection and apoptosis" Biomed. Pharmacother. 52:386-390 (1998).
Czauderna et al., "Structural variations and stabilizing modifications of synthetic siRNAs in mammalian cells," Nucleic Acids Res., 31(11):1-12 (2003).
Dolinnaya et al., "Oligonucleotide circularization by template-directed chemical ligation" Nucleic Acids Res., 21:5403-5407 (1993).
Expert-Bezançon et al., "Precise localization of several covalent RNA-RNA cross-link in *Escherichia coli* 16S RNA" Eur. J. Biochem. 136:267-274 (1983).
Fire et al., "Production of antisense RNA leads to effective and specific inhibition of gene expression in *C. elegans* muscle" Development 113:503-514 (1991).
Gao et al., "Circularization of oligonucleotides by disulfide bridge formation" Nucleic Acids Res., 23:2025-2029 (1995).
Grasby et al., "Purine Functional Groups in Essential Residues of the Hairpin Ribozyme Required for Catalytic Cleavage of RNA" Biochemistry 34:4068-4076 (1995).
Griffey et al., "2'-O-Aminopropyl Ribonucleotides: A Zwitterionic Modification That Enhances the Exonuclease Resistance and Biological Activity of Antisense Oligonucleotides" J. Med. Chem. 39:5100-5109 (1996).
Gryaznov et al., "Template controlled coupling and recombination of oligonucleotide blocks containing thiophosphoryl groups" Nucleic Acids Res. 21:1403-1408 (1993).
Ha et al., "A bulged lin-4-lin-14 RNA duplex is sufficient for Caenorhabditis elegans lin-14 temporal gradient formation" Genes & Development 10:3041-3050 (1996).
Hamilton et al., "A Species of Small Antisense RNA in Post-transcriptional Gene Silencing in Plants" Science 286:950-952 (1999).
Harfe et al., "Analysis of a *Caenorhabditis elegans* Twist homolog identifies conserved and divergent aspects of mesodermal patterning" Genes Dev. 12:2623-2635 (1998).
Hoke et al., "Effects of phosphorothioate capping on antisense oligonucleotide stability, hybridization and antiviral efficacy versus herpes simplex virus infection" Nucleic Acids Res. 19:5743-5748 (1991).
Horn et al., "Chemical synthesis and characterization of branched oligodeoxyribonucleotides (bDNA) for use as signal amplifiers in nucleic acid quantification assays" Nucleic Acids Res. 25:4842-4849 (1997).
Hunter, "Genetics: A touch of elegance with RNAi" Curr. Biol. 9:R440-R442 (1999).
"Introduction of DNA into Mammalian Cells," *Current Protocols in Molecular Biology,* Supplement 48, Edited by Frederick M. Ausubel et al., John Wiley & Sons, Inc., pp. 9.4.7-9.4.8 (1999).
Iwase et al., "Gene regulation by decoy approach (I): synthesis and properties of photo-crosslinked oligonucleotides" Nucleic Acids Symp. Ser. 37:203-204 (1997).
Jacobs et al., "When Two Strands Are Better Than One: The Mediators and Modulators of the Cellular Responses to Double-Stranded RNA" Virology 219:339-349 (1996).
Jäschke et al., "Synthesis and Analytical Characterization of RNA-Polyethylene Glycol Conjugates" Nucleosides & Nucleotides 15:1519-1529 (1996).
Kaufman, "Double-stranded RNA-activated protein kinase mediates virus-induced apoptosis: A new role for an old actor" Proc. Natl. Acad. Sci. USA 96:11693-11695 (1999).
Kennerdell et al., "Use of dsRNA-Mediated Genetic Interference to Demonstrate that frizzled and frizzled 2 Act in the Wingless Pathway" Cell 95:1017-1026 (1998).
Kreutzer et al., "Specific inhibition of viral gene expression by double-stranded RNA in vitro" Annual Fall Meeting of the GBH, Abstract for Poster Paper No. 328, p. S169 (1999).
Kumar et al., "Antisense RNA: function and fate of duplex RNA in cells of higher eukaryotes" Microbiol. Mol. Biol. Rev. 62:1415-1434 (1998).
Lee et al., "The *C. elegans* Heterochronic Gene lin-4 Encodes Small RNAs with Antisense Complementarity to lin-14" Cell 75:843-854 (1993).
Li et al., "Double-stranded RNA injection produces null phenotypes in zebrafish" Dev. Biol. 210:238, Abstract No. 346 (1999).
Lin et al., "Policing rogue genes" Nature 402:128-129 (1999).
Lipinski et al., "Experimental and computational approaches to estimate solubility and permeability in drug discovery and development settings" Adv. Drug Deliv. Rev. 23:3-25 (1997).
Lipson et al., "Psoralen Cross-Linking of Ribosomal RNA" Methods Enzymol. 164:330-341 (1988).
Liu et al., "Detection of a Novel ATP-Dependent Cross-Linked Protein at the 5' Splice Site-U1 Small Nuclear RNA Duplex by Methylene Blue-Mediated Photo-Cross-Linking" Mol. Cell. Biol. 18:6910-6920 (1998).
Ma et al., "Design and Synthesis of RNA Miniduplexes via a Synthetic Linker Approach" Biochemistry 32:1751-1758 (1993).
Majumdar et al., "Targeted gene knockout mediated by triple helix forming oligonucleotides" Nat. Genet. 20:212-214 (1998).
Micura et al., "Cyclic Oligoribonucleotides (RNA) by Solid-Phase Synthesis" Chem. Eur. J. 5:2077-2082 (1999).
Milhaud et al., "Free and Liposome-Encapsulated Double-Stranded RNAs as Inducers of Interferon, Interleukin-6, and Cellular Toxicity" J. Interferon Res., 11:261-265 (1991).
Minks et al., "Stuctural Requirements of Double-strandard RNA for the Activation of 2',5'-Oligo(A) Polymerase and Protein Kinase of Interferon-treated HeLa Cells" J. Biol. Chem. 254(20):10180-10183 (1979).
Misquitta et al., "Targeted disruption of gene function in *Drosophila* by RNA interference (RNA-i): A role for nautilus in embryonic somatic muscle formation" Proc. Natl. Acad. Sci. USA 96:1451-1456 (1999).
Montgomery et al., "RNA as a target of double-stranded RNA-mediated genetic interference in *Caenorhabditis elegans*" Proc. Natl. Acad. Sci. USA 95:15502-15507 (1998).
Moss et al., "The Cold Shock Domain Protein LIN-28 Controls Developmental Timing in *C. elegans* and is Regulated by the lin-4 RNA" Cell 88:637-646 (1997).
Nielsen et al., "A novel class of conformationally restricted oligonucleotide analogues: synthesis of 2',3'-bridged monomers and RNA-selective hybridization" Chem. Commun. pp. 825-826 (1997).
Nikiforov et al., "Oligodeoxynucleotides containing 4-thiothymidine and 6-thiodeoxyguanosine as affinity labels for the Eco RV restriction endonuclease and modification methylase" Nucleic Acids Res. 20:1209-1214 (1992).
Pegram et al., "Phase II Study of Receptor-Enhanced Chemosensitivity Using Recombinant Humanized Anti-p185$^{HER2-neu}$ Monoclonal Antibody Plus Cisplatin in Patients With HER2-neu-Overexpressing Metastatic Breast Cancer Refractory to Chemotherapy Treatment" J. Clin. Oncol. 16:2659-2671 (1998).
Seydoux et al., "Repression of gene expression in the embryonic germ lineage of *C. elegans*" Nature 382:713-716 (1996).
Sharp et al., "RNAi and double-strand RNA" Genes Dev. 13:139-141 (1999).
Shi et al., "A CBP-p300 homolog specifies multiple differentiation pathways in *Caenorhabditis elegans*" Genes Dev. 12:943-955 (1998).
Skripkin et al., "Psoralen crosslinking between human immunodeficiency virus type 1 RNA and primer $tRNA_3^{Lys}$" Nucleic Acids Res. 24:509-514 (1996).
Strauss, "Candidate 'Gene Silencers' Found" Science 286:886 (1999).
Thompson, "Shortcuts from gene sequence to function" Nature 17:1158-1159 (1999).
Timmons et al., "Specific interference by ingested dsRNA" Nature 395:854 (1998).
Verma et al., "Gene therapy—promises, problems and prospects" Nature 389:239-242 (1997).
Voinnet et al., "Systemic signalling in gene silencing" Nature 389:553 (1997).

(56) References Cited

OTHER PUBLICATIONS

Wagner et al., "Double-stranded RNA poses puzzle" Nature 391:744-745 (1998).
Wang et al., "Circular RNA oligonucleotides. Synthesis, nucleic acid binding properties, and a comparison with circular DNAs" Nucleic Acids Res. 22:2326-2333 (1994).
Wang et al., "RNA Conformation in the Tat—TAR Complex Determined by Site-Specific Photo-Cross-Linking" Biochemistry 35:6491-6499 (1996).
Wargelius et al., "Double-Stranded RNA Induces Specific Developmental Defects in Zebrafish Embryos" Biochem. Biophys. Res. Commun. 263:156-161 (1999).
Waterhouse et al., "Virus resistance and gene silencing in plants can be induced by simultaneous expression of sense and antisense Rna" Proc. Natl. Acad. Sci. USA 95:13959-13964 (1998).
Watkins et al., "In vivo UV cross-linking of U snRNAs that participate in trypanosome trans-splicing" Genes Dev. 5:1859-1869 (1991).
Wengel, "Synthesis of 3'-C- and 4'-C-Branched Oligodeoxynucleotides and the Development of Locked Nucleic Acid (LNA)" Acc. Chem. Res. 32:301-310 (1999).
Zwieb et al., "Evidence for RNA-RNA cross-link formation in *Escherichia coli* ribosomes" Nucleic Acids Res. 5:2705-2720 (1978).
Boutla et al., "Short 5'-Phosphorylated double-stranded RNAs induce RNA interference in *Drosophila*" Current Biol. 11:1776-80, 2001.
Bumcrot et al., "RNAi Therapeutics: a potential new class of pharmaceutical drugs" Nature Chem. Biol. 2:711-719, 2006.
Gewirtz et al., "Nucleic Acid Therapeutics: State of the Art and future prospects" Blood 92:712-736, 1998.
Hanazawa et al., "Use of cDNA subtraction and Rna interference screens in combination reveals genes required for germ-line development in *Caenorhabditis elegans*" Proc. Natl. Acad. Sci. 97:8686-91, 2001.
Hornung et al., "Sequence-specific potent induction of IFN-alpha by short interfering RNA in plasmacytoid dendritic cells through TLR7" Nature medicine 11:263-70, 2005.
Huang et al., "Epidermal growth factor receptor inhibition in cancer therapy: biology, rationale and preliminary clinical results" Investig. New Drugs 17:259-69, 1999.
Judge et al., "Sequence-dependent stimulation of the mammalian innate immune response by synthetic siRNA" Nature Biotech 23:457-62, 2005.
Marques et al., "Activation of the mammalian immune system by siRNAs" Nature Biotech 11:139-1405, 2005.
Nykanen, "ATP Requirements and small interfering RNA structure in the RNA interference pathway" Cell 107:309-21, 2001.
Park et al., "Specific inhibition of HIV-1 gene expression by double-stranded RNA" Nucleic Acids Res. Suppl. No. 1:219-20, 2001.
Sharp et al., "RNA Interference" Science 287:2432-33, 2000.
Sledz et al., "Activation of interferon system by short-interfering RNAs" Nature Cell Biol. 5:834-839, 2003.
Veal et al., "Sequence-specific RNAse cleavage of gag mRNA from HIV-1 infected cells by an antisense oligonucleotide in vitro" Nucleic Acids Res. 26:5670-75, 1998.
Wess et al., "Early days of RNAi" BioCentury vol. 11, No. 12, 2003.
Zamore, "RNA interference: listening to the sound of silence" Nature Struc. Biol. 8:748-750, 2001.
Jiang and Milner, "Selective silencing of viral gene expression in HPV-positive human cervical carcinoma cells treated with siRNA, a primer of RNA interference" Oncogene 21:6041-6048 (2002).
Martinez et al., "Synthetic small inhibiting RNAs: Efficient tools to inactivate oncogenic mutations and restore p53 pathways" Proc. Nat. Acad. Sc. 99:14849-14854 (2002).
Reynolds, et al. (2004) "Rational siRNA design for RNA interference," Nature Biotechnology, vol. 22, No. 3, pp. 326-330.
Spänkuch-Schmitt et al., "Effect of RNA Silencing of Polo-Like Kinase-1 (PLK1) on Apoptosis and Spindle Formation in Human Cancer Cells" J. Nat. Cancer Inst. 94:1863-1877 (2002).
Schlingensiepen et al., Blackwell Science Ltd., vol. 6, 1997, "Antisense—From Technology to Therapy".
Uhlmann, E. et at. Jun. 1, 1990, "Antisense Nucleotides: A New Therapeutic Principal" Chemical Reviews, American Chemical Society, Easton, US vol. 90, No. 4, pp. 543-584, ISSN:0009-2665.
Parrish S. et at. Nov. 2000, Functional Anatomy of a dsRNA Trigger: Differential Requirement for the Two Trigger Strands in RNA Interference, Molecular Cell, vol. 6, 1077-87.
Caplen, N.J., (2002), "A new approach to the inhibition of gene expression", TRENDS in Biotechnology, 20(2):49-51.
Caplen, N.J. et al., (2001), "Specific inhibition of gene expression by small double-stranded RNAs in invertebrate and vertebrate systems", Proc. Natl. Acad. Sci. USA, 98(17):9742-9747.
Doench, J.G. et al., (2003), "siRNAs can function as miRNAs", Genes & Development, 17:438-442.
Donze, O. et al., (2002), "RNA interference in mammalian cells using siRNAs synthesized with T7 RNA Polymerase", Nucleic Acids Research, 30(10):e46(4pages).
Elbashir, S.M. et al., (2001), "RNA interference is mediated by 21- and 22-nucleotide RNAs", Genes & Development, 15:188-200.
Elbashir, S.M. et al., (2001), "Functional anatomy of siRNAs for mediating efficient RNAi in *Drosophila melanogaster* embryo lysate", The EMBO Journal, 20(23):6877-6888.
Fire, A. et al., (1998), "Potent and specific genetic interference by double-stranded RNA in *Caenorhabditis elegans*", Nature, 391:806-811.
Harborth, J. et al., (2001), "Identification of essential genes in cultured mammalian cells using small interfering RNAs", Journal of Cell Science, 114(24):4557-4565.
Lewis, D.L. et al., (2002), "Efficient delivery of siRNA for inhibition of gene expression in postnatal mice", Nature Genetics, 32:107-108.
Manche, L. et al., (1992), "Interactions between Double-Stranded DNA Regulators and the Protein Kinase DAI", Molecular and Cellular Biology, 12(11):5238-5248.
McCaffrey, A.P. et al., (2002), "RNA interference in adult mice", Nature, 418:38-39.
Ngo, H. et al., (1998), "Double-stranded RNA induces mRNA degradation in *Trypanosoma brucei*", Proc. Natl. Acad. Sci., 95:14687-14692.
Paddison, P.J. et al., (2002), "Short hairpin RNAs (shRNAs) induce sequence-specific silencing in mammalian cells", Genes & Development, 16:948-958.
Randall, G. et al., (2003), "Clearance of replicating hepatitis C virus replicon RNAs in cell culture by small interfering RNAs", PNAS, 100(1):235-240.
Tijsterman, M. et al., (2002), "The Genetics of RNA Silencing", Annu. Rev. Genet., 36:489-519.
Yu, J. et al., (2002), "RNA interference by expression of short-interfering RNAs and hairpin RNAs in mammalian cells", PNAS, 99(9):6047-6052.
Nolen, T. et al., (2002), "Positional effects of short interfering RNAs targeting the human coagulation trigger Tissue Factor", Nucleic Acids Research, 30(8):1757-1766.
Ambros, V., (2001), "Dicing Up RNAs", Science, 293:811-813.
Elbashir, S.M. et al., (2001), "Duplexes of 21-nucleotide RNAs mediate RNA interference in cultured mammalian cells", Nature, 411:494-498.
Gautschi, O. et al., (2001), "Activity of a Novel bcl-2/bcl-xL-Bispecific Antisense Oligonucleotide Against Tumors of Diverse Histologic Origins", Journal of the National Cancer Institute, 93(6):463-471.
Lipardi, C. et al., (2001), "RNAi as Random Degradative PCR: siRNA Primers Convert mRNA into dsRNAs that Are Degraded to Generate New siRNAs", Cell, 107:297-307.
Sharp, P.A., (2001), "RNA interference—2001", Genes & Development, 15:485-490.
Sijen, T. et al., (2001), "On the Role of RNA Amplification in dsRNA-Triggered Gene Silencing", Cell, 107:465-476.
Bass, B.L., (2000), "Double-Stranded RNA as a Template for Gene Silencing", Cell, 101:235-238.

(56) References Cited

OTHER PUBLICATIONS

Cobaleda, C. et al., (2000), In vivo inhibition by a site-specific catalytic RNA subunit of Rnase P designed against the BCR-ABL oncogenic products: a novel approach for cancer treatment, Blood, 95(3):731-737.
Hammond, S.M. et al., (2000), "An RNA-directed nuclease mediates post-transcriptional gene silencing in *Drosophila* cells", Nature, 404:293-296.
Yang, D. et al., (2000), "Evidence that processed small dsRNAs may mediate sequence-specific mRNA degradation during RNAi in *Drosophila* embryos", Current Biology, 10:1191-1200.
Wianny, F. et al., (2000), "Specific interference with gene function by double-stranded RNA in early mouse development", Nature Cell Biology, 2:70-75.
Zamore, P.D. et al., (2000), "RNAi: Double-Stranded RNA Directs the ATP-Dependent Cleavage of mRNA at 21 to 23 Nucleotide Intervals", Cell, 101:25-33.
Fire, A., "RNA-triggered Gene Silencing," Trends in Genetics, Sep. 1999, pp. 358-363, vol. 15, No. 9.
Tuschl, T. et al., (1999), "Targeted mRNA degradation by double-stranded RNA in vitro", Genes & Development, 13:3191-3197.
Wild, K. et al., (1999), "The 2 .ANG. structure of helix 6 of the human signal recognition particle RNA", Structure, (11):1345-1352.
Montgomery, M.K. et al., (1998), "Double-stranded RNA as a mediator in sequence-specific genetic silencing and co-suppression", TIG, 14(7):255-258.
Lowy, D.R. et al., (1993), "Function and Regulation of RAS", Annu. Rev. Biochem., 62:851-891.
Downward, J. et al., (1990), "Identification of a nucleotide exchange-promoting activity for p21.sup.ras", Proc. Natl. Acad. Sci. USA, 87:5998-6002.
Gibbs, J.B. et al., (1988), "Purification of ras GTPase activating protein from bovine brain", Proc. Natl. Acad. Sci. USA, 85:5026-5030.
Lima, w., et al., "Cleavage of Single Strand RNA Adjacent to RNA-DNA Duplex Regions by *Escherichia coli*RNase H1," The Journal of Biological Chemistry, Oct. 31, 1997, pp. 27513-57216, vol. 272, No. 44.
Wu, H., et al., "Properties of Clones and Expressed Human RNase H1," The Journal of Biological Chemistry, Oct. 1, 1999, pp. 28270-28278, vol. 274, No. 40.
Z-Axis Connector Company, Silver ST AX, www.z-axiscc.comlprodstax.htm, Accessed Jul. 19, 2001.
Z-Axis Connector Company, LCD Connectors, www.z-axiscc.com/prodlcd.htm, Accessed Jul. 19, 2001.
Agrawal, S. et al., Molecular Med. Today, vol. 6, pp. 72-81 (2002).
Branch, A.D., Trends in Biochem. ScL, vol. 23, pp. 45-50 (1998).
Crooke, S.T., Antisense Research & Application, Chapter 1, pp. 1-50, Ed. by S. Crooke, Publ. by Springer-Verlag (1998).
Peracchi, A., Rev. Med. Virol., vol. 14, pp. 47-64 (2003).
Chirila, T.V. et al., Biomaterials, vol. 23, pp. 321-342 (2002).
Opalinska, J.B. et al., Nature Reviews, vol. 1, pp. 503-514 (2002).
Communication from the European Patent Office including Response to Patentee's Submission of May 21, 2010, filed by SI RNA Therapeutics on Sep. 7, 2010, in opposition to European Patent No. 1352061, 15 Pages.
Response to Grounds of Appeal Filed by Opponent in opposition to European Patent No. EP1352061, filed by Alnylam Europe AG on May 21, 2010, 15 Pages.
Grounds for Appeal in opposition to European Patent No. EP1352061, filed by SiRNA Therapeutics, filed on Jan. 4, 2010, 39 Pages.
Notice of Appeal in opposition to European Patent No. EP1352061, filed by SiRNA Therapeutics, filed on Oct. 23, 2009, 39 Pages.
Minutes of the oral proceedings of the Opposition Division, Opposition Application No. 02710786.1 for European Patent No. EP1352061, Aug. 25, 2009, 11 Pages.
Decision on Rejection of the Opposition, Opposition Application No. 02710786.1 for European Patent No. EP1352061, Aug. 25, 2009, 40 Pages.
Annex to Decision on Reject of the Opposition, Opposition Application No. 02710786.1 for European Patent No. EP1352061, Aug. 25, 2009, 20 Pages (English translation of claims included within document).
Petition by Sirna Therapeutics in opposition proceedings for European Patent No. 1352061 (May 14. 2009).
Notice of Opposition by SiRNA Therapeutics, Inc. against EP application No. 02710786.1 (Feb. 28, 2007).
Patentees Observations filed in opposition proceedings for EP application No. 02710786.1 (Oct. 15, 2007).
Summons to Attend oral proceedings in the opposition proceedings for EP application No. 02710786.1 (Mar. 17, 2009).
Submission and Auxiliary Request by Sirna Therapeutics in opposition proceedings for European Patent No. 1352061 (May 13, 2009).
International Search Report for International Application No. PCT/EP2002/00152, Jul. 17, 2003, 10 Pages.
International Search Report for International Application No. PCT/EP2002/00151, Jun. 12, 2003, 7 Pages.
James, H.A, et al., "The therapeutic potential of ribozymes," Blood (1998) 91 :371-82.
Jansen, B., et al., "Chemosensitisation of malignant melanoma by BCL2 antisense therapy," *The Lancet* (2000) 356:1728-1733.
Skorski, T. et al., Suppression of Philadelphia, leukemia cell growth in mice by BCR-ABL antisense oligodeoxynucleotides, *Proc. Nat!. Acad. Sci. USA* (1994) 91:4504-4508.

* cited by examiner

COMPOSITIONS AND METHODS FOR INHIBITING EXPRESSION OF A TARGET GENE

RELATED APPLICATIONS

This application is a continuation of U.S. application Ser. No. 12/894,018, filed on Sep. 29, 2010, which is a continuation of U.S. application Ser. No. 10/384,339, filed on Mar. 7, 2003, which is a continuation-in-part of International Application No. PCT/EP02/00152 (WO02/55693), which designated the United States and was filed on Jan. 9, 2002, which claims the benefit of German Patent No. 101 00 586.5, filed on Jan. 9, 2001, German patent No. 101 55 280.7, filed on Oct. 26, 2001, German Patent No. 101 58 411.3, filed Nov. 29, 2001, and German Patent No. 101 60 151.4, filed Dec. 7, 2001. The entire teachings of the above application(s) are incorporated herein by reference for all purposes.

FIELD OF THE INVENTION

This invention relates to double-stranded ribonucleic acid (dsRNA), and its use in mediating RNA interference in vitro and in vivo.

BACKGROUND OF THE INVENTION

Many diseases (e.g., cancers, hematopoietic disorders, endocrine disorders, and immune disorders) arise from the abnormal expression or activity of a particular gene or group of genes. Similarly, disease can result through expression of a mutant form of protein, as well as from expression of viral genes that have been integrated into the genome of their host. The therapeutic benefits of being able to selectively silence these abnormal or foreign genes are obvious.

A number of therapeutic agents designed to inhibit expression of a target gene have been developed, including antisense ribonucleic acid (RNA) (see, e.g., Skorski, T. et al., *Proc. Natl. Acad. Sci. USA* (1994) 91:4504-4508) and hammerhead-based ribozymes (see, e.g., James, H. A, and 1. Gibson, Blood (1998) 91:371). However, both of these agents have inherent limitations. Antisense approaches, using either single-stranded RNA or DNA, act in a 1:1 stoichiometric relationship and thus have low efficacy (Skorski et al., supra). For example, Jansen et al. report that, in a small percentage of patients, relatively high doses (2 mg/kg body weight per day) of antisense RNA resulted in biologically significant levels (i.e., long-term plasma concentrations above 1 mg/L) of encoded protein (Jansen, B., et al., *The Lancet* (2000) 356: 1728-1733). However, no detectable level of plasma protein was observed at lower dosages (e.g., 0.6 mg). Hammerhead ribozymes, which because of their catalytic activity can degrade a higher number of target molecules, have been used to overcome the stoichiometry problem associated with antisense RNA. However, hammerhead ribozymes require specific nucleotide sequences in the target gene, which are not always present.

More recently, double-stranded RNA molecules (dsRNA) have been shown to block gene expression in a highly conserved regulatory mechanism known as RNA interference (RNAi). Briefly, the RNAse III Dicer enzyme processes dsRNA into small interfering RNAs (siRNA) of approximately 22 nucleotides, which serve as guide sequences to induce target-specific mRNA cleavage by an RNA-induced silencing complex RISC (Hammond, S. M., et al., *Nature* (2000) 404:293-296). In other words, RNAi involves a catalytic-type reaction whereby new siRNAs are generated through successive cleavage of long dsRNA. Thus, unlike antisense, RNAi degrades target RNA in a non-stoichiometric manner. When administered to a cell or organism, exogenous dsRNA has been shown to direct the sequence-specific degradation of endogenous messenger RNA (mRNA) through RNAi.

WO 99/32619 (Fire et al.) discloses the use of a dsRNA of at least 25 nucleotides in length to inhibit the expression of a target gene in *C. elegans*. dsRNA has also been shown to degrade target RNA in other organisms, including plants (see, e.g., WO 99/53050, Waterhouse et al.; and WO 99/61631, Heifetz et al.) and *Drosophila* (see, e.g., Yang, D., et al., *Curr. Biol.* (2000) 10:1191-1200). Despite successes in these organisms, until recently the general perception in the art has been that RNAi cannot be made to work in mammals. It was believed that protocols used for invertebrate and plant systems would not be effective in mammals due to the interferon response, which leads to an overall block to translation and the onset of apoptosis (see, e.g., Wianny, F., et al., *Nature Cell Biol.* (2000) 2:70-75); Fire, A., *Trends Genet.* (1999) 15:358-363; and Tuschl, T., et al., *Genes Dev.* (1999) 13(24):3191-97). At least one group of scientists believed that RNAi could only be made to work in mammals if the PKR response could be neutralized or some way avoided, although no suggestions were given as to how this might be achieved (Fire, *Trends Genet.* (1999), supra; and Montgomery and Fire, *Trends Genet.* (1998) 14:255-258). However, WO 00/44895 (Limmer) demonstrated for the first time that dsRNA can induce RNAi in mammalian cells, provided that the dsRNA meets certain structural requirements, including a defined length limitation.

Despite significant advances in the field, there remains a need for an agent that can selectively and efficiently silence a target gene using the cell's own RNAi machinery. More specifically, an agent that has both high biological activity and in vivo stability, and that can effectively inhibit expression of a target gene at a low dose, would be highly desirable. Compositions comprising such agents would be useful for treating diseases caused by abnormal expression or activity of a gene.

SUMMARY OF THE INVENTION

The present invention discloses double-stranded ribonucleic acid (dsRNA), as well as compositions and methods for inhibiting the expression of a target gene in a cell using the dsRNA. The present invention also discloses compositions and methods for treating diseases caused by the expression or activity of the target gene. The dsRNA of the invention, which is no more than 49 nucleotides in length, comprises an RNA strand (complementary RNA strand) having a region which is complementary to an RNA transcript of at least a part of a target gene. The 3'-end of the complementary RNA strand comprises a nucleotide overhang of 1 to 4 nucleotides; the 5'-end of the complementary RNA strand is blunt.

In one aspect, the invention relates to a double-stranded ribonucleic acid (dsRNA), which is no more than 49 nucleotides in length, comprises a sense RNA strand and a complementary RNA strand. The complementary RNA strand, is substantially identical to at least a part of a target gene, comprises a complementary nucleotide sequence which is complementary to an mRNA transcript of a portion of the target gene. The 3'-end of the complementary RNA has a nucleotide overhang of 1 to 4 nucleotides and the 5'-end is blunt. The dsRNA may be less than 25 nucleotides, preferably 19 to 23 nucleotides in length, and the nucleotide overhang is preferably 1 or 2 nucleotides in length. The nucleotides of the nucleotide overhang may be replaced with nucleoside thiophosphates. The dsRNA may comprise a linker between the complementary RNA strand and the sense RNA strand, preferably between the 5'-end of the complementary RNA strand and the 3'-end of the sense RNA strand. The linker may be a chemical linker, such a hexaethylene glycol linker, apoly-(oxyphosphinico-oxy-1,3-propandiol) linker, or an oligoethyleneglycol linker. The target gene may be an oncogene, a cytokine gene, an idiotype protein gene, a prion gene, a gene that encodes a protein that induces angiogenesis, a gene that encodes an adhesion protein, a gene that encodes a cell surface receptor, a gene that encodes a protein involved in a metastasizing and/or invasive process, a gene that encodes a proteinase, a gene that encodes a protein that regulates apoptosis, a gene that encodes a EGF receptor, a MDR1 gene, a gene of a human papilloma virus, a hepatitis C virus, or a human immunodeficiency virus. In one embodiment, the target gene comprises a sequence of SEQ ID NO:1-140.

In another aspect, the invention relates to a method of inhibiting the expression of a target gene in a cell. The method comprises introducing a double-stranded ribonucleic acid (dsRNA) into the cell, and maintaining the cell for a time sufficient to obtain degradation of the mRNA transcript of the target gene, thereby inhibiting expression of the target gene. The complementary RNA strand, is substantially identical to at least a part of a target gene, comprises a complementary nucleotide sequence which is complementary to an mRNA transcript of a portion of the target gene. The 3'-end of the complementary RNA has a nucleotide overhang of 1 to 4 nucleotides and the 5'-end is blunt. The dsRNA may be less than 25 nucleotides, preferably 19 to 23 nucleotides in length, and the nucleotide overhang is preferably 1 or 2 nucleotides in length. The nucleotides of the nucleotide overhang may be replaced with nucleoside thiophosphates. The dsRNA may comprise a linker between the complementary RNA strand and the sense RNA strand, preferably between the 5'-end of the complementary RNA strand and the 3'-end of the sense RNA strand. The linker may be a chemical linker, such a hexaethylene glycol linker, apoly-(oxyphosphinico-oxy-1,3-propandiol) linker, or an oligoethyleneglycol linker. The target gene may be any gene whose expression is to be inhibited, such as the target genes described above.

In yet another aspect, the invention relates to a pharmaceutical composition for inhibiting the expression of a target gene in a mammal. The pharmaceutical composition comprises a dsRNA, as described above, and a pharmaceutically acceptable carrier. The dosage unit of dsRNA may be in a range of 0.01 to 5.0 milligrams (mg), 0.1 to 200 micrograms, 0.1 to 100 micrograms, 1.0 to 50 micrograms, or 1.0 to 25 micrograms, preferably less than 25 micrograms per kilogram body weight of the mammal. The target gene may be any gene whose expression is to be inhibited, such as the target genes described above. The pharmaceutically acceptable carrier may be an aqueous solution, such as phosphate buffered saline, and may comprise a micellar structure, such as a liposome, capsid, capsoid, polymeric nanocapsule, or polymeric microcapsule. The pharmaceutical composition may be formulated to be administered by inhalation, infusion, injection, or orally, preferably by intravenous or intraperitoneal injection.

In another aspect, the invention relates to a method for treating a disease caused by the expression of a target gene in a mammal. The method comprises administering a pharmaceutical composition, as described above, comprising a double-stranded ribonucleic acid (dsRNA) and a pharmaceutically acceptable carrier. The dosage unit of dsRNA maybe in a range of 0.01 to 5.0 milligrams (mg), 0.1 to 200 micrograms, 0.1 to 100 micrograms, 1.0 to 50 micrograms, or 1.0 to 25 micrograms, preferably less than 25 micrograms per kilogram body weight of the mammal. The target gene may be any gene whose expression causes a disease in an organism, such as the target genes described elsewhere herein.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

Figure 1A:
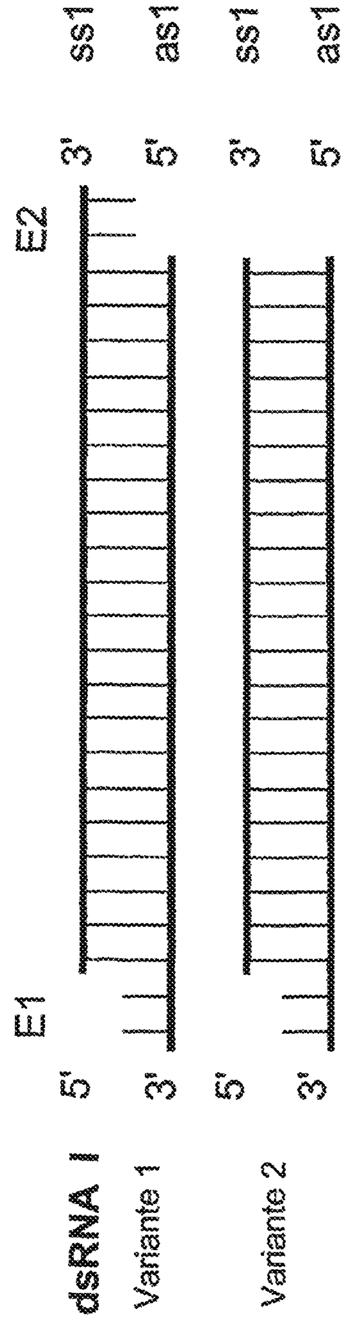
FIG. 1 is a diagram of a first dsRNA (A) and a second dsRNA (B).
Figure 1B:
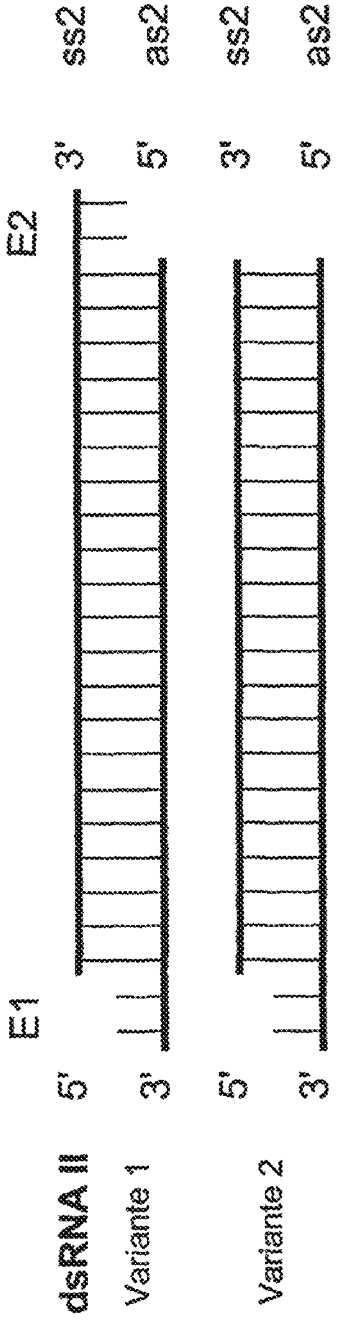
Figure 2:
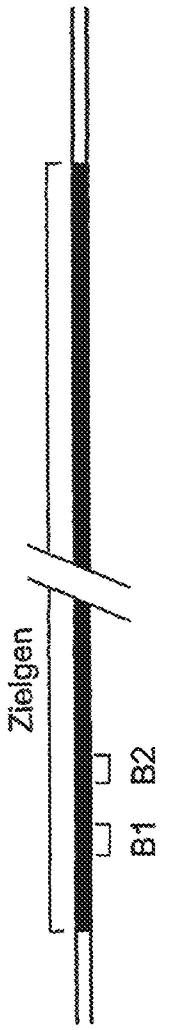
FIG. 2 is a diagram of a target gene.
Figure 3:
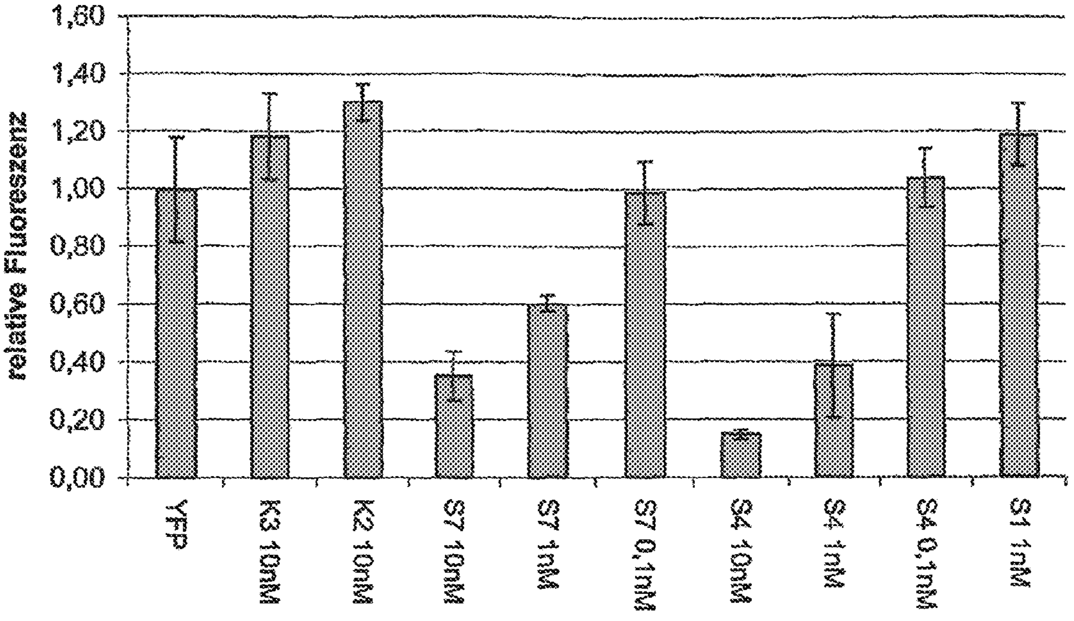
FIG. 3 relative YFP fluorescence after application of various dsRNAs in NIH/3T3 cells (first experiment).
Figure 4:
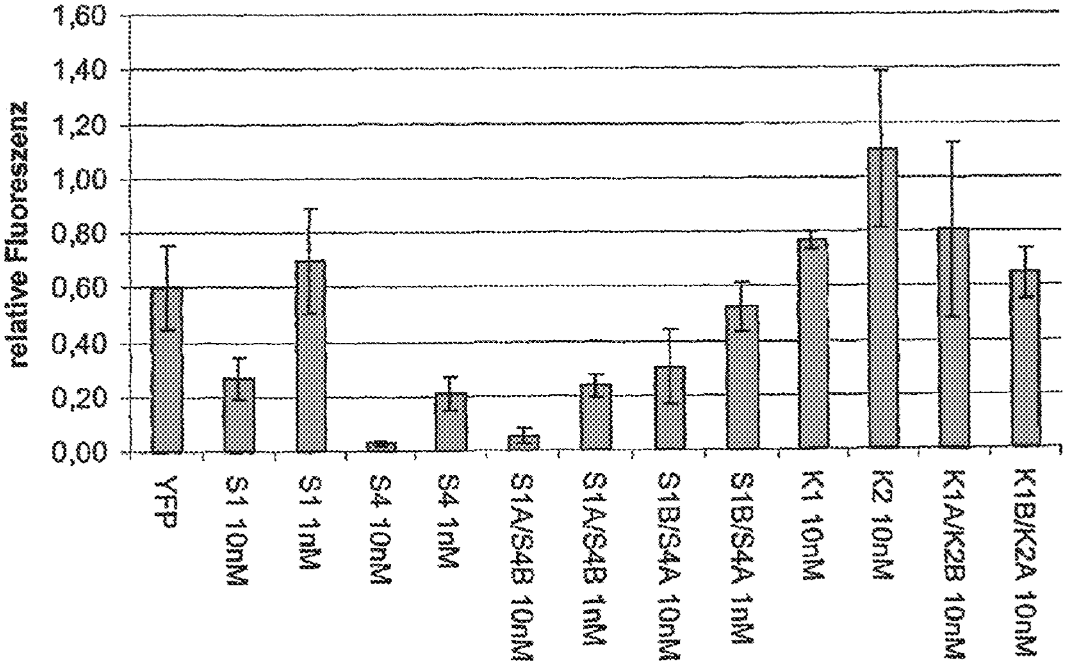
FIG. 4 relative YFP fluorescence after application of various dsRNAs in NIH/3T3 cells (second experiment).
Figure 5:
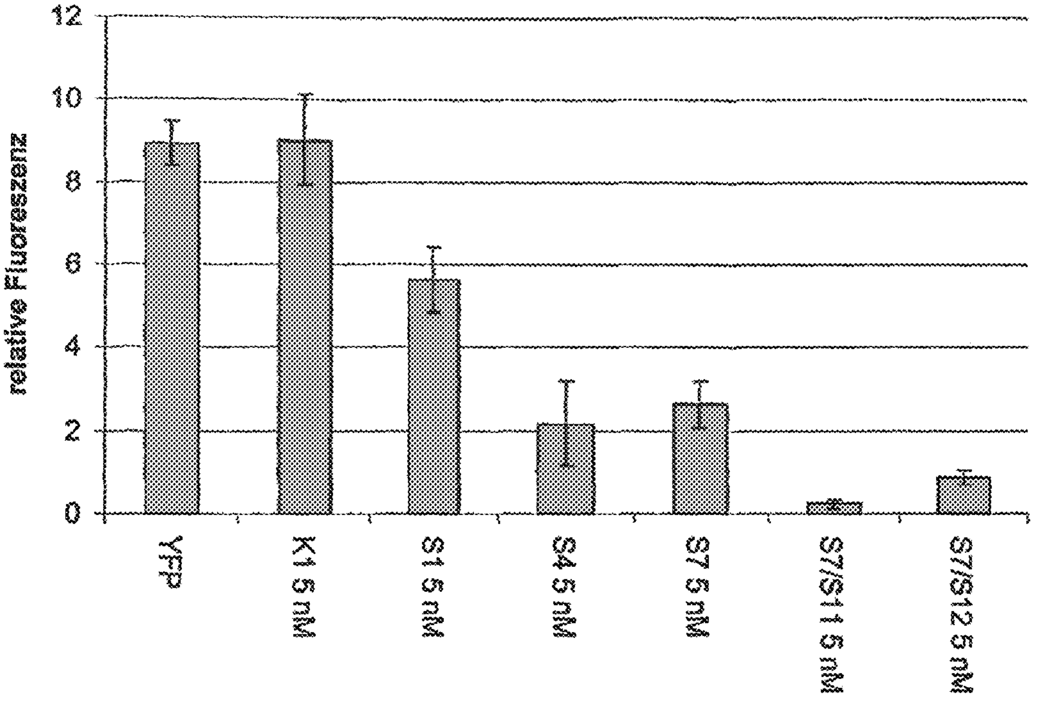
FIG. 5 relative YFP fluorescence after application of various dsRNAs in NIH/3T3 cells (third experiment).
Figure 6:
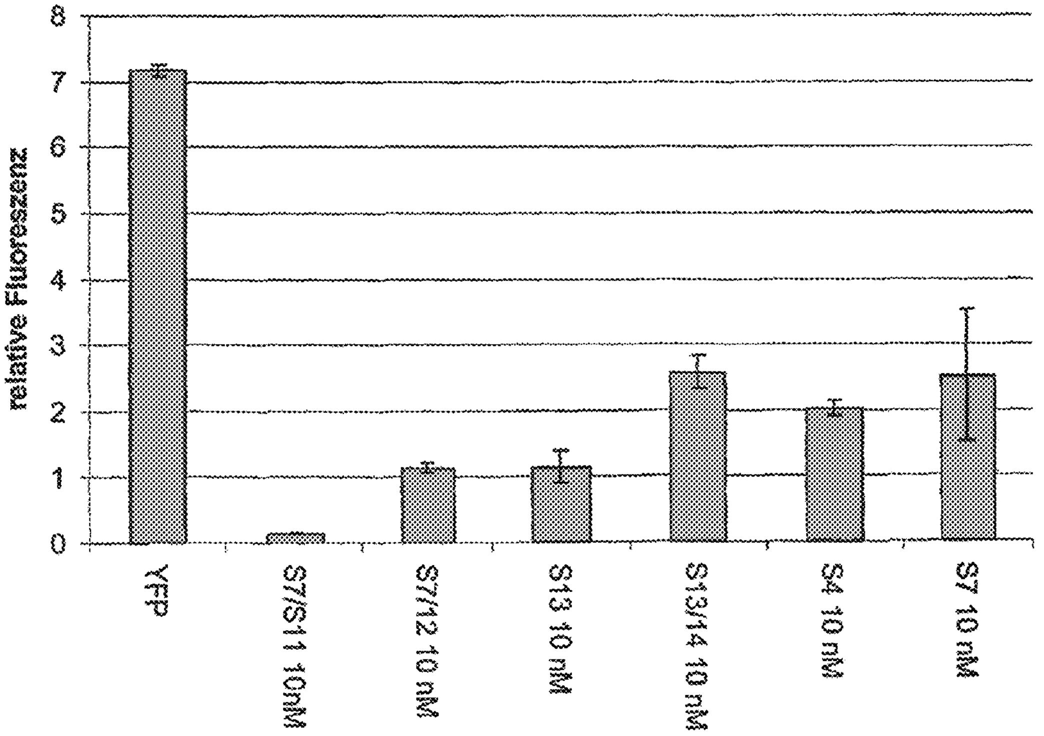
FIG. 6 relative YFP fluorescence after application of various dsRNAs in NIH/3T3 cells (fourth experiment).
Figure 7:
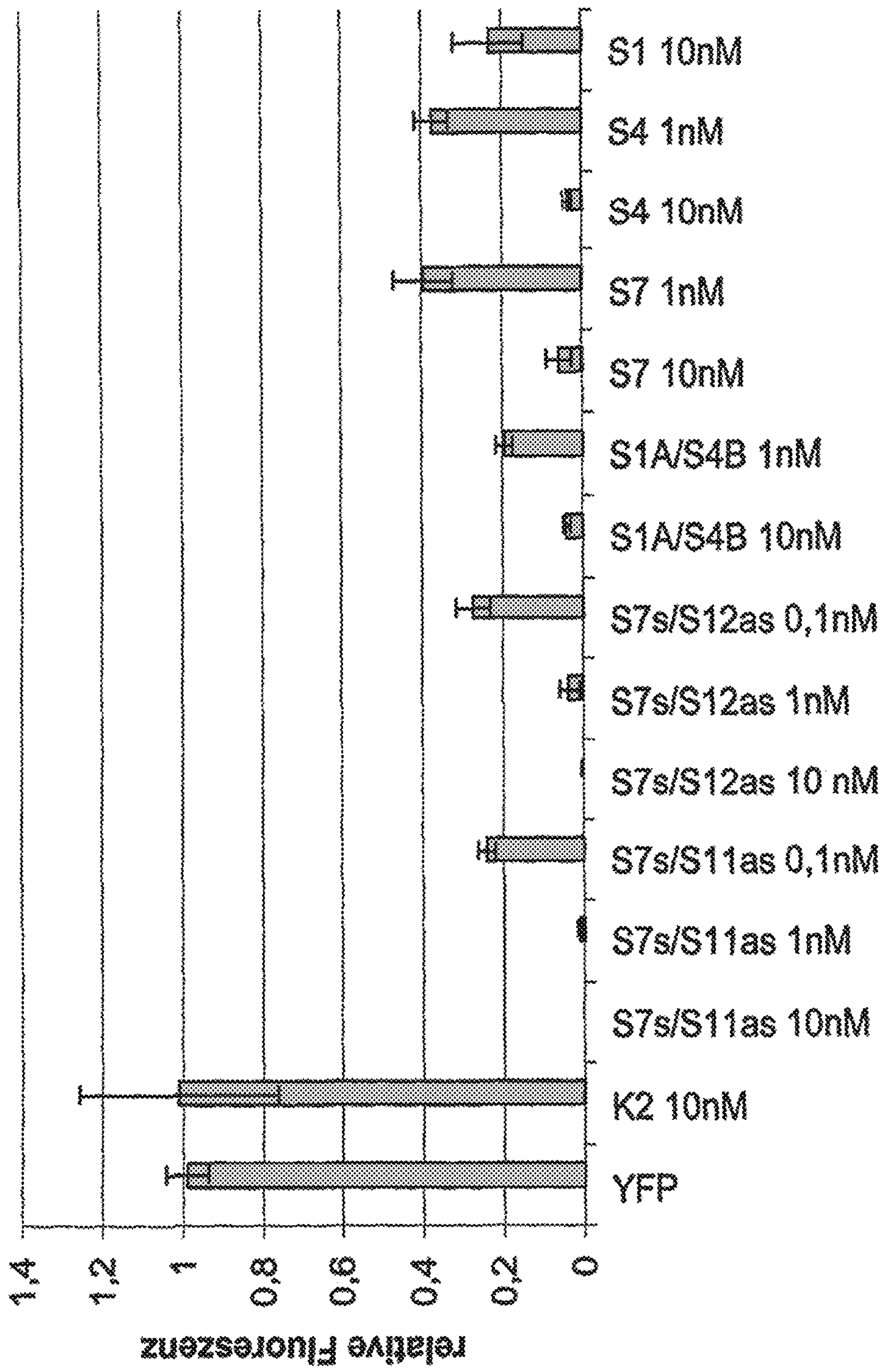
FIG. 7 relative YFP fluorescence after application of various dsRNAs in NIH/3T3 cells (fifth experiment).
Figure 8:
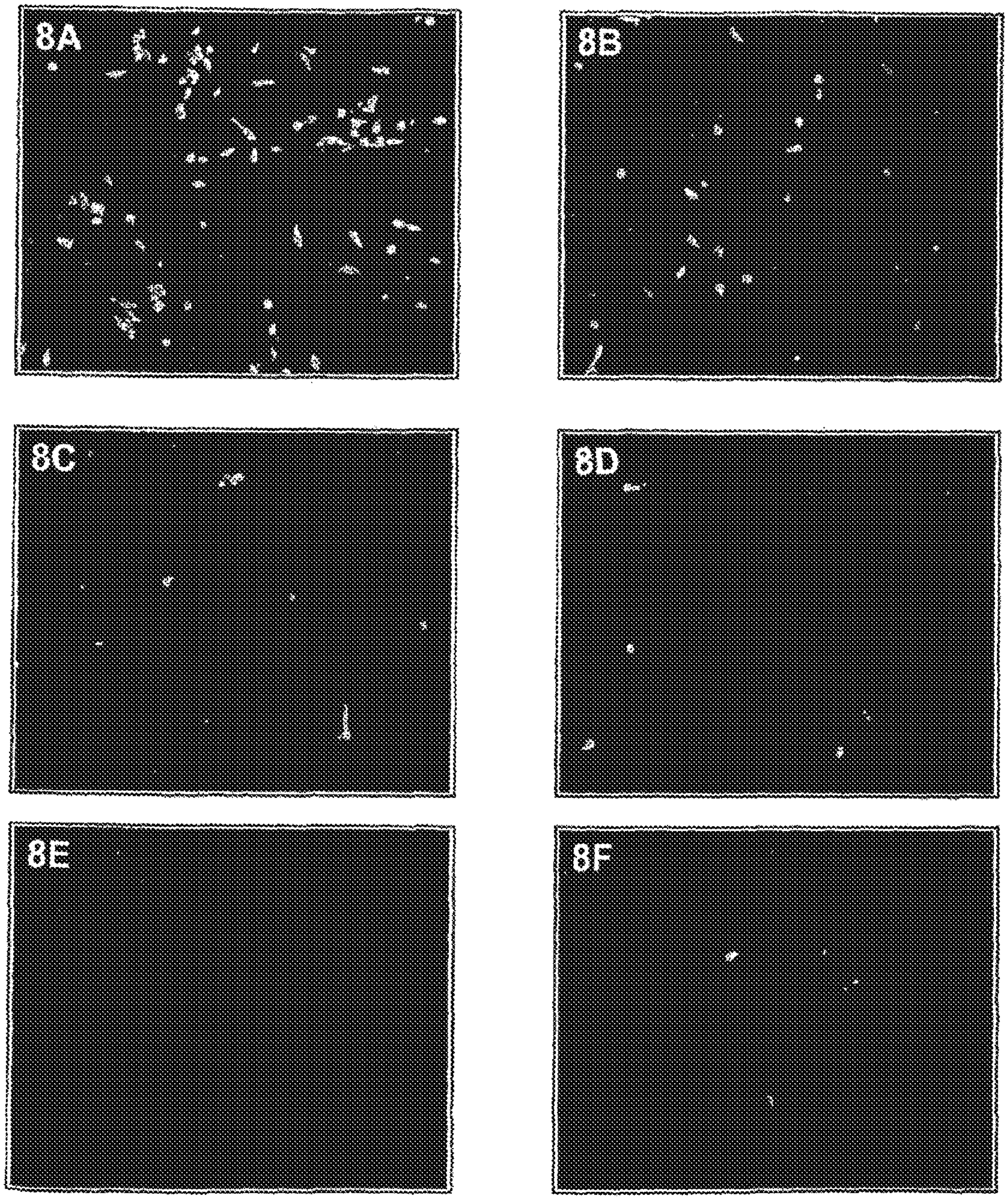
FIG. 8 fluorescence microscopic imaging of NIH/3T3 cells after transfection with pcDNA-YFP or after cotransfection with pcDNA-YFP and various dsRNAs.
Figure 9:
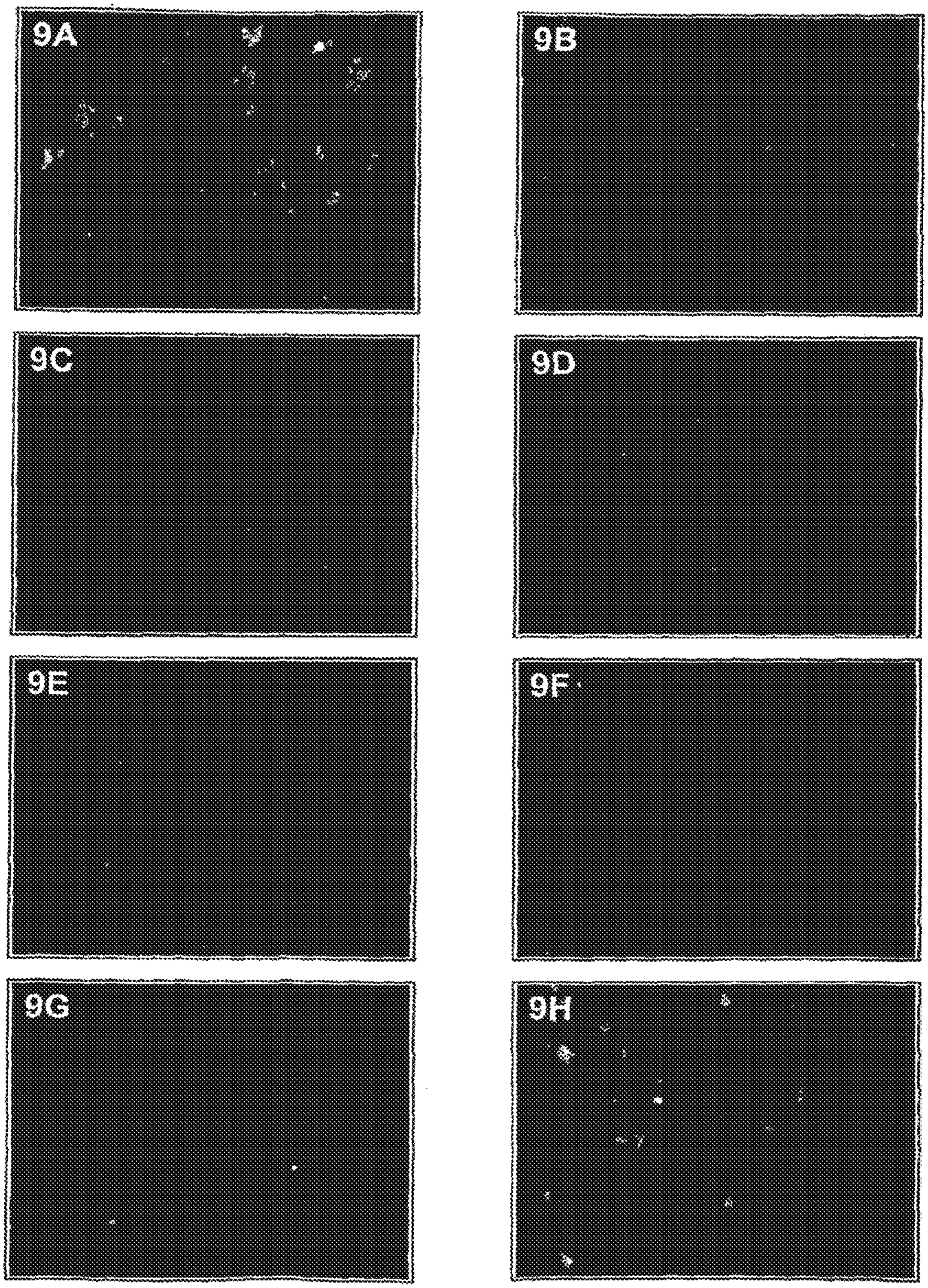
FIG. 9 fluorescence microscopic imaging of HeLa-S3 cells after transfection with pcDNA-YFP or after cotransfection with pcDNA-YFP and various dsRNAs.
Figure 10:
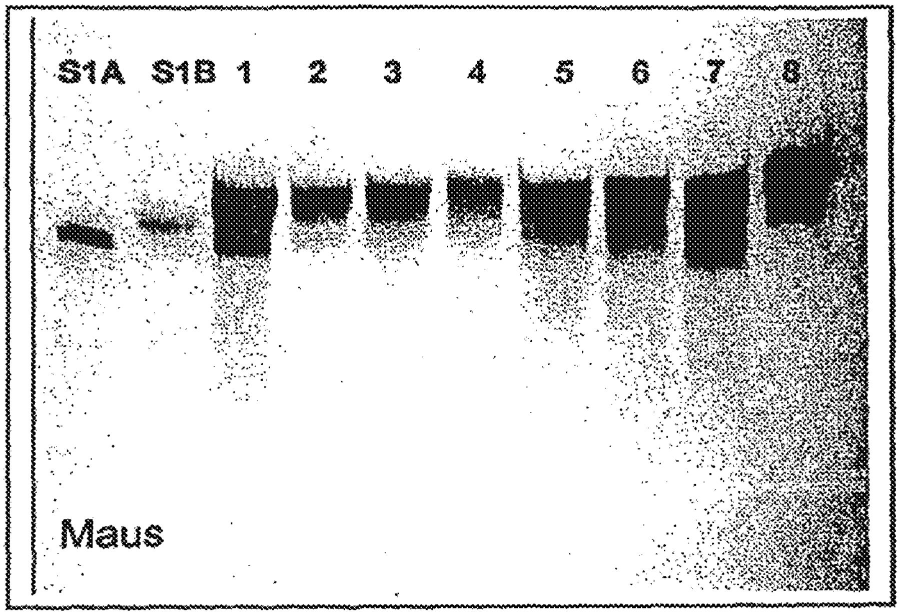
FIG. 10 is a gel electrophoretic separation of S 1 after incubation in mouse serum.
Figure 11:
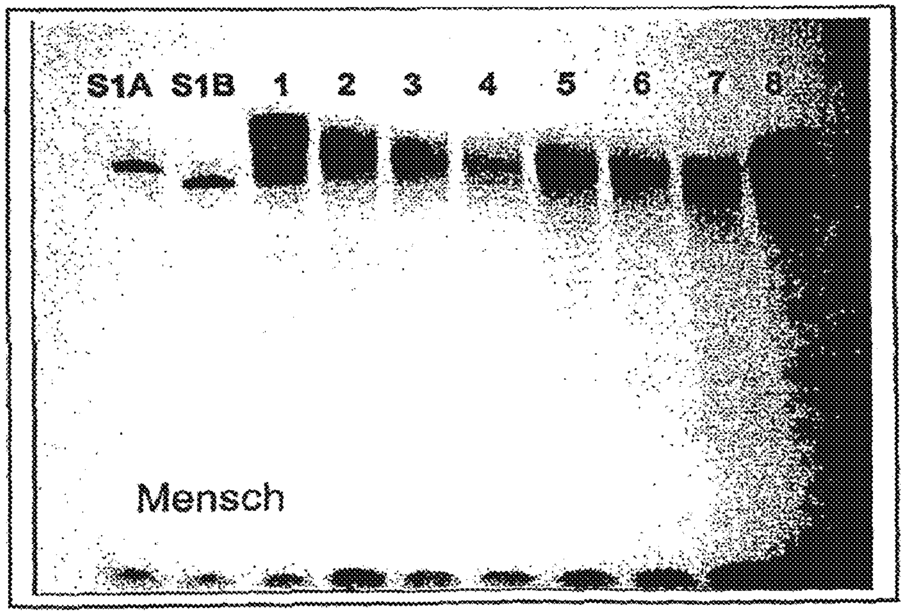
FIG. 11 is a gel electrophoretic separation of S 1 after incubation in human serum.
Figure 12:
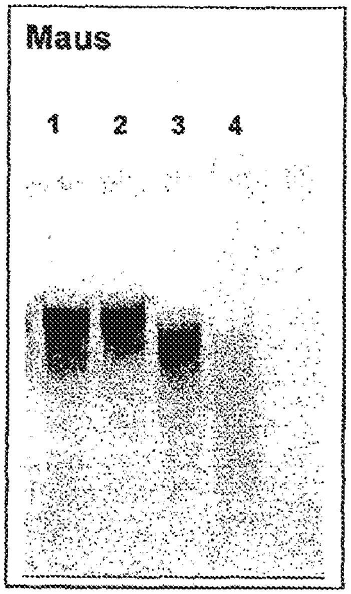
FIG. 12 is a gel electrophoretic separation of S7 after incubation in mouse serum.
Figure 13:
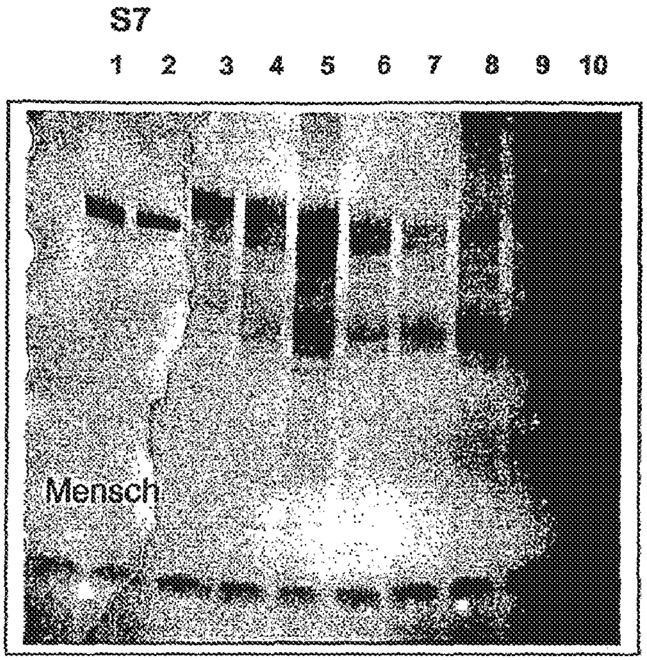
FIG. 13 is a gel electrophoretic separation of S7 after incubation in human serum.
Figure 14:
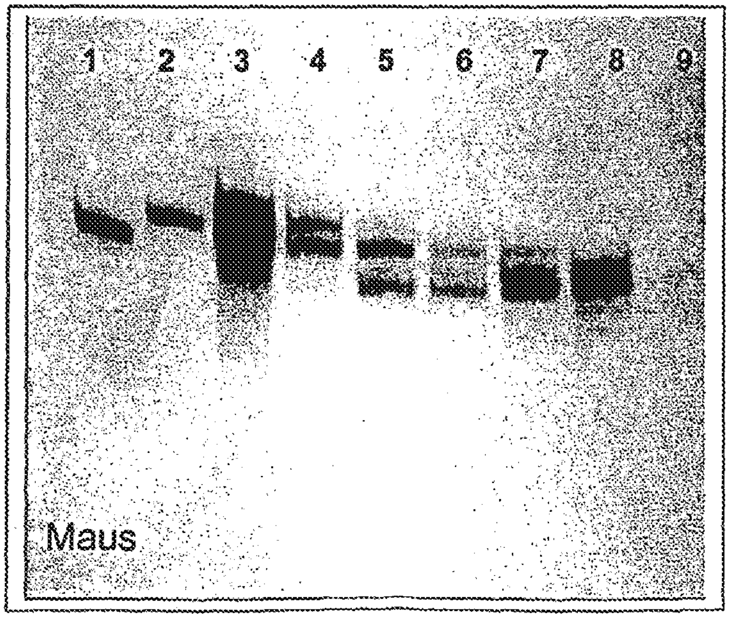
FIG. 14 is a gel electrophoretic separation of K3 after incubation in mouse serum.
Figure 15:
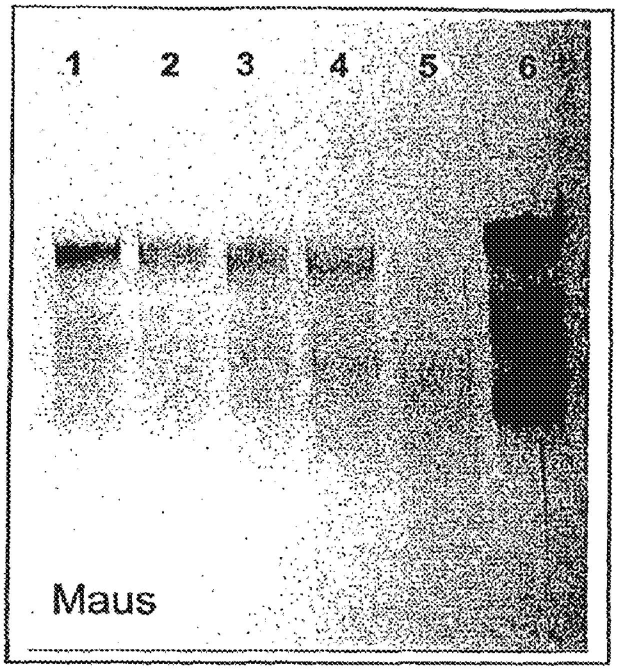
FIG. 15 is a gel electrophoretic separation of PKC112 after incubation in mouse serum.
Figure 16:
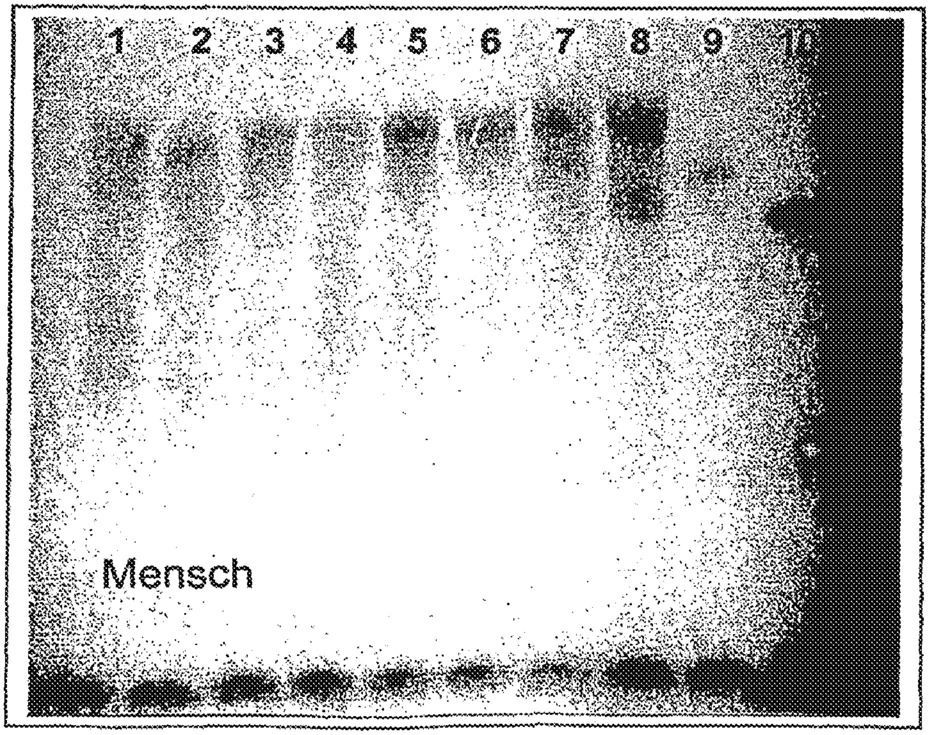
FIG. 16 is a gel electrophoretic separation of S1A/S4B after incubation in human serum.
Figure 17:
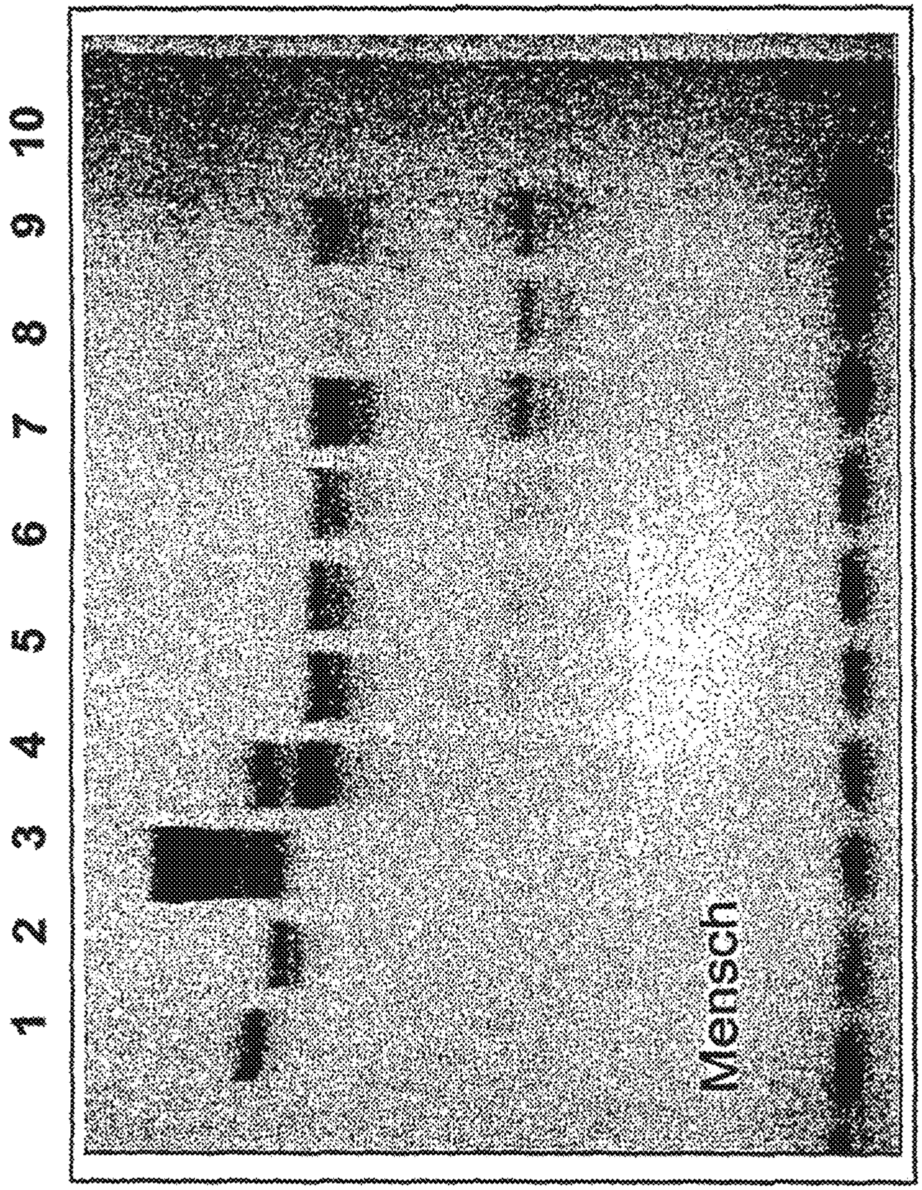
FIG. 17 is a gel electrophoretic separation of K2 after incubation in human serum.

The present invention discloses double-stranded ribonucleic acid (dsRNA), as well as compositions and methods for inhibiting the expression of a target gene in a cell using the dsRNA. The present invention also discloses compositions and methods for treating diseases in organisms caused by expression of a target gene using dsRNA. dsRNA directs the sequence-specific degradation of mRNA through a process known as RNA interference (RNAi). The process occurs in a wide variety of organisms, including mammals and other vertebrates. The dsRNA of the invention is no more than 49 nucleotides in length, and comprises an RNA strand (complementary RNA strand) having a region that is complementary to an RNA transcript of at least a portion of a target gene. The complementary RNA strand has a nucleotide overhang of 1 to 4 nucleotides at the 3'-end; the 5'-end is blunt. Using transgenic mice, the present inventors have demonstrated that very low dosages of these dsRNA can specifically and efficiently mediate RNAi, resulting in significant inhibition of expression of the target gene. The present invention encompasses these dsRNAs and compositions comprising dsRNA and their use for specifically inactivating gene function. The use of these dsRNAs enables the targeted degradation of mRNAs of genes that are implicated in a wide variety of disease processes, including cellular proliferative disorders, hematopoietic disorders, immune disorders, and certain infectious diseases. Thus, the methods and compositions of the present invention comprising these dsRNAs are useful for treating diseases and disorders caused by the expression or activity of a particular gene.

The following detailed description discloses how to make and use the dsRNA and compositions containing dsRNA to inhibit the expression of a target gene, as well as compositions and methods for treating diseases and disorders caused by the expression of the gene. The pharmaceutical compositions of the present invention comprise a dsRNA having a nucleotide sequence of no more than 49 nucleotides in length, preferably less than 25 nucleotides in length, and which is substantially identical to at least a part of the target gene, together with a pharmaceutically acceptable carrier. The dsRNA has a single-stranded nucleotide overhang of 1 to 4 nucleotides at the 3'-end of the complementary RNA strand; the 5'-end is blunt.

Accordingly, certain aspects of the present invention relate to pharmaceutical compositions comprising the dsRNA of the present invention together with a pharmaceutically acceptable carrier, methods of using the compositions to inhibit expression of a target gene, and methods of using the pharmaceutical compositions to treat diseases caused by the expression or activity of a particular gene.

I. Definitions

For convenience, the meaning of certain terms and phrases used in the specification, examples, and appended claims, are provided below.

As used herein, "target gene" refers to a section of a DNA strand of a double-stranded DNA that is complementary to a section of a DNA strand, including all transcribed regions, that serves as a matrix for transcription, as well as a section of an RNA strand of a (+) strand RNA virus. A target gene, usually the sense strand, is a gene whose expression is to be selectively inhibited or silenced through RNA interference. The term "target gene" specifically encompasses any cellular gene or gene fragment whose expression or activity is associated with a disease or disorder (e.g., an oncogene), as well as any foreign or exogenous gene or gene fragment whose expression or activity is associated with a disease, such as a gene from a pathogenic organism (e.g., a viral or pro-viral gene, viroid, or *plasmodium*).

Examples of genes which can be targeted for treatment include, without limitation, an oncogene (Hanahan, D. and R. A. Weinberg, *Cell* (2000) 100:57; and Yokota, J., *Carcinogenesis* (2000) 21(3):497-503); a cytokine gene (Rubinstein, M., et al., *Cytokine Growth Factor Rev*. (1998) 9(2):175-81); a idiotype (1d) protein gene (Benezra, R., et al., *Oncogene* (2001) 20(58):8334-41; Norton, J. D., *J Cell Sci*. (2000) 113(22):3897-905); a prion gene (Prusiner, S. B., et al., *Cell* (1998) 93(3):337-48; Safar, J., and S. B. Prusiner, *Prog. Brain Res*. (1998) 117:421-34); a gene that expresses molecules that induce angiogenesis (Gould, V. E. and B. M. Wagner, *Hum. Pathol*. (2002) 33(11):1061-3); adhesion molecules (Chothia, C. and E. Y. Jones, *Annu. Rev. Biochem*. (1997) 66:823-62; Parise, L. V., et al., *Semin. Cancer Biol*. (2000) 10(6):407-14); cell surface receptors (Deller, M. C., and Y E. Jones, *Curr. Opin. Struct. Biol*. (2000) 10(2):213-9); genes of proteins that are involved in metastasizing and/or invasive processes (Boyd, D., *Cancer Metastasis Rev*. (1996) 15(1):77-89; Yokota, J., *Carcinogenesis* (2000) 21(3):497-503); genes of proteases as well as of molecules that regulate apoptosis and the cell cycle (Matrisian, L. M., *Curr. Biol*. (1999) 9(20): R776-8; Krepela, E., *Neoplasma* (2001) 48(5):332-49; Basbaum and Werb, *Curr. Opin. Cell Biol*. (1996) 8:731-738; Birkedal-Hansen, et al., *Crit. Rev. Oral Biol. Med*. (1993) 4:197-250; Mignatti and Rifkin, *Physiol. Rev*. (1993) 73:161-195; Stetler-Stevenson, et al., *Annu. Rev. Cell Biol*. (1993) 9:541-573; Brinkerhoff, E., and L. M. Matrisan, *Nature Reviews* (2002) 3:207-214; Strasser, A., et al., *Annu. Rev. Biochem*. (2000) 69:217-45; Chao, D. T. and S. J. Korsmeyer, *Annu. Rev. Immunol*. (1998) 16:395-419; Mullauer, L., et al., *Mutat. Res*. (2001) 488(3):211-31; Fotedar, R., et al., *Prog. Cell Cycle Res*. (1996) 2:147-63; Reed, J. C., *Am. J Pathol*. (2000) 157(5):1415-30; D'Ari, R., *Bioassays* (2001) 23(7): 563-5); genes that express the EGF receptor; Mendelsohn, J. and J. Baselga, *Oncogene* (2000) 19(56):6550-65; Normanno, N., et al., *Front. Biosci*. (2001) 6:D685-707); and the multi-drug resistance 1 gene, MDR1 gene (Childs, S., and V. Ling, *Imp. Adv. Oncol*. (1994) 21-36).

The term "complementary RNA strand" (also referred to herein as the "antisense strand") refers to the strand of a dsRNA which is complementary to an mRNA transcript that is formed during expression of the target gene, or its processing products. As used herein, the term "complementary nucleotide sequence" refers to the region on the complementary RNA strand that is complementary to an mRNA transcript of a portion of the target gene. "dsRNA" refers to a ribonucleic acid molecule having a duplex structure comprising two complementary and anti-parallel nucleic acid strands. Not all nucleotides of a dsRNA must exhibit Watson-Crick base pairs; the two RNA strands may be substantially complementary (i.e., having no more than one or two nucleotide mismatches). The maximum number of base pairs is the number of nucleotides in the shortest strand of the dsRNA. The RNA strands may have the same or a different number of nucleotides. The dsRNA is no more than 49, preferably less than 25, and most preferably between 19 and 23, nucleotides in length. dsRNAs of this length are particularly efficient in inhibiting the expression of the target gene. "Introducing into" means uptake or absorption in the cell, as is understood by those skilled in the art. Absorption or uptake of dsRNA can occur through cellular processes, or by auxiliary agents or devices. For example, for in vivo delivery, dsRNA can be injected into a tissue site or administered systemically. In vitro delivery includes methods known in the art such as electroporation and lipofection.

As used herein, a "nucleotide overhang" refers to the unpaired nucleotide or nucleotides that protrude from the duplex structure when a 3'-end of one RNA strand extends beyond the 5'-end of the other strand, or vice versa.

As used herein and as known in the art, the term "identity" is the relationship between two or more polynucleotide sequences, as determined by comparing the sequences. Identity also means the degree of sequence relatedness between polynucleotide sequences, as determined by the match between strings of such sequences. Identity can be readily calculated (see, e.g., *Computation Molecular Biology*, Lesk, A. M., eds., Oxford University Press, New York (1998), and *Biocomputing: Informatics and Genome Projects*, Smith, D. W., ed., Academic Press, New York (1993), both of which are incorporated by reference herein). While there exist a number of methods to measure identity between two polynucleotide sequences, the term is well known to skilled artisans (see, e.g., *Sequence Analysis in Molecular Biology*, von Heinje, G., Academic Press (1987); and *Sequence Analysis Primer*, Gribskov., M. and Devereux, J., eds., M. Stockton Press, New York (1991)). Methods commonly employed to determine identity between sequences include, for example, those disclosed in Carillo, H., and Lipman, D., *SIAM J Applied Math*. (1988) 48:1073. "Substantially identical," as used herein, means there is a very high degree of homology (preferably 100% sequence identity) between the sense strand of the dsRNA and the corresponding part of the target gene. However, dsRNA having greater than 90%, or 95% sequence identity may be used in the present invention, and thus sequence variations that might be expected due to genetic mutation, strain polymorphism, or evolutionary divergence can be tolerated. Although 100% identity is preferred, the dsRNA may contain single or multiple base-pair random mismatches between the RNA and the target gene.

As used herein, the term "treatment" refers to the application or administration of a therapeutic agent to a patient, or application or administration of a therapeutic agent to an isolated tissue or cell line from a patient, who has a disorder, e.g., a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, the terms "pathogen" and "pathogenic organism" refer to an organism capable of producing disease, including, without limitation, a virus, viroid, or *plasmodium*. As used herein, the term "pathogen" includes organisms capable of causing disease in animals and/or plants.

As used herein, a "transformed cell" is a cell into which a dsRNA molecule has been introduced by means of recombinant DNA techniques.

II. Double-Stranded Ribonucleic Acid (dsRNA)

In one embodiment, the invention relates to a double-stranded ribonucleic acid (dsRNA) having a nucleotide sequence which is substantially identical to at least a portion of a target gene. The dsRNA comprises two RNA strands that are sufficiently complementary to hybridize to form the duplex structure. One strand of the dsRNA comprises the nucleotide sequence that is substantially identical to a portion of the target gene (the "sense" strand), and the other strand (the "complementary" or "antisense" strand) comprises a sequence that is complementary to an RNA transcript of the target (DNA) gene or a gene of a (+) strand RNA virus. The dsRNA has no more than 49 nucleotides, preferably less than 25 nucleotides, and most preferably 23 nucleotides in length. The dsRNA can be synthesized by standard methods known in the art, e.g., by use of an automated DNA synthesizer, such as are commercially available from Biosearch, Applied Biosystems, Inc. In specific embodiments, the dsRNA can comprise the sequence set forth in SEQ ID NO:141-173, or a complement or equivalent thereof.

At least one end of the dsRNA has a single-stranded nucleotide overhang of 1 to 4, preferably 1 or 2 nucleotides. The single-stranded overhang is located at the 3'-terminal end of the complementary (antisense) RNA strand, and the 5'-end of the complementary RNA strand is blunt (i.e., no overhang). Such dsRNAs have improved stability and inhibitory activity, thus allowing administration at low dosages, i.e., less than 5 mg/kg body weight of the recipient per day. In another embodiment, one or more of the nucleotides in the overhang is replaced with a nucleoside thiophosphate. dsRNAs having a nucleotide overhang at the 3'-end of the antisense have unexpectedly superior inhibitory properties than their blunt-ended counterparts. Moreover, the present inventors have discovered that the presence of a nucleotide overhang at the 3'-overhang of the antisense strand strengthens the interference activity of the dsRNA, without affecting its overall stability. Such dsRNAs have proven particularly stable and effective in vivo, as well as in a variety of cells, cell culture mediums, blood, and serum.

In another embodiment, the dsRNA is chemically modified for improved stability, i.e., enhanced resistance to degradation and/or strand dissociation. In this embodiment, the integrity of the duplex structure is strengthened by at least one, and preferably two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues. In one embodiment, the linker is a hexa-ethylene glycol linker. In this case, the dsRNAs are produced by solid phase synthesis and the hexa-ethylene glycol linker is incorporated according to standard methods (e.g., Williams, D. J., and K. B. Hall, *Biochem.* (1996) 35:14665-14670). In a preferred embodiment, the 5'-end of the complementary (antisense) RNA strand and the 3'-end of the second (sense) RNA strand are chemically linked via a hexa-ethylene glycol linker.

In yet another embodiment, the target gene is an oncogene; a cytokinin gene; an idiotype protein gene (Id protein gene); a prion gene; a gene that expresses a protein that induces angiogenesis, an adhesion molecule; a cell surface receptor; a gene of a protein involved in a metastasizing and/or invasive process; a gene of a proteinase; a gene of a protein that regulates apoptosis and the cell cycle; a gene that expresses the EGF receptor; or a MDR1 gene, all of which are described elsewhere herein.

In one embodiment, the target gene is the multi-drug resistance 1 gene ("MDR1"). "Multi-drug resistance" (MDR) broadly refers to a pattern of resistance to a variety of chemotherapeutic drugs with unrelated chemical structures and different mechanisms of action. Although the etiology of MDR is multifactorial, the overexpression of P-glycoprotein (Pgp), a membrane protein that mediates the transport of MDR drugs, remains the most common alteration underlying MDR in laboratory models (Childs, S., *Imp. Adv. Oncol.* (1994) 21-36). Moreover, expression of Pgp has been linked to the development of MDR in human cancer, particularly in the leukemias, lymphomas, multiple myeloma, neuroblastoma, and soft tissue sarcoma (Fan., D., et al., *Reversal of Multidrug Resistance in Cancer*, ed. Kellen, J. A. (CRC, Boca Raton, Fla.), pp. 93-125). Recent studies showed that tumor cells expressing MDR-associated protein (MRP) (Cole, S. P. C., et al., *Science* (1992) 258:1650-1654) and lung resistance protein (LRP) (Scheffer, G. L., et al., *Nat. Med.* (1995) 1:578-582) and mutation of DNA topoisomerase II (Beck, W. T., J *Natl. Cancer Inst.* (1989) 81:1683-1685) also may render MDR.

In yet another embodiment, the invention relates to a method for treating viral diseases, including but not limited to hepatitis C, hepatitis B, herpes simplex virus (HSY), HIV-AIDS, poliovirus, and smallpox virus. dsRNAs of the invention are prepared as described herein to target expressed sequences of a virus, thus ameliorating viral activity and replication. The molecules can be used in the treatment and/or diagnosis of viral infected tissue, both animal and plant. Also, such molecules can be used in the treatment of virus-associated carcinoma, such as hepatocellular cancer.

III. Pharmaceutical Compositions Comprising dsRNA

In one embodiment, the invention relates to a pharmaceutical composition comprising a dsRNA, as described in the preceding section, and a pharmaceutically acceptable carrier, as described below. The pharmaceutical composition comprising the dsRNA is useful for treating a disease or disorder associated with the expression or activity of a target gene.

In another embodiment, the invention relates to a pharmaceutical composition comprising at least two dsRNAs, both designed to target the same gene, and a pharmaceutically acceptable carrier. Because of the duplicative targeting of mRNA by a plurality of dsRNAs, pharmaceutical compositions comprising multiple dsRNAs provide improved efficiency of inhibition as compared to compositions comprising a single dsRNA. In this embodiment, the individual dsRNAs are prepared as described in the preceding section, which is incorporated by reference herein. One dsRNA (referred to herein as "dsRNA I") has a nucleotide sequence ("complementary region I") which is substantially identical to at least a portion of the target gene (referred to herein as "region A" of the target gene). Additional dsRNAs are prepared, each of which has a nucleotide sequence that is substantially identical to a different region of the target gene. For example, a second dsRNA ("dsRNA II") may have a nucleotide sequence ("complementary region II") that is substantially identical to a "region B" of the target gene. Region A and region B, which reflect distinct regions of the same target gene, may overlap each other, be adjacent to one another, or be physically separated within the target gene. dsRNA I and dsRNA II may be combined in the same pharmaceutical composition, or formulated separately. If formulated individually, the compositions containing the separate dsRNAs may comprise the same or different carriers, and may be administered using the same or different routes of administration. Moreover, the pharmaceutical compositions comprising the individual dsRNAs may be administered substantially simultaneously, sequentially, or at preset intervals throughout the day or treatment period. Although the foregoing description relates to two dsRNAs (dsRNA I and dsRNA II) which target two regions (region A and region B) of the target gene, the present invention encompasses any number of dsRNAs, each of which targets a distinct region of the target gene.

The pharmaceutical compositions of the present invention are administered in dosages sufficient to inhibit expression of the target gene. The present inventors have found that, because of their improved efficiency, compositions comprising the dsRNA of the invention can be administered at surprisingly low dosages. A maximum dosage of 5 mg dsRNA per kilogram body weight per day is sufficient to inhibit or completely suppress expression of the target gene.

In general, a suitable dose of dsRNA will be in the range of 0.01 to 5.0 milligrams per kilogram body weight of the recipient per day, preferably in the range of 0.1 to 200 micrograms per kilogram body weight per day, more preferably in the range of 0.1 to 100 micrograms per kilogram body weight per day, even more preferably in the range of 1.0 to 50 micrograms per kilogram body weight per day, and most preferably in the range of 1.0 to 25 micrograms per kilogram body weight per day. The pharmaceutical composition may be administered once daily, or the dsRNA may be administered as two, three, four, five, six or more sub-doses at appropriate intervals throughout the day. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases. For example, mouse models are available for hematopoietic malignancies such as leukemias, lymphomas and acute myelogenous leukemia. The MMHCC (Mouse models of Human Cancer Consortium) web page (emice.nci.nih.gov), sponsored by the National Cancer Institute, provides disease-site-specific compendium of known cancer models, and has links to the searchable Cancer Models Database (cancermodels.nci.nih.gov), as well as the NCI-MMHCC mouse repository. Examples of the genetic tools that are currently available for the modeling of leukemia and lymphomas in mice, and which are useful in practicing the present invention, are described in the following references: Maru, Y, *Int. J Hematol.* (2001) 73:308-322; Pandolfi, P. P., *Oncogene* (2001) 20:5726-5735; Pollock, J. L., et al., *Curr. Opin. Hematol.* (2001) 8:206-211; Rego, E. M., et al., *Semin. in Hemat.* (2001) 38:4-70; Shannon, K. M., et al. (2001) Modeling myeloid leukemia tumors suppressor gene inactivation in the mouse, *Semin. Cancer Biol.* 11, 191-200; Van Etten, R. A., (2001) *Curr. Opin. Hematol.* 8, 224-230; Wong, S., et al. (2001) *Oncogene* 20, 5644-5659; Phillips J A., *Cancer Res.* (2000) 52(2):437-43; Harris, A W., et al, *J. Exp. Med.* (1988) 167(2):353-71; Zeng X X et al., *Blood.* (1988) 92(10):3529-36; Eriksson, B., et al., *Exp. Hematol.* (1999) 27(4):682-8; and Kovalchuk, A., et al., *J. Exp. Med.* (2000) 192(8):1183-90. Mouse repositories can also be found at: The Jackson Laboratory, Charles River Laboratories, Taconic, Harlan, Mutant Mouse Regional Resource Centers (MMRRC) National Network and at the European Mouse Mutant Archive. Such models may be used for in vivo testing of dsRNA, as well as for determining a therapeutically effective dose.

The pharmaceutical compositions encompassed by the invention may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered by intravenous or intraparenteral infusion or injection.

For oral administration, the dsRNAs useful in the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of dsRNA in the cells that express the target gene. Such substances include, for example, micellar structures, such as liposomes or capsids, as described below. Surprisingly, the present inventors have discovered that compositions containing only naked dsRNA and a physiologically acceptable solvent are taken up by cells, where the dsRNA effectively inhibits expression of the target gene. Although microinjection, lipofection, viruses, viroids, capsids, capsoids, or other auxiliary agents are required to introduce dsRNA into cell cultures, surprisingly these methods and agents are not necessary for uptake of dsRNA in vivo. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The pharmaceutical compositions useful according to the invention also include encapsulated formulations to protect the dsRNA against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075, which are incorporated by reference herein.

In one embodiment, the encapsulated formulation comprises a viral coat protein. In this embodiment, the dsRNA may be bound to, associated with, or enclosed by at least one viral coat protein. The viral coat protein may be derived from or associated with a virus, such as a polyoma virus, or it may be partially or entirely artificial. For example, the coat protein may be a Virus Protein 1 and/or Virus Protein 2 of the polyoma virus, or a derivative thereof.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in humans. The dosage of compositions of the invention lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, the dsRNAs useful according to the invention can be administered in combination with other known agents effective in treatment of diseases. In any event, the administering physician can adjust the amount and timing of dsRNA administration on the basis of results observed using standard measures of efficacy known in the art or described herein.

For oral administration, the dsRNAs useful in the invention will generally be provided in the form of tablets or capsules, as a powder or granules, or as an aqueous solution or suspension.

IV. Methods for Treating Diseases Caused by Expression of a Target Gene

In one embodiment, the invention relates to a method for treating a subject having a disease or at risk of developing a disease caused by the expression of a target gene. In this embodiment, the dsRNA can act as novel therapeutic agents for controlling one or more of cellular proliferative and/or differentiative disorders, disorders associated with bone metabolism, immune disorders, hematopoietic disorders, cardiovascular disorders, liver disorders, viral diseases, or metabolic disorders. The method comprises administering a pharmaceutical composition of the invention to the patient (e.g., human), such that expression of the target gene is silenced. Because of their high specificity, the dsRNAs of the present invention specifically target mRNAs of target genes of diseased cells and tissues, as described below, and at surprisingly low dosages.

In the prevention of disease, the target gene may be one which is required for initiation or maintenance of the disease, or which has been identified as being associated with a higher risk of contracting the disease. In the treatment of disease, the dsRNA can be brought into contact with the cells or tissue exhibiting the disease. For example, dsRNA substantially identical to all or part of a mutated gene associated with cancer, or one expressed at high levels in tumor cells, e.g. aurora kinase, may be brought into contact with or introduced into a cancerous cell or tumor gene.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin. As used herein, the terms "cancer," "hyperproliferative," and "neoplastic" refer to cells having the capacity for autonomous growth, i.e., an abnormal state of condition characterized by rapidly proliferating cell growth. These terms are meant to include all types of cancerous growths or oncogenic processes, metastatic tissues or malignantly transformed cells, tissues, or organs, irrespective of histopathologic type or stage of invasiveness. Proliferative disorders also include hematopoietic neoplastic disorders, including diseases involving hyperplastic/neoplatic cells of hematopoietic origin, e.g., arising from myeloid, lymphoid or erythroid lineages, or precursor cells thereof.

The pharmaceutical compositions of the present invention can also be used to treat a variety of immune disorders, in particular those associated with overexpression of a gene or expression of a mutant gene. Examples of hematopoietic disorders or diseases include, without limitation, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, automimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing, loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy.

Examples of genes which can be targeted for treatment include, without limitation, an oncogene; a cytokine gene; a idiotype (Id) protein; a prion gene; a gene that expresses molecules that induce angiogenesis; an adhesion molecule; a cell surface receptor; a gene of a protein involved in a metastasizing and/or invasive process; a gene of a proteases as or a protein that regulates apoptosis and the cell cycle; a gene that expresses the EGF receptor; and the multi-drug resistance 1 gene, MDR1 gene, all of which are described elsewhere herein.

In one embodiment, a pharmaceutical compositions comprising dsRNA is used to inhibit the expression of the multi-drug resistance 1 gene ("MDR1"). "Multi-drug resistance" (MDR) broadly refers to a pattern of resistance to a variety of chemotherapeutic drugs with unrelated chemical structures and different mechanisms of action. Although the etiology of MDR is multifactorial, the overexpression of P-glycoprotein (Pgp), a membrane protein that mediates the transport of MDR drugs, remains the most common alteration underlying MDR in laboratory models (Childs, S., *Imp. Adv. Oneal.* (1994) 21-36). Moreover, expression of Pgp has been linked to the development of MDR in human cancer, particularly in the leukemias, lymphomas, multiple myeloma, neuroblastoma, and soft tissue sarcoma (Fan., D., et al., *Reversal of Multidrug Resistance in Cancer*, ed. Kellen, J. A. (CRC, Boca Raton, Fla.), pp. 93-125). Recent studies showed that tumor cells expressing MDR-associated protein (MRP) (Cole, S. P. C., et al., *Science* (1992) 258:1650-1654) and lung resistance protein (LRP) (Scheffer, G. L., et al., *Nat. Med.* (1995) 1:578-582) and mutation of DNA topoisomerase II (Beck, W. T., *J Natl. Cancer Inst.* (1989) 81:1683-1685) also may render MDR.

In another embodiment, the invention relates to a method for treating viral diseases, including but not limited to human papilloma virus, hepatitis C, hepatitis B, herpes simplex virus (HSV), HIV-AIDS, poliovirus, and smallpox virus. dsRNAs of the invention are prepared as described herein to target expressed sequences of a virus, thus ameliorating viral activity and replication. The molecules can be used in the treatment and/or diagnosis of viral infected tissue, both animal and plant. Also, such molecules can be used in the treatment of virus-associated carcinoma, such as hepatocellular cancer.

The pharmaceutical compositions encompassed by the invention may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered by intravenous or intraparenteral infusion or injection.

V. Methods for Inhibiting Expression of a Target Gene

In yet another aspect, the invention relates to a method for inhibiting the expression of a target gene in an organism. The method comprises administering a composition of the invention to the organism such that expression of the target gene is silenced. The organism may be an animal or a plant. Because of their high specificity, the dsRNAs of the present invention specifically target RNAs (primary or processed) of target genes, and at surprisingly low dosages. Compositions and methods for inhibiting the expression of a target gene using dsRNAs can be performed as described elsewhere herein.

In one embodiment, the invention comprises administering a composition comprising a dsRNA, wherein the dsRNA comprises a nucleotide sequence which is complementary to at least a part of an RNA transcript of the target gene of the organism to be treated. When the organism to be treated is a mammal, such as a human, the composition may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the compositions are administered by intravenous or intraparenteral infusion or injection.

The methods for inhibition the expression of a target gene can be applied to any gene one wishes to silence, thereby specifically inhibiting its expression. Examples of human genes which can be targeted for silencing include, without limitation, an oncogene; cytokinin gene; idiotype protein gene (Id protein gene); prion gene; gene that expresses molecules that induce angiogenesis, adhesion molecules, and cell surface receptors; genes of proteins that are involved in metastasizing and/or invasive processes; genes of proteases as well as of molecules that regulate apoptosis and the cell cycle; genes that express the EGF receptor; the multi-drug resistance 1 gene (MDR1 gene); a gene or component of a virus, particularly a human pathogenic virus, that is expressed in pathogenic organisms, preferably in plasmodia.

The methods for inhibition the expression of a target gene can also be applied to any plant gene one wishes to silence, thereby specifically inhibiting its expression.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

RNA Interference in a Mouse Mode

In this Example, double stranded siRNAs are used to inhibit GFP gene expression in transgenic mice.

Synthesis and Preparation of dsRNAs

Oligoribonucleotides are synthesized with an RNA synthesizer (Expedite 8909, Applied Biosystems, Weiterstadt, Germany) and purified by High Pressure Liquid Chromatography (HPLC) using NucleoPac PA-100 columns, 9×250 mm (Dionex Corp.; low salt buffer: 20 mM Tris, 10 nM $NaClO_4$, pH 6.8, 10% acetonitrile; the high-salt buffer was: 20 mM Tris, 400 mM NaClO4, pH 6.S, 10% acetonitrile. flow rate: 3 ml/min). Formation of double stranded siRNAs is then achieved by heating a stoichiometric mixture of the individual complementary strands (10 M) in 10 mM sodium phosphate buffer, pH 6.8, 100 mM NaCl, to 80-90° C., with subsequent slow cooling to room temperature over 6 hours, In addition, dsRNA molecules with linkers may be produced by solid phase synthesis and addition of hexaethylene glycol as a non-nucleotide linker (D. Jeremy Williams, Kathleen B. Hall, Biochemistry, 1996, 35, 14665-14670). A Hexaethylene glycol linker phosphoramidite (Chruachem Ltd, Todd Campus, West of Scotland Science Park, Acre Road, Glasgow, G20 OUA, Scotland, UK) is coupled to the support bound oligoribonucleotide employing the same synthetic cycle as for standard nucleoside phosphoramidites (Proligo Biochemie GmbH, Georg-Hyken-Str.14, Hamburg, Germany) but with prolonged coupling times. Incorporation of linker phosphoramidite is comparable to the incorporation of nucleoside phosphoramidites.

| Name | SEQ ID NO. | DsRNA sequence | Nucleotide number (overhang at the 3'-end of the S1 double-stranded region - overhang at the 3'-end of S2) |
|---|---|---|---|
| S1 | SEQ ID NO: 148 | (S2) 5'-CCACAUGAAGCAGCACGACUUC-3' | 0-22-0 |
| | SEQ ID NO: 149 | (S1) 3'-GGUGUACUUCGUCGUGCUGAAG-5' | |
| S7 | SEQ ID NO: 150 | (S2) 5'-CCACAUGAAGCAGCACGACUU-3' | |
| | SEQ ID NO: 151 | (S1) 3'-CUGGUGUACUUCGUCGUGCUG-5' | 2-19-2 |
| K1 | SEQ ID NO: 153 | (S2) 5'-ACAGGAUGAGGAUCGUUUCGCA-3' | 0-22-0 |
| | SEQ ID NO: 154 | (S1) 3'-UGUCCUACUCCUAGCAAAGCGU-5' | |
| K3 | SEQ ID NO: 155 | (S2) 5'-GAUGAGGAUCGUUUCGCAUGA-3' | 2-19-2 |
| | SEQ ID NO: 156 | (S1) 3'-UCCUACUCCUAGCAAAGCGUA-5' | |
| K4 | SEQ ID NO: 155 | (S2) 5'-GAUGAGGAUCGUUUCGCAUGA-3' | 2-21-0 |
| | SEQ ID NO: 156 | (S1) 3'-UCCUACUCCUAGCAAAGCGUACU-5' | |
| S7/S11 | SEQ ID NO: 150 | (S2) 5'-CCACAUGAAGCAGCACGACUU-3' | 2-21-0 |
| | SEQ ID NO: 159 | (S1) 3'-CUGGUGUACUUCGUCGUGCUGAA-5' | |

RNAi Administration

DsRNA are administered systemically either orally, by means of inhalation, infusion, or injection, preferably by intravenous or intraperitoneal infusion or injection in combination with pharmaceutically acceptable carriers. Examples of suitable carriers are found in standard pharmaceutical texts, e.g. "Remington's Pharmaceutical Sciences", 16th edition, Mack Publishing Company, Easton, Pa., 1980. A preparation that is suitable for inhalation, infusion, or injection preferably consists of dsRNA and a physiologically tolerated solvent, preferably a physiological saline solution or a physiologically tolerated buffer, preferably a phosphate buffered saline solution. The invention anticipates the use of a double-stranded ribonucleic acid in a dosage of a maximum of 5 mg/kg body weight per day.

GFP Laboratory Mice:

The transgenic laboratory mouse strain TgN (GFPU) 5Nagy (Jackson Laboratory, Bar Harbor, Me.), which expresses GFP in all cells studied to date (with the help of a beta actin promoter and a CMV intermediate early enhancer) (Hadjantonakis A K et al., 1998, *Nature Genetics* 19: 220-222), was used. The GFP transgenic mice may be clearly differentiated on the basis of fluorescence (using a UV lamp) from the corresponding wild types (WT). The following experiments were carried out using GFP-heterozygote animals that were bred by mating a WT animal each with a heterozygote GFP-type animal. The animals were kept under controlled conditions in groups of 3-5 animals in Type III Makrolon cages (Ehret Co., Emmendingen, Germany) at a constant temperature of 22° C. and a light-to-dark rhythm of 12 hours. Granulated softwood (8/15, Altromin Co., Lage, Germany) was strewn on the bottom of the cages. The animals received tap water and Altromin 1324 pelleted standard feed (Altromin Co.) ad libitum.

In Vivo Experiment:

Heterozygote GFP animals were placed in cages as described above in groups of 3. DsRNA solution was injected intravenously (i.v.) into the caudal vein in 12-hour rotation (between 5:30 and 7:00 and between 17:30 and 19:00) over 5 days. Injection volume was 60 μl per 10 g body weight, and dosage was 2.5 mg dsRNA or 50 μg per kg body weight. The groups were organized as follows:

Group A: PBS (phosphate buffered saline) 60 μl per 10 g body weight each,

Group B: 2.5 mg per kg body weight of a non-specific control dsRNA (K1 control with smooth ends and a double-stranded region of 22 nucleotide pairs), Group C, 2.5 mg per kg body weight of another non-specific control dsRNA (K3 control with 2 nucleotide [nt] overhangs and both 3'-ends and a double-stranded region of 19 nucleotide pairs), Group D: 2.5 mg per kg body weight of dsRNA (directed specifically against GFP, henceforth designated as S 1, with smooth ends and a double-stranded region of 22 nucleotide pairs), Group E: 2.5 mg dsRNA per kg body weight (directed specifically against GFP, henceforth designated as S7, with 2 nt overhangs and the 3'-ends of both strands, and a double-stranded region of 19 nucleotide pairs), Group F: 50 μg 51 dsRNA per kg body weight (in other words 1/50 the dosage of Group D).

After the last injection of a series of 10 injections, the animals were sacrificed after 14-20 hours, and the organs and blood were removed as described below.

Organ Removal:

Immediately after the animals were killed by C02 inhalation, the blood and various organs were removed (thymus, lungs, heart, spleen, stomach, intestines, pancreas, brain, kidneys, and liver). The organs were quickly rinsed in cold sterile PBS and dissected with a sterile scalpel. A portion was fixed for 24 hours for immunohistochemical staining in methyl Carnoy (MC, 60% methanol, 30% chloroform, 10% glacial acetic acid); another portion was immediately flash-frozen in liquid nitrogen for freeze sections and protein isolation, and stored at −80° C.; and another smaller portion was frozen for RNA isolation at −80° C. in RNAeasy Protect (QIAGEN GmbH, Max Volmer Str. 4, 40724 Hilden). Immediately after removal, the blood was kept on ice for 30 minutes, mixed, centrifuged for 5 minutes at 2000 rpm (Mini Spin, Eppendorf AG, Barkhausenweg 1, 22331, Hamburg, Germany), and the supernatant fluid was drawn off and stored at −80° C. (designated here as plasma).

Processing the Biopsies:

After fixing the tissue for 24 hours in MC, the tissue pieces were dehydrated in an ascending alcohol series at room temperature: 40 minutes each 70% methanol, 80% methanol, 2×96% methanol and 3×100% isopropanol. After that the tissue was warmed up in 100% isopropanol at 60° C. in an incubator, after which it was incubated for 1 hour in an isopropanol/paraffin mixture at 60° C. and 3× for 2 hours in paraffin, and then embedded in paraffin. Tissue sections 3 μm in thickness were prepared for immunoperoxidase staining, using a rotation microtome (Leica Microsystems Nussloch GmbH, Heidelberger Str. 17-19,69226 Nussloch, Germany), placed on microscopic slides (Superfrost, Vogel GmbH & Co. KG, Medical Technology and Electronics, Marburger Str. 81, 35396 Giessen, Germany), and incubated for 30 minutes at 60° C.

Immunoperoxidase Staining for GFP:

The sections were deparaffinized for 3×5 minutes in xylol, rehydrated in a descending alcohol series (3×3 min. 100% ethanol, 2×2 min. 95% ethanol), and then incubated for 20 minutes in 3% H202/methanol to block endogenous peroxidases. Next, all incubation steps were carried out in a moist chamber. After 3×3 min. washing with PBS, the sections were incubated with a first antibody (goat anti-GFP antibody, sc-5384, Santa Cruz Biotechnology, Inc., Berheimer Str. 89-2, 69115 Heidelberg, Germany) 1:500 in 1% BSA/PBS overnight at 4° C. The sections were then incubated with the biotinylated secondary antibody (donkey anti-goat IgG; Santa Cruz Biotechnology; 1:2000 dilution) for 30 minutes at room temperature, after which they were incubated for 30 minutes with Avidin D peroxidase (1:2000 dilution, Vector Laboratories, 30 Ingold Road, Burlingame, Calif. 94010). After each antibody incubation, the sections were washed in PBS for 3×3 min., and buffer residue was removed from the sections along with cell material. All antibodies were diluted with 1% bovine serum albumin (BSA)/PBS. The sections were stained with 3,3'-diamino benzidine (DAB) using the DAB Substrate Kit (Vector Laboratories) in accordance with the manufacturer's instructions. Gill's Hematoxylin III (Merck KgaA, Frankfurter Str. 250, 64293 Darmstadt) was used as the nuclear counterstain. After dehydration in an ascending alcohol series and 3×5 minutes xylol, the sections were covered with Entellan (Merck). Microscopic evaluation of the stains was accomplished using a IX50 microscope from OLYMPUS Optical Co. (Europe) GmbH, Wendenstr. 14-18 20097 Hamburg, Germany, fitted with a CCD camera (Hamamatsu Photonics K. K., Systems Division, 8012 Joko-cho Hamamatsu City, 431-3196 Japan).

Protein Isolation from Tissue Pieces:

Frozen tissue samples were added to 800 μA isolation buffer (50 m HEPES, pH 7.5; 150 mM NaCl; 1 mM EDTA; 2.5 mM EGTA; 10% glycerol; 0.1% Tween; 1 mM DTT; 10 mM β-glycerol phosphate; 1 mM NaF; 0.1 mM Na3V04 with a "complete" protease inhibitor tablet from Roche Diagnostics GmbH, Roche Applied Science, Sandhofer Str. 116, 68305 Mannheim), and homogenized for 2×30 seconds with an ultraturrax (DIAX 900, Dispersion Tool 6G, HEIDOLPH Instruments GmbH & Co. KG, Walpersdorfer Str. 12, 91126 Schwabach), and cooled on ice in between steps. After incubation for 30 minutes on ice, the homogenate was mixed and centrifuged for 20 minutes at 10,000 g, 4° C. (3K30, SIGMA Laboratory Centrifuge GmbH, An der Unteren Söse 50,37507 Osterode am Harz). The supernatant fluid was again incubated for 10 minutes on ice, mixed, and centrifuged for 20 minutes at 15,000 g, 4° C. Protein determination of the supernatant fluid was determined according to Bradford, 1976, modified according to Zor & Selinger, 1996, using the Roti-Nanoquant system (Carl Roth GmbH & Co., Schoemperlenstr. 1-5, 76185 Karlsruhe, Germany) in accordance with manufacturer's instructions. BSA was used for protein calibration in a concentration range of 10 to 100 μg/ml.

SDS Gel Electrophoresis:

Denaturing, discontinuous 15% SDS-PAGE (polyacrylamide gel electrophoresis) according to Läemmli (Nature 277: 680-685, 1970) was carried out in a Multigel-Long electrophoresis chamber (Whatman Biometra GmbH, Rudolf Wissell Str. 30, 37079 Göttingen). The separation gel was poured on to a thickness of 1.5 mm: 7.5 ml acrylamide/bisacrylamide (30%, 0.9%); 3.8 ml 1.5 M Tris/HCl, pH 8.4; 150 μA 10% SDS, 3.3 ml distilled water; 250 μA ammonium persulfate (10%); 9 μl TEMED (N,N,N',N'-tetramethylendiamine), and covered over with 0.1% SDS until polymerization occurred. A collection gel was then poured on: 0.83 μl acrylamide/bisacrylamide (30%, 0.9%), 630 μl 1M tris/HCl, pH 6.8; 3.4 ml distilled water; 50 μl 10% SDS; 50 μl 10% ammonium persulfate; 5 μl TEMED.

A corresponding quantity of 4× sample buffer (200 mM Tris, pH 6.8, 4% SDS, 100 mM DTT (dithiotreithol), 0.02% bromophenol blue, 20% glycerin) was then added to the proteins, which were then denatured on a heat block at 100° C., centrifuged on ice after cooling off, and then applied to the gel. The same plasma and protein quantities were used in each lane (3 μl plasma or 25 μg total protein each). Protein electrophoresis was carried out at room temperature at a constant 50V. The protein gel marker Kaleidoscope Prestained Standard (Bio-Rad Laboratories GmbH, Heidemannstr. 164, 80939 Munich) was used as molecular marker.

Western Blot and Immunodetection:

Proteins separated by SDS-PAGE were transferred to a PVDF (polyvinyl difluoride) membrane (Hybond-P, Amersham Biosciences Europe GmbH, Munzinger Str. 9, 79111 Freiburg, Germany) using the semidry transfer method according to Kyhse-Anderson (J. Biochem. Biophys. Methods 10: 203-210, 1984) at room temperature and constant amperage of 0.8 mA/cm2 for 1.5 hours in Tris/Glycerin transfer buffer (39 mM glycerin, 46 mM tris, 0.1% SDS, and 20% methanol). After immunodetection both the gels and the blots, as well as the blot membranes, were stained with Coomassie (0.1% Coomassie G250, 45% methanol, 10% glacial acetic acid) in order to check for electrophoretic transfer. The blot membranes were incubated after transfer in 1% skim milk powder/PBS for 1 hour at room temperature to saturate nonspecific bonds. Next, each membrane was washed three times for 3 minutes with 0.1% Tween-20/PBS. All subsequent antibody incubations and wash steps were done in 0.1% Tween-20/PBS. The primary antibody (goat anti-GFP antibody, sc-5384, Santa Cruz Biotechnology) was incubated for one hour at room temperature at a dilution of 1:1000. After washing 3×5 minutes, the membranes were incubated with a horseradish peroxidase coupled secondary antibody (donkey anti-goat IgG, Santa Cruz Biotechnology), at a dilution of 1:10,000. Detection of horseradish peroxidase was then achieved using the ECL system (Amersham) in accordance with the manufacturer's instructions.

Figure 18:
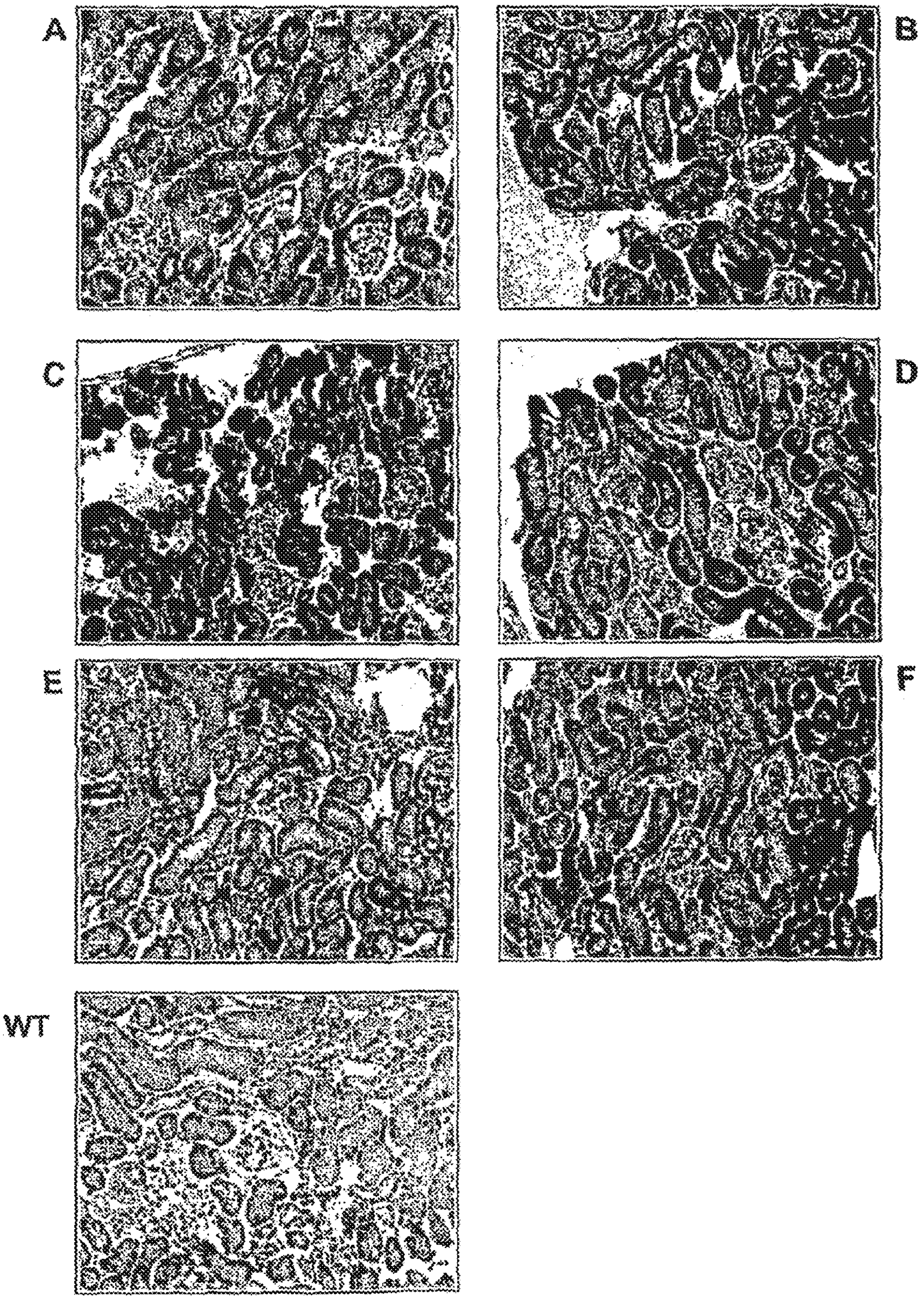
FIG. 18 is a GFP-specific immunoperoxidase staining of kidney paraffin sections from transgenic GFP mice.
Figure 19:
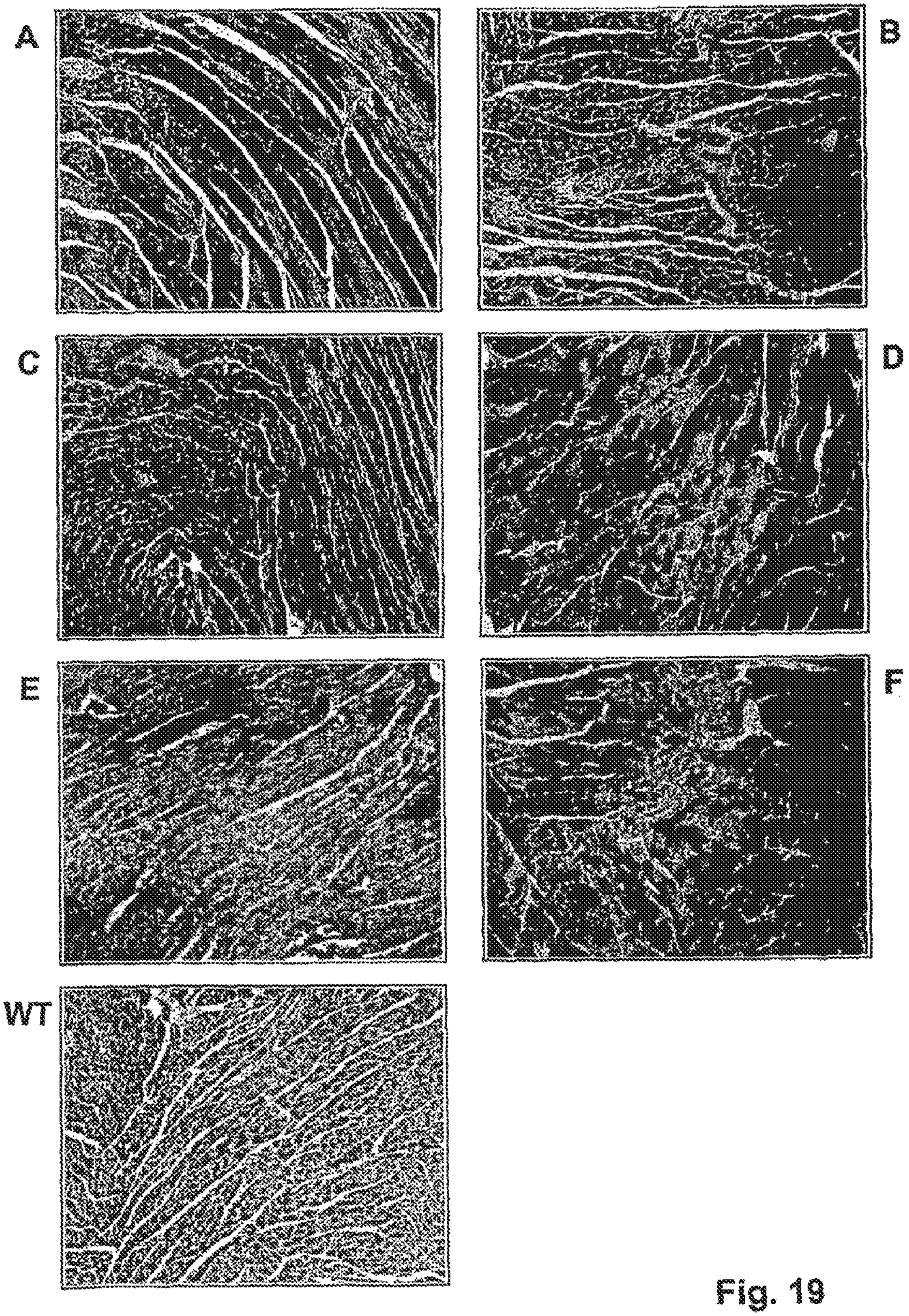
FIG. 19 is a GFP-specific immunoperoxidase staining of heart paraffin sections from transgenic GFP mice.
Figure 20:
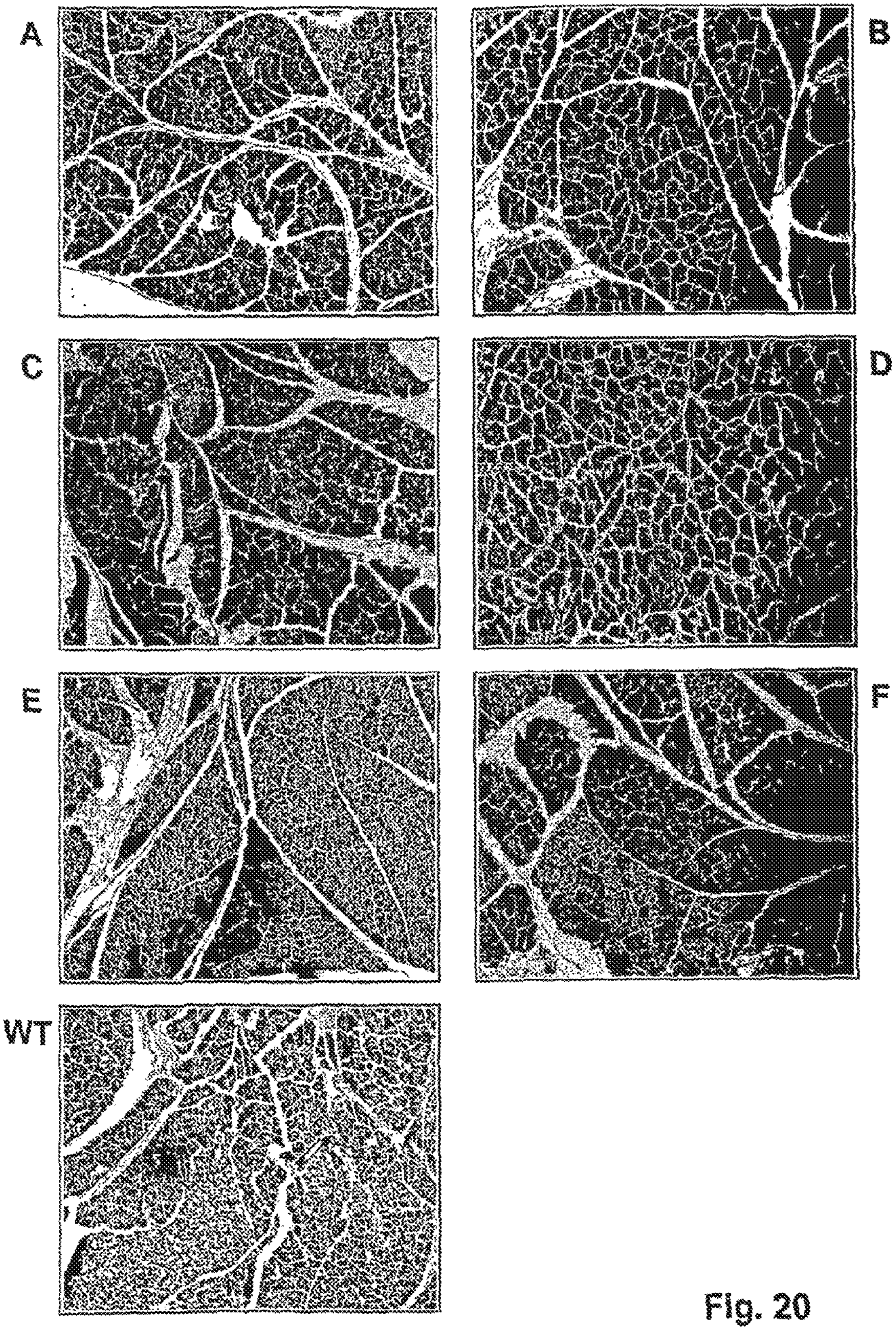
FIG. 20 is a GFP-specific immunoperoxidase staining of pancreas paraffin sections from transgenic GFP mice.
Figure 21:
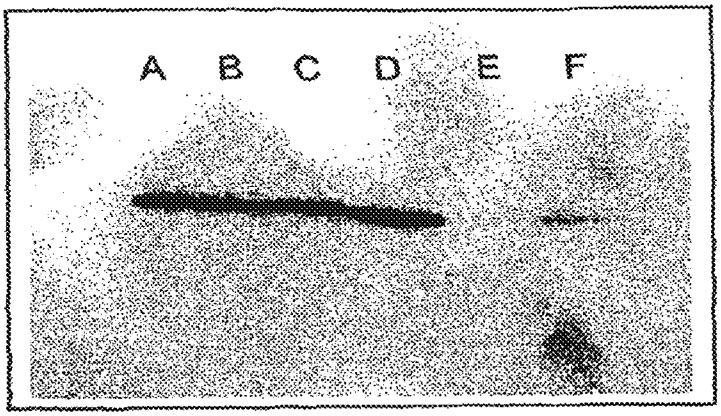
FIG. 21 is a Western blot analysis of GFP expression in plasma.
Figure 22:
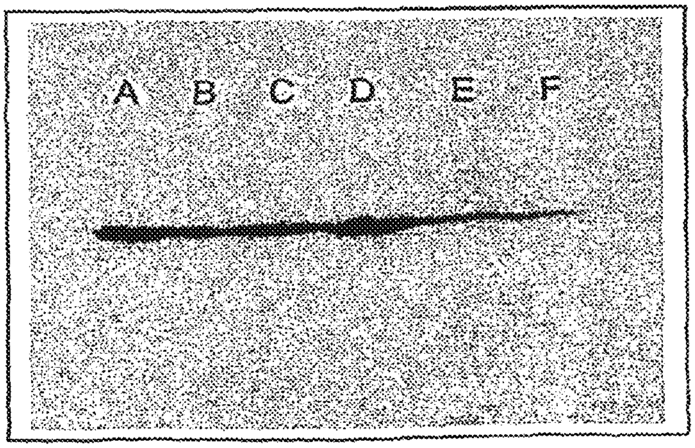
FIG. 22 is a Western blot analysis of GFP expression in kidney.
Figure 23:
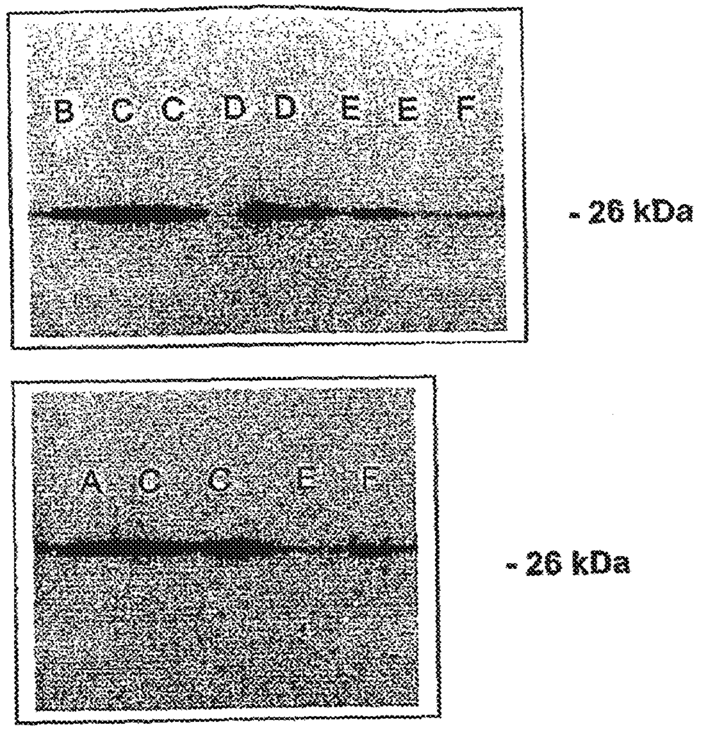
FIG. 23 is a Western blot analysis of GFP expression in heart.

FIGS. 18 to 20 show inhibition of GFP expression after intravenous injection of specific anti-GFP dsRNA, by means of immunoperoxidase GFP staining of 3 μm paraffin sections. Over the course of the experiment, the anti-GFP dsRNA, with a double-stranded region of 22 nucleotide (nt) pairs without overhangs at the 3'-ends (D) and the corresponding non-specific control dsRNA (B), as well as the specific anti-GFP dsRNA, with a double-stranded region consisting of 19 nucleotide pairs with 2 nt overhangs at the 3'-ends (E), and the corresponding non-specific control dsRNA (C) were applied in 12-hour rotation over 5 days. (F) received 1/50 the dosage of Group (D). Animals not administered dsRNA (A) and WT animals were used as further controls. FIG. 18 shows the inhibition of GFP expression in kidney sections; FIG. 19 in heart sections; and FIG. 20 in pancreas tissue. FIGS. 21 to 23 show Western blot analyses of GFP expression in plasma and tissues. FIG. 21 shows the inhibition of GFP expression in plasma; FIG. 22 in kidney; and FIG. 23 in heart. FIG. 23 shows the total protein isolate from various animals. The same quantities of total protein were used for each track. In the animals that were given non-specific control dsRNA (animals in Groups B and C), GFP is not reduced in comparison with animals that received no dsRNA. Animals that received the specific anti-GFP dsRNA with 2 nt overhangs at the 3'-ends of both strands and a double-stranded region consisting of 19 nucleotide pairs showed significantly inhibited GFP expression in the tissues studied (heart, kidneys, pancreas, and blood), compared with untreated animals (FIGS. 18-23). Of the animals in Groups D and F, who were given specific anti-GFP dsRNA, with blunt ends and a double-stranded region consisting of 22 nucleotide pairs, only those animals that received the dsRNA at a dosage of 50 μg/kg body weight per day demonstrated specific inhibition of GFP expression. However, the degree of inhibition was less marked than that seen with the animals in Group E.

A summary evaluation of GFP expression in tissue sections and Western blot shows that the inhibition of GFP expression is greatest in blood and in kidneys (FIGS. 18, 21 and 22).

Example 2

Inhibition of EGFR Gene Expression with EFFR-Specific siRNA

The epidermal growth factor (=EGF) receptor (=EGFR) belongs to the tyrosine kinase receptors, transmembrane proteins with an intrinsic tyrosin kinase activity that are involved in the control of a series of cellular processes such as cell growth, cell differentiation, migratory processes, and cell vitality (reviewed in: Van der Geer et al., 1994). The EGFR family consists of 4 members, EGFR (ErbB1), HER2 (ErbB2), HER3 (ErbB3), and HER4 (ErbB4) with a transmembrane domain, a cysteine-rich extracellular domain, and a catalytic intracellular domain. The EGFR sequence, a 170-kDa protein, was first described by Ullrich et al., 1984.

EGFR is activated by peptide growth factors such as EGF, TGFα (transforming growth factor), amphiregulin, betacellulin, HB-EGF (heparin binding EGF-like growth factor), and neuregulins Ligand binding induces the formation of homodimers or heterodimers with subsequent autophosphorylation of cytoplasmic tyrosine (Ullrich & Schlessinger, 1990; Alroy & Yarden, 1997). The phosphorylated amino acids form the binding sites of numerous proteins that are involved in the initial steps of a complex signal transduction pathway. EGFR is involved in many cancers, and is therefore an appropriate target for therapeutic approaches (Huang & Harari, 1999). The mechanisms that lead to aberrant EGFR activity may be related to overexpression, amplification, constitutive activation of mutant receptor forms, or autocrine loops (Voldberg et al., 1997). Overexpression of EGFR has been described for a series of tumors such as breast cancer (Walker & Dearing, 1999), non-minor lung cancer (Fontanini et al., 1998), pancreatic cancer, colon cancer (Salomon et al., 1995), and glioblastoma (Rieske et al., 1998). For malignant glioblastoma, in particular, there have to date been no effective and specific therapeutic agents.

Example 3

Efficacy of Inhibition of EGFR Gene Expression

To test the effectiveness of dsRNA for the specific inhibition of EGFR gene expression, U-87 MG cells (human glioblastoma cells), ECCAC (European Collection of Animal Cell Culture) No. 89081402 were transfected with the specific anti-EGF-receptor-directed dsRNA (SEQ ID NO:51). After approximately 72 hours of incubation, the cells were harvested, the protein was isolated, and EGFR expression was analyzed by Western blot.

Test Protocol:

Synthesis and Preparation of dsRNAs

Oligoribonucleotides were synthesized with an RNA synthesizer (Expedite 8909, Applied Biosystems, Weiterstadt, Germany) and purified by High Pressure Liquid Chromatography (HPLC) using NucleoPac PA-100 columns, 9×250 mm (Dionex Corp.; low salt buffer: 20 mM tris, 10 mM $NaClO_4$, pH 6.8, 10% acetonitrile; flow rate: 3 ml/min). Formation of double stranded siRNAs was then achieved by heating a stoichiometric mixture of the individual complementary strands (10 M) to 95° C. for 5 minutes in 25 mM Tris-HCl, pH 7.5, and 100 mM NaCl, followed by subsequent cooling for 6 hours to room temperature dsRNA molecules with linkers were produced by solid phase synthesis and addition of hexaethylene glycol as a non-nucleotide linker (D. Jeremy Williams, Kathleen B. Hall, Biochemistry, 1996, 35, 14665-14670). A Hexaethylene glycol linker phosphoramidite (Chruachem Ltd, Todd Campus, West of Scotland Science Park, Acre Road, Glasgow, G20 OUA, Scotland, UK) was coupled to the support bound oligoribonucleotide employing the same synthetic cycle as for standard nucleoside phosphoramidites (Proligo Biochemie GmbH, Georg-Hyken-Str.14, Hamburg, Germany) but with prolonged coupling times. Incorporation of linker phosphoramidite was comparable to the incorporation of nucleoside phosphoramidites.

Seeding the Cells:

All cells were cultured under sterile conditions at an appropriate workstation (HS18/Hera Safe, Kendro, Heraeus). U-87 MG cells were incubated in a $CO_2$-incubator (T20, Hera Cell, Kendro, Heraeus) at 37° C., 5% $CO_2$ and saturated atmospheric humidity in DMEM (Dulbecco's modified eagle medium, Biochrom) with 10% FCS (fetal calf serum, Biochrom), 2 mM L-glutamine (Biochromone) mM sodium pyruvate (Biochrom), 1×NEAA (nonessential amino acids, Biochrom), and penicillin/streptomycin (100 IU/100 μm/ml, Biochrom). In order to maintain the cells in an exponential growth state, the cells were passaged every 3 days. 24 hours before dsRNA application by means of transfection, the cells were trypsinized (10× trypsin/EDTA, Biochrom, Germany) and placed in a 6-well plate (6-well plates, Schubert & Weiss Laboratories, GmbH) in 1.5 μl growth medium.

DsRNA Application in Cultured U-87 MG Cells:

Cells were transfected with dsRNA using the OLIGOFECT AMINE™ reagent (Life Technologies) in accordance with the manufacturer's instructions. Total transfection volume was 1 ml. First, the dsRNA was diluted in serum-free medium: 0.5 μl of a 20 μM stock solution of specific anti-EGFR directed dsRNA and 9.5 μl of a 20 μM stock solution of nonspecific dsRNA (K1A/K2B) diluted with 175 μl serum-free medium (200 nM dsRNA in the transfection incubate or 10 nM specific EGFR-dsRNA) per well. The OLIGOFECTAMINE™ reagent was also diluted in serum-free medium: 3 μl with 12 μl medium per well and then incubated for 10 minutes at room temperature. Then the diluted OLIGOFECTAMINE™ reagent was added to the medium of diluted dsRNA, mixed, and incubated for a further 20 minutes at room temperature. The medium was changed during incubation. The cells were washed 1× with 1 ml serum-free medium and further incubated with 800 µl serum-free medium until the dsRNA/OLIGOFECTAMINE™ reagent was added. After the addition of 200 µl dsRNA/OLIGOFECTAMINE™ reagent per well, the cells incubated up until protein isolation.

Protein Isolation:

Approximately 72 hours after transfection, the cells were harvested and total protein was isolated. The medium was removed, and the cell monolayer was washed once with PBS. After the addition of 200 µl protein isolation buffer (1× "Complete" protease inhibitor, Roche, 50 mM HEPES, pH 7.5, 150 mM NaCl, 1 mM EDTA, 2.5 mM EGTA, 10% glycerin, 0.1% Tween-20, 1 mM DTT, 10 mM β-glycerine phosphate, 1 mM NaF, 0.1 mM $Na_3$ $V0_4$) the cells were removed with the help of a cell scraper, incubated for 10 minutes on ice, transferred to an Eppendorf reagent vessel, and stored at −80° C. for at least 30 minutes. After thawing, the lysate was homogenized at the third setting for 10 seconds with a disperser (DIAX 900, 6G disperser, Heidolph Instruments GmbH, Schwabach), incubated on ice for 10 minutes, and then centrifuged for 15 minutes at 14,000×g at 4° C. (3K30, Sigma). Quantitation of total protein in the supernatant was determined according to Bradford using the Roti-Nanoquant system from Roth (Roth GmbH, Karlsruhe) in accordance with the manufacturer's instructions. 200 µl protein solution at a suitable dilution is mixed with 800 µl 1× working solution, and extinction was measured in semi-microcuvettes at 450 nm and 590 nm against distilled water in a Beckman spectrophotometer (DU 250). BSA dilutions were used for calibration (beaded BSA, Sigma).

SDS Gel Electrophoresis:

Denaturing, discontinuous 15% SDS-PAGE (polyacrylamide gel electrophoresis) according to Läemmli (Nature 277: 680-685, 1970) was carried out in a Multigel-Long electrophoresis chamber (Whatman Biometra GmbH, Rudolf Wissell Str. 30, 37079 Göttingen). The separation gel was poured on to a thickness of 1.5 mm: 7.5 ml acrylamide/bisacrylamide (30%, 0.9%); 3.8 ml 1.5 M Tris/HCl, pH 8.4; 150 µl 10% SDS, 3.3 ml distilled water; 250 µA ammonium persulfate (10%); 9 µl TEMED (N,N,N',N'-tetramethylendiamine), and covered over with 0.1% SDS until polymerization occurred. A collection gel was then poured on: 0.83 µl acrylamide/bisacrylamide (30%, 0.9%), 630 µl 1 M tris/Hel, pH 6.8; 3.4 ml distilled water; 50 µl 10% SDS; 50 µl 10% ammonium persulfate; 5 µl TEMED.

A corresponding quantity of 4× sample buffer (200 mM Tris, pH 6.8, 4% SDS, 100 mM DIT (dithiotreithol), 0.02% bromophenol blue, 20% glycerin) was then added to the proteins, which were then denatured on a heat block at 100° C., centrifuged on ice after cooling off, and then applied to the gel (35 µg total protein/lane). Protein electrophoresis was carried out at room temperature at a constant 50V. The protein gel marker Kaleidoscope Prestained Standard (Bio-Rad Laboratories GmbH, Heidemannstr. 164, 80939 Munich) was used as molecular marker.

Western Blot and Immunodetection:

Transfer of the proteins from SDS-PAGE to a PVDF (polyvinyl difluoride) membrane (Hybond-P, Amersham) was done using a semidry method according to Kyhse-Anderson (J. Biochem. Biophys. Methods 10:203-210, 1984) at room temperature and a constant 0.8 $mA/cm^2$ for 1.5 hours. A cathode buffer (30 mM Tris, 40 mM glycine, 10% methanol, and 0.1% SDS, pH 9.4), anode buffer I (300 mM Tris, pH 10.4, 10% methanol), and anode buffer II (30 mM Tris, pH 10.4, 10% methanol) were used as the transfer buffers. Before assembling the blot stack with 3 MM Whatman paper (Schleicher & Schüll) the gel was incubated in cathode buffer, and the PVDF membrane (previously for 30 seconds in 100% methanol) in anode buffer II (5 minutes): 2 layers of 3 MM paper (anode buffer I), 1 layer 3 MM paper (anode buffer II), PVDF membrane, gel, 3 layers 3 MM paper (cathode buffer). To analyze electrophoretic transfer, both the post-blot gels and the blot membranes were stained after immunodetection using Coomassie (0.1% Coomassie G250, 45% methanol, 10% glacial acetic acid).

After transfer, the blot membrane was incubated in 1% skim milk powder/PBS/0.1% Tween-20 for one hour at room temperature. After that, the membrane was washed three times for 3 minutes with 0.1% Tween-20/PBS. All subsequent antibody incubations and washings were done using 0.1% Tween-20/PBS. The primary antibody (human EGFR extracellular domain, specific goat IgG, Catalogue No. AF231, R&D Systems) was incubated with shaking for two hours at room temperature at a concentration of 1.5 µg/ml. After washing 3×5 minutes, the membrane was incubated for one hour at room temperature with the secondary antibody (labeled donkey anti-goat IgG horseradish peroxidase, Santa Cruz Biotechnology) at a dilution of 1:10,000. After washing (3×3 minutes in PBS/0.1% Tween-20) horseradish peroxidase was detected by ECL reaction (enhanced chemoluminescence). To 18 ml of distilled water, 200 µA Solution A (250 mM luminol, Roth, dissolved in DMSO), 89 µl Solution B (90 mM pcoumaric acid, Sigma, dissolved in DMSO), and 2 ml 30% $H_2O_2$ solution were added. Depending on membrane size, 4-6 ml were pipetted directly onto the membrane, incubated for 1 minute at room temperature, and then placed immediately on X-Ray film (Biomax MS, Kodak).

The sequences used here are depicted in Table 3 below, as well as in SEQ ID NOS:153, 157, 158, 168-173.

TABLE 3

| | | | | |
|---|---|---|---|---|
| ES-7 | SEQ ID NO: 168 | (A) | 5'-AACACCGCAGCAUGUCAAGAU-3' | 2-19-2 |
| | SEQ ID NO: 169 | (B) | 3'-UUUUGUGGCGUCGUACAGUUC-5' | |
| ES-8 | SEQ ID NO: 170 | (A) | 5'-AAGUUAAAAUUCCCGUCGCUAU-3' | $2^5$-19-$2^5$ |
| | SEQ ID NO: 171 | (B) | 3'-CAAUUUUAAGGGCAGCGAUAGU-5' | |
| ES2A/ ES5B | SEQ ID NO: 172 | (A) | 5'-AGUGUGAUCCAAGCUGUCCCAA-3' | 0-22-0 |
| | SEQ ID NO: 173 | (B) | 3'-UUUCACACUAGGUUCGACAGGGUU-5' | |
| K2 | SEQ ID NO: 157 | (A) | 5'-ACAGGAUGAGGAUCGUUUCGCAUG-3' | 2-22-2 |
| | SEQ ID NO: 158 | (B) | 3'-UCUGUCCUACUCCUAGCAAAGCGU-5' | |
| K1A/ KWB | SEQ ID NO: 153 | (A) | 5'-ACAGGAUGAGGAUCGUUUCGCA-3' | 0-22-2 |
| | SEQ ID NO: 158 | (B) | 3'-UCUGUCCUACUCCUAGCAAAGCGU-5' | |

Example 4

Figure 24:
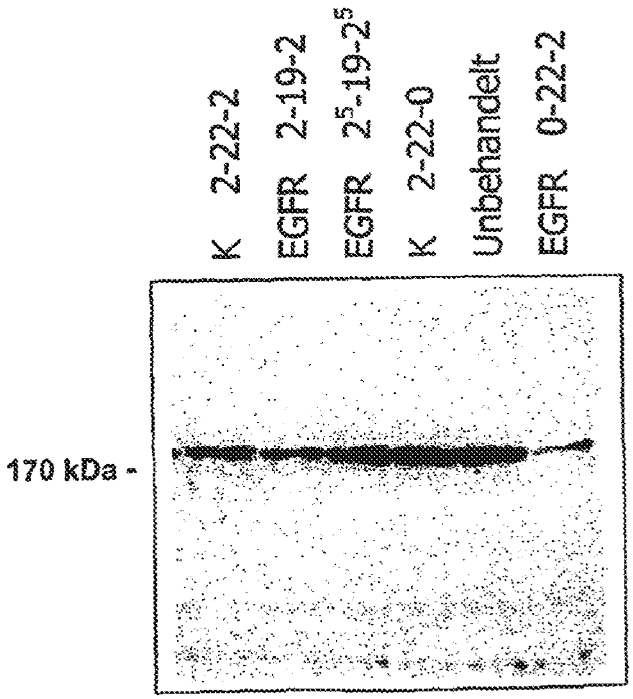
FIG. 24 is a Western blot analysis of EGFR expression in U-87 MG glioblastoma cells.

Inhibition of EGFR Expression in U-87 MG Glioblastoma Cells 24 hours after seeding the cells, U-87 MG glioblastoma cells were transfected with 10 nM dsRNA and oligofectamine. After 72 hours, the cells were harvested and total protein isolated and loaded on to a 7.5% SDS-PAGE gel. 35 μg total protein was applied to each lane. The corresponding Western blot analysis (see FIG. 24) shows that with the specific anti-EGFR-directed dsRNA with a 2 nt overhang at the 3'-end of the antisense strand, EGFR expression in U-87 MG cells is significantly inhibited in comparison to the corresponding controls. This inhibition of expression of an endogenous gene by means of specific dsRNA confirms the results noted in Example II. The inhibition of EGFR expression mediated by ES-7 and ES-8 is notably smaller. The dsRNAs used in FIG. 24 are shown in Table 3.

Example 5

Treatment of a Breast Cancer Patient with EGFR siRNA

In this Example, EGFR-specific double stranded siRNA is injected into a breast cancer patient and shown to specifically inhibit EGFR gene expression.

SiRNA Synthesis

EGFR-specific siRNAs directed against the fusion sequence of EGFR are chemically synthesized with or without a hexaethylene glycol linker as described above siRNA Administration and Dosage The present example provides for pharmaceutical compositions for the treatment of human breast cancer patients comprising a therapeutically effective amount of a EGFR-specific siRNA as disclosed herein, in combination with a pharmaceutically acceptable carrier or excipient. SiRNAs useful according to the invention may be formulated for oral or parenteral administration. The pharmaceutical compositions may be administered in any effective, convenient manner including, for instance, administration by topical, oral, anal, vaginal, intravenous, intraperitoneal, intramuscular, subcutaneous, intranasal or intradermal routes among others. One of skill in the art can readily prepare siRNAs for injection using such carriers that include, but are not limited to, saline, buffered saline, dextrose, water, glycerol, ethanol, and combinations thereof. Additional examples of suitable carriers are found in standard pharmaceutical texts, e.g. "Remington's Pharmaceutical Sciences", 16th edition, Mack Publishing Company, Easton, Pa., 1980.

The dosage of the siRNAs will vary depending on the form of administration. In the case of an injection, the therapeutically effective dose of siRNA per injection is in a dosage range of approximately 1-500 g/kg body weight, preferably 100 g/kg body weight. In addition to the active ingredient, the compositions usually also contain suitable buffers, for example phosphate buffer, to maintain an appropriate pH and sodium chloride, glucose or mannitol to make the solution isotonic. The administering physician will determine the daily dosage which will be most suitable for an individual and will vary with the age, gender, weight and response of the particular individual, as well as the severity of the patient's symptoms. The above dosages are exemplary of the average case. There can, of course, be individual instances where higher or lower dosage ranges are merited, and such are within the scope of this invention. The siRNAs of the present invention may be administered alone or with additional siRNA species or in combination with other pharmaceuticals.

RNA Purification and Analysis

Efficacy of the siRNA treatment is determined at defined intervals after the initiation of treatment using real time PCR or RNAse protection assays on total RNA extracted tissue biopsies. Cytoplasmic RNA from whole blood, taken prior to and during treatment, is purified with the help of the RNeasy Kit (Qiagen, Hilden) and Bcr-abl mRNA levels are quantitated by real time RT-PCR. Real-time Taqman-RT-PCR is performed as described previously (Eder M et al. Leukemia 1999; 13: 1383-1389; Scherr M et al. BioTechniques. 2001; 31: 520-526). Analysis by real time PCR at regular intervals, for example every 1-2 weeks, provides the attending physician with a rapid and accurate assessment of treatment efficacy as well as the opportunity to modify the treatment regimen in response to the patient's symptoms and disease progression.

Example 6

EGFR-Specific siRNA Expression Vectors

In another aspect of the invention, siRNA molecules that interact with target RNA molecules and modulate gene expression activity are expressed from transcription units inserted into DNA or RNA vectors (see for example Couture et A, 1996, TIG., 12, 5 1 0, Skillern et A, International PCT Publication No. WO 00/22113, Conrad, International PCT Publication No. WO 00/22114, and Conrad, U.S. Pat. No. 6,054,299). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann et al., 1995, Proc. Natl. Acad. Sci. USA 92:1292).

The individual strands of a siRNA can be transcribed by promoters on two separate expression vectors and cotransfected into a target cell. Alternatively each individual strand of the siRNA can be transcribed by promoters both of which are located on the same expression plasmid. In a preferred embodiment, the siRNA is expressed as an inverted repeat joined by a linker polynucleotide sequence such that the siRNA has a stem and loop structure.

The recombinant siRNA expression vectors are preferably DNA plasmids or viral vectors. siRNA expressing viral vectors can be constructed based on, but not limited to, adeno-associated virus (for a review, see Muzyczka et al. (1992, Curr. Topics in Micro. and Immunol. 158:97-129)), adenovirus (see, for example, Berkner et al. (1988, BioTechniques 6:616), Rosenfeld et al. (1991, Science 252:431-434), and Rosenfeld et al. (1992, Cell 68:143-155)), or alphavirus as well as others known in the art. Retroviruses have been used to introduce a variety of genes into many different cell types, including epithelial cells, in vitro and/or in vivo (see for example Eglitis, et al., 1985, Science 230:1395-1398; Danos and Mulligan, 1988, Proc. Natl. Acad. Sci. USA 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci.

USA 88:8377-8381; Chowdhury et al., 1991, Science 254: 1802-1805; van Beusechem. et al., 1992, Proc. Natl. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

The promoter driving siRNA expression in either a DNA plasmid or viral vector of the invention may be a eukaryotic RNA polymerase I (e.g. ribosomal RNA promoter), RNA polymerase II (e.g. CMV early promoter or actin promoter or U1 snRNA promoter) or preferably RNA polymerase III promoter (e.g. U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to specific organs or cell types (see, e.g., Lasko et al., 1992, Proc. Natl. Acad. Sci. USA 89:6232). Several tissue-specific regulatory sequences are known in the art including the albumin regulatory sequence for liver (Pinkert et al., 1987, Genes Dev. 1:268276); the endothelin regulatory sequence for endothelial cells (Lee, 1990, J. Biol. Chem. 265:10446-50); the keratin regulatory sequence for epidennis; the myosin light chain-2 regulatory sequence for heart (Lee et al., 1992, J. Biol. Chem. 267: 15875-85), and the insulin regulatory sequence for pancreas (Bucchini et al., 1986, Proc. Natl. Acad. Sci. USA 83:2511-2515), or the vav regulatory sequence for hematopoietic cells (Oligvy et al., 1999, Proc. Natl. Acad. Sci. USA 96:14943-14948). Another suitable regulatory sequence, which directs constitutive expression of transgenes in cells of hematopoietic origin, is the murine MHC class I regulatory sequence (Morello et al., 1986, EMBO J. 5:1877-1882). Since NMC expression is induced by cytokines, expression of a test gene operably linked to this promoter can be upregulated in the presence of cytokines.

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D1-thiogalactopyranoside (EPTG). A person skilled in the art would be able to choose the appropriate regulatory/promoter sequence based on the intended use of the siRNA transgene.

Preferably, recombinant vectors capable of expressing siRNA molecules are delivered as described below, and persist in target cells. Alternatively, viral vectors can be used that provide for transient expression of siRNA molecules. Such vectors can be repeatedly administered as necessary. Once expressed, the siRNAs bind to target RNA and modulate its function or expression. Delivery of siRNA expressing vectors can be systemic, such as by intravenous or intramuscular administration, by administration to target cells ex-planted from the patient followed by reintroduction into the patient, or by any other means that allows for introduction into a desired target cell.

SiRNA expression DNA plasmids are typically transfected into target cells as a complex with cationic lipid carriers (e.g. Oligofectamine) or non-cationic lipid-based carriers (e.g. Transit-TKO™). Multiple lipid transfections for siRNA-mediated knockdowns targeting different regions of a single target gene or multiple target genes over a period of a week or more are also contemplated by the present invention. Successful introduction of the vectors of the invention into host cells can be monitored using various known methods. For example, transient transfection. can be signaled with a reporter, such as a fluorescent marker, such as Green Fluorescent Protein (GFP). Stable transfection. of ex vivo cells can be ensured using markers that provide the transfected cell with resistance to specific environmental factors (e.g., antibiotics and drugs), such as hygromycin B resistance.

For a review of techniques that can be used to generate and assess transgenic animals, skilled artisans can consult Gordon (IwL Rev. CytoL 1 1 5:171-229, 1989), and may obtain additional guidance from, for example: Hogan et al. "Manipulating the Mouse Embryo" (Cold Spring Harbor Press, Cold Spring Harbor, N.Y., 1986; Krimpenfort et al., Bio/Technology 9:86, 1991; Palmiter et al., Cell 41:343, 1985; Kraemer et al., "Genetic Manipulation of the Early Mammalian Embryo," Cold Spring Harbor Press, Cold Spring Harbor, N.Y., 1985; Hammer et al., Nature 315:680, 1985; Purcel et al., Science, 244:1281, 1986; Wagner et al., U.S. Pat. No. 5,175,385; and Krimpenfort et al., U.S. Pat. No. 5,175,384.

The EGFR-specific siRNAs described above can also be generally inserted into vectors and used as gene therapy vectors for human patients. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Example 7

Method of Determining an Effective Dose of a siRNA

A therapeutically effective amount of a composition containing a sequence that encodes an EGFR-specific siRNA, (i.e., an effective dosage), is an amount that inhibits expression of the polypeptide encoded by the EGFR target gene by at least 10 percent. Higher percentages of inhibition, e.g., 15, 20, 30, 40, 50, 75, 85, 90 percent or higher may be preferred in certain embodiments. Exemplary doses include milligram or microgram amounts of the molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). The compositions can be administered one time per week for between about 1 to 10 weeks, e.g., between 2 to 8 weeks, or between about 3 to 7 weeks, or for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. In some cases transient expression of the siRNA may be desired. When an inducible promoter is included in the construct encoding an siRNA, expression is assayed upon delivery to the subject of an appropriate dose of the substance used to induce expression.

Appropriate doses of a composition depend upon the potency of the molecule (the sequence encoding the siRNA) with respect to the expression or activity to be modulated. One or more of these molecules can be administered to an animal (e.g., a human) to modulate expression or activity of one or more target polypeptides. A physician may, for example, prescribe a relatively low dose at first, subsequently increasing the dose until an appropriate response is obtained.

In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The efficacy of treatment can be monitored either by measuring the amount of the target gene mRNA (e.g. using real time PCR) or the amount of polypeptide encoded by the target gene mRNA (Western blot analysis). In addition, the attending physician will monitor the symptoms associated with the disease or disorder afflicting the patient and compare with those symptoms recorded prior to the initiation of siRNA treatment.

Example 8

Inhibiting Expression of Multi-Drug Resistance Gene 1 (MDR1) Using a MDR-1 Specific siRNA Inhibition of MDR1 expression by MDR-1 specific siRNA was tested using the colon cancer cell line LS174T (ATCC—American Type Culture Collection; Tom et al., 1976). Expression of MDR1 in this cell line is inducible by adding rifampicin to the culture medium (Geick et al., 2001). Cells were transfected with MDR-1 specific siRNA using a variety of commercially available transfection kits (Lipofectamine, Oligofectamine, both from Invitrogen; TransMessenger, Qiagen), of which the TransMessenger kit proved to be the most suitable for this cell line.

Four short double-stranded ribonucleic acids (R1-R4) were tested (see Table 4). The ribonucleic acids are homologous with segments of the coding sequence of MDR1 (SEQ ID NO:30). Sequences R1-R3 consist of a 22-mer sense strand and a 24-mer antisense strand, whereby the resulting double strand exhibits a 2-nucleotide overhang at its 3'-end (0-22-2).

Sequence R4 corresponds to R1; however it consists of a 19-mer double-stranded, each with 2-nucleotide overhangs at each 3'-end (2-19-2).

TABLE 4

| Name | SEQ ID NO. | Sequence | Position in Data bank-# AF016535 |
|---|---|---|---|
| Seq R1 | SEQ ID NO: 141 | 5'-CCA UCU CGA AAA GAA GUU AAG A-3' | 1320-1342 |
|  | SEQ ID NO: 142 | 3'-UG GGU AGA CGU UUU CUU CAA UUC U-5' | 1335-1318 |
| Seq R2 | SEQ ID NO: 143 | 5'-UAU AGG UUC CAG GCU UGC UGU A-3' | 2599-2621 |
|  | SEQ ID NO: 152 | 3'-CG AUA UCC AAG GUC CGA ACG ACA U-5' | 2621-2597 |
| Seq R3 | SEQ ID NO: 144 | 5'-CCA GAG AAG GCC GCA CCU GCA U-3' | 3778-3799 |
|  | SEQ ID NO: 145 | 3'-UC GGU CUC UUC CGG CGU GGA CGU A-5' | 3799-3776 |
| Seq R4 | SEQ ID NO: 146 | 5'-CCA UUC CGA AAA GAA GUU AAG-3' | 1320-1341 |
|  | SEQ ID NO: 147 | 3'-UG GGU AGA GCU UUU CUU CAA U-5' | 1339-1318 |
|  |  |  | Position in Data bank-# AF402779 |
| K1A/K2B | SEQ ID NO: 153 | 5'-ACA GGA UGA GGA UCG UUU CGC A-3' | 2829-2808 |
|  | SEQ ID NO: 158 | 3'-UC UGU CCU ACU CCU AGC AAA GCG U-5' | 2808-2831 |

The sequences shown in Table 4 are designated as sequences SEQ ID NOS:141-147, 152, 153, and 158 in the sequence listing. Cells were first seeded in 12-well plates at $3.8 \times 10^5$ cells/well. A day later, dsRNA was transfected into the cells in duplicate at a concentration of 175 nM. For each transfection assay, 93.3 µl EC-R buffer (TransMessenger kits, Qiagen, Hilden) was mixed with 3.2 µl Enhancer R prior to the addition of 3.5 µl of the particular 20 µM dsRNA, mixed well, and incubated for 5 minutes at room temperature. After the addition of 6 µl TransMessenger transfection reagent, the transfection assay was mixed vigorously for 10 seconds, and then incubated for a further 10 minutes at room temperature. The cells were then washed once with PBS (phosphate-buffered saline), and 200 µl fresh medium without FCS was added to the cells in each well. After 10-minute incubation, 100 µl FCS-free medium was pipetted into each transfection assay, mixed, and the mixture was then pipetted drop by drop onto the cells (the dsRNA concentration of 175 μM relates to 400 μl medium total volume). The dsRNA/TransMessenger complexes were incubated with the cells for 4 hours at 37° C. in FCS-free medium. The medium was then changed and replaced with fresh medium containing 10 μM rifampin and 10% FCS. A non-specific dsRNA sequence that exhibits no homologies with the MDR1 gene sequence was used (K) as a control, and a MOCK transfection was conducted that contained all reagents except for dsRNA.

The cells were harvested after 24, 48, and 72 hours, and total RNA was extracted with the RNeasy mini kit from Qiagen. 10 μg total protein from each sample was then separated by electrophoresis on a 1% agarose-formaldehyde gel, blotted on a nylon membrane, and then hybridized as an internal control with specific probes that had been random-marked with 5'-$\alpha^{32}$p-dCTP, first against MDR1, and after the blot had been stripped, against GAPDH, and then exposed on x-ray film. The x-ray film was digitized (Image Master, VDS, Pharmacia) and quantified using Image-Quant software and standardized against the GAPDH signal.

Figure 25A:
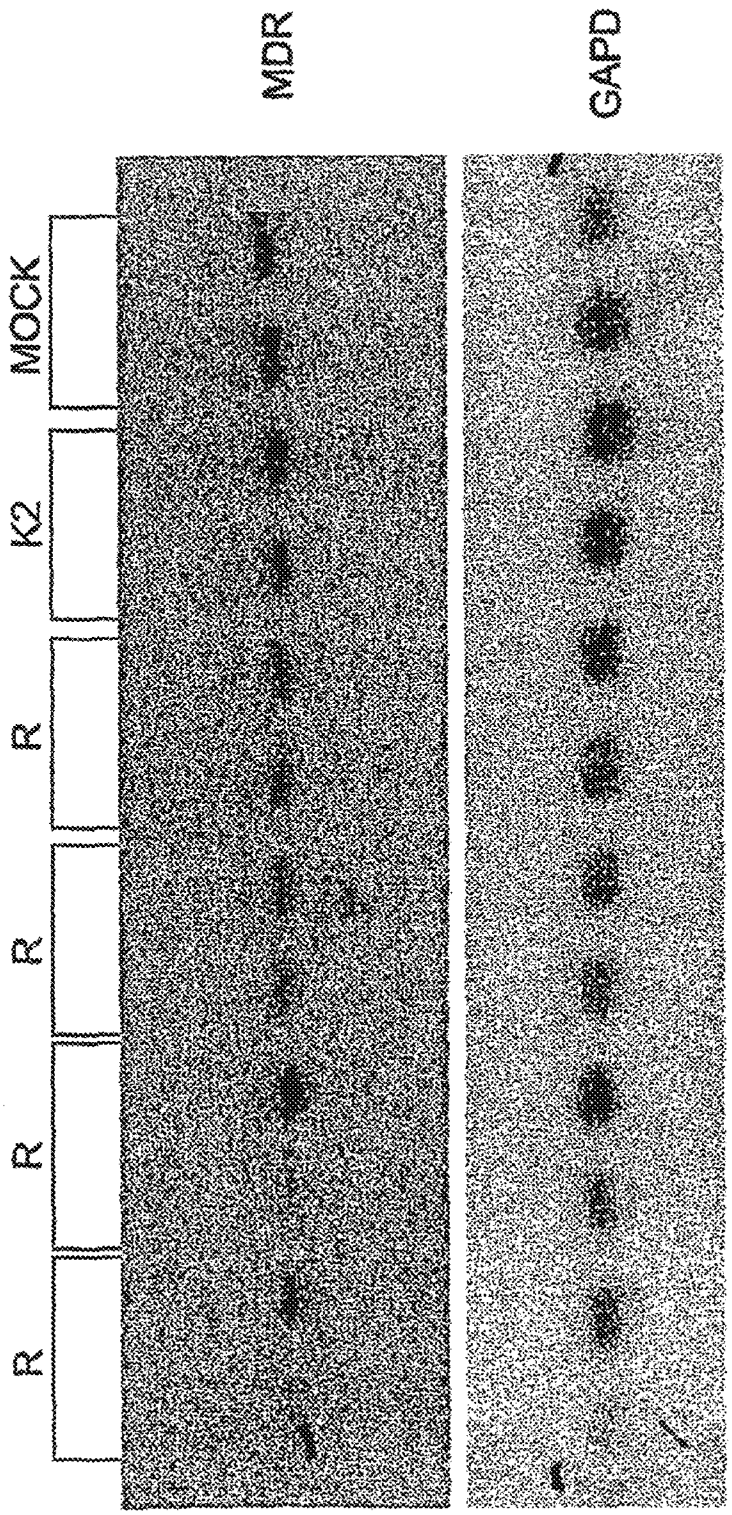
FIG. 25 show a Northern blot analysis of the MDR1 mRNA level in colon carcinoma cell line LSI74T, whereby the cells were harvested after 74 hours (FIG. 25*a*); and quantification of the bands in FIG. 25*a*, whereby the averages are represented by two values (FIG. 25*b*).
Figure 25B:
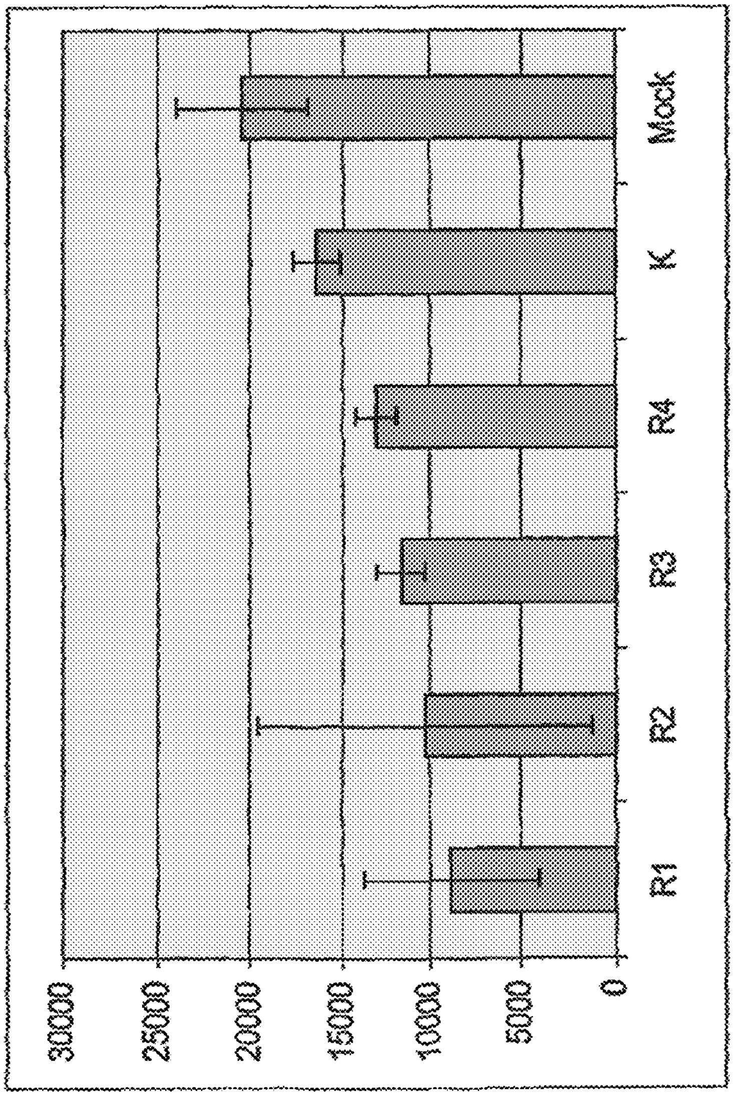
Figure 26A:
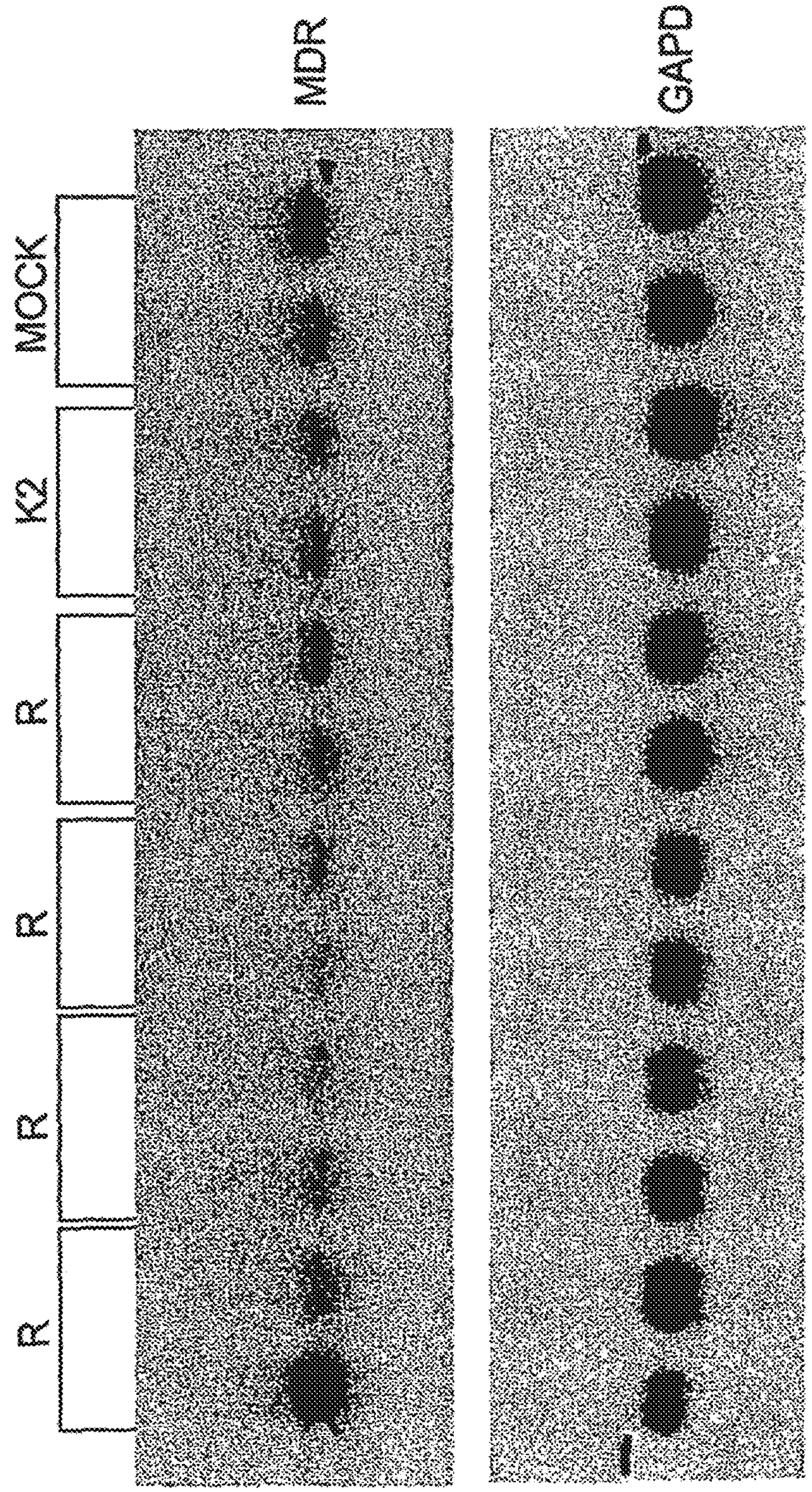
FIG. 26 shows a Northern blot analysis of the MDR1 mRNA level in colon carcinoma cell line LS174T, whereby the cells were harvested after 48 hours (FIG. 26*a*); and quantification of the bands in FIG. 26*a*, whereby the averages of two values are represented (FIG. 26*b*).
Figure 26B:
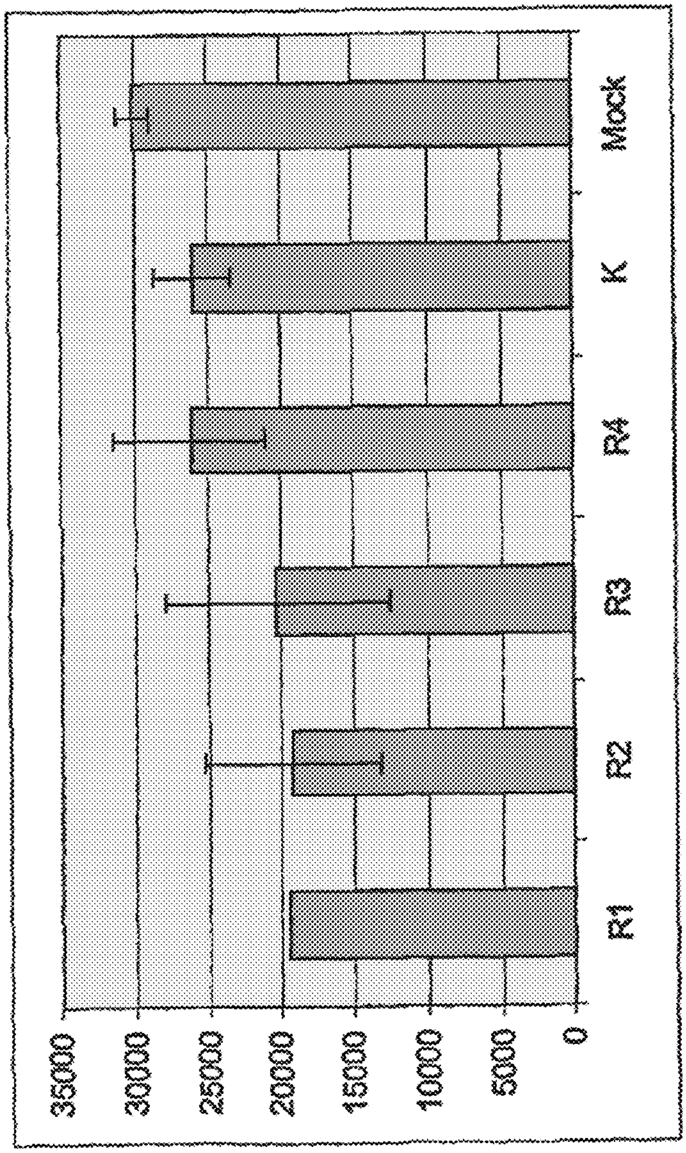

FIGS. 25 and 26 show Northern blots (FIGS. 26*a*, 26*a*) with quantitative analysis of the MDR1-specific signal after adjustment with the corresponding GAPDH values (FIGS. 25*b*, 26*p*). A reduction in the MDR1-mRNA by as much as 55% was observed in comparison to the MOCK transfection, and by as much as 45% in comparison to the nonspecific control transfection. After 48 hours there was a significant reduction in the MDR1-mRNA level in the dsRNA constructs designated as R1, R2, and R3 (Table 4). With the R4 dsRNA constructs, no significant reduction compared to controls was observed after 48 hours (FIGS. 26*a* and 26*b*). After 74 hours, there was an even stronger reduction in MDR1-mRNA levels in the presence of R1, R2, and R3 as compared to the values observed at 48 hours (FIGS. 25*a* and 26*b*). A significant decrease in the MDR1-mRNA level was seen at this time with R4 as well. Thus, the constructs with a 2 nt overhang at the 3'-end of the antisense strand and a double-stranded region consisting of 22 nucleotide pairs reduces the MDR1-mRNA level more efficiently than do constructs with 2 nt overhangs at the 3'-end of both strands (antisense strand and sense strand) and a double-stranded region consisting of 19 nucleotide pairs, apparently independent of the sequence region homologous to the MDR1 gene in each case (after 48 hours; FIG. 26*b*). The results strengthen the findings in Example IV, which describe the inhibition of EGFR gene expression by means of specific dsRNAs after transfection in U-87 MG cells.

Figure 27:
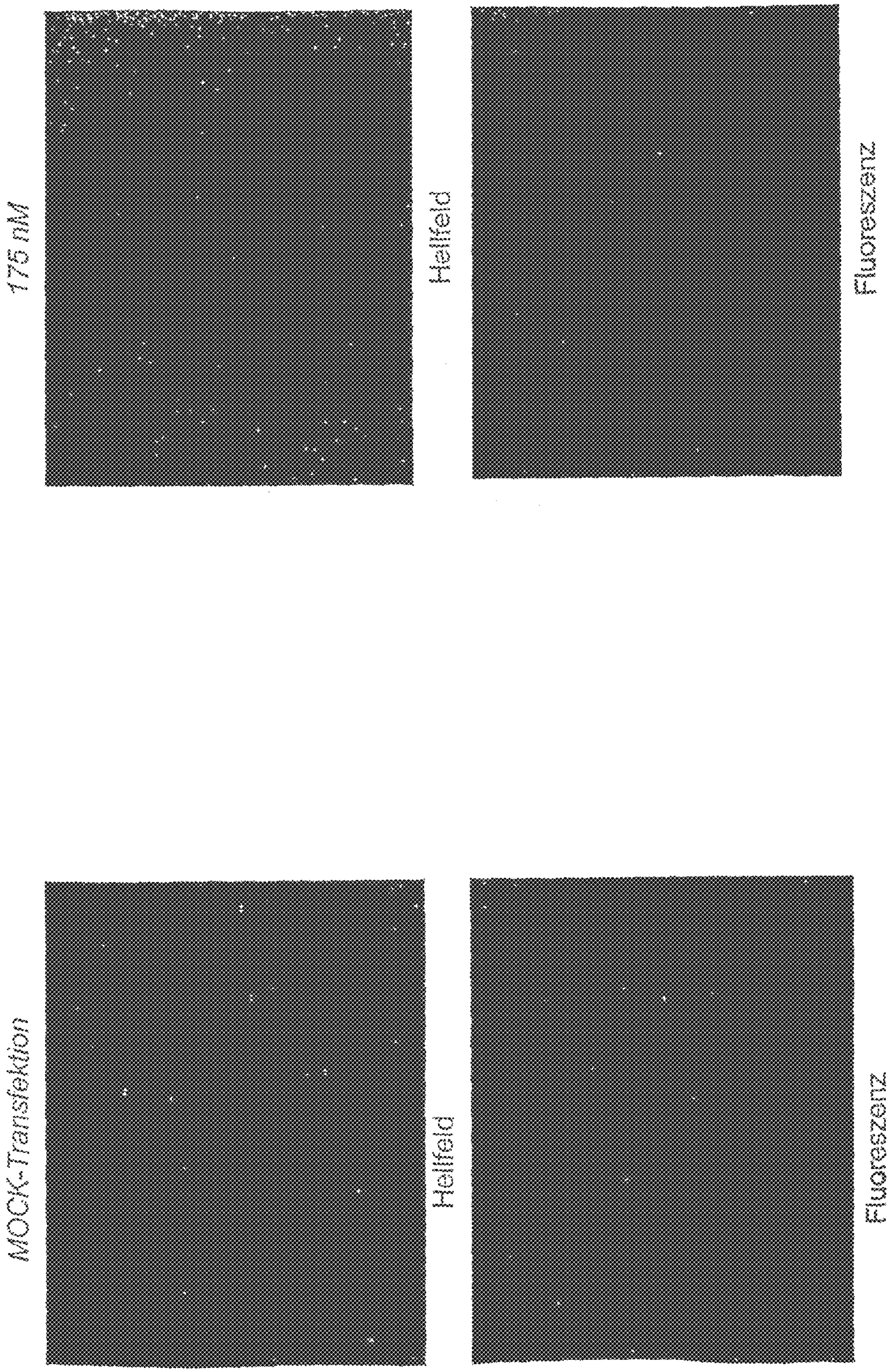
FIG. 27 shows a comparison of a transmitted light- and fluorescence microscopic imaging of a transfection with 175 nM dsRNA (Sequence R1 in Table 4).

Transfection efficiency was determined in a separate experiment with the help of a DNA oligonucleotide marked with Texas red (TexRed-A[GATC]$_5$T; also transfected with 175 nM) (FIGS. 27*a*, 27*b*; 400× enlargement, 48 hours after transfection). Transfection efficiency was approximately 50% on the basis of red fluorescent cells in comparison to total cell number. If one takes the transfection rate of cells of approximately 50% into consideration, then the observed decrease in the MDR1-mRNA level by approximately 45-55% (compared with the controls) indicates that MDR1-mRNA was almost completely and specifically broken down in all cells that were successfully transfected with specific dsRNA.

SEQUENCE LISTING

```
<160> NUMBER OF SEQ ID NOS: 173

<210> SEQ ID NO 1
<211> LENGTH: 2955
<212> TYPE: DNA
<213> ORGANISM: Homo sapiens
<300> PUBLICATION INFORMATION:
<302> TITLE: Eph A1
<310> PATENT DOCUMENT NUMBER: NM00532

<400> SEQUENCE: 1

atggagcggc gctggcccct ggggctaggg ctggtgctgc tgctctgcgc cccgctgccc      60

ccgggggcgc gcgccaagga agttactctg atggacacaa gcaaggcaca gggagagctg     120

ggctggctgc tggatccccc aaaagatggg tggagtgaac agcaacagat actgaatggg     180

acacccctct acatgtacca ggactgccca atgcaaggac gcagagacac tgaccactgg     240

cttcgctcca attggatcta ccgcggggag gaggcttccc gcgtccacgt ggagctgcag     300

ttcaccgtgc gggactgcaa gagtttccct gggggagccg ggcctctggg ctgcaaggag     360

accttcaacc ttctgtacat ggagagtgac caggatgtgg gcattcagct ccgacggccc     420

ttgttccaga aggtaaccac ggtggctgca gaccagagct tcaccattcg agaccttgcg     480

tctggctccg tgaagctgaa tgtggagcgc tgctctctgg gccgcctgac ccgccgtggc     540

ctctacctcg ctttccacaa cccgggtgcc tgtgtggccc tggtgtctgt ccgggtcttc     600

taccagcgct gtcctgagac cctgaatggc ttggcccaat tcccagacac tctgcctggc     660

cccgctgggt tggtggaagt ggcgggcacc tgcttgcccc acgcgcgggc cagccccagg     720

ccctcaggtg caccccgcat gcactgcagc cctgatggcg agtggctggt gcctgtagga     780
```

-continued

```
cggtgccact gtgagcctgg ctatgaggaa ggtggcagtg gcgaagcatg tgttgcctgc    840
cctagcggct cctaccggat ggacatggac acaccccatt gtctcacgtg cccccagcag    900
agcactgctg agtctgaggg ggccaccatc tgtacctgtg agagcggcca ttacagagct    960
cccggggagg gcccccaggt ggcatgcaca ggtcccccct cggccccccg aaacctgagc   1020
ttctctgcct cagggactca gctctccctg cgttgggaac ccccagcaga tacgggggga   1080
cgccaggatg tcagatacag tgtgaggtgt tcccagtgtc agggcacagc acaggacggg   1140
gggccctgcc agccctgtgg ggtgggcgtg cacttctcgc cgggggcccg ggcgctcacc   1200
acacctgcag tgcatgtcaa tggccttgaa ccttatgcca actacacctt taatgtggaa   1260
gcccaaaatg gagtgtcagg gctgggcagc tctggccatg ccagcacctc agtcagcatc   1320
agcatggggc atgcagagtc actgtcaggc ctgtctctga gactggtgaa gaaagaaccg   1380
aggcaactag agctgacctg ggcggggtcc cggccccgaa gccctggggc gaacctgacc   1440
tatgagctgc acgtgctgaa ccaggatgaa gaacggtacc agatggttct agaacccagg   1500
gtcttgctga cagagctgca gcctgacacc acatacatcg tcagagtccg aatgctgacc   1560
ccactgggtc ctggcccttt ctcccctgat catgagtttc ggaccagccc accagtgtcc   1620
aggggcctga ctggaggaga gattgtagcc gtcatctttg ggctgctgct tggtgcagcc   1680
ttgctgcttg ggattctcgt tttccggtcc aggagagccc agcggcagag gcagcagagg   1740
cacgtgaccg cgccaccgat gtggatcgag aggacaagct gtgctgaagc cttatgtggt   1800
acctccaggc atacgaggac cctgcacagg gagccttgga ctttacccgg aggctggtct   1860
aattttcctt cccgggagct tgatccagcg tggctgatgg tggacactgt cataggagaa   1920
ggagagtttg gggaagtgta tcgagggacc ctcaggctcc ccagccagga ctgcaagact   1980
gtggccatta agaccttaaa agacacatcc ccaggtggcc agtggtggaa cttccttcga   2040
gaggcaacta tcatgggcca gtttagccac ccgcatattc tgcatctgga aggcgtcgtc   2100
acaaagcgaa agccgatcat gatcatcaca gaatttatgg agaatgcagc cctggatgcc   2160
ttcctgaggg agcgggagga ccagctggtc cctgggcagc tagtggccat gctgcagggc   2220
atagcatctg gcatgaacta cctcagtaat cacaattatg tccaccggga cctggctgcc   2280
agaaacatct tggtgaatca aaacctgtgc tgcaaggtgt ctgactttgg cctgactcgc   2340
ctcctggatg actttgatgg cacatacgaa acccagggag gaaagatccc tatccgttgg   2400
acagcccctg aagccattgc ccatcggatc ttcaccacag ccagcgatgt gtggagcttt   2460
gggattgtga tgtgggaggt gctgagcttt ggggacaagc cttatgggga gatgagcaat   2520
caggaggtta tgaagagcat tgaggatggg taccggttgc cccctcctgt ggactgccct   2580
gcccctctgt atgagctcat gaagaactgc tgggcatatg accgtgcccg ccggccacac   2640
ttccagaagc ttcaggcaca tctggagcaa ctgcttgcca acccccactc cctgcggacc   2700
attgccaact ttgaccccag ggtgactctt cgcctgccca gcctgagtgg ctcagatggg   2760
atcccgtatc gaaccgtctc tgagtggctc gagtccatac gcatgaaacg ctacatcctg   2820
cacttccact cggctgggct ggacaccatg gagtgtgtgc tggagctgac cgctgaggac   2880
ctgacgcaga tgggaatcac actgcccggg caccagaagc gcattctttg cagtattcag   2940
ggattcaagg actga                                                    2955
```

<210> SEQ ID NO 2
<211> LENGTH: 3042
<212> TYPE: DNA
<213> ORGANISM: Homo sapiens -continued <300> PUBLICATION INFORMATION:
<302> TITLE: ephrin A2
<310> PATENT DOCUMENT NUMBER: XM002088

<400> SEQUENCE: 2

```
gaagttgcgc gcaggccggc gggcgggagc ggacaccgag gccggcgtgc aggcgtgcgg     60
gtgtgcggga gccgggctcg gggggatcgg accgagagcg agaagcgcgg catggagctc    120
caggcagccc gcgcctgctt cgccctgctg tggggctgtg cgctggccgc ggccgcggcg    180
gcgcagggca aggaagtggt actgctggac tttgctgcag ctggagggga gctcggctgg    240
ctcacacacc cgtatggcaa agggtgggac ctgatgcaga acatcatgaa tgacatgccg    300
atctacatgt actccgtgtg caacgtgatg tctggcgacc aggacaactg gctccgcacc    360
aactgggtgt accgaggaga ggctgagcgt atcttcattg agctcaagtt tactgtacgt    420
gactgcaaca gcttccctgg tggcgccagc tcctgcaagg agactttcaa cctctactat    480
gccgagtcgg acctggacta cggcaccaac ttccagaagc gcctgttcac caagattgac    540
accattgcgc ccgatgagat caccgtcagc agcgacttcg aggcacgcca cgtgaagctg    600
aacgtggagg agcgctccgt ggggccgctc acccgcaaag gcttctacct ggccttccag    660
gatatcggtg cctgtgtggc gctgctctcc gtccgtgtct actacaagaa gtgccccgag    720
ctgctgcagg gcctggccca cttccctgag accatcgccg gctctgatgc accttccctg    780
gccactgtgg ccggcacctg tgtggaccat gccgtggtgc caccgggggg tgaagagccc    840
cgtatgcact gtgcagtgga tggcgagtgg ctggtgccca ttgggcagtg cctgtgccag    900
gcaggctacg agaaggtgga ggatgcctgc caggcctgct cgcctggatt ttttaagttt    960
gaggcatctg agagcccctg cttggagtgc cctgagcaca cgctgccatc ccctgagggt   1020
gccacctcct gcgagtgtga ggaaggcttc ttccgggcac ctcaggaccc agcgtcgatg   1080
ccttgcacac gacccccctc cgccccacac tacctcacag ccgtgggcat gggtgccaag   1140
gtggagctgc gctggacgcc ccctcaggac agcgggggcc gcgaggacat tgtctacagc   1200
gtcacctgcg aacagtgctg gcccgagtct ggggaatgcg ggccgtgtga ggccagtgtg   1260
cgctactcgg agcctcctca cggactgacc cgcaccagtg tgacagtgag cgacctggag   1320
ccccacatga actacacctt caccgtggag gcccgcaatg gcgtctcagg cctggtaacc   1380
agccgcagct tccgtactgc cagtgtcagc atcaaccaga cagagccccc caaggtgagg   1440
ctggagggcc gcagcaccac ctcgcttagc gtctcctgga gcatcccccc gccgcagcag   1500
agccgagtgt ggaagtacga ggtcacttac cgcaagaagg gagactccaa cagctacaat   1560
gtgcgccgca ccgagggttt ctccgtgacc ctggacgacc tggccccaga caccacctac   1620
ctggtccagg tgcaggcact gacgcaggag ggccaggggg ccggcagcaa ggtgcacgaa   1680
ttccagacgc tgtccccgga gggatctggc aacttggcgg tgattggcgg cgtggctgtc   1740
ggtgtggtcc tgcttctggt gctggcagga gttggcttct ttatccaccg caggaggaag   1800
aaccagcgtg cccgccagtc cccggaggac gtttacttct ccaagtcaga acaactgaag   1860
cccctgaaga catacgtgga cccccacaca tatgaggacc ccaaccaggc tgtgttgaag   1920
ttcactaccg agatccatcc atcctgtgtc actcggcaga aggtgatcgg agcaggagag   1980
tttggggagg tgtacaaggg catgctgaag acatcctcgg ggaagaagga ggtgccggtg   2040
gccatcaaga cgctgaaagc cggctacaca gagaagcagc gagtggactt cctcggcgag   2100
gccggcatca tgggccagtt cagccaccac aacatcatcc gcctagaggg cgtcatctcc   2160
aaatacaagc ccatgatgat catcactgag tacatggaga atggggccct ggacaagttc   2220
```

```
cttcgggaga aggatggcga gttcagcgtg ctgcagctgg tgggcatgct gcggggcatc   2280

gcagctggca tgaagtacct ggccaacatg aactatgtgc accgtgacct ggctgcccgc   2340

aacatcctcg tcaacagcaa cctggtctgc aaggtgtctg actttggcct gtcccgcgtg   2400

ctggaggacg accccgaggc cacctacacc accagtggcg gcaagatccc catccgctgg   2460

accgccccgg aggccatttc ctaccggaag ttcacctctg ccagcgacgt gtggagcttt   2520

ggcattgtca tgtgggaggt gatgacctat ggcgagcggc cctactggga gttgtccaac   2580

cacgaggtga tgaaagccat caatgatggc ttccggctcc ccacacccat ggactgcccc   2640

tccgccatct accagctcat gatgcagtgc tggcagcagg agcgtgcccg ccgccccaag   2700

ttcgctgaca tcgtcagcat cctggacaag ctcattcgtg cccctgactc cctcaagacc   2760

ctggctgact ttgacccccg cgtgtctatc cggctcccca gcacgagcgg ctcggagggg   2820

gtgcccttcc gcacggtgtc cgagtggctg gagtccatca agatgcagca gtatacggag   2880

cacttcatgg cggccggcta cactgccatc gagaaggtgg tgcagatgac caacgacgac   2940

atcaagagga ttggggtgcg gctgcccggc caccagaagc gcatcgccta cagcctgctg   3000

ggactcaagg accaggtgaa cactgtgggg atccccatct ga                      3042
```

<210> SEQ ID NO 3
<211> LENGTH: 2953
<212> TYPE: DNA
<213> ORGANISM: Homo sapiens
<300> PUBLICATION INFORMATION:
<302> TITLE: ephrin A3
<310> PATENT DOCUMENT NUMBER: NM005233

<400> SEQUENCE: 3

```
atggattgtc agctctccat cctcctcctt ctcagctgct ctgttctcga cagcttcggg     60

gaactgattc cgcagccttc caatgaagtc aatctactgg attcaaaaac aattcaaggg    120

gagctgggct ggatctctta tccatcacat gggtgggaag agatcagtgg tgtggatgaa    180

cattacacac ccatcaggac ttaccaggtg tgcaatgtca tggaccacag tcaaaacaat    240

tggctgagaa caaactgggt ccccaggaac tcagctcaga agatttatgt ggagctcaag    300

ttcactctac gagactgcaa tagcattcca ttggttttag gaacttgcaa ggagacattc    360

aacctgtact acatggagtc tgatgatgat catggggtga aatttcgaga gcatcagttt    420

acaaagattg acaccattgc agctgatgaa agtttcactc aaatggatct tggggaccgt    480

attctgaagc tcaacactga gattagagaa gtaggtcctg tcaacaagaa gggattttat    540

ttggcatttc aagatgttgg tgcttgtgtt gccttggtgt ctgtgagagt atacttcaaa    600

aagtgcccat ttacagtgaa gaatctggct atgtttccag acacggtacc catggactcc    660

cagtccctgg tggaggttag agggtcttgt gtcaacaatt ctaaggagga agatcctcca    720

aggatgtact gcagtacaga aggcgaatgg cttgtaccca ttggcaagtg ttcctgcaat    780

gctggctatg aagaaagagg ttttatgtgc caagcttgtc gaccaggttt ctacaaggca    840

ttggatggta atatgaagtg tgctaagtgc ccgcctcaca gttctactca ggaagatggt    900

tcaatgaact gcaggtgtga gaataattac ttccgggcag acaaagaccc tccatccatg    960

gcttgtaccc gacctccatc ttcaccaaga aatgttatct ctaatataaa cgagacctca   1020

gttatcctgg actggagttg gcccctggac acaggaggcc ggaaagatgt taccttcaac   1080

atcatatgta aaaaatgtgg gtggaatata aaacagtgtg agccatgcag cccaaatgtc   1140

cgcttcctcc ctcgacagtt tggactcacc aacaccacgg tgacagtgac agaccttctg   1200
```

-continued

```
gcacatacta actacacctt tgagattgat gccgttaatg gggtgtcaga gctgagctcc   1260

ccaccaagac agtttgctgc ggtcagcatc acaactaatc aggctgctcc atcacctgtc   1320

ctgacgatta agaaagatcg gacctccaga aatagcatct ctttgtcctg gcaagaacct   1380

gaacatccta atgggatcat attggactac gaggtcaaat actatgaaaa gcaggaacaa   1440

gaaacaagtt ataccattct gagggcaaga ggcacaaatg ttaccatcag tagcctcaag   1500

cctgacacta tatacgtatt ccaaatccga gcccgaacag ccgctggata tgggacgaac   1560

agccgcaagt ttgagtttga aactagtcca gactctttct ccatctctgg tgaaagtagc   1620

caagtggtca tgatcgccat ttcagcggca gtagcaatta ttctcctcac tgttgtcatc   1680

tatgttttga ttgggaggtt ctgtggctat aagtcaaaac atggggcaga tgaaaaaaga   1740

cttcattttg gcaatgggca tttaaaactt ccaggtctca ggacttatgt tgacccacat   1800

acatatgaag accctaccca agctgttcat gagtttgcca aggaattgga tgccaccaac   1860

atatccattg ataaagttgt tggagcaggt gaatttggag aggtgtgcag tggtcgctta   1920

aaacttcctt caaaaaaaga gatttcagtg gccattaaaa ccctgaaagt tggctacaca   1980

gaaaagcaga ggagagactt cctgggagaa gcaagcatta tgggacagtt tgaccacccc   2040

aatatcattc gactggaagg agttgttacc aaaagtaagc cagttatgat tgtcacagaa   2100

tacatggaga atggttcctt ggatagtttc ctacgtaaac acgatgccca gtttactgtc   2160

attcagctag tggggatgct tcgagggata gcatctggca tgaagtacct gtcagacatg   2220

ggctatgttc accgagacct cgctgctcgg aacatcttga tcaacagtaa cttggtgtgt   2280

aaggtttctg atttcggact ttcgcgtgtc ctggaggatg acccagaagc tgcttataca   2340

acaagaggag ggaagatccc aatcaggtgg acatcaccag aagctatagc ctaccgcaag   2400

ttcacgtcag ccagcgatgt atggagttat gggattgttc tctgggaggt gatgtcttat   2460

ggagagagac catactggga gatgtccaat caggatgtaa ttaaagctgt agatgagggc   2520

tatcgactgc cacccccat ggactgccca gctgccttgt atcagctgat gctggactgc   2580

tggcagaaag acaggaacaa cagacccaag tttgagcaga ttgttagtat tctggacaag   2640

cttatccgga atcccggcag cctgaagatc atcaccagtg cagccgcaag gccatcaaac   2700

cttcttctgg accaaagcaa tgtggatatc tctaccttcc gcacaacagg tgactggctt   2760

aatggtgtcc ggacagcaca ctgcaaggaa atcttcacgg gcgtggagta cagttcttgt   2820

gacacaatag ccaagatttc cacagatgac atgaaaaagg ttggtgtcac cgtggttggg   2880

ccacagaaga agatcatcag tagcattaaa gctctagaaa cgcaatcaaa gaatggccca   2940

gttcccgtgt aaa                                                      2953
```

<210> SEQ ID NO 4
<211> LENGTH: 2784
<212> TYPE: DNA
<213> ORGANISM: Homo sapiens
<300> PUBLICATION INFORMATION:
<302> TITLE: ephrin A4
<310> PATENT DOCUMENT NUMBER: XM002578

<400> SEQUENCE: 4

```
atggatgaaa aaaatacacc aatccgaacc taccaagtgt gcaatgtgat ggaacccagc     60

cagaataact ggctacgaac tgattggatc acccgagaag gggctcagag ggtgtatatt    120

gagattaaat tcaccttgag ggactgcaat agtcttccgg gcgtcatggg gacttgcaag    180

gagacgttta acctgtacta ctatgaatca gacaacgaca aagagcgttt catcagagag    240
```

-continued

```
aaccagtttg tcaaaattga caccattgct gctgatgaga gcttcaccca agtggacatt     300
ggtgacagaa tcatgaagct gaacaccgag atccgggatg tagggccatt aagcaaaaag     360
gggttttacc tggcttttca ggatgtgggg gcctgcatcg ccctggtatc agtccgtgtg     420
ttctataaaa agtgtccact cacagtccgc aatctggccc agtttcctga caccatcaca     480
ggggctgata cgtcttccct ggtggaagtt cgaggctcct gtgtcaacaa ctcagaagag     540
aaagatgtgc caaaaatgta ctgtggggca gatggtgaat ggctggtacc cattggcaac     600
tgcctatgca acgctgggca tgaggagcgg agcggagaat gccaagcttg caaaattgga     660
tattacaagg ctctctccac ggatgccacc tgtgccaagt gcccacccca cagctactct     720
gtctgggaag gagccacctc gtgcacctgt gaccgaggct tttcagagc tgacaacgat      780
gctgcctcta tgccctgcac ccgtccacca tctgctcccc tgaacttgat ttcaaatgtc     840
aacgagacat ctgtgaactt ggaatggagt agccctcaga atacaggtgg ccgccaggac     900
atttcctata atgtggtatg caagaaatgt ggagctggtg accccagcaa gtgccgaccc     960
tgtggaagtg gggtccacta caccccacag cagaatggct tgaagaccac caaagtctcc    1020
atcactgacc tcctagctca taccaattac acctttgaaa tctgggctgt gaatggagtg    1080
tccaaatata accctaaccc agaccaatca gtttctgtca ctgtgaccac caaccaagca    1140
gcaccatcat ccattgcttt ggtccaggct aaagaagtca caagatacag tgtggcactg    1200
gcttggctgg aaccagatcg gcccaatggg gtaatcctgg aatatgaagt caagtattat    1260
gagaaggatc agaatgagcg aagctatcgt atagttcgga cagctgccag gaacacagat    1320
atcaaaggcc tgaaccctct cacttcctat gttttccacg tgcgagccag gacagcagct    1380
ggctatggag acttcagtga gcccttggag gttacaacca acacagtgcc ttcccggatc    1440
attggagatg gggctaactc cacagtcctt ctggtctctg tctcgggcag tgtggtgctg    1500
gtggtaattc tcattgcagc ttttgtcatc agccggagac ggagtaaata cagtaaagcc    1560
aaacaagaag cggatgaaga gaaacatttg aatcaaggtg taagaacata tgtggacccc    1620
tttacgtacg aagatcccaa ccaagcagtg cgagagtttg ccaaagaaat tgacgcatcc    1680
tgcattaaga ttgaaaaagt tataggagtt ggtgaatttg gtgaggtatg cagtgggcgt    1740
ctcaaagtgc ctggcaagag agagatctgt gtggctatca agactctgaa agctggttat    1800
acagacaaac agaggagaga cttcctgagt gaggccagca tcatgggaca gtttgaccat    1860
ccgaacatca ttcacttgga aggcgtggtc actaaatgta aaccagtaat gatcataaca    1920
gagtacatgg agaatggctc cttggatgca ttcctcagga aaaatgatgg cagatttaca    1980
gtcattcagc tggtgggcat gcttcgtggc attgggtctg ggatgaagta tttatctgat    2040
atgagctatg tgcatcgtga tctggccgca cggaacatcc tggtgaacag caacttggtc    2100
tgcaaagtgt ctgattttgg catgtcccga gtgcttgagg atgatccgga agcagcttac    2160
accaccaggg gtggcaagat tcctatccgg tggactgcgc cagaagcaat tgcctatcgt    2220
aaattcacat cagcaagtga tgtatggagc tatggaatcg ttatgtggga agtgatgtcg    2280
tacggggaga ggccctattg ggatatgtcc aatcaagatg tgattaaagc cattgaggaa    2340
ggctatcggt taccccctcc aatggactgc cccattgcgc tccaccagct gatgctagac    2400
tgctggcaga aggagaggag cgacaggcct aaatttgggc agattgtcaa catgttggac    2460
aaactcatcc gcaaccccaa cagcttgaag aggacaggga cggagagctc cagacctaac    2520
actgccttgt tggatccaag ctcccctgaa ttctctgctg tggtatcagt gggcgattgg    2580
```

ctccaggcca ttaaaatgga ccggtataag gataacttca cagctgctgg ttataccaca 2640
ctagaggctg tggtgcacgt gaaccaggag gacctggcaa gaattggtat cacagccatc 2700
acgcaccaga ataagatttt gagcagtgtc caggcaatgc gaacccaaat gcagcagatg 2760
cacggcagaa tggttcccgt ctga 2784

<210> SEQ ID NO 5
<211> LENGTH: 2997
<212> TYPE: DNA
<213> ORGANISM: Homo sapiens
<300> PUBLICATION INFORMATION:
<302> TITLE: ephrin A7
<310> PATENT DOCUMENT NUMBER: XM004485

<400> SEQUENCE: 5
atggtttttc aaactcggta cccttcatgg attattttat gctacatctg gctgctccgc 60
tttgcacaca caggggaggc gcaggctgcg aaggaagtac tactgctgga ttctaaagca 120
caacaaacag agttggagtg gatttcctct ccacccaatg ggtgggaaga aattagtggt 180
ttggatgaga actatacccc gatacgaaca taccaggtgt gccaagtcat ggagcccaac 240
caaaacaact ggctgcggac taactggatt tccaaaggca atgcacaaag gatttttgta 300
gaattgaaat tcaccctgag ggattgtaac agtcttcctg gagtactggg aacttgcaag 360
gaaacattta atttgtacta ttatgaaaca gactatgaca ctggcaggaa tataagagaa 420
aacctctatg taaaaataga caccattgct gcagatgaaa gttttaccca aggtgacctt 480
ggtgaaagaa agatgaagct taacactgag gtgagagaga ttggaccttt gtccaaaaag 540
ggattctatc ttgcctttca ggatgtaggg gcttgcatag ctttggtttc tgtcaaagtg 600
tactacaaga agtgctggtc cattattgag aacttagcta tctttccaga tacagtgact 660
ggttcagaat tttcctcttt agtcgaggtt cgagggacat gtgtcagcag tgcagaggaa 720
gaagcggaaa acgcccccag gatgcactgc agtgcagaag gagaatggtt agtgcccatt 780
ggaaaatgta tctgcaaagc aggctaccag caaaaaggag acacttgtga accctgtggc 840
cgtgggttct acaagtcttc ctctcaagat cttcagtgct ctcgttgtcc aactcacagt 900
ttttctgata aagaaggctc ctccagatgt gaatgtgaag atgggtatta cagggctcca 960
tctgacccac catacgttgc atgcacaagg cctccatctg caccacagaa cctcattttc 1020
aacatcaacc aaaccacagt aagtttggaa tggagtcctc ctgcagacaa tgggggaaga 1080
aacgatgtga cctacagaat attgtgtaag cggtgcagtt gggagcaggg cgaatgtgtt 1140
ccctgtggga gtaacattgg atacatgccc cagcagactg gattagagga taactatgtc 1200
actgtcatgg acctgctagc ccacgctaat tatacttttg aagttgaagc tgtaaatgga 1260
gtttctgact taagccgatc ccagaggctc tttgctgctg tcagtatcac cactggtcaa 1320
gcagctccct cgcaagtgag tggagtaatg aaggagagag tactgcagcg gagtgtcgag 1380
ctttcctggc aggaaccaga gcatcccaat ggagtcatca cagaatatga aatcaagtat 1440
tacgagaaag atcaaaggga acggacctac tcaacagtaa aaaccaagtc tacttcagcc 1500
tccattaata atctgaaacc aggaacagtg tatgttttcc agattcgggc ttttactgct 1560
gctggttatg gaaattacag tcccagactt gatgttgcta cactagagga agctacaggt 1620
aaaatgtttg aagctacagc tgtctccagt gaacagaatc ctgttattat cattgctgtg 1680
gttgctgtag ctgggaccat cattttggtg ttcatggtct ttggcttcat cattgggaga 1740
aggcactgtg gttatagcaa agctgaccaa gaaggcgatg aagagcttta ctttcatttt 1800

-continued

```
aaatttccag gcaccaaaac ctacattgac cctgaaacct atgaggaccc aaatagagct   1860

gtccatcaat tcgccaagga gctagatgcc tcctgtatta aaattgagcg tgtgattggt   1920

gcaggagaat tcggtgaagt ctgcagtggc cgtttgaaac ttccagggaa aagagatgtt   1980

gcagtagcca taaaaaccct gaaagttggt tacacagaaa aacaaaggag agactttttg   2040

tgtgaagcaa gcatcatggg gcagtttgac cacccaaatg ttgtccattt ggaagggggtt   2100

gttacaagag ggaaaccagt catgatagta atagagttca tggaaaatgg agccctagat   2160

gcatttctca ggaaacatga tgggcaattt acagtcattc agttagtagg aatgctgaga   2220

ggaattgctg ctggaatgag atatttggct gatatgggat atgttcacag ggaccttgca   2280

gctcgcaata ttcttgtcaa cagcaatctc gtttgtaaag tgtcagattt tggcctgtcc   2340

cgagttatag aggatgatcc agaagctgtc tatacaacta ctggtggaaa aattccagta   2400

aggtggacag cacccgaagc catccagtac cggaaattca catcagccag tgatgtatgg   2460

agctatggaa tagtcatgtg ggaagttatg tcttatggag aaagacctta ttgggacatg   2520

tcaaatcaag atgttataaa agcaatagaa gaaggttatc gtttaccagc acccatggac   2580

tgcccagctg gccttcacca gctaatgttg gattgttggc aaaaggagcg tgctgaaagg   2640

ccaaaatttg aacagatagt tggaattcta gacaaaatga ttcgaaaccc aaatagtctg   2700

aaaactcccc tgggaacttg tagtaggcca ataagccctc ttctggatca aaacactcct   2760

gatttcacta ccttttgttc agttggagaa tggctacaag ctattaagat ggaaagatat   2820

aaagataatt tcacggcagc tggctacaat tcccttgaat cagtagccag gatgactatt   2880

gaggatgtga tgagtttagg gatcacactg gttggtcatc aaaagaaaat catgagcagc   2940

attcagacta tgagagcaca aatgctacat ttacatggaa ctggcattca agtgtga      2997


<210> SEQ ID NO 6
<211> LENGTH: 3018
<212> TYPE: DNA
<213> ORGANISM: Homo sapiens
<220> FEATURE:
<221> NAME/KEY: CDS
<222> LOCATION: (1)..(3018)

<400> SEQUENCE: 6

atg gcc ccc gcc cgg ggc cgc ctg ccc cct gcg ctc tgg gtc gtc acg       48
Met Ala Pro Ala Arg Gly Arg Leu Pro Pro Ala Leu Trp Val Val Thr
1               5                   10                  15

gcc gcg gcg gcg gcg gcc acc tgc gtg tcc gcg gcg cgc ggc gaa gtg       96
Ala Ala Ala Ala Ala Ala Thr Cys Val Ser Ala Ala Arg Gly Glu Val
            20                  25                  30

aat ttg ctg gac acg tcg acc atc cac ggg gac tgg ggc tgg ctc acg      144
Asn Leu Leu Asp Thr Ser Thr Ile His Gly Asp Trp Gly Trp Leu Thr
        35                  40                  45

tat ccg gct cat ggg tgg gac tcc atc aac gag gtg gac gag tcc ttc      192
Tyr Pro Ala His Gly Trp Asp Ser Ile Asn Glu Val Asp Glu Ser Phe
    50                  55                  60

cag ccc atc cac acg tac cag gtt tgc aac gtc atg agc ccc aac cag      240
Gln Pro Ile His Thr Tyr Gln Val Cys Asn Val Met Ser Pro Asn Gln
65                  70                  75                  80

aac aac tgg ctg cgc acg agc tgg gtc ccc cga gac ggc gcc cgg cgc      288
Asn Asn Trp Leu Arg Thr Ser Trp Val Pro Arg Asp Gly Ala Arg Arg
                85                  90                  95

gtc tat gct gag atc aag ttt acc ctg cgc gac tgc aac agc atg cct      336
Val Tyr Ala Glu Ile Lys Phe Thr Leu Arg Asp Cys Asn Ser Met Pro
            100                 105                 110
```

-continued

```
ggt gtg ctg ggc acc tgc aag gag acc ttc aac ctc tac tac ctg gag      384
Gly Val Leu Gly Thr Cys Lys Glu Thr Phe Asn Leu Tyr Tyr Leu Glu
        115                 120                 125

tcg gac cgc gac ctg ggg gcc agc aca caa gaa agc cag ttc ctc aaa      432
Ser Asp Arg Asp Leu Gly Ala Ser Thr Gln Glu Ser Gln Phe Leu Lys
    130                 135                 140

atc gac acc att gcg gcc gac gag agc ttc aca ggt gcc gac ctt ggt      480
Ile Asp Thr Ile Ala Ala Asp Glu Ser Phe Thr Gly Ala Asp Leu Gly
145                 150                 155                 160

gtg cgg cgt ctc aag ctc aac acg gag gtg cgc agt gtg ggt ccc ctc      528
Val Arg Arg Leu Lys Leu Asn Thr Glu Val Arg Ser Val Gly Pro Leu
                165                 170                 175

agc aag cgc ggc ttc tac ctg gcc ttc cag gac ata ggt gcc tgc ctg      576
Ser Lys Arg Gly Phe Tyr Leu Ala Phe Gln Asp Ile Gly Ala Cys Leu
            180                 185                 190

gcc atc ctc tct ctc cgc atc tac tat aag aag tgc cct gcc atg gtg      624
Ala Ile Leu Ser Leu Arg Ile Tyr Tyr Lys Lys Cys Pro Ala Met Val
        195                 200                 205

cgc aat ctg gct gcc ttc tcg gag gca gtg acg ggg gcc gac tcg tcc      672
Arg Asn Leu Ala Ala Phe Ser Glu Ala Val Thr Gly Ala Asp Ser Ser
    210                 215                 220

tca ctg gtg gag gtg agg ggc cag tgc gtg cgg cac tca gag gag cgg      720
Ser Leu Val Glu Val Arg Gly Gln Cys Val Arg His Ser Glu Glu Arg
225                 230                 235                 240

gac aca ccc aag atg tac tgc agc gcg gag ggc gag tgg ctc gtg ccc      768
Asp Thr Pro Lys Met Tyr Cys Ser Ala Glu Gly Glu Trp Leu Val Pro
                245                 250                 255

atc ggc aaa tgc gtg tgc agt gcc ggc tac gag gag cgg cgg gat gcc      816
Ile Gly Lys Cys Val Cys Ser Ala Gly Tyr Glu Glu Arg Arg Asp Ala
            260                 265                 270

tgt gtg gcc tgt gag ctg ggc ttc tac aag tca gcc cct ggg gac cag      864
Cys Val Ala Cys Glu Leu Gly Phe Tyr Lys Ser Ala Pro Gly Asp Gln
        275                 280                 285

ctg tgt gcc cgc tgc cct ccc cac agc cac tcc gca gct cca gcc gcc      912
Leu Cys Ala Arg Cys Pro Pro His Ser His Ser Ala Ala Pro Ala Ala
    290                 295                 300

caa gcc tgc cac tgt gac ctc agc tac tac cgt gca gcc ctg gac ccg      960
Gln Ala Cys His Cys Asp Leu Ser Tyr Tyr Arg Ala Ala Leu Asp Pro
305                 310                 315                 320

ccg tcc tca gcc tgc acc cgg cca ccc tcg gca cca gtg aac ctg atc     1008
Pro Ser Ser Ala Cys Thr Arg Pro Pro Ser Ala Pro Val Asn Leu Ile
                325                 330                 335

tcc agt gtg aat ggg aca tca gtg act ctg gag tgg gcc cct ccc ctg     1056
Ser Ser Val Asn Gly Thr Ser Val Thr Leu Glu Trp Ala Pro Pro Leu
            340                 345                 350

gac cca ggt ggc cgc agt gac atc acc tac aat gcc gtg tgc cgc cgc     1104
Asp Pro Gly Gly Arg Ser Asp Ile Thr Tyr Asn Ala Val Cys Arg Arg
        355                 360                 365

tgc ccc tgg gca ctg agc cgc tgc gag gca tgt ggg agc ggc acc cgc     1152
Cys Pro Trp Ala Leu Ser Arg Cys Glu Ala Cys Gly Ser Gly Thr Arg
    370                 375                 380

ttt gtg ccc cag cag aca agc ctg gtg cag gcc agc ctg ctg gtg gcc     1200
Phe Val Pro Gln Gln Thr Ser Leu Val Gln Ala Ser Leu Leu Val Ala
385                 390                 395                 400

aac ctg ctg gcc cac atg aac tac tcc ttc tgg atc gag gcc gtc aat     1248
Asn Leu Leu Ala His Met Asn Tyr Ser Phe Trp Ile Glu Ala Val Asn
                405                 410                 415

ggc gtg tcc gac ctg agc ccc gag ccc cgc cgg gcc gct gtg gtc aac     1296
Gly Val Ser Asp Leu Ser Pro Glu Pro Arg Arg Ala Ala Val Val Asn
            420                 425                 430
```

-continued

```
atc acc acg aac cag gca gcc ccg tcc cag gtg gtg gtg atc cgt caa      1344
Ile Thr Thr Asn Gln Ala Ala Pro Ser Gln Val Val Val Ile Arg Gln
        435                 440                 445

gag cgg gcg ggg cag acc agc gtc tcg ctg ctg tgg cag gag ccc gag      1392
Glu Arg Ala Gly Gln Thr Ser Val Ser Leu Leu Trp Gln Glu Pro Glu
    450                 455                 460

cag ccg aac ggc atc atc ctg gag tat gag atc aag tac tac gag aag      1440
Gln Pro Asn Gly Ile Ile Leu Glu Tyr Glu Ile Lys Tyr Tyr Glu Lys
465                 470                 475                 480

gac aag gag atg cag agc tac tcc acc ctc aag gcc gtc acc acc aga      1488
Asp Lys Glu Met Gln Ser Tyr Ser Thr Leu Lys Ala Val Thr Thr Arg
                485                 490                 495

gcc acc gtc tcc ggc ctc aag ccg ggc acc cgc tac gtg ttc cag gtc      1536
Ala Thr Val Ser Gly Leu Lys Pro Gly Thr Arg Tyr Val Phe Gln Val
            500                 505                 510

cga gcc cgc acc tca gca ggc tgt ggc cgc ttc agc cag gcc atg gag      1584
Arg Ala Arg Thr Ser Ala Gly Cys Gly Arg Phe Ser Gln Ala Met Glu
        515                 520                 525

gtg gag acc ggg aaa ccc cgg ccc cgc tat gac acc agg acc att gtc      1632
Val Glu Thr Gly Lys Pro Arg Pro Arg Tyr Asp Thr Arg Thr Ile Val
    530                 535                 540

tgg atc tgc ctg acg ctc atc acg ggc ctg gtg gtg ctt ctg ctc ctg      1680
Trp Ile Cys Leu Thr Leu Ile Thr Gly Leu Val Val Leu Leu Leu Leu
545                 550                 555                 560

ctc atc tgc aag aag agg cac tgt ggc tac agc aag gcc ttc cag gac      1728
Leu Ile Cys Lys Lys Arg His Cys Gly Tyr Ser Lys Ala Phe Gln Asp
                565                 570                 575

tcg gac gag gag aag atg cac tat cag aat gga cag gca ccc cca cct      1776
Ser Asp Glu Glu Lys Met His Tyr Gln Asn Gly Gln Ala Pro Pro Pro
            580                 585                 590

gtc ttc ctg cct ctg cat cac ccc ccg gga aag ctc cca gag ccc cag      1824
Val Phe Leu Pro Leu His His Pro Pro Gly Lys Leu Pro Glu Pro Gln
        595                 600                 605

ttc tat gcg gaa ccc cac acc tac gag gag cca ggc cgg gcg ggc cgc      1872
Phe Tyr Ala Glu Pro His Thr Tyr Glu Glu Pro Gly Arg Ala Gly Arg
    610                 615                 620

agt ttc act cgg gag atc gag gcc tct agg atc cac atc gag aaa atc      1920
Ser Phe Thr Arg Glu Ile Glu Ala Ser Arg Ile His Ile Glu Lys Ile
625                 630                 635                 640

atc ggc tct gga gac tcc ggg gaa gtc tgc tac ggg agg ctg cgg gtg      1968
Ile Gly Ser Gly Asp Ser Gly Glu Val Cys Tyr Gly Arg Leu Arg Val
                645                 650                 655

cca ggg cag cgg gat gtg ccc gtg gcc atc aag gcc ctc aaa gcc ggc      2016
Pro Gly Gln Arg Asp Val Pro Val Ala Ile Lys Ala Leu Lys Ala Gly
            660                 665                 670

tac acg gag aga cag agg cgg gac ttc ctg agc gag gcg tcc atc atg      2064
Tyr Thr Glu Arg Gln Arg Arg Asp Phe Leu Ser Glu Ala Ser Ile Met
        675                 680                 685

ggg caa ttc gac cat ccc aac atc atc cgc ctc gag ggt gtc gtc acc      2112
Gly Gln Phe Asp His Pro Asn Ile Ile Arg Leu Glu Gly Val Val Thr
    690                 695                 700

cgt ggc cgc ctg gca atg att gtg act gag tac atg gag aac ggc tct      2160
Arg Gly Arg Leu Ala Met Ile Val Thr Glu Tyr Met Glu Asn Gly Ser
705                 710                 715                 720

ctg gac acc ttc ctg agg acc cac gac ggg cag ttc acc atc atg cag      2208
Leu Asp Thr Phe Leu Arg Thr His Asp Gly Gln Phe Thr Ile Met Gln
                725                 730                 735

ctg gtg ggc atg ctg aga gga gtg ggt gcc ggc atg cgc tac ctc tca      2256
Leu Val Gly Met Leu Arg Gly Val Gly Ala Gly Met Arg Tyr Leu Ser
```

-continued

```
            740                 745                 750

gac ctg ggc tat gtc cac cga gac ctg gcc gcc cgc aac gtc ctg gtt      2304
Asp Leu Gly Tyr Val His Arg Asp Leu Ala Ala Arg Asn Val Leu Val
        755                 760                 765

gac agc aac ctg gtc tgc aag gtg tct gac ttc ggg ctc tca cgg gtg      2352
Asp Ser Asn Leu Val Cys Lys Val Ser Asp Phe Gly Leu Ser Arg Val
    770                 775                 780

ctg gag gac gac ccg gat gct gcc tac acc acc acg ggc ggg aag atc      2400
Leu Glu Asp Asp Pro Asp Ala Ala Tyr Thr Thr Thr Gly Gly Lys Ile
785                 790                 795                 800

ccc atc cgc tgg acg gcc cca gag gcc atc gcc ttc cgc acc ttc tcc      2448
Pro Ile Arg Trp Thr Ala Pro Glu Ala Ile Ala Phe Arg Thr Phe Ser
            805                 810                 815

tcg gcc agc gac gtg tgg agc ttc ggc gtg gtc atg tgg gag gtg ctg      2496
Ser Ala Ser Asp Val Trp Ser Phe Gly Val Val Met Trp Glu Val Leu
            820                 825                 830

gcc tat ggg gag cgg ccc tac tgg aac atg acc aac cgg gat gtc atc      2544
Ala Tyr Gly Glu Arg Pro Tyr Trp Asn Met Thr Asn Arg Asp Val Ile
        835                 840                 845

agc tct gtg gag gag ggg tac cgc ctg ccc gca ccc atg ggc tgc ccc      2592
Ser Ser Val Glu Glu Gly Tyr Arg Leu Pro Ala Pro Met Gly Cys Pro
    850                 855                 860

cac gcc ctg cac cag ctc atg ctc gac tgt tgg cac aag gac cgg gcg      2640
His Ala Leu His Gln Leu Met Leu Asp Cys Trp His Lys Asp Arg Ala
865                 870                 875                 880

cag cgg cct cgc ttc tcc cag att gtc agt gtc ctc gat gcg ctc atc      2688
Gln Arg Pro Arg Phe Ser Gln Ile Val Ser Val Leu Asp Ala Leu Ile
            885                 890                 895

cgc agc cct gag agt ctc agg gcc acc gcc aca gtc agc agg tgc cca      2736
Arg Ser Pro Glu Ser Leu Arg Ala Thr Ala Thr Val Ser Arg Cys Pro
            900                 905                 910

ccc cct gcc ttc gtc cgg agc tgc ttt gac ctc cga ggg ggc agc ggt      2784
Pro Pro Ala Phe Val Arg Ser Cys Phe Asp Leu Arg Gly Gly Ser Gly
        915                 920                 925

ggc ggt ggg ggc ctc acc gtg ggg gac tgg ctg gac tcc atc cgc atg      2832
Gly Gly Gly Gly Leu Thr Val Gly Asp Trp Leu Asp Ser Ile Arg Met
    930                 935                 940

ggc cgg tac cga gac cac ttc gct gcg ggc gga tac tcc tct ctg ggc      2880
Gly Arg Tyr Arg Asp His Phe Ala Ala Gly Gly Tyr Ser Ser Leu Gly
945                 950                 955                 960

atg gtg cta cgc atg aac gcc cag gac gtg cgc gcc ctg ggc atc acc      2928
Met Val Leu Arg Met Asn Ala Gln Asp Val Arg Ala Leu Gly Ile Thr
            965                 970                 975

ctc atg ggc cac cag aag aag atc ctg ggc agc att cag acc atg cgg      2976
Leu Met Gly His Gln Lys Lys Ile Leu Gly Ser Ile Gln Thr Met Arg
            980                 985                 990

gcc cag ctg acc agc acc cag ggg  ccc cgc cgg cac ctc  tga            3018
Ala Gln Leu Thr Ser Thr Gln Gly  Pro Arg Arg His Leu
        995                 1000                1005
```

<210> SEQ ID NO 7
<211> LENGTH: 1497
<212> TYPE: DNA
<213> ORGANISM: Homo sapiens
<300> PUBLICATION INFORMATION:
<308> DATABASE ACCESSION NUMBER: U83508
<309> DATABASE ENTRY DATE: 1996-12-31
<300> PUBLICATION INFORMATION:
<302> TITLE: angiopoietin 2
<310> PATENT DOCUMENT NUMBER: U83508

<400> SEQUENCE: 7
atgacagttt tcctttcctt tgctttcctc gctgccattc tgactcacat agggtgcagc 60
aatcagcgcc gaagtccaga aaacagtggg agaagatata accggattca acatgggcaa 120
tgtgcctaca ctttcattct tccagaacac gatggcaact gtcgtgagag tacgacagac 180
cagtacaaca caaacgctct gcagagagat gctccacacg tggaaccgga tttctcttcc 240
cagaaacttc aacatctgga acatgtgatg gaaaattata ctcagtggct gcaaaaactt 300
gagaattaca ttgtggaaaa catgaagtcg gagatggccc agatacagca gaatgcagtt 360
cagaaccaca cggctaccat gctggagata ggaaccagcc tcctctctca gactgcagag 420
cagaccagaa agctgacaga tgttgagacc caggtactaa atcaaacttc tcgacttgag 480
atacagctgc tggagaattc attatccacc tacaagctag agaagcaact tcttcaacag 540
acaaatgaaa tcttgaagat ccatgaaaaa aacagtttat tagaacataa aatcttagaa 600
atggaaggaa aacacaagga agagttggac accttaaagg aagagaaaga gaaccttcaa 660
ggcttggtta ctcgtcaaac atatataatc caggagctgg aaaagcaatt aaacagagct 720
accaccaaca acagtgtcct tcagaagcag caactggagc tgatggacac agtccacaac 780
cttgtcaatc tttgcactaa agaaggtgtt ttactaaagg gaggaaaaag agaggaagag 840
aaaccattta gagactgtgc agatgtatat caagctggtt ttaataaaag tggaatctac 900
actatttata ttaataatat gccagaaccc aaaaaggtgt tttgcaatat ggatgtcaat 960
gggggaggtt ggactgtaat acaacatcgt gaagatggaa gtctagattt ccaaagaggc 1020
tggaaggaat ataaaatggg ttttggaaat ccctccggtg aatattggct ggggaatgag 1080
tttatttttg ccattaccag tcagaggcag tacatgctaa gaattgagtt aatggactgg 1140
gaagggaacc gagcctattc acagtatgac agattccaca taggaaatga aaagcaaaac 1200
tataggttgt atttaaaagg tcacactggg acagcaggaa aacagagcag cctgatctta 1260
cacggtgctg atttcagcac taaagatgct gataatgaca actgtatgtg caaatgtgcc 1320
ctcatgttaa caggaggatg gtggtttgat gcttgtggcc cctccaatct aaatggaatg 1380
ttctatactg cgggacaaaa ccatggaaaa ctgaatggga taaagtggca ctacttcaaa 1440
gggcccagtt actccttacg ttccacaact atgatgattc gacctttaga tttttga 1497

<210> SEQ ID NO 8
<211> LENGTH: 3417
<212> TYPE: DNA
<213> ORGANISM: Homo sapiens
<300> PUBLICATION INFORMATION:
<310> PATENT DOCUMENT NUMBER: XM001924
<300> PUBLICATION INFORMATION:
<302> TITLE: Tie1

<400> SEQUENCE: 8
atggtctggc gggtgccccc tttcttgctc cccatcctct tcttggcttc tcatgtgggc 60
gcggcggtgg acctgacgct gctggccaac ctgcggctca cggaccccca gcgcttcttc 120
ctgacttgcg tgtctgggga ggccggggcg gggagggggct cggacgcctg gggcccgccc 180
ctgctgctgg agaaggacga ccgtatcgtg cgcaccccgc ccgggccacc cctgcgcctg 240
gcgcgcaacg gttcgcacca ggtcacgctt cgcggcttct ccaagccctc ggacctcgtg 300
ggcgtcttct cctgcgtggg cggtgctggg gcgcggcgca cgcgcgtcat ctacgtgcac 360
aacagccctg gagcccacct gcttccagac aaggtcacac acactgtgaa caaaggtgac 420
accgctgtac tttctgcacg tgtgcacaag gagaagcaga cagacgtgat ctggaagagc 480

```
aacggatcct acttctacac cctggactgg catgaagccc aggatgggcg gttcctgctg    540
cagctcccaa atgtgcagcc accatcgagc ggcatctaca gtgccactta cctggaagcc    600
agccccctgg gcagcgcctt ctttcggctc atcgtgcggg gttgtggggc tgggcgctgg    660
gggccaggct gtaccaagga gtgcccaggt tgcctacatg gaggtgtctg ccacgaccat    720
gacggcgaat gtgtatgccc ccctggcttc actggcaccc gctgtgaaca ggcctgcaga    780
gagggccgtt ttgggcagag ctgccaggag cagtgcccag gcatatcagg ctgccggggc    840
ctcaccttct gcctcccaga cccctatggc tgctcttgtg gatctggctg gagaggaagc    900
cagtgccaag aagcttgtgc ccctggtcat tttggggctg attgccgact ccagtgccag    960
tgtcagaatg gtggcacttg tgaccggttc agtggttgtg tctgcccctc tgggtggcat   1020
ggagtgcact gtgagaagtc agaccggatc cccagatcc tcaacatggc ctcagaactg   1080
gagttcaact tagagacgat gccccggatc aactgtgcag ctgcagggaa ccccttcccc   1140
gtgcggggca gcatagagct acgcaagcca gacggcactg tgctcctgtc caccaaggcc   1200
attgtggagc cagagaagac cacagctgag ttcgaggtgc ccgcttggt tcttgcggac   1260
agtgggttct gggagtgccg tgtgtccaca tctggcggcc aagacagccg gcgcttcaag   1320
gtcaatgtga aagtgccccc cgtgcccctg gctgcacctc ggctcctgac caagcagagc   1380
cgccagcttg tggtctcccc gctggtctcg ttctctgggg atggacccat ctccactgtc   1440
cgcctgcact accggcccca ggacagtacc atggactggt cgaccattgt ggtggacccc   1500
agtgagaacg tgacgttaat gaacctgagg ccaaagacag gatacagtgt tcgtgtgcag   1560
ctgagccggc caggggaagg aggagagggg gcctgggggc ctcccaccct catgaccaca   1620
gactgtcctg agcctttgtt gcagccgtgg ttggagggct ggcatgtgga aggcactgac   1680
cggctgcgag tgagctggtc cttgcccttg gtgcccgggc cactggtggg cgacggtttc   1740
ctgctgcgcc tgtgggacgg gacacggggg caggagcggc gggagaacgt ctcatccccc   1800
caggcccgca ctgccctcct gacgggactc acgcctggca cccactacca gctggatgtg   1860
cagctctacc actgcaccct cctgggcccg gcctcgcccc ctgcacacgt gcttctgccc   1920
cccagtgggc ctccagcccc ccgacacctc cacgcccagg ccctctcaga ctccgagatc   1980
cagctgacat ggaagcaccc ggaggctctg cctgggccaa tatccaagta cgttgtggag   2040
gtgcaggtgg ctgggggtgc aggagaccca ctgtggatag acgtggacag gcctgaggag   2100
acaagcacca tcatccgtgg cctcaacgcc agcacgcgct acctcttccg catgcgggcc   2160
agcattcagg ggctcgggga ctggagcaac acagtagaag agtccaccct gggcaacggg   2220
ctgcaggctg agggcccagt ccaagagagc cgggcagctg aagagggcct ggatcagcag   2280
ctgatcctgg cggtggtggg ctccgtgtct gccacctgcc tcaccatcct ggctgccctt   2340
ttaaccctgg tgtgcatccg cagaagctgc ctgcatcgga gacgcacctt cacctaccag   2400
tcaggctcgg gcgaggagac catcctgcag ttcagctcag ggaccttgac acttacccgg   2460
cggccaaaac tgcagcccga gcccctgagc tacccagtgc tagagtggga ggacatcacc   2520
tttgaggacc tcatcgggga ggggaacttc ggccaggtca tccgggccat gatcaagaag   2580
gacgggctga agatgaacgc agccatcaaa atgctgaaag agtatgcctc tgaaaatgac   2640
catcgtgact ttgcgggaga actggaagtt ctgtgcaaat tggggcatca ccccaacatc   2700
atcaacctcc tgggggcctg taagaaccga ggttacttgt atatcgctat tgaatatgcc   2760
ccctacggga acctgctaga ttttctgcgg aaaagccggg tcctagagac tgacccagct   2820
tttgctcgag agcatgggac agcctctacc cttagctccc ggcagctgct gcgtttcgcc   2880
```

agtgatgcgg ccaatggcat gcagtacctg agtgagaagc agttcatcca cagggacctg 2940
gctgcccgga atgtgctggt cggagagaac ctggcctcca agattgcaga cttcggcctt 3000
tctcggggag aggaggttta tgtgaagaag acgatggggc gtctccctgt gcgctggatg 3060
gccattgagt ccctgaacta cagtgtctat accaccaaga gtgatgtctg gtcctttgga 3120
gtccttcttt gggagatagt gagccttgga ggtacaccct actgtggcat gacctgtgcc 3180
gagctctatg aaaagctgcc ccagggctac cgcatggagc agcctcgaaa ctgtgacgat 3240
gaagtgtacg agctgatgcg tcagtgctgg cgggaccgtc cctatgagcg acccccottt 3300 gcccagattg cgctacagct aggccgcatg ctggaagcca ggaaggccta tgtgaacatg 3360
tcgctgtttg agaacttcac ttacgcgggc attgatgcca cagctgagga ggcctga 3417

<210> SEQ ID NO 9
<211> LENGTH: 3375
<212> TYPE: DNA
<213> ORGANISM: Homo sapiens
<300> PUBLICATION INFORMATION:
<302> TITLE: TEK
<310> PATENT DOCUMENT NUMBER: L06139

<400> SEQUENCE: 9
atggactctt tagccagctt agttctctgt ggagtcagct tgctcctttc tggaactgtg 60
gaaggtgcca tggacttgat cttgatcaat tccctacctc ttgtatctga tgctgaaaca 120
tctctcacct gcattgcctc tgggtggcgc ccccatgagc ccatcaccat aggaagggac 180
tttgaagcct taatgaacca gcaccaggat ccgctggaag ttactcaaga tgtgaccaga 240
gaatgggcta aaaaagttgt ttggaagaga gaaaaggcta gtaagatcaa tggtgcttat 300
ttctgtgaag ggcgagttcg aggagaggca atcaggatac gaaccatgaa gatgcgtcaa 360
caagcttcct tcctaccagc tactttaact atgactgtgg acaagggaga taacgtgaac 420
atatctttca aaaaggtatt gattaaagaa gaagatgcag tgatttacaa aaatggttcc 480
ttcatccatt cagtgccccg gcatgaagta cctgatattc tagaagtaca cctgcctcat 540
gctcagcccc aggatgctgg agtgtactcg gccaggtata taggaggaaa cctcttcacc 600
tcggccttca ccaggctgat agtccggaga tgtgaagccc agaagtgggg acctgaatgc 660
aaccatctct gtactgcttg tatgaacaat ggtgtctgcc atgaagatac tggagaatgc 720
atttgccctc ctgggtttat gggaaggacg tgtgagaagg cttgtgaact gcacacgttt 780
ggcagaactt gtaaagaaag gtgcagtgga caagagggat gcaagtctta tgtgttctgt 840
ctccctgacc cctatgggtg ttcctgtgcc acaggctgga agggtctgca gtgcaatgaa 900
gcatgccacc ctggttttta cgggccagat tgtaagctta ggtgcagctg caacaatggg 960
gagatgtgtg atcgcttcca aggatgtctc tgctctccag gatggcaggg gctccagtgt 1020
gagagagaag gcataccgag gatgacccca aagatagtgg atttgccaga tcatatagaa 1080
gtaaacagtg gtaaatttaa tcccatttgc aaagcttctg gctggccgct acctactaat 1140
gaagaaatga ccctggtgaa gccggatggg acagtgctcc atccaaaaga ctttaaccat 1200
acggatcatt tctcagtagc catattcacc atccaccgga tcctcccccc tgactcagga 1260
gtttgggtct gcagtgtgaa cacagtggct gggatggtgg aaaagccctt caacatttct 1320
gttaaagttc ttccaaagcc cctgaatgcc ccaaacgtga ttgacactgg acataacttt 1380
gctgtcatca acatcagctc tgagccttac tttggggatg gaccaatcaa atccaagaag 1440
cttctataca aacccgttaa tcactatgag gcttggcaac atattcaagt gacaaatgag 1500

-continued

```
attgttacac tcaactattt ggaacctcgg acagaatatg aactctgtgt gcaactggtc   1560
cgtcgtggag agggtgggga agggcatcct ggacctgtga gacgcttcac aacagcttct   1620
atcggactcc ctcctccaag aggtctaaat ctcctgccta aaagtcagac cactctaaat   1680
ttgacctggc aaccaatatt tccaagctcg gaagatgact tttatgttga agtggagaga   1740
aggtctgtgc aaaaaagtga tcagcagaat attaaagttc caggcaactt gacttcggtg   1800
ctacttaaca acttacatcc cagggagcag tacgtggtcc gagctagagt caacaccaag   1860
gcccaggggg aatggagtga agatctcact gcttggaccc ttagtgacat tcttcctcct   1920
caaccagaaa acatcaagat ttccaacatt acacactcct cggctgtgat ttcttggaca   1980
atattggatg gctattctat ttcttctatt actatccgtt acaaggttca aggcaagaat   2040
gaagaccagc acgttgatgt gaagataaag aatgccacca tcattcagta tcagctcaag   2100
ggcctagagc ctgaaacagc ataccaggtg gacatttttg cagagaacaa catagggtca   2160
agcaacccag cctttttctca tgaactggtg accctcccag aatctcaagc accagcggac   2220
ctcggagggg ggaagatgct gcttatagcc atccttggct ctgctggaat gacctgcctg   2280
actgtgctgt tggcctttct gatcatattg caattgaaga gggcaaatgt gcaaaggaga   2340
atggcccaag ccttccaaaa cgtgagggaa gaaccagctg tgcagttcaa ctcagggact   2400
ctggccctaa acaggaaggt caaaaacaac ccagatccta caatttatcc agtgcttgac   2460
tggaatgaca tcaaatttca agatgtgatt ggggagggca attttggcca agttcttaag   2520
gcgcgcatca agaaggatgg gttacggatg gatgctgcca tcaaaagaat gaaagaatat   2580
gcctccaaag atgatcacag ggactttgca ggagaactgg aagttctttg taaacttgga   2640
caccatccaa acatcatcaa tctcttagga gcatgtgaac atcgaggcta cttgtacctg   2700
gccattgagt acgcgcccca tggaaacctt ctggacttcc ttcgcaagag ccgtgtgctg   2760
gagacggacc cagcatttgc cattgccaat agcaccgcgt ccacactgtc ctcccagcag   2820
ctccttcact tcgctgccga cgtggcccgg ggcatggact acttgagcca aaaacagttt   2880
atccacaggg atctggctgc cagaaacatt ttagttggtg aaaactatgt ggcaaaaata   2940
gcagattttg gattgtcccg aggtcaagag gtgtacgtga aaaagacaat gggaaggctc   3000
ccagtgcgct ggatggccat cgagtcactg aattacagtg tgtacacaac caacagtgat   3060
gtatggtcct atggtgtgtt actatgggag attgttagct taggaggcac accctactgc   3120
gggatgactt gtgcagaact ctacgagaag ctgccccagg gctacagact ggagaagccc   3180
ctgaactgtg atgatgaggt gtatgatcta atgagacaat gctggcggga gaagccttat   3240
gagaggccat catttgccca gatattggtg tccttaaaca gaatgttaga ggagcgaaag   3300
acctacgtga ataccacgct ttatgagaag tttacttatg caggaattga ctgttctgct   3360
gaagaagcgg cctag                                                     3375
```

<210> SEQ ID NO 10
<211> LENGTH: 2400
<212> TYPE: DNA
<213> ORGANISM: Homo sapiens
<220> FEATURE:
<221> NAME/KEY: CDS
<222> LOCATION: (1)..(2397)
<300> PUBLICATION INFORMATION:
<300> PUBLICATION INFORMATION:
<302> TITLE: beta5 integrin
<310> PATENT DOCUMENT NUMBER: X53002

<400> SEQUENCE: 10

```
atg ccg cgg gcc ccg gcg ccg ctg tac gcc tgc ctc ctg ggg ctc tgc       48
Met Pro Arg Ala Pro Ala Pro Leu Tyr Ala Cys Leu Leu Gly Leu Cys
1               5                   10                  15

gcg ctc ctg ccc cgg ctc gca ggt ctc aac ata tgc act agt gga agt       96
Ala Leu Leu Pro Arg Leu Ala Gly Leu Asn Ile Cys Thr Ser Gly Ser
            20                  25                  30

gcc acc tca tgt gaa gaa tgt ctg cta atc cac cca aaa tgt gcc tgg      144
Ala Thr Ser Cys Glu Glu Cys Leu Leu Ile His Pro Lys Cys Ala Trp
        35                  40                  45

tgc tcc aaa gag gac ttc gga agc cca cgg tcc atc acc tct cgg tgt      192
Cys Ser Lys Glu Asp Phe Gly Ser Pro Arg Ser Ile Thr Ser Arg Cys
    50                  55                  60

gat ctg agg gca aac ctt gtc aaa aat ggc tgt gga ggt gag ata gag      240
Asp Leu Arg Ala Asn Leu Val Lys Asn Gly Cys Gly Gly Glu Ile Glu
65                  70                  75                  80

agc cca gcc agc agc ttc cat gtc ctg agg agc ctg ccc ctc agc agc      288
Ser Pro Ala Ser Ser Phe His Val Leu Arg Ser Leu Pro Leu Ser Ser
                85                  90                  95

aag ggt tcg ggc tct gca ggc tgg gac gtc att cag atg aca cca cag      336
Lys Gly Ser Gly Ser Ala Gly Trp Asp Val Ile Gln Met Thr Pro Gln
            100                 105                 110

gag att gcc gtg aac ctc cgg ccc ggt gac aag acc acc ttc cag cta      384
Glu Ile Ala Val Asn Leu Arg Pro Gly Asp Lys Thr Thr Phe Gln Leu
        115                 120                 125

cag gtt cgc cag gtg gag gac tat cct gtg gac ctg tac tac ctg atg      432
Gln Val Arg Gln Val Glu Asp Tyr Pro Val Asp Leu Tyr Tyr Leu Met
    130                 135                 140

gac ctc tcc ctg tcc atg aag gat gac ttg gac aat atc cgg agc ctg      480
Asp Leu Ser Leu Ser Met Lys Asp Asp Leu Asp Asn Ile Arg Ser Leu
145                 150                 155                 160

ggc acc aaa ctc gcg gag gag atg agg aag ctc acc agc aac ttc cgg      528
Gly Thr Lys Leu Ala Glu Glu Met Arg Lys Leu Thr Ser Asn Phe Arg
                165                 170                 175

ttg gga ttt ggg tct ttt gtt gat aag gac atc tct cct ttc tcc tac      576
Leu Gly Phe Gly Ser Phe Val Asp Lys Asp Ile Ser Pro Phe Ser Tyr
            180                 185                 190

acg gca ccg agg tac cag acc aat ccg tgc att ggt tac aag ttg ttt      624
Thr Ala Pro Arg Tyr Gln Thr Asn Pro Cys Ile Gly Tyr Lys Leu Phe
        195                 200                 205

cca aat tgc gtc ccc tcc ttt ggg ttc cgc cat ctg ctg cct ctc aca      672
Pro Asn Cys Val Pro Ser Phe Gly Phe Arg His Leu Leu Pro Leu Thr
    210                 215                 220

gac aga gtg gac agc ttc aat gag gaa gtt cgg aaa cag agg gtg tcc      720
Asp Arg Val Asp Ser Phe Asn Glu Glu Val Arg Lys Gln Arg Val Ser
225                 230                 235                 240

cgg aac cga gat gcc cct gag ggg ggc ttt gat gca gta ctc cag gca      768
Arg Asn Arg Asp Ala Pro Glu Gly Gly Phe Asp Ala Val Leu Gln Ala
                245                 250                 255

gcc gtc tgc aag gag aag att ggc tgg cga aag gat gca ctg cat ttg      816
Ala Val Cys Lys Glu Lys Ile Gly Trp Arg Lys Asp Ala Leu His Leu
            260                 265                 270

ctg gtg ttc aca aca gat gat gtg ccc cac atc gca ttg gat gga aaa      864
Leu Val Phe Thr Thr Asp Asp Val Pro His Ile Ala Leu Asp Gly Lys
        275                 280                 285

ttg gga ggc ctg gtg cag cca cac gat ggc cag tgc cac ctg aac gag      912
Leu Gly Gly Leu Val Gln Pro His Asp Gly Gln Cys His Leu Asn Glu
    290                 295                 300

gcc aac gag tac aca gca tcc aac cag atg gac tat cca tcc ctt gcc      960
Ala Asn Glu Tyr Thr Ala Ser Asn Gln Met Asp Tyr Pro Ser Leu Ala
```

-continued

```
305                 310                 315                 320

ttg ctt gga gag aaa ttg gca gag aac aac atc aac ctc atc ttt gca     1008
Leu Leu Gly Glu Lys Leu Ala Glu Asn Asn Ile Asn Leu Ile Phe Ala
                325                 330                 335

gtg aca aaa aac cat tat atg ctg tac aag aat ttt aca gcc ctg ata     1056
Val Thr Lys Asn His Tyr Met Leu Tyr Lys Asn Phe Thr Ala Leu Ile
            340                 345                 350

cct gga aca acg gtg gag att tta gat gga gac tcc aaa aat att att     1104
Pro Gly Thr Thr Val Glu Ile Leu Asp Gly Asp Ser Lys Asn Ile Ile
        355                 360                 365

caa ctg att att aat gca tac aat agt atc cgg tct aaa gtg gag ttg     1152
Gln Leu Ile Ile Asn Ala Tyr Asn Ser Ile Arg Ser Lys Val Glu Leu
    370                 375                 380

tca gtc tgg gat cag cct gag gat ctt aat ctc ttc ttt act gct acc     1200
Ser Val Trp Asp Gln Pro Glu Asp Leu Asn Leu Phe Phe Thr Ala Thr
385                 390                 395                 400

tgc caa gat ggg gta tcc tat cct ggt cag agg aag tgt gag ggt ctg     1248
Cys Gln Asp Gly Val Ser Tyr Pro Gly Gln Arg Lys Cys Glu Gly Leu
                405                 410                 415

aag att ggg gac acg gca tct ttt gaa gta tca ttg gag gcc cga agc     1296
Lys Ile Gly Asp Thr Ala Ser Phe Glu Val Ser Leu Glu Ala Arg Ser
            420                 425                 430

tgt ccc agc aga cac acg gag cat gtg ttt gcc ctg cgg ccg gtg gga     1344
Cys Pro Ser Arg His Thr Glu His Val Phe Ala Leu Arg Pro Val Gly
        435                 440                 445

ttc cgg gac agc ctg gag gtg ggg gtc acc tac aac tgc acg tgc ggc     1392
Phe Arg Asp Ser Leu Glu Val Gly Val Thr Tyr Asn Cys Thr Cys Gly
    450                 455                 460

tgc agc gtg ggg ctg gaa ccc aac agc gcc agg tgc aac ggg agc ggg     1440
Cys Ser Val Gly Leu Glu Pro Asn Ser Ala Arg Cys Asn Gly Ser Gly
465                 470                 475                 480

acc tat gtc tgc ggc ctg tgt gag tgc agc ccc ggc tac ctg ggc acc     1488
Thr Tyr Val Cys Gly Leu Cys Glu Cys Ser Pro Gly Tyr Leu Gly Thr
                485                 490                 495

agg tgc gag tgc cag gat ggg gag aac cag agc gtg tac cag aac ctg     1536
Arg Cys Glu Cys Gln Asp Gly Glu Asn Gln Ser Val Tyr Gln Asn Leu
            500                 505                 510

tgc cgg gag gca gag ggc aag cca ctg tgc agc ggg cgt ggg gac tgc     1584
Cys Arg Glu Ala Glu Gly Lys Pro Leu Cys Ser Gly Arg Gly Asp Cys
        515                 520                 525

agc tgc aac cag tgc tcc tgc ttc gag agc gag ttt ggc aag atc tat     1632
Ser Cys Asn Gln Cys Ser Cys Phe Glu Ser Glu Phe Gly Lys Ile Tyr
    530                 535                 540

ggg cct ttc tgt gag tgc gac aac ttc tcc tgt gcc agg aac aag gga     1680
Gly Pro Phe Cys Glu Cys Asp Asn Phe Ser Cys Ala Arg Asn Lys Gly
545                 550                 555                 560

gtc ctc tgc tca ggc cat ggc gag tgt cac tgc ggg gaa tgc aag tgc     1728
Val Leu Cys Ser Gly His Gly Glu Cys His Cys Gly Glu Cys Lys Cys
                565                 570                 575

cat gca ggt tac atc ggg gac aac tgt aac tgc tcg aca gac atc agc     1776
His Ala Gly Tyr Ile Gly Asp Asn Cys Asn Cys Ser Thr Asp Ile Ser
            580                 585                 590

aca tgc cgg ggc aga gat ggc cag atc tgc agc gag cgt ggg cac tgt     1824
Thr Cys Arg Gly Arg Asp Gly Gln Ile Cys Ser Glu Arg Gly His Cys
        595                 600                 605

ctc tgt ggg cag tgc caa tgc acg gag ccg ggg gcc ttt ggg gag atg     1872
Leu Cys Gly Gln Cys Gln Cys Thr Glu Pro Gly Ala Phe Gly Glu Met
    610                 615                 620

tgt gag aag tgc ccc acc tgc ccg gat gca tgc agc acc aag aga gat     1920
```

-continued

```
Cys Glu Lys Cys Pro Thr Cys Pro Asp Ala Cys Ser Thr Lys Arg Asp
625                 630                 635                 640

tgc gtc gag tgc ctg ctg ctc cac tct ggg aaa cct gac aac cag acc      1968
Cys Val Glu Cys Leu Leu Leu His Ser Gly Lys Pro Asp Asn Gln Thr
                645                 650                 655

tgc cac agc cta tgc agg gat gag gtg atc aca tgg gtg gac acc atc      2016
Cys His Ser Leu Cys Arg Asp Glu Val Ile Thr Trp Val Asp Thr Ile
            660                 665                 670

gtg aaa gat gac cag gag gct gtg cta tgt ttc tac aaa acc gcc aag      2064
Val Lys Asp Asp Gln Glu Ala Val Leu Cys Phe Tyr Lys Thr Ala Lys
        675                 680                 685

gac tgc gtc atg atg ttc acc tat gtg gag ctc ccc agt ggg aag tcc      2112
Asp Cys Val Met Met Phe Thr Tyr Val Glu Leu Pro Ser Gly Lys Ser
    690                 695                 700

aac ctg acc gtc ctc agg gag cca gag tgt gga aac acc ccc aac gcc      2160
Asn Leu Thr Val Leu Arg Glu Pro Glu Cys Gly Asn Thr Pro Asn Ala
705                 710                 715                 720

atg acc atc ctc ctg gct gtg gtc ggt agc atc ctc ctt gtt ggg ctt      2208
Met Thr Ile Leu Leu Ala Val Val Gly Ser Ile Leu Leu Val Gly Leu
                725                 730                 735

gca ctc ctg gct atc tgg aag ctg ctt gtc acc atc cac gac cgg agg      2256
Ala Leu Leu Ala Ile Trp Lys Leu Leu Val Thr Ile His Asp Arg Arg
            740                 745                 750

gag ttt gca aag ttt cag agc gag cga tcc agg gcc cgc tat gaa atg      2304
Glu Phe Ala Lys Phe Gln Ser Glu Arg Ser Arg Ala Arg Tyr Glu Met
        755                 760                 765

gct tca aat cca tta tac aga aag cct atc tcc acg cac act gtg gac      2352
Ala Ser Asn Pro Leu Tyr Arg Lys Pro Ile Ser Thr His Thr Val Asp
    770                 775                 780

ttc acc ttc aac aag ttc aac aaa tcc tac aat ggc act gtg gac tga      2400
Phe Thr Phe Asn Lys Phe Asn Lys Ser Tyr Asn Gly Thr Val Asp
785                 790                 795


<210> SEQ ID NO 11
<211> LENGTH: 2367
<212> TYPE: DNA
<213> ORGANISM: Homo sapiens
<300> PUBLICATION INFORMATION:
<302> TITLE: beta3 integrin
<310> PATENT DOCUMENT NUMBER: NM000212

<400> SEQUENCE: 11

atgcgagcgc ggccgcggcc ccggccgctc tgggcgactg tgctggcgct gggggcgctg      60

gcgggcgttg gcgtaggagg gcccaacatc tgtaccacgc gaggtgtgag ctcctgccag     120

cagtgcctgg ctgtgagccc catgtgtgcc tggtgctctg atgaggccct gcctctgggc     180

tcacctcgct gtgacctgaa ggagaatctg ctgaaggata actgtgcccc agaatccatc     240

gagttcccag tgagtgaggc ccgagtacta gaggacaggc ccctcagcga caagggctct     300

ggagacagct cccaggtcac tcaagtcagt ccccagagga ttgcactccg gctccggcca     360

gatgattcga agaatttctc catccaagtg cggcaggtgg aggattaccc tgtggacatc     420

tactacttga tggacctgtc ttactccatg aaggatgatc tgtggagcat ccagaacctg     480

ggtaccaagc tggccaccca gatgcgaaag ctcaccagta acctgcggat tggcttcggg     540

gcatttgtgg acaagcctgt gtcaccatac atgtatatct ccccaccaga ggccctcgaa     600

aacccctgct atgatatgaa gaccacctgc ttgcccatgt ttggctacaa acacgtgctg     660

acgctaactg accaggtgac ccgcttcaat gaggaagtga agaagcagag tgtgtcacgg     720

aaccgagatg ccccagaggg tggctttgat gccatcatgc aggctacagt ctgtgatgaa     780
```

```
aagattggct ggaggaatga tgcatcccac ttgctggtgt ttaccactga tgccaagact    840

catatagcat tggacggaag gctggcaggc attgtccagc ctaatgacgg gcagtgtcat    900

gttggtagtg acaatcatta ctctgcctcc actaccatgg attatccctc tttggggctg    960

atgactgaga agctatccca gaaaaacatc aatttgatct ttgcagtgac tgaaaatgta   1020

gtcaatctct atcagaacta tagtgagctc atcccaggga ccacagttgg ggttctgtcc   1080

atggattcca gcaatgtcct ccagctcatt gttgatgctt atgggaaaat ccgttctaaa   1140

gtagagctgg aagtgcgtga cctccctgaa gagttgtctc tatccttcaa tgccacctgc   1200

ctcaacaatg aggtcatccc tggcctcaag tcttgtatgg gactcaagat tggagacacg   1260

gtgagcttca gcattgaggc caaggtgcga ggctgtcccc aggagaagga gaagtccttt   1320

accataaagc ccgtgggctt caaggacagc ctgatcgtcc aggtcacctt tgattgtgac   1380

tgtgcctgcc aggcccaagc tgaacctaat agccatcgct gcaacaatgg caatgggacc   1440

tttgagtgtg ggtatgccg ttgtgggcct ggctggctgg gatcccagtg tgagtgctca   1500

gaggaggact atcgcccttc ccagcaggac gaatgcagcc cccgggaggg tcagcccgtc   1560

tgcagccagc ggggcgagtg cctctgtggt caatgtgtct gccacagcag tgactttggc   1620

aagatcacgg gcaagtactg cgagtgtgac gacttctcct gtgtccgcta caagggggag   1680

atgtgctcag gccatggcca gtgcagctgt ggggactgcc tgtgtgactc cgactggacc   1740

ggctactact gcaactgtac cacgcgtact gacacctgca tgtccagcaa tgggctgctg   1800

tgcagcggcc gcggcaagtg tgaatgtggc agctgtgtct gtatccagcc gggctcctat   1860

ggggacacct gtgagaagtg ccccacctgc ccagatgcct gcacctttaa gaaagaatgt   1920

gtggagtgta agaagtttga ccgggagccc tacatgaccg aaaatacctg caaccgttac   1980

tgccgtgacg agattgagtc agtgaaagag cttaaggaca ctggcaagga tgcagtgaat   2040

tgtacctata agaatgagga tgactgtgtc gtcagattcc agtactatga agattctagt   2100

ggaaagtcca tcctgtatgt ggtagaagag ccagagtgtc ccaagggccc tgacatcctg   2160

gtggtcctgc tctcagtgat gggggccatt ctgctcattg gccttgccgc cctgctcatc   2220

tggaaactcc tcatcaccat ccacgaccga aaagaattcg ctaaatttga ggaagaacgc   2280

gccagagcaa aatgggacac agccaacaac ccactgtata aagaggccac gtctaccttc   2340

accaatatca cgtaccgggg cacttaa                                       2367
```

<210> SEQ ID NO 12
<211> LENGTH: 3147
<212> TYPE: DNA
<213> ORGANISM: Homo sapiens
<300> PUBLICATION INFORMATION:
<302> TITLE: alpha v intergrin
<310> PATENT DOCUMENT NUMBER: NM0022210

<400> SEQUENCE: 12

```
atggcttttc cgccgcggcg acggctgcgc ctcggtcccc gcggcctccc gcttcttctc     60

tcgggactcc tgctacctct gtgccgcgcc ttcaacctag acgtggacag tcctgccgag    120

tactctggcc ccgagggaag ttacttcggc ttcgccgtgg atttcttcgt gcccagcgcg    180

tcttcccgga tgtttcttct cgtgggagct cccaaagcaa acaccaccca gcctgggatt    240

gtggaaggag ggcaggtcct caaatgtgac tggtcttcta cccgccggtg ccagccaatt    300

gaatttgatg caacaggcaa tagagattat gccaaggatg atccattgga atttaagtcc    360

catcagtggt ttggagcatc tgtgaggtcg aaacaggata aaattttggc ctgtgcccca    420
```

-continued

```
ttgtaccatt ggagaactga gatgaaacag gagcgagagc ctgttggaac atgctttctt    480
caagatggaa caaagactgt tgagtatgct ccatgtagat cacaagatat tgatgctgat    540
ggacagggat tttgtcaagg aggattcagc attgatttta ctaaagctga cagagtactt    600
cttggtggtc ctggtagctt ttattggcaa ggtcagctta tttcggatca agtggcagaa    660
atcgtatcta aatacgaccc caatgtttac agcatcaagt ataataacca attagcaact    720
cggactgcac aagctatttt tgatgacagc tatttgggtt attctgtggc tgtcggagat    780
ttcaatggtg atggcataga tgactttgtt tcaggagttc caagagcagc aaggactttg    840
ggaatggttt atatttatga tgggaagaac atgtcctcct tatacaattt tactggcgag    900
cagatggctg catatttcgg attttctgta gctgccactg acattaatgg agatgattat    960
gcagatgtgt ttattggagc acctctcttc atggatcgtg gctctgatgg caaactccaa   1020
gaggtggggc aggtctcagt gtctctacag agagcttcag gagacttcca gacgacaaag   1080
ctgaatggat ttgaggtctt tgcacggttt ggcagtgcca tagctccttt gggagatctg   1140
gaccaggatg gtttcaatga tattgcaatt gctgctccat atgggggtga agataaaaaa   1200
ggaattgttt atatcttcaa tggaagatca acaggcttga acgcagtccc atctcaaatc   1260
cttgaagggc agtgggctgc tcgaagcatg ccaccaagct ttggctattc aatgaaagga   1320
gccacagata tagacaaaaa tggatatcca gacttaattg taggagcttt tggtgtagat   1380
cgagctatct tatacagggc cagaccagtt atcactgtaa atgctggtct tgaagtgtac   1440
cctagcattt taaatcaaga caataaaacc tgctcactgc ctggaacagc tctcaaagtt   1500
tcctgtttta atgttaggtt ctgcttaaag gcagatggca aaggagtact tcccaggaaa   1560
cttaatttcc aggtggaact tcttttggat aaactcaagc aaaagggagc aattcgacga   1620
gcactgtttc tctacagcag gtccccaagt cactccaaga acatgactat ttcaaggggg   1680
ggactgatgc agtgtgagga attgatagcg tatctgcggg atgaatctga atttagagac   1740
aaactcactc caattactat ttttatggaa tatcggttgg attatagaac agctgctgat   1800
acaacaggct tgcaacccat tcttaaccag ttcacgcctg ctaacattag tcgacaggct   1860
cacattctac ttgactgtgg tgaagacaat gtctgtaaac ccaagctgga agtttctgta   1920
gatagtgatc aaaagaagat ctatattggg gatgacaacc ctctgacatt gattgttaag   1980
gctcagaatc aaggagaagg tgcctacgaa gctgagctca tcgtttccat tccactgcag   2040
gctgatttca tcggggttgt ccgaaacaat gaagccttag caagactttc ctgtgcattt   2100
aagacagaaa accaaactcg ccaggtggta tgtgaccttg gaaacccaat gaaggctgga   2160
actcaactct tagctggtct tcgtttcagt gtgcaccagc agtcagagat ggatacttct   2220
gtgaaatttg acttacaaat ccaaagctca aatctatttg acaaagtaag cccagttgta   2280
tctcacaaag ttgatcttgc tgttttagct gcagttgaga taagaggagt ctcgagtcct   2340
gatcatatct ttcttccgat tccaaactgg gagcacaagg agaaccctga gactgaagaa   2400
gatgttgggc cagttgttca gcacatctat gagctgagaa acaatggtcc aagttcattc   2460
agcaaggcaa tgctccatct tcagtggcct tacaaatata ataataacac tctgttgtat   2520
atccttcatt atgatattga tggaccaatg aactgcactt cagatatgga gatcaaccct   2580
ttgagaatta agatctcatc tttgcaaaca actgaaaaga atgacacggt tgccgggcaa   2640
ggtgagcggg accatctcat cactaagcgg gatcttgccc tcagtgaagg agatattcac   2700
actttgggtt gtggagttgc tcagtgcttg aagattgtct gccaagttgg gagattagac   2760
```

-continued agaggaaaga gtgcaatctt gtacgtaaag tcattactgt ggactgagac ttttatgaat 2820
aaagaaaatc agaatcattc ctattctctg aagtcgtctg cttcatttaa tgtcatagag 2880
tttccttata agaatcttcc aattgaggat atcaccaact ccacattggt taccactaat 2940
gtcacctggg gcattcagcc agcgcccatg cctgtgcctg tgtgggtgat cattttagca 3000
gttctagcag gattgttgct actggctgtt ttggtatttg taatgtacag gatgggcttt 3060
tttaaacggg tccggccacc tcaagaagaa caagaaaggg agcagcttca acctcatgaa 3120
aatggtgaag gaaactcaga aacttaa 3147

<210> SEQ ID NO 13
<211> LENGTH: 402
<212> TYPE: DNA
<213> ORGANISM: Homo sapiens
<300> PUBLICATION INFORMATION:
<302> TITLE: CaSm (cancer associated SM-like oncogene)
<310> PATENT DOCUMENT NUMBER: AF000177

<400> SEQUENCE: 13
atgaactata tgcctggcac cgccagcctc atcgaggaca ttgacaaaaa gcacttggtt 60
ctgcttcgag atggaaggac acttataggc tttttaagaa gcattgatca atttgcaaac 120
ttagtgctac atcagactgt ggagcgtatt catgtgggca aaaaatacgg tgatattcct 180
cgagggattt ttgtggtcag aggagaaaat gtggtcctac taggagaaat agacttggaa 240
aaggagagtg acacacccct ccagcaagta tccattgaag aaattctaga agaacaaagg 300
gtggaacagc agaccaagct ggaagcagag aagttgaaag tgcaggccct gaaggaccga 360
ggtctttcca ttcctcgagc agatactctt gatgagtact aa 402

<210> SEQ ID NO 14
<211> LENGTH: 1923
<212> TYPE: DNA
<213> ORGANISM: Homo sapiens
<300> PUBLICATION INFORMATION:
<302> TITLE: c-myb
<310> PATENT DOCUMENT NUMBER: NM005375

<400> SEQUENCE: 14
atggcccgaa gaccccggca cagcatatat agcagtgacg aggatgatga ggactttgag 60
atgtgtgacc atgactatga tgggctgctt cccaagtctg gaaagcgtca cttggggaaa 120
acaaggtgga cccgggaaga ggatgaaaaa ctgaagaagc tggtggaaca gaatggaaca 180
gatgactgga aagttattgc caattatctc ccgaatcgaa cagatgtgca gtgccagcac 240
cgatggcaga aagtactaaa ccctgagctc atcaagggtc cttggaccaa agaagaagat 300
cagagagtga tagagcttgt acagaaatac ggtccgaaac gttggtctgt tattgccaag 360
cacttaaagg ggagaattgg aaaacaatgt agggagaggt ggcataacca cttgaatcca 420
gaagttaaga aaacctcctg gacagaagag gaagacagaa ttatttacca ggcacacaag 480
agactgggga acagatgggc agaaatcgca aagctactgc ctggacgaac tgataatgct 540
atcaagaacc actggaattc tacaatgcgt cggaaggtcg aacaggaagg ttatctgcag 600
gagtcttcaa aagccagcca gccagcagtg gccacaagct tccagaagaa cagtcatttg 660
atgggttttg ctcaggctcc gcctacagct caactccctg ccactggcca gcccactgtt 720
aacaacgact attcctatta ccacatttct gaagcacaaa atgtctccag tcatgttcca 780
taccctgtag cgttacatgt aaatatagtc aatgtccctc agccagctgc cgcagccatt 840
cagagacact ataatgatga agaccctgag aaggaaaagc gaataaagga attagaattg 900
ctcctaatgt caaccgagaa tgagctaaaa ggacagcagg tgctaccaac acagaaccac 960
acatgcagct accccgggtg gcacagcacc accattgccg accacaccag acctcatgga 1020
gacagtgcac ctgtttcctg tttgggagaa caccactcca ctccatctct gccagcggat 1080
cctggctccc tacctgaaga aagcgcctcg ccagcaaggt gcatgatcgt ccaccagggc 1140
accattctgg ataatgttaa gaacctctta gaatttgcag aaacactcca atttatagat 1200
tctttcttaa acacttccag taaccatgaa aactcagact tggaaatgcc ttctttaact 1260
tccacccccc tcattggtca caaattgact gttacaacac catttcatag agaccagact 1320
gtgaaaactc aaaaggaaaa tactgttttt agaaccccag ctatcaaaag gtcaatctta 1380
gaaagctctc caagaactcc tacaccattc aaacatgcac ttgcagctca agaaattaaa 1440
tacggtcccc tgaagatgct acctcagaca ccctctcatc tagtagaaga tctgcaggat 1500
gtgatcaaac aggaatctga tgaatctgga tttgttgctg agtttcaaga aaatggacca 1560
cccttactga agaaaatcaa acaagaggtg gaatctccaa ctgataaatc aggaaacttc 1620
ttctgctcac accactggga aggggacagt ctgaataccc aactgttcac gcagacctcg 1680
cctgtgcgag atgcaccgaa tattcttaca agctccgttt taatggcacc agcatcagaa 1740
gatgaagaca atgttctcaa agcatttaca gtacctaaaa acaggtccct ggcgagcccc 1800
ttgcagcctt gtagcagtac ctgggaacct gcatcctgtg gaaagatgga ggagcagatg 1860
acatcttcca gtcaagctcg taaatacgtg aatgcattct cagcccggac gctggtcatg 1920
tga 1923

<210> SEQ ID NO 15
<211> LENGTH: 544
<212> TYPE: DNA
<213> ORGANISM: Homo sapiens
<300> PUBLICATION INFORMATION:
<302> TITLE: c-myc
<310> PATENT DOCUMENT NUMBER: J00120

<400> SEQUENCE: 15
gacccccgag ctgtgctgct cgcggccgcc accgccgggc cccggccgtc cctggctccc 60
ctcctgcctc gagaagggca gggcttctca gaggcttggc gggaaaaaga acggagggag 120
ggatcgcgct gagtataaaa gccggttttc ggggctttat ctaactcgct gtagtaattc 180
cagcgagagg cagagggagc gagcgggcgg ccggctaggg tggaagagcc gggcgagcag 240
agctgcgctg cgggcgtcct gggaagggag atccggagcg aatagggggc ttcgcctctg 300
gcccagccct cccgctgatc ccccagccag cggtccgcaa cccttgccgc atccacgaaa 360
ctttgcccat agcagcgggc gggcactttg cactggaact tacaacaccc gagcaaggac 420
gcgactctcc cgacgcgggg aggctattct gcccatttgg ggacacttcc ccgccgctgc 480
caggacccgc ttctctgaaa ggctctcctt gcagctgctt agacgctgga tttttttcgg 540
gtag 544

<210> SEQ ID NO 16
<211> LENGTH: 618
<212> TYPE: DNA
<213> ORGANISM: Homo sapiens
<300> PUBLICATION INFORMATION:
<302> TITLE: ephrin-A1
<310> PATENT DOCUMENT NUMBER: NM004428

<400> SEQUENCE: 16

```
atggagttcc tctgggcccc tctcttgggt ctgtgctgca gtctggccgc tgctgatcgc     60

cacaccgtct tctggaacag ttcaaatccc aagttccgga atgaggacta caccatacat    120

gtgcagctga atgactacgt ggacatcatc tgtccgcact atgaagatca ctctgtggca    180

gacgctgcca tggagcagta catactgtac ctggtggagc atgaggagta ccagctgtgc    240

cagccccagt ccaaggacca agtccgctgg cagtgcaacc ggcccagtgc caagcatggc    300

ccggagaagc tgtctgagaa gttccagcgc ttcacacctt tcaccctggg caaggagttc    360

aaagaaggac acagctacta ctacatctcc aaacccatcc accagcatga agaccgctgc    420

ttgaggttga aggtgactgt cagtggcaaa atcactcaca gtcctcaggc ccatgtcaat    480

ccacaggaga agagacttgc agcagatgac ccagaggtgc gggttctaca tagcatcggt    540

cacagtgctg ccccacgcct cttcccactt gcctggactg tgctgctcct tccacttctg    600

ctgctgcaaa ccccgtga                                                  618


<210> SEQ ID NO 17
<211> LENGTH: 642
<212> TYPE: DNA
<213> ORGANISM: Homo sapiens

<400> SEQUENCE: 17

atggcgcccg cgcagcgccc gctgctcccg ctgctgctcc tgctgttacc gctgccgccg     60

ccgcccttcg cgcgcgccga ggacgccgcc cgcgccaact cggaccgcta cgccgtctac    120

tggaaccgca gcaaccccag gttccacgca ggcgcggggg acgacggcgg gggctacacg    180

gtggaggtga gcatcaatga ctacctggac atctactgcc cgcactatgg ggcgccgctg    240

ccgccggccg agcgcatgga gcactacgtg ctgtacatgg tcaacggcga gggccacgcc    300

tcctgcgacc accgccagcg cggcttcaag cgctgggagt gcaaccggcc cgcggcgccc    360

ggggggccgc tcaagttctc ggagaagttc cagctcttca cgcccttctc cctgggcttc    420

gagttccggc ccggccacga gtattactac atctctgcca cgcctcccaa tgctgtggac    480

cggccctgcc tgcgactgaa ggtgtacgtg cggccgacca acgagaccct gtacgaggct    540

cctgagccca tcttcaccag caataactcg tgtagcagcc cgggcggctg ccgcctcttc    600

ctcagcacca tccccgtgct ctggaccctc ctgggttcct ag                       642


<210> SEQ ID NO 18
<211> LENGTH: 717
<212> TYPE: DNA
<213> ORGANISM: Homo sapiens
<300> PUBLICATION INFORMATION:
<302> TITLE: ephrin-A3
<310> PATENT DOCUMENT NUMBER: XM001787

<400> SEQUENCE: 18

atggcggcgg ctccgctgct gctgctgctg ctgctcgtgc ccgtgccgct gctgccgctg     60

ctggcccaag ggcccggagg ggcgctggga aaccggcatg cggtgtactg gaacagctcc    120

aaccagcacc tgcggcgaga gggctacacc gtgcaggtga acgtgaacga ctatctggat    180

atttactgcc cgcactacaa cagctcgggg gtgggccccg gggcgggacc ggggcccgga    240

ggcggggcag agcagtacgt gctgtacatg gtgagccgca acggctaccg cacctgcaac    300

gccagccagg gcttcaagcg ctgggagtgc aaccggccgc acgccccgca cagccccatc    360

aagttctcgg agaagttcca gcgctacagc gccttctctc tgggctacga gttccacgcc    420

ggccacgagt actactacat ctccacgccc actcacaacc tgcactggaa gtgtctgagg    480
```

atgaaggtgt tcgtctgctg cgcctccaca tcgcactccg gggagaagcc ggtccccact 540
ctcccccagt tcaccatggg ccccaatatg aagatcaacg tgctggaaga ctttgaggga 600
gagaaccctc aggtgcccaa gcttgagaag agcatcagcg ggaccagccc caaacgggaa 660
cacctgcccc tggccgtggg catcgccttc ttcctcatga cgttcttggc ctcctag 717

<210> SEQ ID NO 19
<211> LENGTH: 606
<212> TYPE: DNA
<213> ORGANISM: Homo sapiens
<300> PUBLICATION INFORMATION:
<302> TITLE: ephrin-A3
<310> PATENT DOCUMENT NUMBER: XM001784

<400> SEQUENCE: 19
atgcggctgc tgcccctgct gcggactgtc ctctgggccg cgttcctcgg ctcccctctg 60
cgcgggggct ccagcctccg ccacgtagtc tactggaact ccagtaaccc caggttgctt 120
cgaggagacg ccgtggtgga gctgggcctc aacgattacc tagacattgt ctgcccccac 180
tacgaaggcc cagggccccc tgagggcccc gagacgtttg ctttgtacat ggtggactgg 240
ccaggctatg agtcctgcca ggcagagggc ccccgggcct acaagcgctg ggtgtgctcc 300
ctgccctttg gccatgttca attctcagag aagattcagc gcttcacacc cttctccctc 360
ggctttgagt tcttacctgg agagacttac tactacatct cggtgcccac tccagagagt 420
tctggccagt gcttgaggct ccaggtgtct gtctgctgca aggagaggaa gtctgagtca 480
gcccatcctg ttgggagccc tggagagagt ggcacatcag ggtggcgagg gggggacact 540
cccagccccc tctgtctctt gctattactg ctgcttctga ttcttcgtct tctgcgaatt 600
ctgtga 606

<210> SEQ ID NO 20
<211> LENGTH: 687
<212> TYPE: DNA
<213> ORGANISM: Homo sapiens
<300> PUBLICATION INFORMATION:
<302> TITLE: ephrin-A5
<310> PATENT DOCUMENT NUMBER: NM001962

<400> SEQUENCE: 20
atgttgcacg tggagatgtt gacgctggtg tttctggtgc tctggatgtg tgtgttcagc 60
caggacccgg gctccaaggc cgtcgccgac cgctacgctg tctactggaa cagcagcaac 120
cccagattcc agaggggtga ctaccatatt gatgtctgta tcaatgacta cctggatgtt 180
ttctgccctc actatgagga ctccgtccca gaagataaga ctgagcgcta tgtcctctac 240
atggtgaact ttgatggcta cagtgcctgc gaccacactt ccaaagggtt caagagatgg 300
gaatgtaacc ggcctcactc tccaaatgga ccgctgaagt tctctgaaaa attccagctc 360
ttcactccct tttctctagg atttgaattc aggccaggcc gagaatattt ctacatctcc 420
tctgcaatcc cagataatgg aagaaggtcc tgtctaaagc tcaaagtctt tgtgagacca 480
acaaatagct gtatgaaaac tataggtgtt catgatcgtg ttttcgatgt taacgacaaa 540
gtagaaaatt cattagaacc agcagatgac accgtacatg agtcagccga gccatcccgc 600
ggcgagaacg cggcacaaac accaaggata cccagccgcc ttttggcaat cctactgttc 660
ctcctggcga tgcttttgac attatag 687

<210> SEQ ID NO 21
<211> LENGTH: 2955

<212> TYPE: DNA
<213> ORGANISM: Homo sapiens

<400> SEQUENCE: 21
atggccctgg attatctact actgctcctc ctggcatccg cagtggctgc gatggaagaa 60
acgttaatgg acaccagaac ggctactgca gagctgggct ggacggccaa tcctgcgtcc 120
gggtgggaag aagtcagtgg ctacgatgaa aacctgaaca ccatccgcac ctaccaggtg 180
tgcaatgtct tcgagcccaa ccagaacaat tggctgctca ccaccttcat caaccggcgg 240
ggggcccatc gcatctacac agagatgcgc ttcactgtga gagactgcag cagcctccct 300
aatgtcccag gatcctgcaa ggagaccttc aacttgtatt actatgagac tgactctgtc 360
attgccacca agaagtcagc cttctggtct gaggccccct acctcaaagt agacaccatt 420
gctgcagatg agagcttctc ccaggtggac tttgggggaa ggctgatgaa ggtaaacaca 480
gaagtcagga gctttgggcc tcttactcgg aatggttttt acctcgcttt tcaggattat 540
ggagcctgta tgtctcttct ttctgtccgt gtcttcttca aaaagtgtcc cagcattgtg 600
caaaattttg cagtgtttcc agagactatg acaggggcag agagcacatc tctggtgatt 660
gctcggggca catgcatccc caacgcagag gaagtggacg tgcccatcaa actctactgc 720
aacggggatg gggaatggat ggtgcctatt gggcgatgca cctgcaagcc tggctatgag 780
cctgagaaca gcgtggcatg caaggcttgc cctgcaggga cattcaaggc cagccaggaa 840
gctgaaggct gctcccactg cccctccaac agccgctccc ctgcagaggc gtctcccatc 900
tgcacctgtc ggaccggtta ttaccgagcg gactttgacc ctccagaagt ggcatgcact 960
agcgtcccat caggtccccg caatgttatc tccatcgtca atgagacgtc catcattctg 1020
gagtggcacc ctccaaggga gacaggtggg cgggatgatg tgacctacaa catcatctgc 1080
aaaaagtgcc gggcagaccg ccggagctgc tcccgctgtg acgacaatgt ggagtttgtg 1140
cccaggcagc tgggcctgac ggagtgccgc gtctccatca gcagcctgtg ggcccacacc 1200
ccctacacct ttgacatcca ggccatcaat ggagtctcca gcaagagtcc cttcccccca 1260
cagcacgtct ctgtcaacat caccacaaac caagccgccc cctccaccgt tcccatcatg 1320
caccaagtca gtgccactat gaggagcatc accttgtcat ggccacagcc ggagcagccc 1380
aatggcatca tcctggacta tgagatccgg tactatgaga aggaacacaa tgagttcaac 1440
tcctccatgg ccaggagtca gaccaacaca gcaaggattg atgggctgcg gcctggcatg 1500
gtatatgtgg tacaggtgcg tgcccgcact gttgctggct acggcaagtt cagtggcaag 1560
atgtgcttcc agactctgac tgacgatgat tacaagtcag agctgaggga gcagctgccc 1620
ctgattgctg gctcggcagc ggccggggtc gtgttcgttg tgtccttggt ggccatctct 1680
atcgtctgta gcaggaaacg ggcttatagc aaagaggctg tgtacagcga taagctccag 1740
cattacagca caggccgagg ctccccaggg atgaagatct acattgaccc cttcacttat 1800
gaggatccca acgaagctgt ccgggagttt gccaaggaga ttgatgtatc ttttgtgaaa 1860
attgaagagg tcatcggagc aggggagttt ggagaagtgt acaaggggcg tttgaaactg 1920
ccaggcaaga gggaaatcta cgtggccatc aagaccctga aggcagggta ctcggagaag 1980
cagcgtcggg actttctgag tgaggcgagc atcatgggcc agttcgacca tcctaacatc 2040
attcgcctgg agggtgtggt caccaagagt cggcctgtca tgatcatcac agagttcatg 2100
gagaatggtg cattggattc tttcctcagg caaaatgacg ggcagttcac cgtgatccag 2160
cttgtgggta tgctcagggg catcgctgct ggcatgaagt acctggctga gatgaattat 2220

-continued

```
gtgcatcggg acctggctgc taggaacatt ctggtcaaca gtaacctggt gtgcaaggtg   2280

tccgactttg gcctctcccg ctacctccag gatgacacct cagatcccac ctacaccagc   2340

tccttgggag ggaagatccc tgtgagatgg acagctccag aggccatcgc ctaccgcaag   2400

ttcacttcag ccagcgacgt ttggagctat gggatcgtca tgtgggaagt catgtcattt   2460

ggagagagac cctattggga tatgtccaac caagatgtca tcaatgccat cgagcaggac   2520

taccggctgc ccccacccat ggactgtcca gctgctctac accagctcat gctggactgt   2580

tggcagaagg accggaacag ccggccccgg tttgcggaga ttgtcaacac cctagataag   2640

atgatccgga acccggcaag tctcaagact gtggcaacca tcaccgccgt gccttcccag   2700

cccctgctcg accgctccat cccagacttc acggccttta ccaccgtgga tgactggctc   2760

agcgccatca aaatggtcca gtacagggac agcttcctca ctgctggctt cacctccctc   2820

cagctggtca cccagatgac atcagaagac ctcctgagaa taggcatcac cttggcaggc   2880

catcagaaga agatcctgaa cagcattcat tctatgaggg tccagataag tcagtcacca   2940

acggcaatgg catga                                                    2955
```

<210> SEQ ID NO 22
<211> LENGTH: 3168
<212> TYPE: DNA
<213> ORGANISM: Homo sapiens

<400> SEQUENCE: 22

```
atggctctgc ggaggctggg ggccgcgctg ctgctgctgc cgctgctcgc cgccgtggaa     60

gaaacgctaa tggactccac tacagcgact gctgagctgg gctggatggt gcatcctcca    120

tcagggtggg aagaggtgag tggctacgat gagaacatga acacgatccg cacgtaccag    180

gtgtgcaacg tgtttgagtc aagccagaac aactggctac ggaccaagtt tatccggcgc    240

cgtggcgccc accgcatcca cgtggagatg aagttttcgg tgcgtgactg cagcagcatc    300

cccagcgtgc ctggctcctg caaggagacc ttcaacctct attactatga ggctgacttt    360

gactcggcca ccaagacctt ccccaactgg atggagaatc catgggtgaa ggtggatacc    420

attgcagccg acgagagctt ctcccaggtg gacctgggtg gccgcgtcat gaaaatcaac    480

accgaggtgc ggagcttcgg acctgtgtcc cgcagcggct tctacctggc cttccaggac    540

tatggcggct gcatgtccct catcgccgtg cgtgtcttct accgcaagtg cccccgcatc    600

atccagaatg gcgccatctt ccaggaaacc ctgtcggggg ctgagagcac atcgctggtg    660

gctgcccggg gcagctgcat cgccaatgcg gaagaggtgg atgtacccat caagctctac    720

tgtaacgggg acggcgagtg gctggtgccc atcgggcgct gcatgtgcaa agcaggcttc    780

gaggccgttg agaatggcac cgtctgccga ggttgtccat ctgggacttt caaggccaac    840

caaggggatg aggcctgtac ccactgtccc atcaacagcc ggaccacttc tgaaggggcc    900

accaactgtg tctgccgcaa tggctactac agagcagacc tggacccccct ggacatgccc    960

tgcacaacca tcccctccgc gccccaggct gtgatttcca gtgtcaatga gacctccctc   1020

atgctggagt ggacccctcc ccgcgactcc ggaggccgag aggacctcgt ctacaacatc   1080

atctgcaaga gctgtggctc gggccggggt gcctgcaccc gctgcgggga caatgtacag   1140

tacgcaccac gccagctagg cctgaccgag ccacgcattt acatcagtga cctgctggcc   1200

cacacccagt acaccttcga gatccaggct gtgaacggcg ttactgacca gagcccccttc  1260

tcgcctcagt tcgcctctgt gaacatcacc accaaccagg cagctccatc ggcagtgtcc   1320

atcatgcatc aggtgagccg caccgtggac agcattaccc tgtcgtggtc ccagccagac   1380
```

```
cagcccaatg gcgtgatcct ggactatgag ctgcagtact atgagaagga gctcagtgag   1440
tacaacgcca cagccataaa aagccccacc aacacggtca ccgtgcaggg cctcaaagcc   1500
ggcgccatct atgtcttcca ggtgcgggca cgcaccgtgg caggctacgg gcgctacagc   1560
ggcaagatgt acttccagac catgacagaa gccgagtacc agacaagcat ccaggagaag   1620
ttgccactca tcatcggctc ctcggccgct ggcctggtct tcctcattgc tgtggttgtc   1680
atcgccatcg tgtgtaacag acgggggttt gagcgtgctg actcggagta cacggacaag   1740
ctgcaacact acaccagtgg ccacatgacc ccaggcatga agatctacat cgatcctttc   1800
acctacgagg accccaacga ggcagtgcgg gagtttgcca aggaaattga catctcctgt   1860
gtcaaaattg agcaggtgat cggagcaggg gagtttggcg aggtctgcag tggccacctg   1920
aagctgccag gcaagagaga gatctttgtg gccatcaaga cgctcaagtc gggctacacg   1980
gagaagcagc gccgggactt cctgagcgaa gcctccatca tgggccagtt cgaccatccc   2040
aacgtcatcc acctggaggg tgtcgtgacc aagagcacac ctgtgatgat catcaccgag   2100
ttcatggaga atggctccct ggactccttt ctccggcaaa acgatgggca gttcacagtc   2160
atccagctgg tgggcatgct tcggggcatc gcagctggca tgaagtacct ggcagacatg   2220
aactatgttc accgtgacct ggctgcccgc aacatcctcg tcaacagcaa cctggtctgc   2280
aaggtgtcgg actttgggct ctcacgcttt ctagaggacg atacctcaga ccccacctac   2340
accagtgccc tgggcggaaa gatccccatc cgctggacag ccccggaagc catccagtac   2400
cggaagttca cctcggccag tgatgtgtgg agctacggca ttgtcatgtg ggaggtgatg   2460
tcctatgggg agcggcccta ctgggacatg accaaccagg atgtaatcaa tgccattgag   2520
caggactatc ggctgccacc gcccatggac tgcccgagcg ccctgcacca actcatgctg   2580
gactgttggc agaaggaccg caaccaccgg cccaagttcg gccaaattgt caacacgcta   2640
gacaagatga tccgcaatcc caacagcctc aaagccatgg cgcccctctc ctctggcatc   2700
aacctgccgc tgctggaccg cacgatcccc gactacacca gctttaacac ggtggacgag   2760
tggctggagg ccatcaagat ggggcagtac aaggagagct tcgccaatgc cggcttcacc   2820
tcctttgacg tcgtgtctca gatgatgatg gaggacattc tccgggttgg ggtcactttg   2880
gctggccacc agaaaaaaat cctgaacagt atccaggtga tgcgggcgca gatgaaccag   2940
attcagtctg tggagggcca gccactcgcc aggaggccac gggccacggg aagaaccaag   3000
cggtgccagc cacgagacgt caccaagaaa acatgcaact caaacgacgg aaaaaaaaag   3060
ggaatgggaa aaaagaaaac agatcctggg agggggcggg aaatacaagg aatatttttt   3120
aaagaggatt ctcataagga aagcaatgac tgttcttgcg ggggataa                 3168
```

<210> SEQ ID NO 23
<211> LENGTH: 2997
<212> TYPE: DNA
<213> ORGANISM: Homo sapiens

<400> SEQUENCE: 23

```
atggccagag cccgcccgcc gccgccgccg tcgccgccgc cggggcttct gccgctgctc     60
cctccgctgc tgctgctgcc gctgctgctg ctgcccgccg gctgccgggc gctggaagag    120
accctcatgg acacaaaatg ggtaacatct gagttggcgt ggacatctca tccagaaagt    180
gggtgggaag aggtgagtgg ctacgatgag gccatgaatc ccatccgcac ataccaggtg    240
tgtaatgtgc gcgagtcaag ccagaacaac tggcttcgca cggggttcat ctggcggcgg    300
```

-continued

```
gatgtgcagc gggtctacgt ggagctcaag ttcactgtgc gtgactgcaa cagcatcccc    360
aacatccccg gctcctgcaa ggagaccttc aacctcttct actacgaggc tgacagcgat    420
gtggcctcag cctcctcccc cttctggatg gagaacccct acgtgaaagt ggacaccatt    480
gcacccgatg agagcttctc gcggctggat gccggccgtg tcaacaccaa ggtgcgcagc    540
tttgggccac tttccaaggc tggcttctac ctggccttcc aggaccaggg cgcctgcatg    600
tcgctcatct ccgtgcgcgc cttctacaag aagtgtgcat ccaccaccgc aggcttcgca    660
ctcttccccg agaccctcac tggggcggag cccacctcgc tggtcattgc tcctggcacc    720
tgcatcccta acgccgtgga ggtgtcggtg ccactcaagc tctactgcaa cggcgatggg    780
gagtggatgg tgcctgtggg tgcctgcacc tgtgccaccg gccatgagcc agctgccaag    840
gagtcccagt gccgcccctg tcccccctggg agctacaagg cgaagcaggg agaggggccc    900
tgcctcccat gtccccccaa cagccgtacc acctccccag ccgccagcat ctgcacctgc    960
cacaataact tctaccgtgc agactcggac tctgcggaca gtgcctgtac caccgtgcca   1020
tctccacccc gaggtgtgat ctccaatgtg aatgaaacct cactgatcct cgagtggagt   1080
gagccccggg acctgggtgt ccgggatgac ctcctgtaca atgtcatctg caagaagtgc   1140
catggggctg gaggggcctc agcctgctca cgctgtgatg acaacgtgga gtttgtgcct   1200
cggcagctgg gcctgtcgga gccccgggtc cacaccagcc atctgctggc ccacacgcgc   1260
tacacctttg aggtgcaggc ggtcaacggt gtctcgggca agagccctct gccgcctcgt   1320
tatgcggccg tgaatatcac cacaaaccag gctgccccgt ctgaagtgcc cacactacgc   1380
ctgcacagca gctcaggcag cagcctcacc ctatcctggg cacccccaga gcggcccaac   1440
ggagtcatcc tggactacga gatgaagtac tttgagaaga gcgagggcat cgcctccaca   1500
gtgaccagcc agatgaactc cgtgcagctg gacgggcttc ggcctgacgc ccgctatgtg   1560
gtccaggtcc gtgcccgcac agtagctggc tatgggcagt acagccgccc tgccgagttt   1620
gagaccacaa gtgagagagg ctctggggcc cagcagctcc aggagcagct tcccctcatc   1680
gtgggctccg ctacagctgg gcttgtcttc gtggtggctg tcgtggtcat cgctatcgtc   1740
tgcctcagga agcagcgaca cggctctgat tcggagtaca cggagaagct gcagcagtac   1800
attgctcctg gaatgaaggt ttatattgac ccttttacct acgaggaccc taatgaggct   1860
gttcgggagt ttgccaagga gatcgacgtg tcctgcgtca agatcgagga ggtgatcgga   1920
gctggggaat ttggggaagt gtgccgtggt cgactgaaac agcctggccg ccgagaggtg   1980
tttgtggcca tcaagacgct gaaggtgggc tacaccgaga ggcagcggcg ggacttccta   2040
agcgaggcct ccatcatggg tcagtttgat caccccaata taatccggct cgagggcgtg   2100
gtcaccaaaa gtcggccagt tatgatcctc actgagttca tggaaaactg cgccctggac   2160
tccttcctcc ggctcaacga tgggcagttc acggtcatcc agctggtggg catgttgcgg   2220
ggcattgctg ccggcatgaa gtacctgtcc gagatgaact atgtgcaccg cgacctggct   2280
gctcgcaaca tccttgtcaa cagcaacctg gtctgcaaag tctcagactt tggcctctcc   2340
cgcttcctgg aggatgaccc ctccgatcct acctacacca gttccctggg cgggaagatc   2400
cccatccgct ggactgcccc agaggccata gcctatcgga agttcacttc tgctagtgat   2460
gtctggagct acggaattgt catgtgggag gtcatgagct atggagagcg accctactgg   2520
gacatgagca accaggatgt catcaatgcc gtggagcagg attaccggct gccaccaccc   2580
atggactgtc ccacagcact gcaccagctc atgctggact gctgggtgcg ggaccggaac   2640
ctcaggccca aattctccca gattgtcaat accctggaca agctcatccg caatgctgcc   2700
```

agcctcaagg tcattgccag cgctcagtct ggcatgtcac agcccctcct ggaccgcacg 2760
gtcccagatt acacaacctt cacgacagtt ggtgattggc tggatgccat caagatgggg 2820
cggtacaagg agagcttcgt cagtgcgggg tttgcatctt ttgacctggt ggcccagatg 2880
acggcagaag acctgctccg tattggggtc accctggccg gccaccagaa gaagatcctg 2940
agcagtatcc aggacatgcg gctgcagatg aaccagacgc tgcctgtgca ggtctga 2997

<210> SEQ ID NO 24
<211> LENGTH: 2964
<212> TYPE: DNA
<213> ORGANISM: Homo sapiens

<400> SEQUENCE: 24
atggagctcc gggtgctgct ctgctgggct tcgttggccg cagctttgga agagaccctg 60
ctgaacacaa aattggaaac tgctgatctg aagtgggtga cattccctca ggtggacggg 120
cagtgggagg aactgagcgg cctggatgag gaacagcaca gcgtgcgcac ctacgaagtg 180
tgtgaagtgc agcgtgcccc gggccaggcc cactggcttc gcacaggttg ggtcccacgg 240
cggggcgccg tccacgtgta cgccacgctg cgcttcacca tgctcgagtg cctgtccctg 300
cctcgggctg ggcgctcctg caaggagacc ttcaccgtct tctactatga gagcgatgcg 360
gacacggcca cggccctcac gccagcctgg atggagaacc cctacatcaa ggtggacacg 420
gtggccgcgg agcatctcac ccggaagcgc cctggggccg aggccaccgg gaaggtgaat 480
gtcaagacgc tgcgtctggg accgctcagc aaggctggct tctacctggc cttccaggac 540
cagggtgcct gcatggccct gctatccctg cacctcttct acaaaaagtg cgcccagctg 600
actgtgaacc tgactcgatt cccggagact gtgcctcggg agctggttgt gcccgtggcc 660
ggtagctgcg tggtggatgc cgtccccgcc cctggcccca gccccagcct ctactgccgt 720
gaggatggcc agtgggccga acagccggtc acgggctgca gctgtgctcc ggggttcgag 780
gcagctgagg ggaacaccaa gtgccgagcc tgtgcccagg gcaccttcaa gcccctgtca 840
ggagaagggt cctgccagcc atgcccagcc aatagccact ctaacaccat tggatctgcc 900
gtctgccagt gccgcgtcgg ggacttccgg gcacgcacag acccccgggg tgcaccctgc 960
accacccctc cttcggctcc gcggagcgtg gtttcccgcc tgaacggctc ctccctgcac 1020
ctggaatgga gtgcccccct ggagtctggt ggccgagagg acctcaccta cgccctccgc 1080
tgccgggagt gccgacccgg aggctcctgt gcgccctgcg gggagacct gacttttgac 1140 cccggccccc gggacctggt ggagccctgg gtggtggttc gagggctacg tccggacttc 1200
acctatacct ttgaggtcac tgcattgaac ggggtatcct ccttagccac ggggcccgtc 1260
ccatttgagc ctgtcaatgt caccactgac cgagaggtac ctcctgcagt gtctgacatc 1320
cgggtgacgc ggtcctcacc cagcagcttg agcctggcct gggctgttcc ccgggcaccc 1380
agtggggcgt ggctggacta cgaggtcaaa taccatgaga agggcgccga gggtcccagc 1440
agcgtgcggt tcctgaagac gtcagaaaac cgggcagagc tgcgggggct gaagcgggga 1500
gccagctacc tggtgcaggt acgggcgcgc tctgaggccg gctacgggcc cttcggccag 1560
gaacatcaca gccagaccca actggatgag agcgagggct ggcgggagca gctggccctg 1620
attgcgggca cggcagtcgt gggtgtggtc ctggtcctgg tggtcattgt ggtcgcagtt 1680
ctctgcctca ggaagcagag caatgggaga gaagcagaat attcggacaa acacggacag 1740
tatctcatcg gacatggtac taaggtctac atcgacccct tcacttatga agaccctaat 1800

```
gaggctgtga gggaatttgc aaaagagatc gatgtctcct acgtcaagat tgaagaggtg   1860

attggtgcag gtgagtttgg cgaggtgtgc cgggggcggc tcaaggcccc agggaagaag   1920

gagagctgtg tggcaatcaa gaccctgaag ggtggctaca cggagcggca gcggcgtgag   1980

tttctgagcg aggcctccat catgggccag ttcgagcacc ccaatatcat ccgcctggag   2040

ggcgtggtca ccaacagcat gcccgtcatg attctcacag agttcatgga gaacggcgcc   2100

ctggactcct tcctgcggct aaacgacgga cagttcacag tcatccagct cgtgggcatg   2160

ctgcggggca tcgcctcggg catgcggtac cttgccgaga tgagctacgt ccaccgagac   2220

ctggctgctc gcaacatcct agtcaacagc aacctcgtct gcaaagtgtc tgactttggc   2280

ctttcccgat tcctggagga gaactcttcc gatcccacct acacgagctc cctgggagga   2340

aagattccca tccgatggac tgccccggag gccattgcct tccggaagtt cacttccgcc   2400

agtgatgcct ggagttacgg gattgtgatg tgggaggtga tgtcatttgg ggagaggccg   2460

tactgggaca tgagcaatca ggacgtgatc aatgccattg aacaggacta ccggctgccc   2520

ccgcccccag actgtcccac ctccctccac cagctcatgc tggactgttg gcagaaagac   2580

cggaatgccc ggccccgctt cccccaggtg gtcagcgccc tggacaagat gatccggaac   2640

cccgccagcc tcaaaatcgt ggcccgggag aatggcgggg cctcacaccc tctcctggac   2700

cagcggcagc ctcactactc agcttttggc tctgtgggcg agtggcttcg ggccatcaaa   2760

atgggaagat acgaagcccg tttcgcagcc gctggctttg gctccttcga gctggtcagc   2820

cagatctctg ctgaggacct gctccgaatc ggagtcactc tggcgggaca ccagaagaaa   2880

atcttggcca gtgtccagca catgaagtcc caggccaagc cgggaacccc gggtgggaca   2940

ggaggaccgg ccccgcagta ctga                                          2964
```

<210> SEQ ID NO 25
<211> LENGTH: 1041
<212> TYPE: DNA
<213> ORGANISM: Homo sapiens
<300> PUBLICATION INFORMATION:
<302> TITLE: ephrin-B1
<310> PATENT DOCUMENT NUMBER: NM004429

<400> SEQUENCE: 25

```
atggctcggc ctgggcagcg ttggctcggc aagtggcttg tggcgatggt cgtgtgggcg     60

ctgtgccggc tcgccacacc gctggccaag aacctggagc ccgtatcctg gagctccctc    120

aaccccaagt tcctgagtgg gaagggcttg gtgatctatc cgaaaattgg agacaagctg    180

gacatcatct gcccccgagc agaagcaggg cggccctatg agtactacaa gctgtacctg    240

gtgcggcctg agcaggcagc tgcctgtagc acagttctcg accccaacgt gttggtcacc    300

tgcaataggc cagagcagga aatacgcttt accatcaagt tccaggagtt cagccccaac    360

tacatgggcc tggagttcaa gaagcaccat gattactaca ttacctcaac atccaatgga    420

agcctggagg ggctggaaaa ccgggagggc ggtgtgtgcc gcacacgcac catgaagatc    480

atcatgaagg ttgggcaaga tcccaatgct gtgacgcctg agcagctgac taccagcagg    540

cccagcaagg aggcagacaa cactgtcaag atggccacac aggcccctgg tagtcggggc    600

tccctgggtg actctgatgg caagcatgag actgtgaacc aggaagagaa gagtggccca    660

ggtgcaagtg gggcagcag cggggaccct gatggcttct tcaactccaa ggtggcattg    720

ttcgcggctg tcggtgccgg ttgcgtcatc ttcctgctca tcatcatctt cctgacggtc    780

ctactactga agctacgcaa gcggcaccgc aagcacacac agcagcgggc ggctgccctc    840
```

```
tcgctcagta ccctggccag tcccaagggg ggcagtggca cagcgggcac cgagcccagc    900

gacatcatca ttcccttacg gactacagag aacaactact gcccccacta tgagaaggtg    960

agtggggact acgggcaccc tgtctacatc gtccaagaga tgccgcccca gagcccggcg   1020

aacatctact acaaggtctg a                                             1041
```

<210> SEQ ID NO 26
<211> LENGTH: 1002
<212> TYPE: DNA
<213> ORGANISM: Homo sapiens
<300> PUBLICATION INFORMATION:

<400> SEQUENCE: 26

```
atggctgtga gaagggactc cgtgtggaag tactgctggg gtgttttgat ggttttatgc     60

agaactgcga tttccaaatc gatagtttta gagcctatct attggaattc ctcgaactcc    120

aaatttctac ctggacaagg actggtacta tacccacaga taggagacaa attggatatt    180

atttgcccca aagtggactc taaaactgtt ggccagtatg aatattataa agtttatatg    240

gttgataaag accaagcaga cagatgcact attaagaagg aaaatacccc tctcctcaac    300

tgtgccaaac cagaccaaga tatcaaattc accatcaagt ttcaagaatt cagccctaac    360

ctctggggtc tagaatttca gaagaacaaa gattattaca ttatatctac atcaaatggg    420

tctttggagg gcctggataa ccaggaggga ggggtgtgcc agacaagagc catgaagatc    480

ctcatgaaag ttggacaaga tgcaagttct gctggatcaa ccaggaataa agatccaaca    540

agacgtccag aactagaagc tggtacaaat ggaagaagtt cgacaacaag tccctttgta    600

aaaccaaatc caggttctag cacagacggc aacagcgccg gacattcggg gaacaacatc    660

ctcggttccg aagtggcctt atttgcaggg attgcttcag gatgcatcat cttcatcgtc    720

atcatcatca cgctggtggt cctcttgctg aagtaccgga ggagacacag gaagcactcg    780

ccgcagcaca cgaccacgct gtcgctcagc acactggcca cacccaagcg cagcggcaac    840

aacaacggct cagagcccag tgacattatc atcccgctaa ggactgcgga cagcgtcttc    900

tgccctcact acgagaaggt cagcggcgac tacgggcacc cggtgtacat cgtccaggag    960

atgcccccgc agagcccggc gaacatttac tacaaggtct ga                      1002
```

<210> SEQ ID NO 27
<211> LENGTH: 1023
<212> TYPE: DNA
<213> ORGANISM: Homo sapiens

<400> SEQUENCE: 27

```
atggggcccc cccattctgg gccgggggc gtgcgagtcg gggccctgct gctgctgggg     60

gttttggggc tggtgtctgg gctcagcctg gagcctgtct actggaactc ggcgaataag    120

aggttccagg cagagggtgg ttatgtgctg taccctcaga tcggggaccg gctagacctg    180

ctctgccccc gggcccggcc tcctggccct cactcctctc ctaattatga gttctacaag    240

ctgtacctgg taggggggtgc tcagggccgg cgctgtgagg caccccctgc cccaaacctc    300

cttctcactt gtgatcgccc agacctggat ctccgcttca ccatcaagtt ccaggagtat    360

agccctaatc tctggggcca cgagttccgc tcgcaccacg attactacat cattgccaca    420

tcggatggga cccgggaggg cctggagagc ctgcagggag gtgtgtgcct aaccagaggc    480

atgaaggtgc ttctccgagt gggacaaagt ccccgaggag gggctgtccc ccgaaaacct    540

gtgtctgaaa tgcccatgga aagagaccga ggggcagccc acagcctgga gcctgggaag    600
```

-continued gagaacctgc caggtgaccc caccagcaat gcaacctccc ggggtgctga aggccccctg 660
ccccctccca gcatgcctgc agtggctggg gcagcagggg ggctggcgct gctcttgctg 720
ggcgtggcag gggctggggg tgccatgtgt tggcggagac ggcgggccaa gccttcggag 780
agtcgccacc ctggtcctgg ctccttcggg aggggagggt ctctgggcct ggggggtgga 840
ggtgggatgg gacctcggga ggctgagcct ggggagctag ggatagctct gcggggtggc 900
ggggctgcag atcccccctt ctgcccccac tatgagaagg tgagtggtga ctatgggcat 960
cctgtgtata tcgtgcagga tgggcccccc cagagccctc caaacatcta ctacaaggta 1020
tga 1023

<210> SEQ ID NO 28
<211> LENGTH: 3399
<212> TYPE: DNA
<213> ORGANISM: Homo sapiens
<300> PUBLICATION INFORMATION:
<302> TITLE: telomerase reverse transcriptase
<310> PATENT DOCUMENT NUMBER: AF015950

<400> SEQUENCE: 28
atgccgcgcg ctccccgctg ccgagccgtg cgctccctgc tgcgcagcca ctaccgcgag 60
gtgctgccgc tggccacgtt cgtgcggcgc ctggggcccc agggctggcg gctggtgcag 120
cgcggggacc cggcggcttt ccgcgcgctg gtggcccagt gcctggtgtg cgtgccctgg 180
gacgcacggc cgccccccgc cgccccctcc ttccgccagg tgtcctgcct gaaggagctg 240
gtggcccgag tgctgcagag gctgtgcgag cgcggcgcga agaacgtgct ggccttcggc 300
ttcgcgctgc tggacggggc ccgcgggggc ccccccgagg ccttcaccac cagcgtgcgc 360
agctacctgc ccaacacggt gaccgacgca ctgcggggga gcggggcgtg ggggctgctg 420
ctgcgccgcg tgggcgacga cgtgctggtt cacctgctgg cacgctgcgc gctctttgtg 480
ctggtggctc ccagctgcgc ctaccaggtg tgcgggccgc cgctgtacca gctcggcgct 540
gccactcagg cccggccccc gccacacgct agtggacccc gaaggcgtct gggatgcgaa 600
cgggcctgga accatagcgt cagggaggcc ggggtccccc tgggcctgcc agccccgggt 660
gcgaggaggc gcgggggcag tgccagccga agtctgccgt tgcccaagag gcccaggcgt 720
ggcgctgccc ctgagccgga gcggacgccc gttgggcagg ggtcctgggc ccacccgggc 780
aggacgcgtg gaccgagtga ccgtggtttc tgtgtggtgt cacctgccag acccgccgaa 840
gaagccacct ctttggaggg tgcgctctct ggcacgcgcc actcccaccc atccgtgggc 900
cgccagcacc acgcgggccc cccatccaca tcgcggccac cacgtccctg ggacacgcct 960
tgtcccccgg tgtacgccga gaccaagcac ttcctctact cctcaggcga caaggagcag 1020
ctgcggccct ccttcctact cagctctctg aggcccagcc tgactggcgc tcggaggctc 1080
gtggagacca tctttctggg ttccaggccc tggatgccag ggactccccg caggttgccc 1140
cgcctgcccc agcgctactg gcaaatgcgg cccctgtttc tggagctgct tgggaaccac 1200
gcgcagtgcc cctacggggt gctcctcaag acgcactgcc cgctgcgagc tgcggtcacc 1260
ccagcagccg gtgtctgtgc ccgggagaag ccccagggct ctgtggcggc ccccgaggag 1320
gaggacacag acccccgtcg cctggtgcag ctgctccgcc agcacagcag cccctggcag 1380
gtgtacggct tcgtgcgggc ctgcctgcgc cggctggtgc ccccaggcct ctggggctcc 1440
aggcacaacg aacgccgctt cctcaggaac accaagaagt tcatctccct ggggaagcat 1500
gccaagctct cgctgcagga gctgacgtgg aagatgagcg tgcgggactg cgcttggctg 1560

-continued cgcaggagcc caggggttgg ctgtgttccg gccgcagagc accgtctgcg tgaggagatc 1620
ctggccaagt tcctgcactg gctgatgagt gtgtacgtcg tcgagctgct caggtctttc 1680
ttttatgtca cggagaccac gtttcaaaag aacaggctct ttttctaccg gaagagtgtc 1740
tggagcaagt tgcaaagcat tggaatcaga cagcacttga agagggtgca gctgcgggag 1800
ctgtcggaag cagaggtcag gcagcatcgg gaagccaggc ccgccctgct gacgtccaga 1860
ctccgcttca tccccaagcc tgacgggctg cggccgattg tgaacatgga ctacgtcgtg 1920
ggagccagaa cgttccgcag agaaaagagg gccgagcgtc tcacctcgag ggtgaaggca 1980
ctgttcagcg tgctcaacta cgagcgggcg cggcgccccg gcctcctggg cgcctctgtg 2040
ctgggcctgg acgatatcca cagggcctgg cgcaccttcg tgctgcgtgt gcgggcccag 2100
gacccgccgc ctgagctgta ctttgtcaag gtggatgtga cgggcgcgta cgacaccatc 2160
ccccaggaca ggctcacgga ggtcatcgcc agcatcatca aaccccagaa cacgtactgc 2220
gtgcgtcggt atgccgtggt ccagaaggcc gcccatgggc acgtccgcaa ggccttcaag 2280
agccacgtct ctaccttgac agacctccag ccgtacatgc gacagttcgt ggctcacctg 2340
caggagacca gcccgctgag ggatgccgtc gtcatcgagc agagctcctc cctgaatgag 2400
gccagcagtg gcctcttcga cgtcttccta cgcttcatgt gccaccacgc cgtgcgcatc 2460
aggggcaagt cctacgtcca gtgccagggg atcccgcagg gctccatcct ctccacgctg 2520
ctctgcagcc tgtgctacgg cgacatggag aacaagctgt ttgcggggat tcggcgggac 2580
gggctgctcc tgcgtttggt ggatgatttc ttgttggtga cacctcacct cacccacgcg 2640
aaaaccttcc tcaggaccct ggtccgaggt gtccctgagt atggctgcgt ggtgaacttg 2700
cggaagacag tggtgaactt ccctgtagaa gacgaggccc tgggtggcac ggcttttgtt 2760
cagatgccgg cccacggcct attcccctgg tgcggcctgc tgctggatac ccggaccctg 2820
gaggtgcaga gcgactactc cagctatgcc cggacctcca tcagagccag tctcaccttc 2880
aaccgcggct tcaaggctgg gaggaacatg cgtcgcaaac tctttggggt cttgcggctg 2940
aagtgtcaca gcctgtttct ggatttgcag gtgaacagcc tccagacggt gtgcaccaac 3000
atctacaaga tcctcctgct gcaggcgtac aggtttcacg catgtgtgct gcagctccca 3060
tttcatcagc aagtttggaa gaaccccaca tttttcctgc gcgtcatctc tgacacggcc 3120
tccctctgct actccatcct gaaagccaag aacgcaggga tgtcgctggg ggccaagggc 3180
gccgccggcc ctctgccctc cgaggccgtg cagtggctgt gccaccaagc attcctgctc 3240
aagctgactc gacaccgtgt cacctacgtg ccactcctgg ggtcactcag gacagcccag 3300
acgcagctga gtcggaagct cccggggacg acgctgactg ccctggaggc cgcagccaac 3360
ccggcactgc cctcagactt caagaccatc ctggactga 3399

<210> SEQ ID NO 29
<211> LENGTH: 567
<212> TYPE: DNA
<213> ORGANISM: Homo sapiens
<300> PUBLICATION INFORMATION:
<302> TITLE: K-ras
<310> PATENT DOCUMENT NUMBER: M54968

<400> SEQUENCE: 29
atgactgaat ataaacttgt ggtagttgga gcttgtggcg taggcaagag tgccttgacg 60
atacagctaa ttcagaatca ttttgtggac gaatatgatc caacaataga ggattcctac 120
aggaagcaag tagtaattga tggagaaacc tgtctcttgg atattctcga cacagcaggt 180
caagaggagt acagtgcaat gagggaccag tacatgagga ctggggaggg ctttctttgt 240
gtatttgcca taaataatac taaatcattt gaagatattc accattatag agaacaaatt 300
aaaagagtta aggactctga agatgtacct atggtcctag taggaaataa atgtgatttg 360
ccttctagaa cagtagacac aaaacaggct caggacttag caagaagtta tggaattcct 420
tttattgaaa catcagcaaa gacaagacag ggtgttgatg atgccttcta tacattagtt 480
cgagaaattc gaaaacataa agaaaagatg agcaaagatg gtaaaaagaa gaaaaagaag 540
tcaaagacaa agtgtgtaat tatgtaa 567

<210> SEQ ID NO 30
<211> LENGTH: 3840
<212> TYPE: DNA
<213> ORGANISM: Homo sapiens
<300> PUBLICATION INFORMATION:
<302> TITLE: mdr-1
<310> PATENT DOCUMENT NUMBER: AF016535

<400> SEQUENCE: 30
atggatcttg aaggggaccg caatggagga gcaaagaaga agaacttttt taaactgaac 60
aataaaagtg aaaaagataa gaaggaaaag aaaccaactg tcagtgtatt ttcaatgttt 120
cgctattcaa attggcttga caagttgtat atggtggtgg gaactttggc tgccatcatc 180
catggggctg gacttcctct catgatgctg gtgtttggag aaatgacaga tatctttgca 240
aatgcaggaa atttagaaga tctgatgtca aacatcacta atagaagtga tatcaatgat 300
acagggttct tcatgaatct ggaggaagac atgaccaggt atgcctatta ttacagtgga 360
attggtgctg gggtgctggt tgctgcttac attcaggttt cattttggtg cctggcagct 420
ggaagacaaa tacacaaaat tagaaaacag tttttcatg ctataatgcg acaggagata 480
ggctggtttg atgtgcacga tgttggggag cttaacaccc gacttacaga tgatgtctcc 540
aagattaatg aaggaattgg tgacaaaatt ggaatgttct ttcagtcaat ggcaacattt 600
ttcactgggt ttatagtagg atttacacgt ggttggaagc taacccttgt gattttggcc 660
atcagtcctg ttcttggact gtcagctgct gtctgggcaa agatactatc ttcatttact 720
gataaagaac tcttagcgta tgcaaaagct ggagcagtag ctgaagaggt cttggcagca 780
attagaactg tgattgcatt tggaggacaa aagaaagaac ttgaaaggta caacaaaaat 840
ttagaagaag ctaaaagaat tgggataaag aaagctatta cagccaatat ttctataggt 900
gctgctttcc tgctgatcta tgcatcttat gctctggcct tctggtatgg gaccaccttg 960
gtcctctcag gggaatattc tattggacaa gtactcactg tattttctgt attaattggg 1020
gcttttagtg ttggacaggc atctccaagc attgaagcat ttgcaaatgc aagaggagca 1080
gcttatgaaa tcttcaagat aattgataat aagccaagta ttgacagcta ttcgaagagt 1140
gggcacaaac cagataatat taagggaaat ttggaattca gaaatgttca cttcagttac 1200
ccatctcgaa aagaagttaa gatcttgaag ggtctgaacc tgaaggtgca gagtgggcag 1260
acggtggccc tggttggaaa cagtggctgt gggaagagca caacagtcca gctgatgcag 1320
aggctctatg accccacaga ggggatggtc agtgttgatg gacaggatat taggaccata 1380
aatgtaaggt ttctacggga aatcattggt gtggtgagtc aggaacctgt attgtttgcc 1440
accacgatag ctgaaaacat tcgctatggc cgtgaaaatg tcaccatgga tgagattgag 1500
aaagctgtca aggaagccaa tgcctatgac tttatcatga aactgcctca taaatttgac 1560
accctggttg gagagagagg ggcccagttg agtggtgggc agaagcagag gatcgccatt 1620

-continued

```
gcacgtgccc tggttcgcaa ccccaagatc ctcctgctgg atgaggccac gtcagccttg   1680
gacacagaaa gcgaagcagt ggttcaggtg gctctggata aggccagaaa aggtcggacc   1740
accattgtga tagctcatcg tttgtctaca gttcgtaatg ctgacgtcat cgctggtttc   1800
gatgatggag tcattgtgga gaaaggaaat catgatgaac tcatgaaaga gaaaggcatt   1860
tacttcaaac ttgtcacaat gcagacagca ggaaatgaag ttgaattaga aaatgcagct   1920
gatgaatcca aaagtgaaat tgatgccttg gaaatgtctt caaatgattc aagatccagt   1980
ctaataagaa aaagatcaac tcgtaggagt gtccgtggat cacaagccca agacagaaag   2040
cttagtacca aagaggctct ggatgaaagt atacctccag tttccttttg gaggattatg   2100
aagctaaatt taactgaatg gccttatttt gttgttggtg tattttgtgc cattataaat   2160
ggaggcctgc aaccagcatt tgcaataata ttttcaaaga ttataggggt ttttacaaga   2220
attgatgatc ctgaaacaaa acgacagaat agtaacttgt tttcactatt gtttctagcc   2280
cttggaatta tttcttttat tacatttttc cttcagggtt tcacatttgg caaagctgga   2340
gagatcctca ccaagcggct ccgatacatg gttttccgat ccatgctcag acaggatgtg   2400
agttggtttg atgaccctaa aaacaccact ggagcattga ctaccaggct cgccaatgat   2460
gctgctcaag ttaaaggggc tataggttcc aggcttgctg taattaccca gaatatagca   2520
aatcttggga caggaataat tatatccttc atctatggtt ggcaactaac actgttactc   2580
ttagcaattg tacccatcat tgcaatagca ggagttgttg aaatgaaaat gttgtctgga   2640
caagcactga aagataagaa agaactagaa ggtgctggga agatcgctac tgaagcaata   2700
gaaaacttcc gaaccgttgt ttctttgact caggagcaga agtttgaaca tatgtatgct   2760
cagagtttgc aggtaccata cagaaactct ttgaggaaag cacacatctt tggaattaca   2820
ttttccttca cccaggcaat gatgtatttt tcctatgctg gatgtttccg gtttggagcc   2880
tacttggtgg cacataaact catgagcttt gaggatgttc tgttagtatt ttcagctgtt   2940
gtctttggtg ccatggccgt ggggcaagtc agttcatttg ctcctgacta tgccaaagcc   3000
aaaatatcag cagcccacat catcatgatc attgaaaaaa ccccctttgat tgacagctac   3060
agcacggaag gcctaatgcc gaacacattg gaaggaaatg tcacatttgg tgaagttgta   3120
ttcaactatc ccacccgacc ggacatccca gtgcttcagg gactgagcct ggaggtgaag   3180
aagggccaga cgctggctct ggtgggcagc agtggctgtg ggaagagcac agtggtccag   3240
ctcctggagc ggttctacga ccccttggca gggaaagtgc tgcttgatgg caaagaaata   3300
aagcgactga atgttcagtg gctccgagca cacctgggca tcgtgtccca ggagcccatc   3360
ctgtttgact gcagcattgc tgagaacatt gcctatggag acaacagccg ggtggtgtca   3420
caggaagaga ttgtgagggc agcaaaggag gccaacatac atgccttcat cgagtcactg   3480
cctaataaat atagcactaa agtaggagac aaaggaactc agctctctgg tggccagaaa   3540
caacgcattg ccatagctcg tgcccttgtt agacagcctc atattttgct tttggatgaa   3600
gccacgtcag ctctggatac agaaagtgaa aaggttgtcc aagaagccct ggacaaagcc   3660
agagaaggcc gcacctgcat tgtgattgct caccgcctgt ccaccatcca gaatgcagac   3720
ttaatagtgg tgtttcagaa tggcagagtc aaggagcatg gcacgcatca gcagctgctg   3780
gcacagaaag gcatctattt ttcaatggtc agtgtccagg ctggaacaaa gcgccagtga   3840
```

<210> SEQ ID NO 31
<211> LENGTH: 1318
<212> TYPE: DNA
<213> ORGANISM: Homo sapiens <300> PUBLICATION INFORMATION:
<302> TITLE: UPAR (urokinase-type plasminogen activator receptor)
<310> PATENT DOCUMENT NUMBER: XM009232

<400> SEQUENCE: 31

```
atgggtcacc cgccgctgct gccgctgctg ctgctgctcc acacctgcgt cccagcctct     60

tggggcctgc ggtgcatgca gtgtaagacc aacggggatt gccgtgtgga agagtgcgcc    120

ctgggacagg acctctgcag gaccacgatc gtgcgcttgt gggaagaagg agaagagctg    180

gagctggtgg agaaaagctg tacccactca gagaagacca acaggaccct gagctatcgg    240

actggcttga agatcaccag ccttaccgag gttgtgtgtg ggttagactt gtgcaaccag    300

ggcaactctg gccgggctgt cacctattcc cgaagccgtt acctcgaatg catttcctgt    360

ggctcatcag acatgagctg tgagaggggc cggcaccaga gcctgcagtg ccgcagccct    420

gaagaacagt gcctggatgt ggtgacccac tggatccagg aaggtgaaga agggcgtcca    480

aaggatgacc gccacctccg tggctgtggc taccttcccg gctgcccggg ctccaatggt    540

ttccacaaca acgacacctt ccacttcctg aaatgctgca acaccaccaa atgcaacgag    600

ggcccaatcc tggagcttga aaatctgccg cagaatggcc gccagtgtta cagctgcaag    660

gggaacagca cccatggatg ctcctctgaa gagactttcc tcattgactg ccgaggcccc    720

atgaatcaat gtctggtagc caccggcact cacgaaccga aaaaccaaag ctatatggta    780

agaggctgtg caaccgcctc aatgtgccaa catgcccacc tgggtgacgc cttcagcatg    840

aaccacattg atgtctcctg ctgtactaaa agtggctgta accacccaga cctggatgtc    900

cagtaccgca gtggggctgc tcctcagcct ggccctgccc atctcagcct caccatcacc    960

ctgctaatga ctgccagact gtggggaggc actctcctct ggacctaaac ctgaaatccc   1020

cctctctgcc ctggctggat ccgggggacc cctttgccct tccctcggct cccagcccta   1080

cagacttgct gtgtgacctc aggccagtgt gccgacctct ctgggcctca gttttcccag   1140

ctatgaaaac agctatctca caaagttgtg tgaagcagaa gagaaaagct ggaggaaggc   1200

cgtgggccaa tgggagagct cttgttatta ttaatattgt tgccgctgtt gtgttgttgt   1260

tattaattaa tattcatatt atttatttta tacttacata aagattttgt accagtgg     1318
```

<210> SEQ ID NO 32
<211> LENGTH: 636
<212> TYPE: DNA
<213> ORGANISM: Homo sapiens
<300> PUBLICATION INFORMATION:
<302> TITLE: Bak
<310> PATENT DOCUMENT NUMBER: U16811

<400> SEQUENCE: 32

```
atggcttcgg ggcaaggccc aggtcctccc aggcaggagt gcggagagcc tgccctgccc     60

tctgcttctg aggagcaggt agcccaggac acagaggagg ttttccgcag ctacgttttt    120

taccgccatc agcaggaaca ggaggctgaa ggggtggctg cccctgccga cccagagatg    180

gtcaccttac ctctgcaacc tagcagcacc atggggcagg tgggacggca gctcgccatc    240

atcggggacg acatcaaccg acgctatgac tcagagttcc agaccatgtt gcagcacctg    300

cagcccacgg cagagaatgc ctatgagtac ttcaccaaga ttgccaccag cctgtttgag    360

agtggcatca attggggccg tgtggtggct cttctgggct tcggctaccg tctggcccta    420

cacgtctacc agcatggcct gactggcttc ctaggccagg tgacccgctt cgtggtcgac    480

ttcatgctgc atcactgcat tgcccggtgg attgcacaga ggggtggctg ggtggcagcc    540
```

ctgaacttgg gcaatggtcc catcctgaac gtgctggtgg ttctgggtgt ggttctgttg 600
ggccagtttg tggtacgaag attcttcaaa tcatga 636

<210> SEQ ID NO 33
<211> LENGTH: 579
<212> TYPE: DNA
<213> ORGANISM: Homo sapiens
<300> PUBLICATION INFORMATION:
<302> TITLE: Bax alpha
<310> PATENT DOCUMENT NUMBER: L22473

<400> SEQUENCE: 33
atggacgggt ccggggagca gcccagaggc gggggcccca ccagctctga gcagatcatg 60
aagacagggg cccttttgct tcagggtttc atccaggatc gagcagggcg aatggggggg 120
gaggcacccg agctggccct ggacccggtg cctcaggatg cgtccaccaa gaagctgagc 180
gagtgtctca agcgcatcgg ggacgaactg gacagtaaca tggagctgca gaggatgatt 240
gccgccgtgg acacagactc cccccgagag gtctttttcc gagtggcagc tgacatgttt 300
tctgacggca acttcaactg gggccgggtt gtcgcccttt tctactttgc cagcaaactg 360
gtgctcaagg ccctgtgcac caaggtgccg gaactgatca gaaccatcat gggctggaca 420
ttggacttcc tccgggagcg gctgttgggc tggatccaag accagggtgg ttgggacggc 480
ctcctctcct actttgggac gcccacgtgg cagaccgtga ccatctttgt ggcgggagtg 540
ctcaccgcct cgctcaccat ctggaagaag atgggctga 579

<210> SEQ ID NO 34
<211> LENGTH: 657
<212> TYPE: DNA
<213> ORGANISM: Homo sapiens
<300> PUBLICATION INFORMATION:
<302> TITLE: Bax beta
<310> PATENT DOCUMENT NUMBER: L22474

<400> SEQUENCE: 34
atggacgggt ccggggagca gcccagaggc gggggcccca ccagctctga gcagatcatg 60
aagacagggg cccttttgct tcagggtttc atccaggatc gagcagggcg aatggggggg 120
gaggcacccg agctggccct ggacccggtg cctcaggatg cgtccaccaa gaagctgagc 180
gagtgtctca agcgcatcgg ggacgaactg gacagtaaca tggagctgca gaggatgatt 240
gccgccgtgg acacagactc cccccgagag gtctttttcc gagtggcagc tgacatgttt 300
tctgacggca acttcaactg gggccgggtt gtcgcccttt tctactttgc cagcaaactg 360
gtgctcaagg ccctgtgcac caaggtgccg gaactgatca gaaccatcat gggctggaca 420
ttggacttcc tccgggagcg gctgttgggc tggatccaag accagggtgg ttgggtgaga 480
ctcctcaagc ctcctcaccc ccaccaccgc gccctcacca ccgcccctgc cccaccgtcc 540
ctgccccccg ccactcctct gggaccctgg gccttctgga gcaggtcaca gtggtgccct 600
ctccccatct tcagatcatc agatgtggtc tataatgcgt tttccttacg tgtctga 657

<210> SEQ ID NO 35
<211> LENGTH: 432
<212> TYPE: DNA
<213> ORGANISM: Homo sapiens
<300> PUBLICATION INFORMATION:
<302> TITLE: Bax delta
<310> PATENT DOCUMENT NUMBER: U19599

<400> SEQUENCE: 35

-continued atggacgggt ccggggagca gcccagaggc gggggggccca ccagctctga gcagatcatg 60
aagacagggg cccttttgct tcaggggatg attgccgccg tggacacaga ctcccccga 120 gaggtctttt tccgagtggc agctgacatg ttttctgacg gcaacttcaa ctggggccgg 180
gttgtcgccc ttttctactt tgccagcaaa ctggtgctca aggccctgtg caccaaggtg 240
ccggaactga tcagaaccat catgggctgg acattggact tcctccggga gcggctgttg 300
ggctggatcc aagaccaggg tggttgggac ggcctcctct cctactttgg gacgcccacg 360
tggcagaccg tgaccatctt tgtggcggga gtgctcaccg cctcgctcac catctggaag 420
aagatgggct ga 432

<210> SEQ ID NO 36
<211> LENGTH: 495
<212> TYPE: DNA
<213> ORGANISM: Homo sapiens
<300> PUBLICATION INFORMATION:
<302> TITLE: Bax epsolin
<310> PATENT DOCUMENT NUMBER: AF007826

<400> SEQUENCE: 36
atggacgggt ccggggagca gcccagaggc gggggggccca ccagctctga gcagatcatg 60
aagacagggg cccttttgct tcagggtttc atccaggatc gagcagggcg aatggggggg 120
gaggcacccg agctggccct ggacccggtg cctcaggatg cgtccaccaa gaagctgagc 180
gagtgtctca agcgcatcgg ggacgaactg gacagtaaca tggagctgca gaggatgatt 240
gccgccgtgg acacagactc cccccgagag gtctttttcc gagtggcagc tgacatgttt 300
tctgacggca acttcaactg gggccgggtt gtcgcccttt tctactttgc cagcaaactg 360
gtgctcaagg ctggcgtgaa atggcgtgat ctgggctcac tgcaacctct gcctcctggg 420
ttcaagcgat tcacctgcct cagcatccca aggagctggg attacaggcc ctgtgcacca 480
aggtgccgga actga 495

<210> SEQ ID NO 37
<211> LENGTH: 582
<212> TYPE: DNA
<213> ORGANISM: Homo sapiens
<300> PUBLICATION INFORMATION:
<302> TITLE: bcl-w
<310> PATENT DOCUMENT NUMBER: U59747

<400> SEQUENCE: 37
atggcgaccc cagcctcggc cccagacaca cgggctctgg tggcagactt tgtaggttat 60
aagctgaggc agaagggtta tgtctgtgga gctggccccg gggagggccc agcagctgac 120
ccgctgcacc aagccatgcg ggcagctgga gatgagttcg agacccgctt ccggcgcacc 180
ttctctgatc tggcggctca gctgcatgtg accccaggct cagcccagca acgcttcacc 240
caggtctccg acgaactttt tcaagggggc cccaactggg gccgccttgt agccttcttt 300
gtctttgggg ctgcactgtg tgctgagagt gtcaacaagg agatggaacc actggtggga 360
caagtgcagg agtggatggt ggcctacctg gagacgcggc tggctgactg gatccacagc 420
agtgggggct gggcggagtt cacagctcta tacggggacg gggccctgga ggaggcgcgg 480
cgtctgcggg aggggaactg ggcatcagtg aggacagtgc tgacgggggc cgtggcactg 540
ggggccctgg taactgtagg ggcctttttt gctagcaagt ga 582

<210> SEQ ID NO 38
<211> LENGTH: 2481

<212> TYPE: DNA
<213> ORGANISM: Homo sapiens
<300> PUBLICATION INFORMATION:
<302> TITLE: HIF-alpha
<310> PATENT DOCUMENT NUMBER: U22431

<400> SEQUENCE: 38
atggagggcg ccggcggcgc gaacgacaag aaaaagataa gttctgaacg tcgaaaagaa 60
aagtctcgag atgcagccag atctcggcga agtaaagaat ctgaagtttt ttatgagctt 120
gctcatcagt tgccacttcc acataatgtg agttcgcatc ttgataaggc ctctgtgatg 180
aggcttacca tcagctattt gcgtgtgagg aaacttctgg atgctggtga tttggatatt 240
gaagatgaca tgaaagcaca gatgaattgc ttttatttga aagccttgga tggttttgtt 300
atggttctca cagatgatgg tgacatgatt tacatttctg ataatgtgaa caaatacatg 360
ggattaactc agtttgaact aactggacac agtgtgtttg attttactca tccatgtgac 420
catgaggaaa tgagagaaat gcttacacac agaaatggcc ttgtgaaaaa gggtaaagaa 480
caaaacacac agcgaagctt ttttctcaga atgaagtgta ccctaactag ccgaggaaga 540
actatgaaca taaagtctgc aacatggaag gtattgcact gcacaggcca cattcacgta 600
tatgatacca acagtaacca acctcagtgt gggtataaga aaccacctat gacctgcttg 660
gtgctgattt gtgaacccat tcctcaccca tcaaatattg aaattccttt agatagcaag 720
actttcctca gtcgacacag cctggatatg aaattttctt attgtgatga aagaattacc 780
gaattgatgg gatatgagcc agaagaactt ttaggccgct caatttatga atattatcat 840
gctttggact ctgatcatct gaccaaaact catcatgata tgtttactaa aggacaagtc 900
accacaggac agtacaggat gcttgccaaa agaggtggat atgtctgggt tgaaactcaa 960
gcaactgtca tatataacac caagaattct caaccacagt gcattgtatg tgtgaattac 1020
gttgtgagtg gtattattca gcacgacttg attttctccc ttcaacaaac agaatgtgtc 1080
cttaaaccgg ttgaatcttc agatatgaaa atgactcagc tattcaccaa agttgaatca 1140
gaagatacaa gtagcctctt tgacaaactt aagaaggaac ctgatgcttt aactttgctg 1200
gccccagccg ctggagacac aatcatatct ttagattttg gcagcaacga cacagaaact 1260
gatgaccagc aacttgagga agtaccatta tataatgatg taatgctccc ctcacccaac 1320
gaaaaattac agaatataaa tttggcaatg tctccattac ccaccgctga aacgccaaag 1380
ccacttcgaa gtagtgctga ccctgcactc aatcaagaag ttgcattaaa attagaacca 1440
aatccagagt cactggaact ttcttttacc atgccccaga ttcaggatca gacacctagt 1500
ccttccgatg gaagcactag acaaagttca cctgagccta atagtcccag tgaatattgt 1560
ttttatgtgg atagtgatat ggtcaatgaa ttcaagttgg aattggtaga aaaacttttt 1620
gctgaagaca cagaagcaaa gaacccattt tctactcagg acacagattt agacttggag 1680
atgttagctc cctatatccc aatggatgat gacttccagt tacgttcctt cgatcagttg 1740
tcaccattag aaagcagttc cgcaagccct gaaagcgcaa gtcctcaaag cacagttaca 1800
gtattccagc agactcaaat acaagaacct actgctaatg ccaccactac cactgccacc 1860
actgatgaat taaaaacagt gacaaaagac cgtatggaag acattaaaat attgattgca 1920
tctccatctc ctacccacat acataaagaa actactagtg ccacatcatc accatataga 1980
gatactcaaa gtcggacagc ctcaccaaac agagcaggaa aaggagtcat agaacagaca 2040
gaaaaatctc atccaagaag ccctaacgtg ttatctgtcg ctttgagtca aagaactaca 2100
gttcctgagg aagaactaaa tccaaagata ctagctttgc agaatgctca gagaaagcga 2160
aaaatggaac atgatggttc actttttcaa gcagtaggaa ttggaacatt attacagcag 2220
ccagacgatc atgcagctac tacatcactt tcttggaaac gtgtaaaagg atgcaaatct 2280
agtgaacaga atggaatgga gcaaaagaca attattttaa taccctctga tttagcatgt 2340
agactgctgg ggcaatcaat ggatgaaagt ggattaccac agctgaccag ttatgattgt 2400
gaagttaatg ctcctataca aggcagcaga aacctactgc agggtgaaga attactcaga 2460
gctttggatc aagttaactg a 2481

<210> SEQ ID NO 39
<211> LENGTH: 481
<212> TYPE: DNA
<213> ORGANISM: Homo sapiens
<300> PUBLICATION INFORMATION:
<302> TITLE: ID1
<310> PATENT DOCUMENT NUMBER: X77956

<400> SEQUENCE: 39
atgaaagtcg ccagtggcag caccgccacc gccgccgcgg gccccagctg cgcgctgaag 60
gccggcaaga cagcgagcgg tgcgggcgag gtggtgcgct gtctgtctga gcagagcgtg 120
gccatctcgc gctgccgggg cgccggggcg cgcctgcctg ccctgctgga cgagcagcag 180
gtaaacgtgc tgctctacga catgaacggc tgttactcac gcctcaagga gctggtgccc 240
accctgcccc agaaccgcaa ggtgagcaag gtggagattc tccagcacgt catcgactac 300
atcagggacc ttcagttgga gctgaactcg gaatccgaag ttgggacccc cgggggccga 360
gggctgccgg tccgggctcc gctcagcacc ctcaacggcg agatcagcgc cctgacggcc 420
gaggcggcat gcgttcctgc ggacgatcgc atcttgtgtc gctgaatggt gaaaaaaaaa 480
a 481

<210> SEQ ID NO 40
<211> LENGTH: 110
<212> TYPE: DNA
<213> ORGANISM: Homo sapiens
<300> PUBLICATION INFORMATION:
<302> TITLE: ID2B
<310> PATENT DOCUMENT NUMBER: M96843

<400> SEQUENCE: 40
tgaaagcctt cagtcccgtg aggtccatta ggaaaaacag cctgttggac caccgcctgg 60
gcatctccca gagcaaaacc ccggtggatg acctgatgag cctgctgtaa 110

<210> SEQ ID NO 41
<211> LENGTH: 486
<212> TYPE: DNA
<213> ORGANISM: Homo sapiens
<300> PUBLICATION INFORMATION:
<302> TITLE: ID4
<310> PATENT DOCUMENT NUMBER: Y07958

<400> SEQUENCE: 41
atgaaggcgg tgagcccggt gcgcccctcg ggccgcaagg cgccgtcggg ctgcggcggc 60
ggggagctgg cgctgcgctg cctggccgag cacggccaca gcctgggtgg ctccgcagcc 120
gcggcggcgg cggcggcggc agcgcgctgt aaggcggccg aggcggcggc cgacgagccg 180
gcgctgtgcc tgcagtgcga tatgaacgac tgctatagcc gcctgcggag gctggtgccc 240
accatcccgc ccaacaagaa agtcagcaaa gtggagatcc tgcagcacgt tatcgactac 300
atcctggacc tgcagctggc gctggagacg cacccggccc tgctgaggca gccaccaccg 360
cccgcgccgc cacaccaccc ggccgggacc tgtccagccg cgccgccgcg gaccccgctc 420
actgcgctca acaccgaccc ggccggcgcg gtgaacaagc agggcgacag cattctgtgc 480
cgctga 486

<210> SEQ ID NO 42
<211> LENGTH: 462
<212> TYPE: DNA
<213> ORGANISM: Homo sapiens
<300> PUBLICATION INFORMATION:
<302> TITLE: IGF1
<310> PATENT DOCUMENT NUMBER: NM000618

<400> SEQUENCE: 42
atgggaaaaa tcagcagtct tccaacccaa ttatttaagt gctgcttttg tgatttcttg 60
aaggtgaaga tgcacaccat gtcctcctcg catctcttct acctggcgct gtgcctgctc 120
accttcacca gctctgccac ggctggaccg gagacgctct gcggggctga gctggtggat 180
gctcttcagt tcgtgtgtgg agacaggggc ttttatttca acaagcccac agggtatggc 240
tccagcagtc ggagggcgcc tcagacaggc atcgtggatg agtgctgctt ccggagctgt 300
gatctaagga ggctggagat gtattgcgca cccctcaagc ctgccaagtc agctcgctct 360
gtccgtgccc agcgccacac cgacatgccc aagacccaga aggaagtaca tttgaagaac 420
gcaagtagag ggagtgcagg aaacaagaac tacaggatgt ag 462

<210> SEQ ID NO 43
<211> LENGTH: 591
<212> TYPE: DNA
<213> ORGANISM: Homo sapiens
<300> PUBLICATION INFORMATION:
<302> TITLE: PDGFA
<310> PATENT DOCUMENT NUMBER: NM002607

<400> SEQUENCE: 43
atgaggacct tggcttgcct gctgctcctc ggctgcggat acctcgccca tgttctggcc 60
gaggaagccg agatcccccg cgaggtgatc gagaggctgg cccgcagtca gatccacagc 120
atccgggacc tccagcgact cctggagata gactccgtag ggagtgagga ttctttggac 180
accagcctga gagctcacgg ggtccacgcc actaagcatg tgcccgagaa gcggcccctg 240
cccattcgga ggaagagaag catcgaggaa gctgtccccg ctgtctgcaa gaccaggacg 300
gtcatttacg agattcctcg gagtcaggtc gaccccacgt ccgccaactt cctgatctgg 360
cccccgtgcg tggaggtgaa acgctgcacc ggctgctgca acacgagcag tgtcaagtgc 420
cagccctccc gcgtccacca ccgcagcgtc aaggtggcca aggtggaata cgtcaggaag 480
aagccaaaat taaaagaagt ccaggtgagg ttagaggagc atttggagtg cgcctgcgcg 540
accacaagcc tgaatccgga ttatcgggaa gaggacacgg atgtgaggtg a 591

<210> SEQ ID NO 44
<211> LENGTH: 528
<212> TYPE: DNA
<213> ORGANISM: Homo sapiens
<300> PUBLICATION INFORMATION:
<302> TITLE: PDGFRA
<310> PATENT DOCUMENT NUMBER: XM003568

<400> SEQUENCE: 44
atggccaagc ctgaccacgc taccagtgaa gtctacgaga tcatggtgaa atgctggaac 60
agtgagccgg agaagagacc ctccttttac cacctgagtg agattgtgga gaatctgctg 120

```
cctggacaat ataaaaagag ttatgaaaaa attcacctgg acttcctgaa gagtgaccat    180

cctgctgtgg cacgcatgcg tgtggactca gacaatgcat acattggtgt cacctacaaa    240

aacgaggaag acaagctgaa ggactgggag ggtggtctgg atgagcagag actgagcgct    300

gacagtggct acatcattcc tctgcctgac attgaccctg tccctgagga ggaggacctg    360

ggcaagagga acagacacag ctcgcagacc tctgaagaga gtgccattga gacgggttcc    420

agcagttcca ccttcatcaa gagagaggac gagaccattg aagacatcga catgatggat    480

gacatcggca tagactcttc agacctggtg gaagacagct tcctgtaa                528
```

<210> SEQ ID NO 45
<211> LENGTH: 1911
<212> TYPE: DNA
<213> ORGANISM: Homo sapiens
<300> PUBLICATION INFORMATION:
<302> TITLE: PDGFRB
<310> PATENT DOCUMENT NUMBER: XM003790

<400> SEQUENCE: 45

```
atgcggcttc cgggtgcgat gccagctctg gccctcaaag gcgagctgct gttgctgtct     60

ctcctgttac ttctggaacc acagatctct cagggcctgg tcgtcacacc cccggggcca    120

gagcttgtcc tcaatgtctc cagcaccttc gttctgacct gctcgggttc agctccggtg    180

gtgtgggaac ggatgtccca ggagcccccca caggaaatgg ccaaggccca ggatggcacc    240

ttctccagcg tgctcacact gaccaacctc actgggctag acacgggaga atacttttgc    300

acccacaatg actcccgtgg actggagacc gatgagcgga aacggctcta catctttgtg    360

ccagatccca ccgtgggctt cctccctaat gatgccgagg aactattcat ctttctcacg    420

gaaataactg agatcaccat tccatgccga gtaacagacc cacagctggt ggtgacactg    480

cacgagaaga aaggggacgt tgcactgcct gtcccctatg atcaccaacg tggcttttct    540

ggtatctttg aggacagaag ctacatctgc aaaaccacca ttggggacag ggaggtggat    600

tctgatgcct actatgtcta cagactccag gtgtcatcca tcaacgtctc tgtgaacgca    660

gtgcagactg tggtccgcca gggtgagaac atcaccctca tgtgcattgt gatcgggaat    720

gaggtggtca acttcgagtg gacatacccc cgcaaagaaa gtgggcggct ggtggagccg    780

gtgactgact tcctcttgga tatgccttac cacatccgct ccatcctgca catccccagt    840

gccgagttag aagactcggg gacctacacc tgcaatgtga cggagagtgt gaatgaccat    900

caggatgaaa aggccatcaa catcaccgtg gttgagagcg gctacgtgcg gctcctggga    960

gaggtgggca cactacaatt tgctgagctg catcggagcc ggacactgca ggtagtgttc   1020

gaggcctacc caccgcccac tgtcctgtgg ttcaaagaca accgcaccct gggcgactcc   1080

agcgctggcg aaatcgccct gtccacgcgc aacgtgtcgg agacccggta tgtgtcagag   1140

ctgacactgg ttcgcgtgaa ggtggcagag gctggccact acaccatgcg ggccttccat   1200

gaggatgctg aggtccagct ctccttccag ctacagatca atgtccctgt ccgagtgctg   1260

gagctaagtg agagccaccc tgacagtggg gaacagacag tccgctgtcg tggccggggc   1320

atgccccagc cgaacatcat ctggtctgcc tgcagagacc tcaaaaggtg tccacgtgag   1380

ctgccgccca cgctgctggg gaacagttcc gaagaggaga gccagctgga gactaacgtg   1440

acgtactggg aggaggagca ggagtttgag gtggtgagca cactgcgtct gcagcacgtg   1500

gatcggccac tgtcggtgcg ctgcacgctg cgcaacgctg tgggccagga cacgcaggag   1560

gtcatcgtgg tgccacactc cttgcccttt aaggtggtgg tgatctcagc catcctggcc   1620
```

-continued

```
ctggtggtgc tcaccatcat ctcccttatc atcctcatca tgctttggca gaagaagcca   1680

cgttacgaga tccgatggaa ggtgattgag tctgtgagct ctgacggcca tgagtacatc   1740

tacgtggacc ccatgcagct gccctatgac tccacgtggg agctgccgcg ggaccagctt   1800

gtgctgggac gcaccctcgg ctctggggcc tttgggcagg tggtggaggc cacggttcat   1860

ggcctgagcc attttcaagc cccaatgaaa gtggccgtca aaaatgctta a            1911
```

<210> SEQ ID NO 46
<211> LENGTH: 1176
<212> TYPE: DNA
<213> ORGANISM: Homo sapiens
<300> PUBLICATION INFORMATION:
<302> TITLE: TGFbeta1
<310> PATENT DOCUMENT NUMBER: NM000660

<400> SEQUENCE: 46

```
atgccgccct ccgggctgcg gctgctgccg ctgctgctac cgctgctgtg gctactggtg     60

ctgacgcctg gcccgccggc cgcgggacta tccacctgca agactatcga catggagctg    120

gtgaagcgga agcgcatcga ggccatccgc ggccagatcc tgtccaagct gcggctcgcc    180

agccccccga gccaggggga ggtgccgccc ggcccgctgc ccgaggccgt gctcgccctg    240

tacaacagca cccgcgaccg ggtggccggg gagagtgcag aaccggagcc cgagcctgag    300

gccgactact acgccaagga ggtcacccgc gtgctaatgg tggaaaccca caacgaaatc    360

tatgacaagt tcaagcagag tacacacagc atatatatgt tcttcaacac atcagagctc    420

cgagaagcgg tacctgaacc cgtgttgctc tcccgggcag agctgcgtct gctgaggagg    480

ctcaagttaa aagtggagca gcacgtggag ctgtaccaga aatacagcaa caattcctgg    540

cgatacctca gcaaccggct gctggcaccc agcgactcgc cagagtggtt atcttttgat    600

gtcaccggag ttgtgcggca gtggttgagc cgtggagggg aaattgaggg ctttcgcctt    660

agcgcccact gctcctgtga cagcagggat aacacactgc aagtggacat caacgggttc    720

actaccggcc gccgaggtga cctggccacc attcatggca tgaaccggcc tttcctgctt    780

ctcatggcca ccccgctgga gagggcccag catctgcaaa gctcccggca ccgccgagcc    840

ctggacacca actattgctt cagctccacg gagaagaact gctgcgtgcg gcagctgtac    900

attgacttcc gcaaggacct cggctggaag tggatccacg agcccaaggg ctaccatgcc    960

aacttctgcc tcgggccctg cccctacatt tggagcctgg acacgcagta cagcaaggtc   1020

ctggccctgt acaaccagca taacccgggc gcctcggcgg cgccgtgctg cgtgccgcag   1080

gcgctggagc cgctgcccat cgtgtactac gtgggccgca agcccaaggt ggagcagctg   1140

tccaacatga tcgtgcgctc ctgcaagtgc agctga                             1176
```

<210> SEQ ID NO 47
<211> LENGTH: 1245
<212> TYPE: DNA
<213> ORGANISM: Homo sapiens
<300> PUBLICATION INFORMATION:
<302> TITLE: TGFbeta2
<310> PATENT DOCUMENT NUMBER: NM003238

<400> SEQUENCE: 47

```
atgcactact gtgtgctgag cgcttttctg atcctgcatc tggtcacggt cgcgctcagc     60

ctgtctacct gcagcacact cgatatggac cagttcatgc gcaagaggat cgaggcgatc    120

cgcgggcaga tcctgagcaa gctgaagctc accagtcccc cagaagacta tcctgagccc    180
```

-continued

```
gaggaagtcc ccccggaggt gatttccatc tacaacagca ccagggactt gctccaggag    240

aaggcgagcc ggagggcggc cgcctgcgag cgcgagagga gcgacgaaga gtactacgcc    300

aaggaggttt acaaaataga catgccgccc ttcttcccct ccgaaaatgc catcccgccc    360

actttctaca gaccctactt cagaattgtt cgatttgacg tctcagcaat ggagaagaat    420

gcttccaatt tggtgaaagc agagttcaga gtctttcgtt tgcagaaccc aaaagccaga    480

gtgcctgaac aacggattga gctatatcag attctcaagt ccaaagattt aacatctcca    540

acccagcgct acatcgacag caaagttgtg aaaacaagag cagaaggcga atggctctcc    600

ttcgatgtaa ctgatgctgt tcatgaatgg cttcaccata aagacaggaa cctgggattt    660

aaaataagct tacactgtcc ctgctgcact tttgtaccat ctaataatta catcatccca    720

aataaaagtg aagaactaga agcaagattt gcaggtattg atggcacctc cacatatacc    780

agtggtgatc agaaaactat aaagtccact aggaaaaaaa acagtgggaa gaccccacat    840

ctcctgctaa tgttattgcc ctcctacaga cttgagtcac aacagaccaa ccggcggaag    900

aagcgtgctt tggatgcggc ctattgcttt agaaatgtgc aggataattg ctgcctacgt    960

ccactttaca ttgatttcaa gagggatcta gggtggaaat ggatacacga acccaaaggg   1020

tacaatgcca acttctgtgc tggagcatgc ccgtatttat ggagttcaga cactcagcac   1080

agcagggtcc tgagcttata taataccata aatccagaag catctgcttc tccttgctgc   1140

gtgtcccaag atttagaacc tctaaccatt ctctactaca ttggcaaaac acccaagatt   1200

gaacagcttt ctaatatgat tgtaaagtct tgcaaatgca gctaa                   1245


<210> SEQ ID NO 48
<211> LENGTH: 1239
<212> TYPE: DNA
<213> ORGANISM: Homo sapiens
<300> PUBLICATION INFORMATION:
<302> TITLE: TGFbeta3
<310> PATENT DOCUMENT NUMBER: XM007417

<400> SEQUENCE: 48

atgaagatgc acttgcaaag ggctctggtg gtcctggccc tgctgaactt tgccacggtc     60

agcctctctc tgtccacttg caccaccttg gacttcggcc acatcaagaa gaagagggtg    120

gaagccatta ggggacagat cttgagcaag ctcaggctca ccagcccccc tgagccaacg    180

gtgatgaccc acgtccccta tcaggtcctg gccctttaca acagcacccg ggagctgctg    240

gaggagatgc atggggagag ggaggaaggc tgcacccagg aaaacaccga gtcggaatac    300

tatgccaaag aaatccataa attcgacatg atccaggggc tggcggagca caacgaactg    360

gctgtctgcc ctaaaggaat tacctccaag gttttccgct tcaatgtgtc ctcagtggag    420

aaaaatagaa ccaacctatt ccgagcagaa ttccgggtct tgcgggtgcc caaccccagc    480

tctaagcgga atgagcagag gatcgagctc ttccagatcc ttcggccaga tgagcacatt    540

gccaaacagc gctatatcgg tggcaagaat ctgcccacac ggggcactgc cgagtggctg    600

tcctttgatg tcactgacac tgtgcgtgag tggctgttga gaagagagtc caacttaggt    660

ctagaaatca gcattcactg tccatgtcac acctttcagc ccaatggaga tatcctggaa    720

aacattcacg aggtgatgga aatcaaattc aaaggcgtgg acaatgagga tgaccatggc    780

cgtggagatc tggggcgcct caagaagcag aaggatcacc acaaccctca tctaatcctc    840

atgatgattc ccccacaccg gctcgacaac ccgggccagg ggggtcagag gaagaagcgg    900

gctttggaca ccaattactg cttccgcaac ttggaggaga actgctgtgt gcgcccctc     960
```

-continued

```
tacattgact tccgacagga tctgggctgg aagtgggtcc atgaacctaa gggctactat   1020

gccaacttct gctcaggccc ttgcccatac ctccgcagtg cagacacaac ccacagcacg   1080

gtgctgggac tgtacaacac tctgaaccct gaagcatctg cctcgccttg ctgcgtgccc   1140

caggacctgg agcccctgac catcctgtac tatgttggga ggacccccaa agtggagcag   1200

ctctccaaca tggtggtgaa gtcttgtaaa tgtagctga                          1239


<210> SEQ ID NO 49
<211> LENGTH: 1704
<212> TYPE: DNA
<213> ORGANISM: Homo sapiens
<300> PUBLICATION INFORMATION:
<302> TITLE: TGFbetaR2
<310> PATENT DOCUMENT NUMBER: XM003094

<400> SEQUENCE: 49

atgggtcggg ggctgctcag gggcctgtgg ccgctgcaca tcgtcctgtg gacgcgtatc     60

gccagcacga tcccaccgca cgttcagaag tcggttaata acgacatgat agtcactgac    120

aacaacggtg cagtcaagtt tccacaactg tgtaaatttt gtgatgtgag attttccacc    180

tgtgacaacc agaaatcctg catgagcaac tgcagcatca cctccatctg tgagaagcca    240

caggaagtct gtgtggctgt atggagaaag aatgacgaga acataacact agagacagtt    300

tgccatgacc ccaagctccc ctaccatgac tttattctgg aagatgctgc ttctccaaag    360

tgcattatga aggaaaaaaa aaagcctggt gagactttct tcatgtgttc ctgtagctct    420

gatgagtgca atgacaacat catcttctca gaagaatata acaccagcaa tcctgacttg    480

ttgctagtca tatttcaagt gacaggcatc agcctcctgc caccactggg agttgccata    540

tctgtcatca tcatcttcta ctgctaccgc gttaaccggc agcagaagct gagttcaacc    600

tgggaaaccg gcaagacgcg gaagctcatg gagttcagcg agcactgtgc catcatcctg    660

gaagatgacc gctctgacat cagctccacg tgtgccaaca acatcaacca caacacagag    720

ctgctgccca ttgagctgga caccctggtg gggaaaggtc gctttgctga ggtctataag    780

gccaagctga agcagaacac ttcagagcag tttgagacag tggcagtcaa gatctttccc    840

tatgaggagt atgcctcttg gaagacagag aaggacatct tctcagacat caatctgaag    900

catgagaaca tactccagtt cctgacggct gaggagcgga agacggagtt ggggaaacaa    960

tactggctga tcaccgcctt ccacgccaag ggcaacctac aggagtacct gacgcggcat   1020

gtcatcagct gggaggacct gcgcaagctg ggcagctccc tcgcccgggg gattgctcac   1080

ctccacagtg atcacactcc atgtgggagg cccaagatgc ccatcgtgca cagggacctc   1140

aagagctcca atatcctcgt gaagaacgac ctaacctgct gcctgtgtga ctttgggctt   1200

tccctgcgtc tggaccctac tctgtctgtg gatgacctgg ctaacagtgg gcaggtggga   1260

actgcaagat acatggctcc agaagtccta gaatccagga tgaatttgga gaatgttgag   1320

tccttcaagc agaccgatgt ctactccatg gctctggtgc tctgggaaat gacatctcgc   1380

tgtaatgcag tgggagaagt aaaagattat gagcctccat ttggttccaa ggtgcgggag   1440

cacccctgtg tcgaaagcat gaaggacaac gtgttgagag atcgagggcg accagaaatt   1500

cccagcttct ggctcaacca ccagggcatc cagatggtgt gtgagacgtt gactgagtgc   1560

tgggaccacg acccagaggc ccgtctcaca gcccagtgtg tggcagaacg cttcagtgag   1620

ctggagcatc tggacaggct ctcggggagg agctgctcgg aggagaagat tcctgaagac   1680

ggctccctaa acactaccaa atag                                          1704
```

<210> SEQ ID NO 50
<211> LENGTH: 609
<212> TYPE: DNA
<213> ORGANISM: Homo sapiens
<300> PUBLICATION INFORMATION:
<302> TITLE: TGFbeta3
<310> PATENT DOCUMENT NUMBER: XM001924

<400> SEQUENCE: 50
atgtctcatt acaccattat tgagaatatt tgtcctaaag atgaatctgt gaaattctac 60
agtcccaaga gagtgcactt tcctatcccg caagctgaca tggataagaa gcgattcagc 120
tttgtcttca agcctgtctt caacacctca ctgctctttc tacagtgtga gctgacgctg 180
tgtacgaaga tggagaagca cccccagaag ttgcctaagt gtgtgcctcc tgacgaagcc 240
tgcacctcgc tggacgcctc gataatctgg gccatgatgc agaataagaa gacgttcact 300
aagccccttg ctgtgatcca ccatgaagca gaatctaaag aaaaaggtcc aagcatgaag 360
gaaccaaatc caatttctcc accaattttc catggtctgg acaccctaac cgtgatgggc 420
attgcgtttg cagcctttgt gatcggagca ctcctgacgg gggccttgtg gtacatctat 480
tctcacacag gggagacagc aggaaggcag caagtcccca cctccccgcc agcctcggaa 540
aacagcagtg ctgcccacag catcggcagc acgcagagca cgccttgctc cagcagcagc 600
acggcctag 609

<210> SEQ ID NO 51
<211> LENGTH: 3633
<212> TYPE: DNA
<213> ORGANISM: Homo sapiens
<300> PUBLICATION INFORMATION:
<302> TITLE: EGFR
<310> PATENT DOCUMENT NUMBER: X00588

<400> SEQUENCE: 51
atgcgaccct ccgggacggc cggggcagcg ctcctggcgc tgctggctgc gctctgcccg 60
gcgagtcggg ctctggagga aaagaaagtt tgccaaggca cgagtaacaa gctcacgcag 120
ttgggcactt ttgaagatca ttttctcagc ctccagagga tgttcaataa ctgtgaggtg 180
gtccttggga atttggaaat tacctatgtg cagaggaatt atgatctttc cttcttaaag 240
accatccagg aggtggctgg ttatgtcctc attgccctca acacagtgga gcgaattcct 300
ttggaaaacc tgcagatcat cagaggaaat atgtactacg aaaattccta tgccttagca 360
gtcttatcta actatgatgc aaataaaacc ggactgaagg agctgcccat gagaaattta 420
caggaaatcc tgcatggcgc cgtgcggttc agcaacaacc ctgccctgtg caacgtggag 480
agcatccagt ggcgggacat agtcagcagt gactttctca gcaacatgtc gatggacttc 540
cagaaccacc tgggcagctg ccaaaagtgt gatccaagct gtcccaatgg gagctgctgg 600
ggtgcaggag aggagaactg ccagaaactg accaaaatca tctgtgccca gcagtgctcc 660
gggcgctgcc gtggcaagtc ccccagtgac tgctgccaca accagtgtgc tgcaggctgc 720
acaggccccc gggagagcga ctgcctggtc tgccgcaaat tccgagacga agccacgtgc 780
aaggacacct gccccccact catgctctac aaccccacca cgtaccagat ggatgtgaac 840
cccgagggca aatacagctt tggtgccacc tgcgtgaaga agtgtccccg taattatgtg 900
gtgacagatc acggctcgtg cgtccgagcc tgtggggccg acagctatga gatggaggaa 960
gacggcgtcc gcaagtgtaa gaagtgcgaa gggccttgcc gcaaagtgtg taacggaata 1020
ggtattggtg aatttaaaga ctcactctcc ataaatgcta cgaatattaa acacttcaaa 1080

```
aactgcacct ccatcagtgg cgatctccac atcctgccgg tggcatttag gggtgactcc   1140
ttcacacata ctcctcctct ggatccacag gaactggata ttctgaaaac cgtaaaggaa   1200
atcacagggt ttttgctgat tcaggcttgg cctgaaaaca ggacggacct ccatgccttt   1260
gagaacctag aaatcatacg cggcaggacc aagcaacatg gtcagttttc tcttgcagtc   1320
gtcagcctga acataacatc cttgggatta cgctccctca aggagataag tgatggagat   1380
gtgataattt caggaaacaa aaatttgtgc tatgcaaata caataaactg gaaaaaactg   1440
tttgggacct ccggtcagaa aaccaaaatt ataagcaaca gaggtgaaaa cagctgcaag   1500
gccacaggcc aggtctgcca tgccttgtgc tcccccgagg gctgctgggg cccggagccc   1560
agggactgcg tctcttgccg gaatgtcagc cgaggcaggg aatgcgtgga caagtgcaag   1620
cttctggagg gtgagccaag ggagtttgtg gagaactctg agtgcataca gtgccaccca   1680
gagtgcctgc ctcaggccat gaacatcacc tgcacaggac ggggaccaga caactgtatc   1740
cagtgtgccc actacattga cggcccccac tgcgtcaaga cctgcccggc aggagtcatg   1800
ggagaaaaca acaccctggt ctggaagtac gcagacgccg gccatgtgtg ccacctgtgc   1860
catccaaact gcacctacgg atgcactggg ccaggtcttg aaggctgtcc aacgaatggg   1920
cctaagatcc cgtccatcgc cactgggatg gtgggggccc tcctcttgct gctggtggtg   1980
gccctgggga tcggcctctt catgcgaagg cgccacatcg ttcggaagcg cacgctgcgg   2040
aggctgctgc aggagaggga gcttgtggag cctcttacac ccagtggaga agctcccaac   2100
caagctctct tgaggatctt gaaggaaact gaattcaaaa agatcaaagt gctgggctcc   2160
ggtgcgttcg gcacggtgta taagggactc tggatcccag aaggtgagaa agttaaaatt   2220
cccgtcgcta tcaaggaatt aagagaagca acatctccga aagccaacaa ggaaatcctc   2280
gatgaagcct acgtgatggc cagcgtggac aacccccacg tgtgccgcct gctgggcatc   2340
tgcctcacct ccaccgtgca actcatcacg cagctcatgc ccttcggctg cctcctggac   2400
tatgtccggg aacacaaaga caatattggc tcccagtacc tgctcaactg gtgtgtgcag   2460
atcgcaaagg gcatgaacta cttggaggac cgtcgcttgg tgcaccgcga cctggcagcc   2520
aggaacgtac tggtgaaaac accgcagcat gtcaagatca cagattttgg gctggccaaa   2580
ctgctgggtg cggaagagaa agaataccat gcagaaggag gcaaagtgcc tatcaagtgg   2640
atggcattgg aatcaatttt acacagaatc tatacccacc agagtgatgt ctggagctac   2700
ggggtgaccg tttgggagtt gatgaccttt ggatccaagc catatgacgg aatccctgcc   2760
agcgagatct cctccatcct ggagaaagga gaacgcctcc ctcagccacc catatgtacc   2820
atcgatgtct acatgatcat ggtcaagtgc tggatgatag acgcagatag tcgcccaaag   2880
ttccgtgagt tgatcatcga attctccaaa atggcccgag acccccagcg ctaccttgtc   2940
attcaggggg atgaaagaat gcatttgcca agtcctacag actccaactt ctaccgtgcc   3000
ctgatggatg aagaagacat ggacgacgtg gtggatgccg acgagtacct catcccacag   3060
cagggcttct tcagcagccc ctccacgtca cggactcccc tcctgagctc tctgagtgca   3120
accagcaaca attccaccgt ggcttgcatt gatagaaatg ggctgcaaag ctgtcccatc   3180
aaggaagaca gcttcttgca gcgatacagc tcagacccca caggcgcctt gactgaggac   3240
agcatagacg acaccttcct cccagtgcct gaatacataa accagtccgt tcccaaaagg   3300
cccgctggct ctgtgcagaa tcctgtctat cacaatcagc ctctgaaccc cgcgcccagc   3360
agagacccac actaccagga cccccacagc actgcagtgg gcaaccccga gtatctcaac   3420
```

actgtccagc ccacctgtgt caacagcaca ttcgacagcc ctgcccactg ggcccagaaa 3480
ggcagccacc aaattagcct ggacaaccct gactaccagc aggacttctt tcccaaggaa 3540
gccaagccaa atggcatctt taagggctcc acagctgaaa atgcagaata cctaagggtc 3600
gcgccacaaa gcagtgaatt tattggagca tga 3633

<210> SEQ ID NO 52
<211> LENGTH: 3768
<212> TYPE: DNA
<213> ORGANISM: Homo sapiens
<300> PUBLICATION INFORMATION:
<302> TITLE: ERBB2
<310> PATENT DOCUMENT NUMBER: NM004448

<400> SEQUENCE: 52
atggagctgg cggccttgtg ccgctggggg ctcctcctcg ccctcttgcc ccccggagcc 60
gcgagcaccc aagtgtgcac cggcacagac atgaagctgc ggctccctgc cagtcccgag 120
acccacctgg acatgctccg ccacctctac cagggctgcc aggtggtgca gggaaacctg 180
gaactcacct acctgcccac caatgccagc ctgtccttcc tgcaggatat ccaggaggtg 240
cagggctacg tgctcatcgc tcacaaccaa gtgaggcagg tcccactgca gaggctgcgg 300
attgtgcgag gcacccagct ctttgaggac aactatgccc tggccgtgct agacaatgga 360
gacccgctga acaataccac ccctgtcaca ggggcctccc caggaggcct gcgggagctg 420
cagcttcgaa gcctcacaga gatcttgaaa ggaggggtct tgatccagcg gaacccccag 480
ctctgctacc aggacacgat tttgtggaag gacatcttcc acaagaacaa ccagctggct 540
ctcacactga tagacaccaa ccgctctcgg gcctgccacc cctgttctcc gatgtgtaag 600
ggctcccgct gctggggaga gagttctgag gattgtcaga gcctgacgcg cactgtctgt 660
gccggtggct gtgcccgctg caaggggcca ctgcccactg actgctgcca tgagcagtgt 720
gctgccggct gcacgggccc caagcactct gactgcctgg cctgcctcca cttcaaccac 780
agtggcatct gtgagctgca ctgcccagcc ctggtcacct acaacacaga cacgtttgag 840
tccatgccca atcccgaggg ccggtataca ttcggcgcca gctgtgtgac tgcctgtccc 900
tacaactacc tttctacgga cgtgggatcc tgcaccctcg tctgccccct gcacaaccaa 960
gaggtgacag cagaggatgg aacacagcgg tgtgagaagt gcagcaagcc ctgtgcccga 1020
gtgtgctatg gtctgggcat ggagcacttg cgagaggtga gggcagttac cagtgccaat 1080
atccaggagt ttgctggctg caagaagatc tttgggagcc tggcatttct gccggagagc 1140
tttgatgggg acccagcctc caacactgcc ccgctccagc cagagcagct ccaagtgttt 1200
gagactctgg aagagatcac aggttaccta tacatctcag catggccgga cagcctgcct 1260
gacctcagcg tcttccagaa cctgcaagta atccggggac gaattctgca caatggcgcc 1320
tactcgctga ccctgcaagg gctgggcatc agctggctgg ggctgcgctc actgagggaa 1380
ctgggcagtg gactggccct catccaccat aacacccacc tctgcttcgt gcacacggtg 1440
ccctgggacc agctctttcg gaacccgcac caagctctgc tccacactgc caaccggcca 1500
gaggacgagt gtgtgggcga gggcctggcc tgccaccagc tgtgcgcccg agggcactgc 1560
tggggtccag ggcccaccca gtgtgtcaac tgcagccagt tccttcgggg ccaggagtgc 1620
gtggaggaat gccgagtact gcaggggctc cccagggagt atgtgaatgc caggcactgt 1680
ttgccgtgcc accctgagtg tcagccccag aatggctcag tgacctgttt tggaccggag 1740
gctgaccagt gtgtggcctg tgcccactat aaggaccctc ccttctgcgt ggcccgctgc 1800

-continued cccagcggtg tgaaacctga cctctcctac atgcccatct ggaagtttcc agatgaggag 1860
ggcgcatgcc agccttgccc catcaactgc acccactcct gtgtggacct ggatgacaag 1920
ggctgccccg ccgagcagag agccagccct ctgacgtcca tcgtctctgc ggtggttggc 1980
attctgctgg tcgtggtctt gggggtggtc tttgggatcc tcatcaagcg acggcagcag 2040
aagatccgga agtacacgat gcggagactg ctgcaggaaa cggagctggt ggagccgctg 2100
acacctagcg gagcgatgcc caaccaggcg cagatgcgga tcctgaaaga gacggagctg 2160
aggaaggtga aggtgcttgg atctggcgct tttggcacag tctacaaggg catctggatc 2220
cctgatgggg agaatgtgaa aattccagtg gccatcaaag tgttgaggga aaacacatcc 2280
cccaaagcca acaaagaaat cttagacgaa gcatacgtga tggctggtgt gggctcccca 2340
tatgtctccc gccttctggg catctgcctg acatccacgg tgcagctggt gacacagctt 2400
atgccctatg gctgcctctt agaccatgtc cgggaaaacc gcggacgcct gggctcccag 2460
gacctgctga actggtgtat gcagattgcc aaggggatga gctacctgga ggatgtgcgg 2520
ctcgtacaca gggacttggc cgctcggaac gtgctggtca agagtcccaa ccatgtcaaa 2580
attacagact tcgggctggc tcggctgctg gacattgacg agacagagta ccatgcagat 2640
gggggcaagg tgcccatcaa gtggatggcg ctggagtcca ttctccgccg gcggttcacc 2700
caccagagtg atgtgtggag ttatggtgtg actgtgtggg agctgatgac ttttggggcc 2760
aaaccttacg atgggatccc agcccgggag atccctgacc tgctggaaaa gggggagcgg 2820
ctgccccagc cccccatctg caccattgat gtctacatga tcatggtcaa atgttggatg 2880
attgactctg aatgtcggcc aagattccgg gagttggtgt ctgaattctc ccgcatggcc 2940
agggaccccc agcgctttgt ggtcatccag aatgaggact tgggcccagc cagtcccttg 3000
gacagcacct tctaccgctc actgctggag gacgatgaca tgggggacct ggtggatgct 3060
gaggagtatc tggtacccca gcagggcttc ttctgtccag accctgcccc gggcgctggg 3120
ggcatggtcc accacaggca ccgcagctca tctaccagga gtggcggtgg ggacctgaca 3180
ctagggctgg agccctctga agaggaggcc cccaggtctc cactggcacc ctccgaaggg 3240
gctggctccg atgtatttga tggtgacctg ggaatggggg cagccaaggg gctgcaaagc 3300
ctccccacac atgaccccag ccctctacag cggtacagtg aggaccccac agtacccctg 3360
ccctctgaga ctgatggcta cgttgccccc ctgacctgca gcccccagcc tgaatatgtg 3420
aaccagccag atgttcggcc ccagcccccct tcgccccgag agggccctct gcctgctgcc 3480
cgacctgctg gtgccactct ggaaagggcc aagactctct ccccagggaa gaatggggtc 3540
gtcaaagacg tttttgcctt tgggggtgcc gtggagaacc ccgagtactt gacaccccag 3600
ggaggagctg cccctcagcc ccaccctcct cctgccttca gcccagcctt cgacaacctc 3660
tattactggg accaggaccc accagagcgg ggggctccac ccagcacctt caaagggaca 3720
cctacggcag agaacccaga gtacctgggt ctggacgtgc cagtgtga 3768

<210> SEQ ID NO 53
<211> LENGTH: 1986
<212> TYPE: DNA
<213> ORGANISM: Homo sapiens
<300> PUBLICATION INFORMATION:
<302> TITLE: ERBB3
<310> PATENT DOCUMENT NUMBER: XM006723

<400> SEQUENCE: 53
atgcacaact tcagtgtttt ttccaatttg acaaccattg gaggcagaag cctctacaac 60

-continued

```
cggggcttct cattgttgat catgaagaac ttgaatgtca catctctggg cttccgatcc     120

ctgaaggaaa ttagtgctgg gcgtatctat ataagtgcca ataggcagct ctgctaccac     180

cactctttga actggaccaa ggtgcttcgg gggcctacgg aagagcgact agacatcaag     240

cataatcggc cgcgcagaga ctgcgtggca gagggcaaag tgtgtgaccc actgtgctcc     300

tctgggggat gctggggccc aggccctggt cagtgcttgt cctgtcgaaa ttatagccga     360

ggaggtgtct gtgtgaccca ctgcaacttt ctgaatgggg agcctcgaga atttgcccat     420

gaggccgaat gcttctcctg ccacccggaa tgccaaccca tggagggcac tgccacatgc     480

aatggctcgg gctctgatac ttgtgctcaa tgtgcccatt ttcgagatgg gccccactgt     540

gtgagcagct gcccccatgg agtcctaggt gccaagggcc caatctacaa gtacccagat     600

gttcagaatg aatgtcggcc ctgccatgag aactgcaccc aggggtgtaa aggaccagag     660

cttcaagact gtttaggaca aacactggtg ctgatcggca aaacccatct gacaatggct     720

ttgacagtga tagcaggatt ggtagtgatt ttcatgatgc tgggcggcac ttttctctac     780

tggcgtgggc gccggattca gaataaaagg gctatgaggc gatacttgga acggggtgag     840

agcatagagc ctctggaccc cagtgagaag gctaacaaag tcttggccag aatcttcaaa     900

gagacagagc taaggaagct taaagtgctt ggctcgggtg tctttggaac tgtgcacaaa     960

ggagtgtgga tccctgaggg tgaatcaatc aagattccag tctgcattaa agtcattgag    1020

gacaagagtg gacggcagag ttttcaagct gtgacagatc atatgctggc cattggcagc    1080

ctggaccatg cccacattgt aaggctgctg ggactatgcc cagggtcatc tctgcagctt    1140

gtcactcaat atttgcctct gggttctctg ctggatcatg tgagacaaca ccgggggcca    1200

ctggggccac agctgctgct caactgggga gtacaaattg ccaagggaat gtactacctt    1260

gaggaacatg gtatggtgca tagaaacctg gctgcccgaa acgtgctact caagtcaccc    1320

agtcaggttc aggtggcaga ttttggtgtg gctgacctgc tgcctcctga tgataagcag    1380

ctgctataca gtgaggccaa gactccaatt aagtggatgg cccttgagag tatccacttt    1440

gggaaataca cacaccagag tgatgtctgg agctatggtg tgacagtttg ggagttgatg    1500

accttcgggg cagagcccta tgcagggcta cgattggctg aagtaccaga cctgctagag    1560

aagggggagc ggttggcaca gccccagatc tgcacaattg atgtctacat ggtgatggtc    1620

aagtgttgga tgattgatga gaacattcgc ccaaccttta aagaactagc caatgagttc    1680

accaggatgg cccgagaccc accacggtat ctggtcataa agagagagag tgggcctgga    1740

atagcccctg ggccagagcc ccatggtctg acaaacaaga agctagagga agtagagctg    1800

gagccagaac tagacctaga cctagacttg gaagcagagg aggacaacct ggcaaccacc    1860

acactgggct ccgccctcag cctaccagtt ggaacactta atcggccacg tgggagccag    1920

agccttttaa gtccatcatc tggatacatg cccatgaacc agggtaatct tggggttctt    1980

ccttag                                                               1986
```

<210> SEQ ID NO 54
<211> LENGTH: 1437
<212> TYPE: DNA
<213> ORGANISM: Homo sapiens
<300> PUBLICATION INFORMATION:
<302> TITLE: ERBB4
<310> PATENT DOCUMENT NUMBER: XM002260

<400> SEQUENCE: 54

```
atgatgtacc tggaagaaag acgactcgtt catcgggatt tggcagcccg taatgtctta      60
```

```
gtgaaatctc caaaccatgt gaaaatcaca gattttgggc tagccagact cttggaagga    120

gatgaaaaag agtacaatgc tgatggagga aagatgccaa ttaaatggat ggctctggag    180

tgtatacatt acaggaaatt cacccatcag agtgacgttt ggagctatgg agttactata    240

tgggaactga tgacctttgg aggaaaaccc tatgatggaa ttccaacgcg agaaatccct    300

gatttattag agaaaggaga acgtttgcct cagcctccca tctgcactat tgacgtttac    360

atggtcatgg tcaaatgttg gatgattgat gctgacagta gacctaaatt taaggaactg    420

gctgctgagt tttcaaggat ggctcgagac cctcaaagat acctagttat tcagggtgat    480

gatcgtatga agcttcccag tccaaatgac agcaagttct ttcagaatct cttggatgaa    540

gaggatttgg aagatatgat ggatgctgag gagtacttgg tccctcaggc tttcaacatc    600

ccacctccca tctatacttc cagagcaaga attgactcga ataggagtga aattggacac    660

agccctcctc ctgcctacac cccatgtca ggaaaccagt ttgtataccg agatggaggt     720

tttgctgctg aacaaggagt gtctgtgccc tacagagccc caactagcac aattccagaa    780

gctcctgtgg cacagggtgc tactgctgag atttttgatg actcctgctg taatggcacc    840

ctacgcaagc cagtggcacc ccatgtccaa gaggacagta gcacccagag gtacagtgct    900

gaccccaccg tgtttgcccc agaacggagc ccacgaggag agctggatga ggaaggttac    960

atgactccta tgcgagacaa acccaaacaa gaatacctga atccagtgga ggagaaccct   1020

tttgtttctc ggagaaaaaa tggagacctt caagcattgg ataatcccga atatcacaat   1080

gcatccaatg gtccacccaa ggccgaggat gagtatgtga atgagccact gtacctcaac   1140

acctttgcca acaccttggg aaaagctgag tacctgaaga acaacatact gtcaatgcca   1200

gagaaggcca agaaagcgtt tgacaaccct gactactgga accacagcct gccacctcgg   1260

agcacccttc agcacccaga ctacctgcag gagtacagca caaaatattt ttataaacag   1320

aatgggcgga tccggcctat tgtggcagag aatcctgaat acctctctga gttctccctg   1380

aagccaggca ctgtgctgcc gcctccacct tacagacacc ggaatactgt ggtgtaa      1437


<210> SEQ ID NO 55
<211> LENGTH: 627
<212> TYPE: DNA
<213> ORGANISM: Homo sapiens
<300> PUBLICATION INFORMATION:
<302> TITLE: FGF10
<310> PATENT DOCUMENT NUMBER: NM004465

<400> SEQUENCE: 55

atgtggaaat ggatactgac acattgtgcc tcagcctttc cccacctgcc cggctgctgc     60

tgctgctgct tttgttgct gttcttggtg tcttccgtcc ctgtcacctg ccaagccctt     120

ggtcaggaca tggtgtcacc agaggccacc aactcttctt cctcctcctt ctcctctcct    180

tccagcgcgg gaaggcatgt gcggagctac aatcaccttc aaggagatgt ccgctggaga    240

aagctattct ctttcaccaa gtactttctc aagattgaga agaacgggaa ggtcagcggg    300

accaagaagg agaactgccc gtacagcatc ctggagataa catcagtaga aatcggagtt    360

gttgccgtca aagccattaa cagcaactat tacttagcca tgaacaagaa ggggaaactc    420

tatggctcaa aagaatttaa caatgactgt aagctgaagg agaggataga ggaaaatgga    480

tacaatacct atgcatcatt taactggcag cataatggga ggcaaatgta tgtggcattg    540

aatggaaaag gagctccaag gagaggacag aaaacacgaa ggaaaaacac ctctgctcac    600

tttcttccaa tggtggtaca ctcatag                                       627
```

<210> SEQ ID NO 56
<211> LENGTH: 679
<212> TYPE: DNA
<213> ORGANISM: Homo sapiens
<300> PUBLICATION INFORMATION:
<302> TITLE: FGF11
<310> PATENT DOCUMENT NUMBER: XM008660

<400> SEQUENCE: 56

```
aatggcggcg ctggccagta gcctgatccg gcagaagcgg gaggtccgcg agcccggggg     60
cagccggccg gtgtcggcgc agcggcgcgt gtgtccccgc ggcaccaagt ccctttgcca    120
gaagcagctc ctcatcctgc tgtccaaggt gcgactgtgc ggggggcggc ccgcgcggcc    180
ggaccgcggc ccggagcctc agctcaaagg catcgtcacc aaactgttct gccgccaggg    240
tttctacctc caggcgaatc ccgacggaag catccagggc accccagagg ataccagctc    300
cttcacccac ttcaacctga tccctgtggg cctccgtgtg gtcaccatcc agagcgccaa    360
gctgggtcac tacatggcca tgaatgctga gggactgctc tacagttcgc cgcatttcac    420
agctgagtgt cgctttaagg agtgtgtctt tgagaattac tacgtcctgt acgcctctgc    480
tctctaccgc cagcgtcgtt ctggccgggc ctggtacctc ggcctggaca aggagggcca    540
ggtcatgaag ggaaaccgag ttaagaagac caaggcagct gcccactttc tgcccaagct    600
cctggaggtg gccatgtacc aggagccttc tctccacagt gtccccgagg cctccccttc    660
cagtcccccct gccccctga                                                 679
```

<210> SEQ ID NO 57
<211> LENGTH: 732
<212> TYPE: DNA
<213> ORGANISM: Homo sapiens
<300> PUBLICATION INFORMATION:
<302> TITLE: FGF12
<310> PATENT DOCUMENT NUMBER: NM021032

<400> SEQUENCE: 57

```
atggctgcgg cgatagccag ctccttgatc cggcagaagc ggcaggcgag ggagtccaac     60
agcgaccgag tgtcggcctc caagcgccgc tccagcccca gcaaagacgg gcgctccctg    120
tgcgagaggc acgtcctcgg ggtgttcagc aaagtgcgct tctgcagcgg ccgcaagagg    180
ccggtgaggc ggagaccaga accccagctc aaagggattg tgacaaggtt attcagccag    240
cagggatact tcctgcagat gcacccagat ggtaccattg atgggaccaa ggacgaaaac    300
agcgactaca ctctcttcaa tctaattccc gtgggcctgc gtgtagtggc catccaagga    360
gtgaaggcta gcctctatgt ggccatgaat ggtgaaggct atctctacag ttcagatgtt    420
ttcactccag aatgcaaatt caaggaatct gtgtttgaaa actactatgt gatctattct    480
tccacactgt accgccagca agaatcaggc cgagcttggt ttctgggact caataaagaa    540
ggtcaaatta tgaaggggaa cagagtgaag aaaaccaagc cctcatcaca ttttgtaccg    600
aaacctattg aagtgtgtat gtacagagaa ccatcgctac atgaaattgg agaaaaacaa    660
gggcgttcaa ggaaaagttc tggaacacca accatgaatg gaggcaaagt tgtgaatcaa    720
gattcaacat ag                                                         732
```

<210> SEQ ID NO 58
<211> LENGTH: 738
<212> TYPE: DNA
<213> ORGANISM: Homo sapiens
<300> PUBLICATION INFORMATION:
<302> TITLE: FGF13

<310> PATENT DOCUMENT NUMBER: XM010269

<400> SEQUENCE: 58
atggcggcgg ctatcgccag ctcgctcatc cgtcagaaga ggcaagcccg cgagcgcgag 60
aaatccaacg cctgcaagtg tgtcagcagc cccagcaaag gcaagaccag ctgcgacaaa 120
aacaagttaa atgtcttttc ccgggtcaaa ctcttcggct ccaagaagag gcgcagaaga 180
agaccagagc ctcagcttaa gggtatagtt accaagctat acagccgaca aggctaccac 240
ttgcagctgc aggcggatgg aaccattgat ggcaccaaag atgaggacag cacttacact 300
ctgtttaacc tcatccctgt gggtctgcga gtggtggcta tccaaggagt tcaaaccaag 360
ctgtacttgg caatgaacag tgagggatac ttgtacacct cggaactttt cacacctgag 420
tgcaaattca aagaatcagt gtttgaaaat tattatgtga catattcatc aatgatatac 480
cgtcagcagc agtcaggccg agggtggtat ctgggtctga acaaagaagg agagatcatg 540
aaaggcaacc atgtgaagaa gaacaagcct gcagctcatt ttctgcctaa accactgaaa 600
gtggccatgt acaaggagcc atcactgcac gatctcacgg agttctcccg atctggaagc 660
gggaccccaa ccaagagcag aagtgtctct ggcgtgctga acggaggcaa atccatgagc 720
cacaatgaat caacgtag 738

<210> SEQ ID NO 59
<211> LENGTH: 624
<212> TYPE: DNA
<213> ORGANISM: Homo sapiens
<300> PUBLICATION INFORMATION:
<302> TITLE: FGF16
<310> PATENT DOCUMENT NUMBER: NM003868

<400> SEQUENCE: 59
atggcagagg tgggggcgt cttcgcctcc ttggactggg atctacacgg cttctcctcg 60
tctctgggga acgtgccctt agctgactcc ccaggtttcc tgaacgagcg cctgggccaa 120
atcgagggga agctgcagcg tggctcaccc acagacttcg cccacctgaa ggggatcctg 180
cggcgccgcc agctctactg ccgcaccggc ttccacctgg agatcttccc caacggcacg 240
gtgcacggga cccgccacga ccacagccgc ttcggaatcc tggagtttat cagcctggct 300
gtggggctga tcagcatccg gggagtggac tctggcctgt acctaggaat gaatgagcga 360
ggagaactct atgggtcgaa gaaactcaca cgtgaatgtg ttttccggga acagtttgaa 420
gaaaactggt acaacaccta tgcctcaacc ttgtacaaac attcggactc agagagacag 480
tattacgtgg ccctgaacaa agatggctca ccccgggagg gatacaggac taaacgacac 540
cagaaattca ctcacttttt acccaggcct gtagatcctt ctaagttgcc ctccatgtcc 600
agagacctct ttcactatag gtaa 624

<210> SEQ ID NO 60
<211> LENGTH: 651
<212> TYPE: DNA
<213> ORGANISM: Homo sapiens
<300> PUBLICATION INFORMATION:
<302> TITLE: FGF17
<310> PATENT DOCUMENT NUMBER: XM005316

<400> SEQUENCE: 60
atgggagccg cccgcctgct gcccaacctc actctgtgct tacagctgct gattctctgc 60
tgtcaaactc agggggagaa tcacccgtct cctaatttta accagtacgt gagggaccag 120
ggcgccatga ccgaccagct gagcaggcgg cagatccgcg agtaccaact ctacagcagg 180

```
accagtggca agcacgtgca ggtcaccggg cgtcgcatct ccgccaccgc cgaggacggc    240

aacaagtttg ccaagctcat agtggagacg gacacgtttg gcagccgggt tcgcatcaaa    300

ggggctgaga gtgagaagta catctgtatg aacaagaggg gcaagctcat cgggaagccc    360

agcgggaaga gcaaagactg cgtgttcacg gagatcgtgc tggagaacaa ctatacggcc    420

ttccagaacg cccggcacga gggctggttc atggccttca cgcggcaggg gcggccccgc    480

caggcttccc gcagccgcca gaaccagcgc gaggcccact tcatcaagcg cctctaccaa    540

ggccagctgc ccttccccaa ccacgccgag aagcagaagc agttcgagtt tgtgggctcc    600

gcccccaccc gccggaccaa gcgcacacgg cggccccagc ccctcacgta g             651
```

```
<210> SEQ ID NO 61
<211> LENGTH: 624
<212> TYPE: DNA
<213> ORGANISM: Homo sapiens
<300> PUBLICATION INFORMATION:
<302> TITLE: FGF18
<310> PATENT DOCUMENT NUMBER: AF075292

<400> SEQUENCE: 61

atgtattcag cgccctccgc ctgcacttgc ctgtgtttac acttcctgct gctgtgcttc     60

caggtacagg tgctggttgc cgaggagaac gtggacttcc gcatccacgt ggagaaccag    120

acgcgggctc gggacgatgt gagccgtaag cagctgcggc tgtaccagct ctacagccgg    180

accagtggga aacacatcca ggtcctgggc cgcaggatca gtgcccgcgg cgaggatggg    240

gacaagtatg cccagctcct agtggagaca gacaccttcg gtagtcaagt ccggatcaag    300

ggcaaggaga cggaattcta cctgtgcatg aaccgcaaag gcaagctcgt ggggaagccc    360

gatggcacca gcaaggagtg tgtgttcatc gagaaggttc tggagaacaa ctacacggcc    420

ctgatgtcgg ctaagtactc cggctggtac gtgggcttca ccaagaaggg gcggccgcgg    480

aagggcccca agacccggga gaaccagcag gacgtgcatt tcatgaagcg ctaccccaag    540

gggcagccgg agcttcagaa gcccttcaag tacacgacgg tgaccaagag gtcccgtcgg    600

atccggccca cacaccctgc ctag                                           624
```

```
<210> SEQ ID NO 62
<211> LENGTH: 651
<212> TYPE: DNA
<213> ORGANISM: Homo sapiens
<300> PUBLICATION INFORMATION:
<302> TITLE: FGF19
<310> PATENT DOCUMENT NUMBER: AF110400

<400> SEQUENCE: 62

atgcggagcg ggtgtgtggt ggtccacgta tggatcctgg ccggcctctg gctggccgtg     60

gccgggcgcc ccctcgcctt ctcggacgcg gggccccacg tgcactacgg ctggggcgac    120

cccatccgcc tgcggcacct gtacacctcc ggcccccacg ggctctccag ctgcttcctg    180

cgcatccgtg ccgacggcgt cgtggactgc gcgcggggcc agagcgcgca cagtttgctg    240

gagatcaagg cagtcgctct gcggaccgtg gccatcaagg gcgtgcacag cgtgcggtac    300

ctctgcatgg gcgccgacgg caagatgcag gggctgcttc agtactcgga ggaagactgt    360

gctttcgagg aggagatccg cccagatggc tacaatgtgt accgatccga gaagcaccgc    420

ctcccggtct ccctgagcag tgccaaacag cggcagctgt acaagaacag aggctttctt    480

ccactctctc atttcctgcc catgctgccc atggtcccag aggagcctga ggacctcagg    540
```

ggccacttgg aatctgacat gttctcttcg cccctggaga ccgacagcat ggacccattt 600
gggcttgtca ccggactgga ggccgtgagg agtcccagct ttgagaagta a 651

<210> SEQ ID NO 63
<211> LENGTH: 468
<212> TYPE: DNA
<213> ORGANISM: Homo sapiens

<400> SEQUENCE: 63
atggctgaag gggaaatcac caccttcaca gccctgaccg agaagtttaa tctgcctcca 60
gggaattaca agaagcccaa actcctctac tgtagcaacg gggccactt cctgaggatc 120 cttccggatg gcacagtgga tgggacaagg gacaggagcg accagcacat tcagctgcag 180
ctcagtgcgg aaagcgtggg ggaggtgtat ataaagagta ccgagactgg ccagtacttg 240
gccatggaca ccgacgggct tttatacggc tcacagacac caaatgagga atgtttgttc 300
ctggaaaggc tggaggagaa ccattacaac acctatatat ccaagaagca tgcagagaag 360
aattggtttg ttggcctcaa gaagaatggg agctgcaaac gcggtcctcg gactcactat 420
ggccagaaag caatcttgtt tctcccccctg ccagtctctt ctgattaa 468

<210> SEQ ID NO 64
<211> LENGTH: 636
<212> TYPE: DNA
<213> ORGANISM: Homo sapiens
<300> PUBLICATION INFORMATION:
<302> TITLE: FGF20
<310> PATENT DOCUMENT NUMBER: NM019851

<400> SEQUENCE: 64
atggctccct tagccgaagt cgggggcttt ctgggcggcc tggagggctt gggccagcag 60
gtgggttcgc atttcctgtt gcctcctgcc ggggagcggc cgccgctgct gggcgagcgc 120
aggagcgcgg cggagcggag cgcccgcggc gggccggggg ctgcgcagct ggcgcacctg 180
cacggcatcc tgcgccgccg gcagctctat tgccgcaccg gcttccacct gcagatcctg 240
cccgacggca gcgtgcaggg cacccggcag gaccacagcc tcttcggtat cttggaattc 300
atcagtgtgg cagtgggact ggtcagtatt agaggtgtgg acagtggtct ctatcttgga 360
atgaatgaca aaggagaact ctatggatca gagaaactta cttccgaatg catctttagg 420
gagcagtttg aagagaactg gtataacacc tattcatcta acatatataa acatggagac 480
actggccgca ggtattttgt ggcacttaac aaagacggaa ctccaagaga tggcgccagg 540
tccaagaggc atcagaaatt tacacatttc ttacctagac cagtggatcc agaaagagtt 600
ccagaattgt acaaggacct actgatgtac acttga 636

<210> SEQ ID NO 65
<211> LENGTH: 630
<212> TYPE: DNA
<213> ORGANISM: Homo sapiens
<300> PUBLICATION INFORMATION:
<302> TITLE: FGF21
<310> PATENT DOCUMENT NUMBER: XM009100

<400> SEQUENCE: 65
atggactcgg acgagaccgg gttcgagcac tcaggactgt gggtttctgt gctggctggt 60
cttctgctgg gagcctgcca ggcacacccc atccctgact ccagtcctct cctgcaattc 120
gggggccaag tccggcagcg gtacctctac acagatgatg cccagcagac agaagcccac 180
ctggagatca gggaggatgg gacggtgggg ggcgctgctg accagagccc cgaaagtctc 240
ctgcagctga aagccttgaa gccgggagtt attcaaatct tgggagtcaa gacatccagg 300
ttcctgtgcc agcggccaga tggggccctg tatggatcgc tccactttga ccctgaggcc 360
tgcagcttcc gggagctgct tcttgaggac ggatacaatg tttaccagtc cgaagcccac 420
ggcctcccgc tgcacctgcc agggaacaag tccccacacc gggaccctgc accccgagga 480
ccagctcgct tcctgccact accaggcctg ccccccgcac tcccggagcc acccggaatc 540
ctggcccccc agccccccga tgtgggctcc tcggaccctc tgagcatggt gggaccttcc 600
cagggccgaa gccccagcta cgcttcctga 630

<210> SEQ ID NO 66
<211> LENGTH: 513
<212> TYPE: DNA
<213> ORGANISM: Homo sapiens
<300> PUBLICATION INFORMATION:
<302> TITLE: FGF22
<310> PATENT DOCUMENT NUMBER: XM009271

<400> SEQUENCE: 66
atgcgccgcc gcctgtggct gggcctggcc tggctgctgc tggcgcgggc gccggacgcc 60
gcgggaaccc cgagcgcgtc gcggggaccg cgcagctacc cgcacctgga gggcgacgtg 120
cgctggcggc gcctcttctc ctccactcac ttcttcctgc gcgtggatcc cggcggccgc 180
gtgcagggca cccgctggcg ccacggccag gacagcatcc tggagatccg ctctgtacac 240
gtgggcgtcg tggtcatcaa agcagtgtcc tcaggcttct acgtggccat gaaccgccgg 300
ggccgcctct acgggtcgcg actctacacc gtggactgca ggttccggga gcgcatcgaa 360
gagaacggcc acaacaccta cgcctcacag cgctggcgcc gccgcggcca gcccatgttc 420
ctggcgctgg acaggagggg ggggccccgg ccaggcggcc ggacgcggcg gtaccacctg 480
tccgcccact tcctgcccgt cctggtctcc tga 513

<210> SEQ ID NO 67
<211> LENGTH: 621
<212> TYPE: DNA
<213> ORGANISM: Homo sapiens
<300> PUBLICATION INFORMATION:
<302> TITLE: FGF4
<310> PATENT DOCUMENT NUMBER: NM002007

<400> SEQUENCE: 67
atgtcggggc ccgggacggc cgcggtagcg ctgctcccgg cggtcctgct ggccttgctg 60
gcgccctggg cgggccgagg gggcgccgcc gcacccactg cacccaacgg cacgctggag 120
gccgagctgg agcgccgctg ggagagcctg gtggcgctct cgttggcgcg cctgccggtg 180
gcagcgcagc ccaaggaggc ggccgtccag agcggcgccg gcgactacct gctgggcatc 240
aagcggctgc ggcggctcta ctgcaacgtg ggcatcggct tccacctcca ggcgctcccc 300
gacggccgca tcggcggcgc gcacgcggac acccgcgaca gcctgctgga gctctcgccc 360
gtggagcggg gcgtggtgag catcttcggc gtggccagcc ggttcttcgt ggccatgagc 420
agcaagggca agctctatgg ctcgcccttc ttcaccgatg agtgcacgtt caaggagatt 480
ctccttccca acaactacaa cgcctacgag tcctacaagt accccggcat gttcatcgcc 540
ctgagcaaga atgggaagac caagaagggg aaccgagtgt cgcccaccat gaaggtcacc 600
cacttcctcc ccaggctgtg a 621

<210> SEQ ID NO 68

<211> LENGTH: 597
<212> TYPE: DNA
<213> ORGANISM: Homo sapiens
<300> PUBLICATION INFORMATION:
<302> TITLE: FGF6
<310> PATENT DOCUMENT NUMBER: NM020996

<400> SEQUENCE: 68
atgtcccggg gagcaggacg tctgcagggc acgctgtggg ctctcgtctt cctaggcatc 60
ctagtgggca tggtggtgcc ctcgcctgca ggcacccgtg ccaacaacac gctgctggac 120
tcgaggggct ggggcaccct gctgtccagg tctcgcgcgg ggctagctgg agagattgcc 180
ggggtgaact gggaaagtgg ctatttggtg ggatcaagc ggcagcggag gctctactgc 240
aacgtgggca tcggctttca cctccaggtg ctccccgacg gccggatcag cgggacccac 300
gaggagaacc cctacagcct gctggaaatt tccactgtgg agcgaggcgt ggtgagtctc 360
tttggagtga gaagtgccct cttcgttgcc atgaacagta aaggaagatt gtacgcaacg 420
cccagcttcc aagaagaatg caagttcaga gaaaccctcc tgcccaacaa ttacaatgcc 480
tacgagtcag acttgtacca agggacctac attgccctga gcaaatacgg acgggtaaag 540
cggggcagca aggtgtcccc gatcatgact gtcactcatt tccttcccag gatctaa 597

<210> SEQ ID NO 69
<211> LENGTH: 150
<212> TYPE: DNA
<213> ORGANISM: Homo sapiens
<300> PUBLICATION INFORMATION:
<302> TITLE: FGF7
<310> PATENT DOCUMENT NUMBER: XM007559

<400> SEQUENCE: 69
atgtcttggc aatgcacttc atacacaatg actaatctat actgtgatga tttgactcaa 60
aaggagaaaa gaaattatgt agttttcaat tctgattcct attcaccttt tgtttatgaa 120
tggaaagctt tgtgcaaaat atacatataa 150

<210> SEQ ID NO 70
<211> LENGTH: 628
<212> TYPE: DNA
<213> ORGANISM: Homo sapiens
<300> PUBLICATION INFORMATION:
<302> TITLE: FGF9
<310> PATENT DOCUMENT NUMBER: XM007105

<400> SEQUENCE: 70
gatggctccc ttaggtgaag ttgggaacta tttcggtgtg caggatgcgg taccgtttgg 60
gaatgtgccc gtgttgccgg tggacagccc ggttttgtta agtgaccacc tgggtcagtc 120
cgaagcaggg gggctcccca ggggacccgc agtcacggac ttggatcatt taaaggggat 180
tctcaggcgg aggcagctat actgcaggac tggatttcac ttagaaatct tccccaatgg 240
tactatccag ggaaccagga aagaccacag ccgatttggc attctggaat ttatcagtat 300
agcagtgggc ctggtcagca ttcgaggcgt ggacagtgga ctctacctcg ggatgaatga 360
gaagggggag ctgtatggat cagaaaaact aacccaagag tgtgtattca gagaacagtt 420
cgaagaaaac tggtataata cgtactcatc aaacctatat aagcacgtgg acactggaag 480
gcgatactat gttgcattaa ataaagatgg gaccccgaga gaagggacta ggactaaacg 540
gcaccagaaa ttcacacatt ttttacctag accagtggac cccgacaaag tacctgaact 600
gtataaggat attctaagcc aaagttga 628

<210> SEQ ID NO 71
<211> LENGTH: 2469
<212> TYPE: DNA
<213> ORGANISM: Homo sapiens
<300> PUBLICATION INFORMATION:
<302> TITLE: FGFR1
<310> PATENT DOCUMENT NUMBER: NM000604

<400> SEQUENCE: 71
atgtggagct ggaagtgcct cctcttctgg gctgtgctgg tcacagccac actctgcacc 60
gctaggccgt ccccgacctt gcctgaacaa gcccagccct ggggagcccc tgtggaagtg 120
gagtccttcc tggtccaccc cggtgacctg ctgcagcttc gctgtcggct gcgggacgat 180
gtgcagagca tcaactggct gcgggacggg gtgcagctgg cggaaagcaa ccgcacccgc 240
atcacagggg aggaggtgga ggtgcaggac tccgtgcccg cagactccgg cctctatgct 300
tgcgtaacca gcagcccctc gggcagtgac accacctact tctccgtcaa tgtttcagat 360
gctctcccct cctcggagga tgatgatgat gatgatgact cctcttcaga ggagaaagaa 420
acagataaca ccaaaccaaa ccgtatgccc gtagctccat attggacatc cccagaaaag 480
atggaaaaga aattgcatgc agtgccggct gccaagacag tgaagttcaa atgcccttcc 540
agtgggaccc caaaccccac actgcgctgg ttgaaaaatg gcaaagaatt caaacctgac 600
cacagaattg gaggctacaa ggtccgttat gccacctgga gcatcataat ggactctgtg 660
gtgccctctg acaagggcaa ctacacctgc attgtggaga atgagtacgg cagcatcaac 720
cacacatacc agctggatgt cgtggagcgg tcccctcacc ggcccatcct gcaagcaggg 780
ttgcccgcca acaaaacagt ggccctgggt agcaacgtgg agttcatgtg taaggtgtac 840
agtgacccgc agccgcacat ccagtggcta aagcacatcg aggtgaatgg gagcaagatt 900
ggcccagaca acctgcctta tgtccagatc ttgaagactg ctggagttaa taccaccgac 960
aaagagatgg aggtgcttca cttaagaaat gtctcctttg aggacgcagg ggagtatacg 1020
tgcttggcgg gtaactctat cggactctcc catcactctg catggttgac cgttctggaa 1080
gccctggaag agaggccggc agtgatgacc tcgcccctgt acctggagat catcatctat 1140
tgcacagggg ccttcctcat ctcctgcatg gtggggtcgg tcatcgtcta caagatgaag 1200
agtggtacca agaagagtga cttccacagc cagatggctg tgcacaagct ggccaagagc 1260
atccctctgc gcagacaggt aacagtgtct gctgactcca gtgcatccat gaactctggg 1320
gttcttctgg ttcggccatc acggctctcc tccagtggga ctcccatgct agcaggggtc 1380
tctgagtatg agcttcccga agaccctcgc tgggagctgc ctcgggacag actggtctta 1440
ggcaaacccc tgggagaggg ctgctttggg caggtggtgt tggcagaggc tatcgggctg 1500
gacaaggaca aacccaaccg tgtgaccaaa gtggctgtga agatgttgaa gtcggacgca 1560
acagagaaag acttgtcaga cctgatctca gaaatggaga tgatgaagat gatcgggaag 1620
cataagaata tcatcaacct gctgggggcc tgcacgcagg atggtccctt gtatgtcatc 1680
gtggagtatg cctccaaggg caacctgcgg gagtacctgc aggcccggag gcccccaggg 1740
ctggaatact gctacaaccc cagccacaac ccagaggagc agctctcctc caaggacctg 1800
gtgtcctgcg cctaccaggt ggcccgaggc atggagtatc tggcctccaa gaagtgcata 1860
caccgagacc tggcagccag gaatgtcctg gtgacagagg acaatgtgat gaagatagca 1920
gactttggcc tcgcacggga cattcaccac atcgactact ataaaaagac aaccaacggc 1980
cgactgcctg tgaagtggat ggcacccgag gcattatttg accggatcta cacccaccag 2040

-continued

```
agtgatgtgt ggtctttcgg ggtgctcctg tgggagatct tcactctggg cggctcccca   2100

taccccggtg tgcctgtgga ggaacttttc aagctgctga aggagggtca ccgcatggac   2160

aagcccagta actgcaccaa cgagctgtac atgatgatgc gggactgctg gcatgcagtg   2220

ccctcacaga gacccacctt caagcagctg gtggaagacc tggaccgcat cgtggccttg   2280

acctccaacc aggagtacct ggacctgtcc atgcccctgg accagtactc ccccagcttt   2340

cccgacaccc ggagctctac gtgctcctca ggggaggatt ccgtcttctc tcatgagccg   2400

ctgcccgagg agccctgcct gccccgacac ccagcccagc ttgccaatgg cggactcaaa   2460

cgccgctga                                                           2469


<210> SEQ ID NO 72
<211> LENGTH: 2409
<212> TYPE: DNA
<213> ORGANISM: Homo sapiens
<300> PUBLICATION INFORMATION:
<302> TITLE: FGFR4
<310> PATENT DOCUMENT NUMBER: XM003910

<400> SEQUENCE: 72

atgcggctgc tgctggccct gttgggggtc ctgctgagtg tgcctgggcc tccagtcttg     60

tccctggagg cctctgagga agtggagctt gagccctgcc tggctcccag cctggagcag    120

caagagcagg agctgacagt agcccttggg cagcctgtgc ggctgtgctg tgggcgggct    180

gagcgtggtg gccactggta caaggagggc agtcgcctgg cacctgctgg ccgtgtacgg    240

ggctggaggg gccgcctaga gattgccagc ttcctacctg aggatgctgg ccgctacctc    300

tgcctggcac gaggctccat gatcgtcctg cagaatctca ccttgattac aggtgactcc    360

ttgacctcca gcaacgatga tgaggacccc aagtcccata gggacctctc gaataggcac    420

agttaccccc agcaagcacc ctactggaca cacccccagc gcatggagaa gaaactgcat    480

gcagtacctg cggggaacac cgtcaagttc cgctgtccag ctgcaggcaa ccccacgccc    540

accatccgct ggcttaagga tggacaggcc tttcatgggg agaaccgcat tggaggcatt    600

cggctgcgcc atcagcactg gagtctcgtg atggagagcg tggtgccctc ggaccgcggc    660

acatacacct gcctggtaga gaacgctgtg ggcagcatcc gttataacta cctgctagat    720

gtgctggagc ggtccccgca ccggcccatc ctgcaggccg ggctcccggc caacaccaca    780

gccgtggtgg gcagcgacgt ggagctgctg tgcaaggtgt acagcgatgc ccagccccac    840

atccagtggc tgaagcacat cgtcatcaac ggcagcagct tcggagccga cggtttcccc    900

tatgtgcaag tcctaaagac tgcagacatc aatagctcag aggtggaggt cctgtacctg    960

cggaacgtgt cagccgagga cgcaggcgag tacacctgcc tcgcaggcaa ttccatcggc   1020

ctctcctacc agtctgcctg gctcacggtg ctgccagagg aggaccccac atggaccgca   1080

gcagcgcccg aggccaggta tacggacatc atcctgtacg cgtcgggctc cctggccttg   1140

gctgtgctcc tgctgctggc caggctgtat cgagggcagg cgctccacgg ccggcacccc   1200

cgcccgcccg ccactgtgca gaagctctcc cgcttccctc tggcccgaca gttctccctg   1260

gagtcaggct cttccggcaa gtcaagctca tccctggtac gaggcgtgcg tctctcctcc   1320

agcggccccg ccttgctcgc cggcctcgtg agtctagatc tacctctcga cccactatgg   1380

gagttccccc gggacaggct ggtgcttggg aagcccctag gcgagggctg ctttggccag   1440

gtagtacgtg cagaggcctt tggcatggac cctgcccggc ctgaccaagc cagcactgtg   1500

gccgtcaaga tgctcaaaga caacgcctct gacaaggacc tggccgacct ggtctcggag   1560
```

atggaggtga tgaagctgat cggccgacac aagaacatca tcaacctgct tggtgtctgc 1620
acccaggaag ggcccctgta cgtgatcgtg gagtgcgccg ccaagggaaa cctgcgggag 1680
ttcctgcggg cccggcgccc cccaggcccc gacctcagcc ccgacggtcc tcggagcagt 1740
gaggggccgc tctccttccc agtcctggtc tcctgcgcct accaggtggc ccgaggcatg 1800
cagtatctgg agtcccggaa gtgtatccac cgggacctgg ctgcccgcaa tgtgctggtg 1860
actgaggaca atgtgatgaa gattgctgac tttgggctgg cccgcggcgt ccaccacatt 1920
gactactata agaaaaccag caacggccgc ctgcctgtga agtggatggc gcccgaggcc 1980
ttgtttgacc gggtgtacac acaccagagt gacgtgtggt cttttgggat cctgctatgg 2040
gagatcttca ccctcggggg ctccccgtat cctggcatcc cggtggagga gctgttctcg 2100
ctgctgcggg agggacatcg gatggaccga cccccacact gccccccaga gctgtacggg 2160
ctgatgcgtg agtgctggca cgcagcgccc tcccagaggc ctaccttcaa gcagctggtg 2220
gaggcgctgg acaaggtcct gctggccgtc tctgaggagt acctcgacct ccgcctgacc 2280
ttcggaccct attccccctc tggtggggac gccagcagca cctgctcctc cagcgattct 2340
gtcttcagcc acgaccccct gccattggga tccagctcct tccccttcgg gtctggggtg 2400
cagacatga 2409

<210> SEQ ID NO 73
<211> LENGTH: 1695
<212> TYPE: DNA
<213> ORGANISM: Homo sapiens
<300> PUBLICATION INFORMATION:
<302> TITLE: MT2MMP
<310> PATENT DOCUMENT NUMBER: D86331

<400> SEQUENCE: 73
atgaagcggc cccgctgtgg ggtgccagac cagttcgggg tacgagtgaa agccaacctg 60
cggcggcgtc ggaagcgcta cgccctcacc gggaggaagt ggaacaacca ccatctgacc 120
tttagcatcc agaactacac ggagaagttg ggctggtacc actcgatgga ggcggtgcgc 180
agggccttcc gcgtgtggga gcaggccacg cccctggtct tccaggaggt gccctatgag 240
gacatccggc tgcggcgaca gaaggaggcc gacatcatgg tactctttgc ctctggcttc 300
cacggcgaca gctcgccgtt tgatggcacc ggtggctttc tggcccacgc ctatttccct 360
ggccccggcc taggcgggga cacccatttt gacgcagatg agccctggac cttctccagc 420
actgacctgc atggaaacaa cctcttcctg gtggcagtgc atgagctggg ccacgcgctg 480
gggctggagc actccagcaa ccccaatgcc atcatggcgc cgttctacca gtggaaggac 540
gttgacaact tcaagctgcc cgaggacgat ctccgtggca tccagcagct ctacggtacc 600
ccagacggtc agccacagcc tacccagcct ctccccactg tgacgccacg gcggccaggc 660
cggcctgacc accggccgcc ccggcctccc cagccaccac ccccaggtgg gaagccagag 720
cggcccccaa agccgggccc ccagtccag ccccgagcca cagagcggcc cgaccagtat 780
ggccccaaca tctgcgacgg ggactttgac acagtggcca tgcttcgcgg ggagatgttc 840
gtgttcaagg gccgctggtt ctggcgagtc cggcacaacc gcgtcctgga caactatccc 900
atgcccatcg ggcacttctg gcgtggtctg cccggtgaca tcagtgctgc ctacgagcgc 960
caagacggtc gttttgtctt tttcaaaggt gaccgctact ggctctttcg agaagcgaac 1020
ctggagcccg gctacccaca gccgctgacc agctatggcc tgggcatccc ctatgaccgc 1080
attgacacgg ccatctggtg ggagcccaca ggccacacct tcttcttcca agaggacagg 1140

-continued

```
tactggcgct tcaacgagga gacacagcgt ggagaccctg ggtaccccaa gcccatcagt   1200

gtctggcagg ggatccctgc ctcccctaaa ggggccttcc tgagcaatga cgcagcctac   1260

acctacttct acaagggcac caaatactgg aaattcgaca atgagcgcct gcggatggag   1320

cccggctacc ccaagtccat cctgcgggac ttcatgggct gccaggagca cgtggagcca   1380

ggcccccgat ggcccgacgt ggcccggccg cccttcaacc cccacggggg tgcagagccc   1440

ggggcggaca gcgcagaggg cgacgtgggg gatggggatg gggactttgg ggccggggtc   1500

aacaaggaca ggggcagccg cgtggtggtg cagatggagg aggtggcacg gacggtgaac   1560

gtggtgatgg tgctggtgcc actgctgctg ctgctctgcg tcctgggcct cacctacgcg   1620

ctggtgcaga tgcagcgcaa gggtgcgcca cgtgtcctgc tttactgcaa gcgctcgctg   1680

caggagtggg tctga                                                    1695
```

```
<210> SEQ ID NO 74
<211> LENGTH: 1824
<212> TYPE: DNA
<213> ORGANISM: Homo sapiens
<300> PUBLICATION INFORMATION:
<302> TITLE: MT3MMP
<310> PATENT DOCUMENT NUMBER: D85511

<400> SEQUENCE: 74

atgatcttac tcacattcag cactggaaga cggttggatt tcgtgcatca ttcgggggtg     60

tttttcttgc aaaccttgct ttggatttta tgtgctacag tctgcggaac ggagcagtat    120

ttcaatgtgg aggtttggtt acaaaagtac ggctaccttc caccgactga ccccagaatg    180

tcagtgctgc gctctgcaga gaccatgcag tctgccctag ctgccatgca gcagttctat    240

ggcattaaca tgacaggaaa agtggacaga aacacaattg actggatgaa gaagccccga    300

tgcggtgtac ctgaccagac aagaggtagc tccaaatttc atattcgtcg aaagcgatat    360

gcattgacag gacagaaatg gcagcacaag cacatcactt acagtataaa gaacgtaact    420

ccaaaagtag gagaccctga gactcgtaaa gctattcgcc gtgcctttga tgtgtggcag    480

aatgtaactc ctctgacatt tgaagaagtt ccctacagtg aattagaaaa tggcaaacgt    540

gatgtggata taaccattat ttttgcatct ggtttccatg gggacagctc tccctttgat    600

ggagagggag gatttttggc acatgcctac ttccctggac caggaattgg aggagatacc    660

cattttgact cagatgagcc atggacacta ggaaatccta atcatgatgg aaatgactta    720

tttcttgtag cagtccatga actgggacat gctctgggat tggagcattc caatgacccc    780

actgccatca tggctccatt ttaccagtac atggaaacag acaacttcaa actacctaat    840

gatgatttac agggcatcca gaagatatat ggtccacctg acaagattcc tccacctaca    900

agacctctac cgacagtgcc cccacaccgc tctattcctc cggctgaccc aaggaaaaat    960

gacaggccaa aacctcctcg gcctccaacc ggcagaccct cctatcccgg agccaaaccc   1020

aacatctgtg atgggaactt taacactcta gctattcttc gtcgtgagat gtttgttttc   1080

aaggaccagt ggttttggcg agtgagaaac aacagggtga tggatggata cccaatgcaa   1140

attacttact tctggcgggg cttgcctcct agtatcgatg cagtttatga aaatagcgac   1200

gggaattttg tgttctttaa aggtaacaaa tattgggtgt tcaaggatac aactcttcaa   1260

cctggttacc ctcatgactt gataaccctt ggaagtggaa ttccccctca tggtattgat   1320

tcagccattt ggtgggagga cgtcgggaaa acctatttct tcaagggaga cagatattgg   1380

agatatagtg aagaaatgaa aacaatggac cctggctatc ccaagccaat cacagtctgg   1440
```

-continued

```
aaagggatcc ctgaatctcc tcagggagca tttgtacaca aagaaaatgg ctttacgtat   1500

ttctacaaag gaaaggagta ttggaaattc aacaaccaga tactcaaggt agaacctgga   1560

tatccaagat ccatcctcaa ggattttatg ggctgtgatg gaccaacaga cagagttaaa   1620

gaaggacaca gcccaccaga tgatgtagac attgtcatca aactggacaa cacagccagc   1680

actgtgaaag ccatagctat tgtcattccc tgcatcttgg ccttatgcct ccttgtattg   1740

gtttacactg tgttccagtt caagaggaaa ggaacacccc gccacatact gtactgtaaa   1800

cgctctatgc aagagtgggt gtga                                          1824
```

<210> SEQ ID NO 75
<211> LENGTH: 1818
<212> TYPE: DNA
<213> ORGANISM: Homo sapiens
<300> PUBLICATION INFORMATION:
<302> TITLE: MT4MMP
<310> PATENT DOCUMENT NUMBER: AB021225

<400> SEQUENCE: 75

```
atgcggcgcc gcgcagcccg gggacccggc ccgccgcccc cagggcccgg actctcgcgg     60

ctgccgctgc tgccgctgcc gctgctgctg ctgctggcgc tggggacccg cgggggctgc    120

gccgcgccgg aacccgcgcg gcgcgccgag gacctcagcc tgggagtgga gtggctaagc    180

aggttcggtt acctgccccc ggctgacccc acaacagggc agctgcagac gcaagaggag    240

ctgtctaagg ccatcacagc catgcagcag tttggtggcc tggaggccac cggcatcctg    300

gacgaggcca ccctggccct gatgaaaacc ccacgctgct ccctgccaga cctccctgtc    360

ctgacccagg ctcgcaggag acgccaggct ccagccccca ccaagtggaa caagaggaac    420

ctgtcgtgga gggtccggac gttcccacgg gactcaccac tggggcacga cacggtgcgt    480

gcactcatgt actacgccct caaggtctgg agcgacattg cgcccctgaa cttccacgag    540

gtggcgggca gcaccgccga catccagatc gacttctcca aggccgacca taacgacggc    600

taccccttcg acgcccggcg gcaccgtgcc cacgccttct tccccggcca ccaccacacc    660

gccgggtaca cccactttaa cgatgacgag gcctggacct tccgctcctc ggatgcccac    720

gggatggacc tgtttgcagt ggctgtccac gagtttggcc acgccattgg gttaagccat    780

gtggccgctg cacactccat catgcggccg tactaccagg gcccggtggg tgacccgctg    840

cgctacgggc tcccctacga ggacaaggtg cgcgtctggc agctgtacgg tgtgcgggag    900

tctgtgtctc ccacggcgca gcccgaggag cctcccctgc tgccggagcc cccagacaac    960

cggtccagcg ccccgcccag gaaggacgtg ccccacagat gcagcactca ctttgacgcg   1020

gtggcccaga tccggggtga agctttcttc ttcaaaggca agtacttctg gcggctgacg   1080

cgggaccggc acctggtgtc cctgcagccg gcacagatgc accgcttctg gcggggcctg   1140

ccgctgcacc tggacagcgt ggacgccgtg tacgagcgca ccagcgacca caagatcgtc   1200

ttctttaaag gagacaggta ctgggtgttc aaggacaata acgtagagga aggatacccg   1260

cgccccgtct ccgacttcag cctcccgcct ggcggcatcg acgctgcctt ctcctgggcc   1320

cacaatgaca ggacttattt ctttaaggac cagctgtact ggcgctacga tgaccacacg   1380

aggcacatgg accccggcta ccccgcccag agccccctgt ggaggggtgt ccccagcacg   1440

ctggacgacg ccatgcgctg gtccgacggt gcctcctact tcttccgtgg ccaggagtac   1500

tggaaagtgc tggatggcga gctggaggtg gcacccgggt acccacagtc cacggcccgg   1560

gactggctgg tgtgtggaga ctcacaggcc gatggatctg tggctgcggg cgtggacgcg   1620
```

gcagaggggc cccgcgcccc tccaggacaa catgaccaga gccgctcgga ggacggttac 1680
gaggtctgct catgcacctc tggggcatcc tctcccccgg gggccccagg cccactggtg 1740
gctgccacca tgctgctgct gctgccgcca ctgtcaccag gcgccctgtg gacagcggcc 1800
caggccctga cgctatga 1818

<210> SEQ ID NO 76
<211> LENGTH: 1938
<212> TYPE: DNA
<213> ORGANISM: Homo sapiens
<300> PUBLICATION INFORMATION:
<302> TITLE: MT5MMP
<310> PATENT DOCUMENT NUMBER: AB021227

<400> SEQUENCE: 76
atgccgagga gccggggcgg ccgcgccgcg ccggggccgc cgccgccgcc gccgccgccg 60
ggccaggccc cgcgctggag ccgctggcgg gtccctgggc ggctgctgct gctgctgctg 120
cccgcgctct gctgcctccc gggcgccgcg cgggcggcgg cggcggcggc gggggcaggg 180
aaccgggcag cggtggcggt ggcggtggcg cgggcggacg aggcggaggc gcccttcgcc 240
gggcagaact ggttaaagtc ctatggctat ctgcttccct atgactcacg ggcatctgcg 300
ctgcactcag cgaaggcctt gcagtcggca gtctccacta tgcagcagtt ttacgggatc 360
ccggtcaccg gtgtgttgga tcagacaacg atcgagtgga tgaagaaacc ccgatgtggt 420
gtccctgatc acccccactt aagccgtagg cggagaaaca agcgctatgc cctgactgga 480
cagaagtgga ggcaaaaaca catcacctac agcattcaca actataccccc aaaagtgggt 540 gagctagaca cgcggaaagc tattcgccag gctttcgatg tgtggcagaa ggtgacccca 600
ctgacctttg aagaggtgcc ataccatgag atcaaaagtg accggaagga ggcagacatc 660
atgatctttt ttgcttctgg tttccatggc gacagctccc catttgatgg agaaggggga 720
ttcctggccc atgcctactt ccctggccca gggattggag gagacaccca ctttgactcc 780
gatgagccat ggacgctagg aaacgccaac catgacggga acgacctctt cctggtggct 840
gtgcatgagc tgggccacgc gctgggactg gagcactcca gcgaccccag cgccatcatg 900
gcgcccttct accagtacat ggagacgcac aacttcaagc tgccccagga cgatctccag 960
ggcatccaga agatctatgg acccccagcc gagcctctgg agcccacaag gccactccct 1020
acactccccg tccgcaggat ccactcacca tcggagagga aacacgagcg ccagcccagg 1080
ccccctcggc cgcccctcgg ggaccggcca tccacaccag gcaccaaacc caacatctgt 1140
gacggcaact tcaacacagt ggccctcttc cggggcgaga tgtttgtctt taaggatcgc 1200
tggttctggc gtctgcgcaa taaccgagtg caggagggct accccatgca gatcgagcag 1260
ttctggaagg gcctgcctgc ccgcatcgac gcagcctatg aaagggccga tgggagattt 1320
gtcttcttca aaggtgacaa gtattgggtg tttaaggagg tgacggtgga gcctgggtac 1380
ccccacagcc tgggggagct gggcagctgt ttgccccgtg aaggcattga cacagctctg 1440
cgctgggaac ctgtgggcaa gacctacttt ttcaaaggcg agcggtactg gcgctacagc 1500
gaggagcggc gggccacgga ccctggctac cctaagccca tcaccgtgtg gaagggcatc 1560
ccacaggctc cccaaggagc cttcatcagc aaggaaggat attacaccta tttctacaag 1620
ggccgggact actggaagtt tgacaaccag aaactgagcg tggagccagg ctacccgcgc 1680
aacatcctgc gtgactggat gggctgcaac cagaaggagg tggagcggcg gaaggagcgg 1740
cggctgcccc aggacgacgt ggacatcatg gtgaccatca acgatgtgcc gggctccgtg 1800
aacgccgtgg ccgtggtcat cccctgcatc ctgtccctct gcatcctggt gctggtctac 1860
accatcttcc agttcaagaa caagacaggc cctcagcctg tcacctacta taagcggcca 1920
gtccaggaat gggtgtga 1938

<210> SEQ ID NO 77
<211> LENGTH: 1689
<212> TYPE: DNA
<213> ORGANISM: Homo sapiens
<300> PUBLICATION INFORMATION:
<302> TITLE: MT6MMP
<310> PATENT DOCUMENT NUMBER: AJ27137

<400> SEQUENCE: 77
atgcggctgc ggctccggct tctggcgctg ctgcttctgc tgctggcacc gcccgcgcgc 60
gccccgaagc cctcggcgca ggacgtgagc ctgggcgtgg actggctgac tcgctatggt 120
tacctgccgc caccccaccc tgcccaggcc cagctgcaga gccctgagaa gttgcgcgat 180
gccatcaaag tcatgcagag gttcgcgggg ctgccggaga ccggccgcat ggacccaggg 240
acagtggcca ccatgcgtaa gccccgctgc tccctgcctg acgtgctggg ggtggcgggg 300
ctggtcaggc ggcgtcgccg gtacgctctg agcggcagcg tgtggaagaa gcgaaccctg 360
acatggaggg tacgttcctt cccccagagc tcccagctga gccaggagac cgtgcgggtc 420
ctcatgagct atgccctgat ggcctggggc atggagtcag gcctcacatt tcatgaggtg 480
gattcccccc agggccagga gcccgacatc ctcatcgact ttgcccgcgc cttccaccag 540
gacagctacc ccttcgacgg gttgggggggc accctagccc atgccttctt ccctggggag 600
caccccatct ccggggacac tcactttgac gatgaggaga cctggacttt tgggtcaaaa 660
gacggcgagg ggaccgacct gtttgccgtg gctgtccatg agtttggcca cgccctgggc 720
ctgggccact cctcagcccc caactccatt atgaggccct tctaccaggg tccggtgggc 780
gaccctgaca agtaccgcct gtctcaggat gaccgcgatg gcctgcagca actctatggg 840
aaggcgcccc aaaccccata tgacaagccc acaaggaaac ccctggctcc tccgccccag 900
cccccggcct cgcccacaca cagcccatcc ttccccatcc ctgatcgatg tgagggcaat 960
tttgacgcca tcgccaacat ccgaggggaa actttcttct tcaaaggccc ctggttctgg 1020
cgcctccagc cctccggaca gctggtgtcc ccgcgacccg cacggctgca ccgcttctgg 1080
gaggggctgc ccgcccaggt gagggtggtg caggccgcct atgctcggca ccgagacggc 1140
cgaatcctcc tctttagcgg gccccagttc tgggtgttcc aggaccggca gctggagggc 1200
ggggcgcggc cgctcacgga gctggggctg cccccgggag aggaggtgga cgccgtgttc 1260
tcgtggccac agaacgggaa gacctacctg gtccgcggcc ggcagtactg gcgctacgac 1320
gaggcggcgg cgcgcccgga ccccggctac cctcgcgacc tgagcctctg ggaaggcgcg 1380 ccccccctccc ctgacgatgt caccgtcagc aacgcaggtg acacctactt cttcaagggc 1440
gcccactact ggcgcttccc caagaacagc atcaagaccg agccggacgc cccccagccc 1500
atggggccca actggctgga ctgccccgcc ccgagctctg gtccccgcgc cccccaggccc 1560 cccaaagcga cccccgtgtc cgaaacctgc gattgtcagt gcgagctcaa ccaggccgca 1620
ggacgttggc ctgctcccat cccgctgctc ctcttgcccc tgctggtggg gggtgtagcc 1680
tcccgctga 1689

<210> SEQ ID NO 78
<211> LENGTH: 1749
<212> TYPE: DNA

<213> ORGANISM: Homo sapiens
<300> PUBLICATION INFORMATION:
<302> TITLE: MTMMP
<310> PATENT DOCUMENT NUMBER: X90925

<400> SEQUENCE: 78
atgtctcccg ccccaagacc ctcccgttgt ctcctgctcc ccctgctcac gctcggcacc 60
gcgctcgcct ccctcggctc ggcccaaagc agcagcttca gccccgaagc ctggctacag 120
caatatggct acctgcctcc cggggaccta cgtacccaca cacagcgctc accccagtca 180
ctctcagcgg ccatcgctgc catgcagaag ttttacggct tgcaagtaac aggcaaagct 240
gatgcagaca ccatgaaggc catgaggcgc ccccgatgtg gtgttccaga caagtttggg 300
gctgagatca aggccaatgt tcgaaggaag cgctacgcca tccagggtct caaatggcaa 360
cataatgaaa tcactttctg catccagaat tacaccccca aggtgggcga gtatgccaca 420
tacgaggcca ttcgcaaggc gttccgcgtg tgggagagtg ccacaccact gcgcttccgc 480
gaggtgccct atgcctacat ccgtgagggc catgagaagc aggccgacat catgatcttc 540
tttgccgagg gcttccatgg cgacagcacg cccttcgatg gtgagggcgg cttcctggcc 600
catgcctact tcccaggccc caacattgga ggagacaccc actttgactc tgccgagcct 660
tggactgtca ggaatgagga tctgaatgga aatgacatct tcctggtggc tgtgcacgag 720
ctgggccatg ccctggggct cgagcattcc agtgacccct cggccatcat ggcacccttt 780
taccagtgga tggacacgga gaattttgtg ctgcccgatg atgaccgccg gggcatccag 840
caactttatg gggtgagtc agggttcccc accaagatgc cccctcaacc caggactacc 900
tcccggcctt ctgttcctga taaacccaaa aaccccacct atgggcccaa catctgtgac 960
gggaactttg acaccgtggc catgctccga ggggagatgt ttgtcttcaa ggagcgctgg 1020
ttctggcggg tgaggaataa ccaagtgatg gatggatacc caatgcccat tggccagttc 1080
tggcggggcc tgcctgcgtc catcaacact gcctacgaga ggaaggatgg caaattcgtc 1140
ttcttcaaag gagacaagca ttgggtgttt gatgaggcgt ccctggaacc tggctacccc 1200
aagcacatta aggagctggg ccgagggctg cctaccgaca agattgatgc tgctctcttc 1260
tggatgccca atggaaagac ctacttcttc cgtggaaaca agtactaccg tttcaacgaa 1320
gagctcaggg cagtggatag cgagtacccc aagaacatca aagtctggga agggatccct 1380
gagtctccca gagggtcatt catgggcagc gatgaagtct tcacttactt ctacaagggg 1440
aacaaatact ggaaattcaa caaccagaag ctgaaggtag aaccgggcta ccccaagcca 1500
gccctgaggg actggatggg ctgcccatcg ggaggccggc cggatgaggg gactgaggag 1560
gagacggagg tgatcatcat tgaggtggac gaggagggcg gcggggcggt gagcgcggct 1620
gccgtggtgc tgcccgtgct gctgctgctc ctggtgctgg cggtgggcct tgcagtcttc 1680
ttcttcagac gccatgggac ccccaggcga ctgctctact gccagcgttc cctgctggac 1740
aaggtctga 1749

<210> SEQ ID NO 79
<211> LENGTH: 744
<212> TYPE: DNA
<213> ORGANISM: Homo sapiens
<300> PUBLICATION INFORMATION:
<302> TITLE: FGF1
<310> PATENT DOCUMENT NUMBER: XM003647

<400> SEQUENCE: 79
atggccgcgg ccatcgctag cggcttgatc cgccagaagc ggcaggcgcg ggagcagcac 60
tgggaccggc cgtctgccag caggaggcgg agcagcccca gcaagaaccg cgggctctgc 120
aacggcaacc tggtggatat cttctccaaa gtgcgcatct tcggcctcaa gaagcgcagg 180
ttgcggcgcc aagatcccca gctcaagggt atagtgacca ggttatattg caggcaaggc 240
tactacttgc aaatgcaccc cgatggagct ctcgatggaa ccaaggatga cagcactaat 300
tctacactct tcaacctcat accagtggga ctacgtgttg ttgccatcca gggagtgaaa 360
acagggttgt atatagccat gaatggagaa ggttacctct acccatcaga actttttacc 420
cctgaatgca agtttaaaga atctgttttt gaaaattatt atgtaatcta ctcatccatg 480
ttgtacagac aacaggaatc tggtagagcc tggtttttgg gattaaataa ggaagggcaa 540
gctatgaaag ggaacagagt aaagaaaacc aaaccagcag ctcattttct acccaagcca 600
ttggaagttg ccatgtaccg agaaccatct ttgcatgatg ttggggaaac ggtcccgaag 660
cctggggtga cgccaagtaa aagcacaagt gcgtctgcaa taatgaatgg aggcaaacca 720
gtcaacaaga gtaagacaac atag 744

<210> SEQ ID NO 80
<211> LENGTH: 468
<212> TYPE: DNA
<213> ORGANISM: Homo sapiens
<300> PUBLICATION INFORMATION:
<302> TITLE: FGF2
<310> PATENT DOCUMENT NUMBER: NM002006

<400> SEQUENCE: 80
atggcagccg ggagcatcac cacgctgccc gccttgcccg aggatggcgg cagcggcgcc 60
ttcccgcccg gccacttcaa ggaccccaag cggctgtact gcaaaaacgg gggcttcttc 120
ctgcgcatcc accccgacgg ccgagttgac ggggtccggg agaagagcga ccctcacatc 180
aagctacaac ttcaagcaga agagagagga gttgtgtcta tcaaaggagt gtgtgctaac 240
cgttacctgg ctatgaagga agatggaaga ttactggctt ctaaatgtgt tacggatgag 300
tgtttctttt ttgaacgatt ggaatctaat aactacaata cttaccggtc aaggaaatac 360
accagttggt atgtggcact gaaacgaact gggcagtata aacttggatc caaaacagga 420
cctgggcaga aagctatact tttcttccca atgtctgcta agagctga 468

<210> SEQ ID NO 81
<211> LENGTH: 756
<212> TYPE: DNA
<213> ORGANISM: Homo sapiens
<300> PUBLICATION INFORMATION:
<302> TITLE: FGF23
<310> PATENT DOCUMENT NUMBER: NM020638

<400> SEQUENCE: 81
atgttggggg cccgcctcag gctctgggtc tgtgccttgt gcagcgtctg cagcatgagc 60
gtcctcagag cctatcccaa tgcctcccca ctgctcggct ccagctgggg tggcctgatc 120
cacctgtaca cagccacagc caggaacagc taccacctgc agatccacaa gaatggccat 180
gtggatggcg caccccatca gaccatctac agtgccctga tgatcagatc agaggatgct 240
ggctttgtgg tgattacagg tgtgatgagc agaagatacc tctgcatgga tttcagaggc 300
aacatttttg gatcacacta tttcgacccg gagaactgca ggttccaaca ccagacgctg 360
gaaaacgggt acgacgtcta ccactctcct cagtatcact tcctggtcag tctgggccgg 420
gcgaagagag ccttcctgcc aggcatgaac ccaccccgt actcccagtt cctgtcccgg 480

```
aggaacgaga tccccctaat tcacttcaac acccccatac cacggcggca cacccggagc    540

gccgaggacg actcggagcg ggaccccctg aacgtgctga agccccgggc ccggatgacc    600

ccggccccgg cctcctgttc acaggagctc ccgagcgccg aggacaacag cccgatggcc    660

agtgacccat taggggtggt caggggcggt cgagtgaaca cgcacgctgg gggaacgggc    720

ccggaaggct gccgcccctt cgccaagttc atctag                              756
```

<210> SEQ ID NO 82
<211> LENGTH: 720
<212> TYPE: DNA
<213> ORGANISM: Homo sapiens
<300> PUBLICATION INFORMATION:
<302> TITLE: FGF3
<310> PATENT DOCUMENT NUMBER: NM005247

<400> SEQUENCE: 82

```
atgggcctaa tctggctgct actgctcagc ctgctggagc ccggctggcc cgcagcgggc     60

cctggggcgc ggttgcggcg cgatgcgggc ggccgtggcg gcgtctacga gcaccttggc    120

ggggcgcccc ggcgccgcaa gctctactgc gccacgaagt accacctcca gctgcacccg    180

agcggccgcg tcaacggcag cctggagaac agcgcctaca gtattttgga gataacggca    240

gtggaggtgg gcattgtggc catcaggggt ctcttctccg ggcggtacct ggccatgaac    300

aagaggggac gactctatgc ttcggagcac tacagcgccg agtgcgagtt tgtggagcgg    360

atccacgagc tgggctataa tacgtatgcc tcccggctgt accggacggt gtctagtacg    420

cctggggccc gccggcagcc cagcgccgag agactgtggt acgtgtctgt gaacggcaag    480

ggccggcccc gcaggggctt caagacccgc cgcacacaga agtcctccct gttcctgccc    540

cgcgtgctgg accacaggga ccacgagatg gtgcggcagc tacagagtgg gctgcccaga    600

ccccctggta agggggtcca gccccgacgg cggcggcaga agcagagccc ggataacctg    660

gagccctctc acgttcaggc ttcgagactg ggctcccagc tggaggccag tgcgcactag    720
```

<210> SEQ ID NO 83
<211> LENGTH: 807
<212> TYPE: DNA
<213> ORGANISM: Homo sapiens
<300> PUBLICATION INFORMATION:
<302> TITLE: FGF5
<310> PATENT DOCUMENT NUMBER: NM004464

<400> SEQUENCE: 83

```
atgagcttgt ccttcctcct cctcctcttc ttcagccacc tgatcctcag cgcctgggct     60

cacggggaga agcgtctcgc ccccaaaggg caacccggac ccgctgccac tgataggaac    120

cctataggct ccagcagcag acagagcagc agtagcgcta tgtcttcctc ttctgcctcc    180

tcctcccccg cagcttctct gggcagccaa ggaagtggct tggagcagag cagtttccag    240

tggagcccct cggggcgccg gaccggcagc ctctactgca gagtgggcat cggtttccat    300

ctgcagatct acccggatgg caaagtcaat ggatcccacg aagccaatat gttaagtgtt    360

ttggaaatat ttgctgtgtc tcaggggatt gtaggaatac gaggagtttt cagcaacaaa    420

tttttagcga tgtcaaaaaa aggaaaactc catgcaagtg ccaagttcac agatgactgc    480

aagttcaggg agcgttttca agaaaatagc tataatacct atgcctcagc aatacataga    540

actgaaaaaa cagggcggga gtggtatgtt gccctgaata aaagaggaaa agccaaacga    600

gggtgcagcc cccgggttaa accccagcat atctctaccc attttcttcc aagattcaag    660

cagtcggagc agccagaact ttctttcacg gttactgttc ctgaaaagaa aaatccacct    720
```

agccctatca agtcaaagat tcccctttct gcacctcgga aaaataccaa ctcagtgaaa 780
tacagactca agtttcgctt tggataa 807

<210> SEQ ID NO 84
<211> LENGTH: 649
<212> TYPE: DNA
<213> ORGANISM: Homo sapiens
<300> PUBLICATION INFORMATION:
<302> TITLE: FGF8
<310> PATENT DOCUMENT NUMBER: NM006119

<400> SEQUENCE: 84
atgggcagcc cccgctccgc gctgagctgc ctgctgttgc acttgctggt cctctgcctc 60
caagcccagg taactgttca gtcctcacct aattttacac agcatgtgag ggagcagagc 120
ctggtgacgg atcagctcag ccgccgcctc atccggacct accaactcta cagccgcacc 180
agcgggaagc acgtgcaggt cctggccaac aagcgcatca acgccatggc agaggacggc 240 gacccetteg caaagctcat cgtggagacg gacacctttg gaagcagagt tcgagtccga 300
ggagccgaga cgggcctcta catctgcatg aacaagaagg ggaagctgat cgccaagagc 360
aacggcaaag gcaaggactg cgtcttcacg gagattgtgc tggagaacaa ctacacagcg 420
ctgcagaatg ccaagtacga gggctggtac atggccttca cccgcaaggg ccggccccgc 480
aagggctcca agacgcggca gcaccagcgt gaggtccact tcatgaagcg gctgccccgg 540
ggccaccaca ccaccgagca gagcctgcgc ttcgagttcc tcaactaccc gcccttcacg 600
cgcagcctgc gcggcagcca gaggacttgg gccccggaac cccgatagg 649

<210> SEQ ID NO 85
<211> LENGTH: 2466
<212> TYPE: DNA
<213> ORGANISM: Homo sapiens
<300> PUBLICATION INFORMATION:
<302> TITLE: FGFR2
<310> PATENT DOCUMENT NUMBER: NM000141

<400> SEQUENCE: 85
atggtcagct ggggtcgttt catctgcctg gtcgtggtca ccatggcaac cttgtccctg 60
gcccggccct ccttcagttt agttgaggat accacattag agccagaaga gccaccaacc 120
aaataccaaa tctctcaacc agaagtgtac gtggctgcgc caggggagtc gctagaggtg 180
cgctgcctgt tgaaagatgc cgccgtgatc agttggacta aggatggggt gcacttgggg 240
cccaacaata ggacagtgct tattggggag tacttgcaga taaagggcgc cacgcctaga 300
gactccggcc tctatgcttg tactgccagt aggactgtag acagtgaaac ttggtacttc 360
atggtgaatg tcacagatgc catctcatcc ggagatgatg aggatgacac cgatggtgcg 420
gaagattttg tcagtgagaa cagtaacaac aagagagcac catactggac caacacagaa 480
aagatggaaa agcggctcca tgctgtgcct gcggccaaca ctgtcaagtt tcgctgccca 540
gccgggggga acccaatgcc aaccatgcgg tggctgaaaa acgggaagga gtttaagcag 600
gagcatcgca ttggaggcta caaggtacga aaccagcact ggagcctcat tatggaaagt 660
gtggtcccat ctgacaaggg aaattatacc tgtgtggtgg agaatgaata cgggtccatc 720
aatcacacgt accacctgga tgttgtggag cgatcgcctc accggcccat cctccaagcc 780
ggactgccgg caaatgcctc cacagtggtc ggaggagacg tagagtttgt ctgcaaggtt 840
tacagtgatg cccagcccca catccagtgg atcaagcacg tggaaaagaa cggcagtaaa 900

-continued

```
tacgggcccg acgggctgcc ctacctcaag gttctcaagg ccgccggtgt taacaccacg    960
gacaaagaga ttgaggttct ctatattcgg aatgtaactt ttgaggacgc tggggaatat   1020
acgtgcttgg cgggtaattc tattgggata tcctttcact ctgcatggtt gacagttctg   1080
ccagcgcctg gaagagaaaa ggagattaca gcttccccag actacctgga gatagccatt   1140
tactgcatag gggtcttctt aatcgcctgt atggtggtaa cagtcatcct gtgccgaatg   1200
aagaacacga ccaagaagcc agacttcagc agccagccgg ctgtgcacaa gctgaccaaa   1260
cgtatccccc tgcggagaca ggtaacagtt tcggctgagt ccagctcctc catgaactcc   1320
aacaccccgc tggtgaggat aacaacacgc ctctcttcaa cggcagacac cccatgctg    1380
gcaggggtct ccgagtatga acttccagag gacccaaaat gggagtttcc aagagataag   1440
ctgacactgg gcaagcccct gggagaaggt tgctttgggc aagtggtcat ggcggaagca   1500
gtgggaattg acaaagacaa gcccaaggag gcggtcaccg tggccgtgaa gatgttgaaa   1560
gatgatgcca cagagaaaga cctttctgat ctggtgtcag agatggagat gatgaagatg   1620
attgggaaac acaagaatat cataaatctt cttggagcct gcacacagga tgggcctctc   1680
tatgtcatag ttgagtatgc ctctaaaggc aacctccgag aatacctccg agcccggagg   1740
ccacccggga tggagtactc ctatgacatt aaccgtgttc ctgaggagca gatgaccttc   1800
aaggacttgg tgtcatgcac ctaccagctg gccagaggca tggagtactt ggcttcccaa   1860
aaatgtattc atcgagattt agcagccaga aatgttttgg taacagaaaa caatgtgatg   1920
aaaatagcag actttggact cgccagagat atcaacaata tagactatta caaaaagacc   1980
accaatgggc ggcttccagt caagtggatg gctccagaag ccctgtttga tagagtatac   2040
actcatcaga gtgatgtctg gtccttcggg gtgttaatgt gggagatctt cactttaggg   2100
ggctcgccct acccagggat tcccgtggag gaacttttta agctgctgaa ggaaggacac   2160
agaatggata agccagccaa ctgcaccaac gaactgtaca tgatgatgag ggactgttgg   2220
catgcagtgc cctcccagag accaacgttc aagcagttgg tagaagactt ggatcgaatt   2280
ctcactctca caaccaatga ggaatacttg gacctcagcc aacctctcga acagtattca   2340
cctagttacc ctgacacaag aagttcttgt tcttcaggag atgattctgt tttttctcca   2400
gaccccatgc cttacgaacc atgccttcct cagtatccac acataaacgg cagtgttaaa   2460
acatga                                                              2466
```

<210> SEQ ID NO 86
<211> LENGTH: 2421
<212> TYPE: DNA
<213> ORGANISM: Homo sapiens
<300> PUBLICATION INFORMATION:
<302> TITLE: FGFR3
<310> PATENT DOCUMENT NUMBER: NM000142

<400> SEQUENCE: 86

```
atgggcgccc ctgcctgcgc cctcgcgctc tgcgtggccg tggccatcgt ggccggcgcc     60
tcctcggagt ccttggggac ggagcagcgc gtcgtggggc gagcggcaga agtcccgggc    120
ccagagcccg gccagcagga gcagttggtc ttcggcagcg gggatgctgt ggagctgagc    180
tgtcccccgc ccgggggtgg tcccatgggg cccactgtct gggtcaagga tggcacaggg    240
ctggtgccct cggagcgtgt cctggtgggg ccccagcggc tgcaggtgct gaatgcctcc    300
cacgaggact ccggggccta cagctgccgg cagcggctca cgcagcgcgt actgtgccac    360
ttcagtgtgc gggtgacaga cgctccatcc tcgggagatg acgaagacgg ggaggacgag    420
```

gctgaggaca caggtgtgga cacaggggcc ccttactgga cacggcccga gcggatggac 480
aagaagctgc tggccgtgcc ggccgccaac accgtccgct tccgctgccc agccgctggc 540
aaccccactc cctccatctc ctggctgaag aacggcaggg agttccgcgg cgagcaccgc 600
attggaggca tcaagctgcg gcatcagcag tggagcctgg tcatggaaag cgtggtgccc 660
tcggaccgcg gcaactacac ctgcgtcgtg gagaacaagt ttggcagcat ccggcagacg 720
tacacgctgg acgtgctgga gcgctccccg caccggccca tcctgcaggc ggggctgccg 780
gccaaccaga cggcggtgct gggcagcgac gtggagttcc actgcaaggt gtacagtgac 840
gcacagcccc acatccagtg gctcaagcac gtggaggtga acggcagcaa ggtgggcccg 900
gacggcacac cctacgttac cgtgctcaag acggcgggcg ctaacaccac cgacaaggag 960
ctagaggttc tctccttgca caacgtcacc tttgaggacg ccggggagta cacctgcctg 1020
gcgggcaatt ctattgggtt ttctcatcac tctgcgtggc tggtggtgct gccagccgag 1080
gaggagctgg tggaggctga cgaggcgggc agtgtgtatg caggcatcct cagctacggg 1140
gtgggcttct tcctgttcat cctggtggtg gcggctgtga cgctctgccg cctgcgcagc 1200
ccccccaaga aaggcctggg ctcccccacc gtgcacaaga tctcccgctt cccgctcaag 1260
cgacaggtgt ccctggagtc caacgcgtcc atgagctcca acacaccact ggtgcgcatc 1320
gcaaggctgt cctcagggga gggccccacg ctggccaatg tctccgagct cgagctgcct 1380
gccgacccca aatgggagct gtctcgggcc cggctgaccc tgggcaagcc ccttggggag 1440
ggctgcttcg gccaggtggt catggcggag gccatcggca ttgacaagga ccgggccgcc 1500
aagcctgtca ccgtagccgt gaagatgctg aaagacgatg ccactgacaa ggacctgtcg 1560
gacctggtgt ctgagatgga gatgatgaag atgatcggga aacacaaaaa catcatcaac 1620
ctgctgggcg cctgcacgca gggcgggccc ctgtacgtgc tggtggagta cgcggccaag 1680
ggtaacctgc gggagtttct gcgggcgcgg cggcccccgg gcctggacta ctccttcgac 1740
acctgcaagc cgcccgagga gcagctcacc ttcaaggacc tggtgtcctg tgcctaccag 1800
gtggcccggg gcatggagta cttggcctcc cagaagtgca tccacaggga cctggctgcc 1860
cgcaatgtgc tggtgaccga ggacaacgtg atgaagatcg cagacttcgg gctggcccgg 1920
gacgtgcaca acctcgacta ctacaagaag acaaccaacg gccggctgcc cgtgaagtgg 1980
atggcgcctg aggccttgtt tgaccgagtc tacactcacc agagtgacgt ctggtccttt 2040
ggggtcctgc tctgggagat cttcacgctg gggggctccc cgtaccccgg catccctgtg 2100
gaggagctct tcaagctgct gaaggagggc caccgcatgg acaagcccgc caactgcaca 2160
cacgacctgt acatgatcat gcgggagtgc tggcatgccg cgccctccca gaggcccacc 2220
ttcaagcagc tggtggagga cctggaccgt gtccttaccg tgacgtccac cgacgagtac 2280
ctggacctgt cggcgccttt cgagcagtac tccccgggtg gccaggacac ccccagctcc 2340
agctcctcag gggacgactc cgtgtttgcc cacgacctgc tgcccccggc cccacccagc 2400
agtgggggct cgcggacgtg a 2421

<210> SEQ ID NO 87
<211> LENGTH: 2102
<212> TYPE: DNA
<213> ORGANISM: Homo sapiens
<300> PUBLICATION INFORMATION:
<302> TITLE: HGF
<310> PATENT DOCUMENT NUMBER: E08541

<400> SEQUENCE: 87

-continued

```
atgcagaggg acaaaggaaa agaagaaata caattcatga attcaaaaaa tcagcaaaga      60
ctaccctaat caaaatagat ccagcactga agataaaaac caaaaaagtg aatactgcag     120
accaatgtgc taatagatgt actaggaata aaggacttcc attcacttgc aaggcttttg     180
tttttgataa agcaagaaaa caatgcctct ggttcccctt caatagcatg tcaagtggag     240
tgaaaaaaga atttggccat gaatttgacc tctatgaaaa caaagactac attagaaact     300
gcatcattgg taaaggacgc agctacaagg gaacagtatc tatcactaag agtggcatca     360
aatgtcagcc ctggagttcc atgataccac acgaacacag ctttttgcct tcgagctatc     420
ggggtaaaga cctacaggaa aactactgtc gaaatcctcg aggggaagaa gggggaccct     480
ggtgtttcac aagcaatcca gaggtacgct acgaagtctg tgacattcct cagtgttcag     540
aagttgaatg catgacctgc aatggggaga gttatcgagg tctcatggat catacagaat     600
caggcaagat ttgtcagcgc tgggatcatc agacaccaca ccggcacaaa ttcttgcctg     660
aaagatatcc cgacaagggc tttgatgata attattgccg caatcccgat ggccagccga     720
ggccatggtg ctatactctt gaccctcaca cccgctggga gtactgtgca attaaaacat     780
gcgctgacaa tactatgaat gacactgatg ttcctttgga aacaactgaa tgcatccaag     840
gtcaaggaga aggctacagg ggcactgtca ataccatttg gaatggaatt ccatgtcagc     900
gttgggattc tcagtatcct cacgagcatg acatgactcc tgaaaatttc aagtgcaagg     960
acctacgaga aaattactgc cgaaatccag atgggtctga atcaccctgg tgttttacca    1020
ctgatccaaa catccgagtt ggctactgct cccaaattcc aaactgtgat atgtcacatg    1080
gacaagattg ttatcgtggg aatggcaaaa attatatggg caacttatcc caaacaagat    1140
ctggactaac atgttcaatg tgggacaaga acatggaaga cttacatcgt catatcttct    1200
gggaaccaga tgcaagtaag ctgaatgaga attactgccg aaatccagat gatgatgctc    1260
atggaccctg gtgctacacg ggaaatccac tcattccttg ggattattgc cctatttctc    1320
gttgtgaagg tgataccaca cctacaatag tcaatttaga ccatcccgta atatcttgtg    1380
ccaaaaggaa acaattgcga gttgtaaatg ggattccaac acgaacaaac ataggatgga    1440
tggttagttt gagatacaga aataaacata tctgcggagg atcattgata aaggagagtt    1500
gggttcttac tgcacgacag tgtttccctt ctcgagactt gaaagattat gaagcttggc    1560
ttggaattca tgatgtccac ggaagaggag atgagaaatg caaacaggtt ctcaatgttt    1620
cccagctggt atatggccct gaaggatcag atctggtttt aatgaagctt gccaggcctg    1680
ctgtcctgga tgattttgtt agtacgattg atttacctaa ttatggatgc acaattcctg    1740
aaaagaccag ttgcagtgtt tatggctggg gctacactgg attgatcaac tatgatggcc    1800
tattacgagt ggcacatctc tatataatgg gaaatgagaa atgcagccag catcatcgag    1860
ggaaggtgac tctgaatgag tctgaaatat gtgctggggc tgaaaagatt ggatcaggac    1920
catgtgaggg ggattatggt ggcccacttg tttgtgagca acataaaatg agaatggttc    1980
ttggtgtcat tgttcctggt cgtggatgtg ccattccaaa tcgtcctggt atttttgtcc    2040
gagtagcata ttatgcaaaa tggatacaca aaattatttt aacatataag gtaccacagt    2100
ca                                                                   2102
```

<210> SEQ ID NO 88
<211> LENGTH: 360
<212> TYPE: DNA
<213> ORGANISM: Homo sapiens
<300> PUBLICATION INFORMATION:
<302> TITLE: ID3

<310> PATENT DOCUMENT NUMBER: XM001539

<400> SEQUENCE: 88
atgaaggcgc tgagcccggt gcgcggctgc tacgaggcgg tgtgctgcct gtcggaacgc 60
agtctggcca tcgcccgggg ccgagggaag ggcccggcag ctgaggagcc gctgagcttg 120
ctggacgaca tgaaccactg ctactcccgc ctgcgggaac tggtacccgg agtcccgaga 180
ggcactcagc ttagccaggt ggaaatccta cagcgcgtca tcgactacat tctcgacctg 240
caggtagtcc tggccgagcc agcccctgga ccccctgatg gcccccacct tcccatccag 300
acagccgagc tcactccgga acttgtcatc tccaacgaca aaaggagctt ttgccactga 360

<210> SEQ ID NO 89
<211> LENGTH: 743
<212> TYPE: DNA
<213> ORGANISM: Homo sapiens
<300> PUBLICATION INFORMATION:
<302> TITLE: IGF2
<310> PATENT DOCUMENT NUMBER: NM000612

<400> SEQUENCE: 89
atgggaatcc caatggggaa gtcgatgctg gtgcttctca ccttcttggc cttcgcctcg 60
tgctgcattg ctgcttaccg ccccagtgag accctgtgcg gcggggagct ggtggacacc 120
ctccagttcg tctgtgggga ccgcggcttc tacttcagca ggcccgcaag ccgtgtgagc 180
cgtcgcagcc gtggcatcgt tgaggagtgc tgtttccgca gctgtgacct ggccctcctg 240
gagacgtact gtgctacccc cgccaagtcc gagagggacg tgtcgacccc tccgaccgtg 300
cttccggaca acttccccag ataccccgtg ggcaagttct tccaatatga cacctggaag 360
cagtccaccc agcgcctgcg caggggcctg cctgccctcc tgcgtgcccg ccggggtcac 420
gtgctcgcca aggagctcga ggcgttcagg gaggccaaac gtcaccgtcc cctgattgct 480
ctacccaccc aagaccccgc ccacgggggc gccccccccag agatggccag caatcggaag 540
tgagcaaaac tgccgcaagt ctgcagcccg gcgccaccat cctgcagcct cctcctgacc 600
acggacgttt ccatcaggtt ccatcccgaa aatctctcgg ttccacgtcc ccctggggct 660
tctcctgacc cagtccccgt gccccgcctc cccgaaacag gctactctcc tcggccccct 720
ccatcgggct gaggaagcac agc 743

<210> SEQ ID NO 90
<211> LENGTH: 7476
<212> TYPE: DNA
<213> ORGANISM: Homo sapiens
<300> PUBLICATION INFORMATION:
<302> TITLE: IGF2R
<310> PATENT DOCUMENT NUMBER: NM000876

<400> SEQUENCE: 90
atgggggccg ccgccggccg gagcccccac ctggggcccg cgcccgcccg ccgcccgcag 60
cgctctctgc tcctgctgca gctgctgctg ctcgtcgctg ccccggggtc cacgcaggcc 120
caggccgccc cgttccccga gctgtgcagt tatacatggg aagctgttga taccaaaaat 180
aatgtacttt ataaaatcaa catctgtgga agtgtggata ttgtccagtg cgggccatca 240
agtgctgttt gtatgcacga cttgaagaca cgcacttatc attcagtggg tgactctgtt 300
ttgagaagtg caaccagatc tctcctggaa ttcaacacaa cagtgagctg tgaccagcaa 360
ggcacaaatc acagagtcca gagcagcatt gccttcctgt gtgggaaaac cctgggaact 420
cctgaatttg taactgcaac agaatgtgtg cactactttg agtggaggac cactgcagcc 480

```
tgcaagaaag acatatttaa agcaaataag gaggtgccat gctatgtgtt tgatgaagag    540
ttgaggaagc atgatctcaa tcctctgatc aagcttagtg gtgcctactt ggtggatgac    600
tccgatccgg acacttctct attcatcaat gtttgtagag acatagacac actacgagac    660
ccaggttcac agctgcgggc ctgtcccccc ggcactgccg cctgcctggt aagaggacac    720
caggcgtttg atgttggcca gccccgggac ggactgaagc tggtgcgcaa ggacaggctt    780
gtcctgagtt acgtgaggga agaggcagga aagctagact tttgtgatgg tcacagccct    840
gcggtgacta ttacatttgt ttgcccgtcg gagcggagag agggcaccat tcccaaactc    900
acagctaaat ccaactgccg ctatgaaatt gagtggatta ctgagtatgc ctgccacaga    960
gattacctgg aaagtaaaac ttgttctctg agcggcgagc agcaggatgt ctccatagac   1020
ctcacaccac ttgcccagag cggaggttca tcctatattt cagatggaaa agaatatttg   1080
ttttatttga atgtctgtgg agaaactgaa atacagttct gtaataaaaa acaagctgca   1140
gtttgccaag tgaaaaagag cgatacctct caagtcaaag cagcaggaag ataccacaat   1200
cagaccctcc gatattcgga tggagacctc accttgatat attttggagg tgatgaatgc   1260
agctcagggt ttcagcggat gagcgtcata aactttgagt gcaataaaac cgcaggtaac   1320
gatgggaaag gaactcctgt attcacaggg gaggttgact gcacctactt cttcacatgg   1380
gacacggaat acgcctgtgt taaggagaag gaagacctcc tctgcggtgc caccgacggg   1440
aagaagcgct atgacctgtc cgcgctggtc cgccatgcag aaccagagca gaattgggaa   1500
gctgtggatg gcagtcagac ggaaacagag aagaagcatt ttttcattaa tatttgtcac   1560
agagtgctgc aggaaggcaa ggcacgaggg tgtcccgagg acgcggcagt gtgtgcagtg   1620
gataaaaatg gaagtaaaaa tctgggaaaa tttatttcct ctcccatgaa agagaaagga   1680
aacattcaac tctcttattc agatggtgat gattgtggtc atggcaagaa aattaaaact   1740
aatatcacac ttgtatgcaa gccaggtgat ctggaaagtg caccagtgtt gagaacttct   1800
ggggaaggcg gttgctttta tgagtttgag tggcgcacag ctgcggcctg tgtgctgtct   1860
aagacagaag gggagaactg cacggtcttt gactcccagg cagggttttc ttttgactta   1920
tcacctctca caaagaaaaa tggtgcctat aaagttgaga caaagaagta tgacttttat   1980
ataaatgtgt gtggcccggt gtctgtgagc ccctgtcagc cagactcagg agcctgccag   2040
gtggcaaaaa gtgatgagaa gacttggaac ttgggtctga gtaatgcgaa gctttcatat   2100
tatgatggga tgatccaact gaactacaga ggcggcacac cctataacaa tgaaagacac   2160
acaccgagag ctacgctcat cacctttctc tgtgatcgag acgcgggagt gggcttccct   2220
gaatatcagg aagaggataa ctccacctac aacttccggt ggtacaccag ctatgcctgc   2280
ccggaggagc ccctggaatg cgtagtgacc gacccctcca cgctggagca gtacgacctc   2340
tccagtctgg caaaatctga aggtggcctt ggaggaaact ggtatgccat ggacaactca   2400
ggggaacatg tcacgtggag gaaatactac attaacgtgt gtcggcctct gaatccagtg   2460
ccgggctgca accgatatgc atcggcttgc cagatgaagt atgaaaaaga tcagggctcc   2520
ttcactgaag tggtttccat cagtaacttg ggaatggcaa agaccggccc ggtggttgag   2580
gacagcggca gcctccttct ggaatacgtg aatgggtcgg cctgcaccac cagcgatggc   2640
agacagacca catataccac gaggatccat ctcgtctgct ccaggggcag gctgaacagc   2700
caccccatct ttctctcaa ctgggagtgt gtggtcagtt tcctgtggaa cacagaggct    2760
gcctgtccca ttcagacaac gacggataca gaccaggctt gctctataag ggatcccaac   2820
```

-continued

```
agtggatttg tgtttaatct taatccgcta aacagttcgc aaggatataa cgtctctggc   2880
attgggaaga tttttatgtt taatgtctgc ggcacaatgc ctgtctgtgg gaccatcctg   2940
ggaaaacctg cttctggctg tgaggcagaa acccaaactg aagagctcaa gaattggaag   3000
ccagcaaggc cagtcggaat tgagaaaagc ctccagctgt ccacagaggg cttcatcact   3060
ctgacctaca aagggcctct ctctgccaaa ggtaccgctg atgcttttat cgtccgcttt   3120
gtttgcaatg atgatgttta ctcagggccc ctcaaattcc tgcatcaaga tatcgactct   3180
gggcaaggga tccgaaacac ttactttgag tttgaaaccg cgttggcctg tgttccttct   3240
ccagtggact gccaagtcac cgacctggct ggaaatgagt acgacctgac tggcctaagc   3300
acagtcagga aaccttggac ggctgttgac acctctgtcg atgggagaaa gaggactttc   3360
tatttgagcg tttgcaatcc tctcccttac attcctggat gccagggcag cgcagtgggg   3420
tcttgcttag tgtcagaagg caatagctgg aatctgggtg tggtgcagat gagtccccaa   3480
gccgcggcga atggatcttt gagcatcatg tatgtcaacg gtgacaagtg tgggaaccag   3540
cgcttctcca ccaggatcac gtttgagtgt gctcagatat cgggctcacc agcatttcag   3600
cttcaggatg gttgtgagta cgtgtttatc tggagaactg tggaagcctg tcccgttgtc   3660
agagtggaag gggacaactg tgaggtgaaa gacccaaggc atggcaactt gtatgacctg   3720
aagcccctgg gcctcaacga caccatcgtg agcgctggcg aatacactta ttacttccgg   3780
gtctgtggga agctttcctc agacgtctgc cccacaagtg acaagtccaa ggtggtctcc   3840
tcatgtcagg aaaagcggga accgcaggga tttcacaaag tggcaggtct cctgactcag   3900
aagctaactt atgaaaatgg cttgttaaaa atgaacttca cggggggggga cacttgccat   3960
aaggtttatc agcgctccac agccatcttc ttctactgtg accgcggcac ccagcggcca   4020
gtatttctaa aggagacttc agattgttcc tacttgtttg agtggcgaac gcagtatgcc   4080
tgcccacctt tcgatctgac tgaatgttca ttcaaagatg gggctggcaa ctccttcgac   4140
ctctcgtccc tgtcaaggta cagtgacaac tgggaagcca tcactgggac gggggacccg   4200
gagcactacc tcatcaatgt ctgcaagtct ctggccccgc aggctggcac tgagccgtgc   4260
cctccagaag cagccgcgtg tctgctgggt ggctccaagc ccgtgaacct cggcagggta   4320
agggacggac ctcagtggag agatggcata attgtcctga aatacgttga tggcgactta   4380
tgtccagatg ggattcggaa aaagtcaacc accatccgat tcacctgcag cgagagccaa   4440
gtgaactcca ggcccatgtt catcagcgcc gtggaggact gtgagtacac ctttgcctgg   4500
cccacagcca cagcctgtcc catgaagagc aacgagcatg atgactgcca ggtcaccaac   4560
ccaagcacag gacacctgtt tgatctgagc tccttaagtg gcagggcggg attcacagct   4620
gcttacagcg agaaggggtt ggtttacatg agcatctgtg gggagaatga aaactgccct   4680
cctggcgtgg gggcctgctt tggacagacc aggattagcg tgggcaaggc caacaagagg   4740
ctgagatacg tggaccaggt cctgcagctg gtgtacaagg atgggtcccc ttgtccctcc   4800
aaatccggcc tgagctataa gagtgtgatc agtttcgtgt gcaggcctga ggccgggcca   4860
accaataggc ccatgctcat ctccctggac aagcagacat gcactctctt cttctcctgg   4920
cacacgccgc tggcctgcga gcaagcgacc gaatgttccg tgaggaatgg aagctctatt   4980
gttgacttgt ctccccttat tcatcgcact ggtggttatg aggcttatga tgagagtgag   5040
gatgatgcct ccgataccaa ccctgatttc tacatcaata tttgtcagcc actaaatccc   5100
atgcacgcag tgccctgtcc tgccggagcc gctgtgtgca aagttcctat tgatggtccc   5160
cccatagata tcggccgggt agcaggacca ccaatactca atccaatagc aaatgagatt   5220
```

```
tacttgaatt ttgaaagcag tactccttgc ttagcggaca agcatttcaa ctacacctcg   5280
ctcatcgcgt ttcactgtaa gagaggtgtg agcatgggaa cgcctaagct gttaaggacc   5340
agcgagtgcg actttgtgtt cgaatgggag actcctgtcg tctgtcctga tgaagtgagg   5400
atggatggct gtaccctgac agatgagcag ctcctctaca gcttcaactt gtccagcctt   5460
tccacgagca cctttaaggt gactcgcgac tcgcgcacct acagcgttgg ggtgtgcacc   5520
tttgcagtcg ggccagaaca aggaggctgt aaggacggag gagtctgtct gctctcaggc   5580
accaaggggg catcctttgg acggctgcaa tcaatgaaac tggattacag gcaccaggat   5640
gaagcggtcg ttttaagtta cgtgaatggt gatcgttgcc ctccagaaac cgatgacggc   5700
gtcccctgtg tcttcccctt catattcaat gggaagagct acgaggagtg catcatagag   5760
agcagggcga agctgtggtg tagcacaact gcggactacg acagagacca cgagtggggc   5820
ttctgcagac actcaaacag ctaccggaca tccagcatca tatttaagtg tgatgaagat   5880
gaggacattg ggaggccaca agtcttcagt gaagtgcgtg ggtgtgatgt gacatttgag   5940
tggaaaacaa aagttgtctg ccctccaaag aagttggagt gcaaattcgt ccagaaacac   6000
aaaacctacg acctgcggct gctctcctct ctcaccgggt cctggtccct ggtccacaac   6060
ggagtctcgt actatataaa tctgtgccag aaaatatata aagggcccct gggctgctct   6120
gaaagggcca gcatttgcag aaggaccaca actggtgacg tccaggtcct gggactcgtt   6180
cacacgcaga agctgggtgt cataggtgac aaagttgttg tcacgtactc caaaggttat   6240
ccgtgtggtg gaaataagac cgcatcctcc gtgatagaat tgacctgtac aaagacggtg   6300
ggcagacctg cattcaagag gtttgatatc gacagctgca cttactactt cagctgggac   6360
tcccgggctg cctgcgccgt gaagcctcag gaggtgcaga tggtgaatgg gaccatcacc   6420
aaccctataa atggcaagag cttcagcctc ggagatattt attttaagct gttcagagcc   6480
tctggggaca tgaggaccaa tggggacaac tacctgtatg agatccaact ttcctccatc   6540
acaagctcca gaaacccggc gtgctctgga gccaacatat gccaggtgaa gcccaacgat   6600
cagcacttca gtcggaaagt tggaacctct gacaagacca agtactacct tcaagacggc   6660
gatctcgatg tcgtgtttgc ctcttcctct aagtgcggaa aggataagac caagtctgtt   6720
tcttccacca tcttcttcca ctgtgaccct ctggtggagg acgggatccc cgagttcagt   6780
cacgagactg ccgactgcca gtacctcttc tcttggtaca cctcagccgt gtgtcctctg   6840
ggggtgggct ttgacagcga gaatcccggg gacgacgggc agatgcacaa ggggctgtca   6900
gaacggagcc aggcagtcgg cgcggtgctc agcctgctgc tggtggcgct cacctgctgc   6960
ctgctggccc tgttgctcta caagaaggag aggagggaaa cagtgataag taagctgacc   7020
acttgctgta ggagaagttc caacgtgtcc tacaaatact caaaggtgaa taaggaagaa   7080
gagacagatg agaatgaaac agagtggctg atggaagaga tccagctgcc tcctccacgg   7140
cagggaaagg aagggcagga gaacggccat attaccacca agtcagtgaa agccctcagc   7200
tccctgcatg gggatgacca ggacagtgag gatgaggttc tgaccatccc agaggtgaaa   7260
gttcactcgg gcaggggagc tggggcagag agctcccacc cagtgagaaa cgcacagagc   7320
aatgcccttc aggagcgtga ggacgatagg gtggggctgg tcaggggtga gaaggcgagg   7380
aaagggaagt ccagctctgc acagcagaag acagtgagct ccaccaagct ggtgtccttc   7440
catgacgaca gcgacgagga cctcttacac atctga                             7476
```

<210> SEQ ID NO 91

<211> LENGTH: 4104
<212> TYPE: DNA
<213> ORGANISM: Homo sapiens
<300> PUBLICATION INFORMATION:
<302> TITLE: IGF1R
<310> PATENT DOCUMENT NUMBER: NM000875

<400> SEQUENCE: 91

```
atgaagtctg gctccggagg agggtccccg acctcgctgt gggggctcct gtttctctcc     60

gccgcgctct cgctctggcc gacgagtgga gaaatctgcg ggccaggcat cgacatccgc    120

aacgactatc agcagctgaa gcgcctggag aactgcacgg tgatcgaggg ctacctccac    180

atcctgctca tctccaaggc cgaggactac cgcagctacc gcttccccaa gctcacggtc    240

attaccgagt acttgctgct gttccgagtg gctggcctcg agagcctcgg agacctcttc    300

cccaacctca cggtcatccg cggctggaaa ctcttctaca actacgccct ggtcatcttc    360

gagatgacca atctcaagga tattgggctt tacaacctga ggaacattac tcggggggcc    420

atcaggattg agaaaaatgc tgacctctgt tacctctcca ctgtggactg gtccctgatc    480

ctggatgcgg tgtccaataa ctacattgtg gggaataagc cccaaagga atgtggggac    540

ctgtgtccag ggaccatgga ggagaagccg atgtgtgaga agaccaccat caacaatgag    600

tacaactacc gctgctggac cacaaaccgc tgccagaaaa tgtgcccaag cacgtgtggg    660

aagcgggcgt gcaccgagaa caatgagtgc tgccaccccg agtgcctggg cagctgcagc    720

gcgcctgaca acgacacggc ctgtgtagct tgccgccact actactatgc cggtgtctgt    780

gtgcctgcct gcccgcccaa cacctacagg tttgagggct ggcgctgtgt ggaccgtgac    840

ttctgcgcca acatcctcag cgccgagagc agcgactccg aggggtttgt gatccacgac    900

ggcgagtgca tgcaggagtg cccctcgggc ttcatccgca acggcagcca gagcatgtac    960

tgcatccctt gtgaaggtcc ttgcccgaag gtctgtgagg aagaaaagaa aacaaagacc   1020

attgattctg ttacttctgc tcagatgctc caaggatgca ccatcttcaa gggcaatttg   1080

ctcattaaca tccgacgggg gaataacatt gcttcagagc tggagaactt catggggctc   1140

atcgaggtgg tgacgggcta cgtgaagatc cgccattctc atgccttggt ctccttgtcc   1200

ttcctaaaaa accttcgcct catcctagga gaggagcagc tagaagggaa ttactccttc   1260

tacgtcctcg acaaccagaa cttgcagcaa ctgtgggact gggaccaccg caacctgacc   1320

atcaaagcag ggaaaatgta ctttgctttc aatcccaaat tatgtgtttc cgaaatttac   1380

cgcatggagg aagtgacggg gactaaaggg cgccaaagca aaggggacat aaacaccagg   1440

aacaacgggg agagagcctc ctgtgaaagt gacgtcctgc atttcacctc caccaccacg   1500

tcgaagaatc gcatcatcat aacctggcac cggtaccggc cccctgacta cagggatctc   1560

atcagcttca ccgtttacta caaggaagca ccctttaaga atgtcacaga gtatgatggg   1620

caggatgcct gcggctccaa cagctggaac atggtggacg tggacctccc gcccaacaag   1680

gacgtggagc ccggcatctt actacatggg ctgaagccct ggactcagta cgccgtttac   1740

gtcaaggctg tgaccctcac catggtggag aacgaccata tccgtggggc caagagtgag   1800

atcttgtaca ttcgcaccaa tgcttcagtt ccttccattc ccttggacgt tctttcagca   1860

tcgaactcct cttctcagtt aatcgtgaag tggaaccctc cctctctgcc caacggcaac   1920

ctgagttact acattgtgcg ctggcagcgg cagcctcagg acggctacct ttaccggcac   1980

aattactgct ccaaagacaa aatccccatc aggaagtatg ccgacggcac catcgacatt   2040

gaggaggtca cagagaaccc caagactgag gtgtgtggtg gggagaaagg gccttgctgc   2100
```

```
gcctgcccca aaactgaagc cgagaagcag gccgagaagg aggaggctga ataccgcaaa   2160
gtctttgaga atttcctgca caactccatc ttcgtgccca gacctgaaag gaagcggaga   2220
gatgtcatgc aagtggccaa caccaccatg tccagccgaa gcaggaacac cacggccgca   2280
gacacctaca acatcaccga cccggaagag ctggagacag agtacccttt ctttgagagc   2340
agagtggata acaaggagag aactgtcatt tctaaccttc ggcctttcac attgtaccgc   2400
atcgatatcc acagctgcaa ccacgaggct gagaagctgg gctgcagcgc ctccaacttc   2460
gtctttgcaa ggactatgcc cgcagaagga gcagatgaca ttcctgggcc agtgacctgg   2520
gagccaaggc ctgaaaactc catcttttta aagtggccgg aacctgagaa tcccaatgga   2580
ttgattctaa tgtatgaaat aaaatacgga tcacaagttg aggatcagcg agaatgtgtg   2640
tccagacagg aatacaggaa gtatggaggg gccaagctaa accggctaaa cccggggaac   2700
tacacagccc ggattcaggc cacatctctc tctgggaatg ggtcgtggac agatcctgtg   2760
ttcttctatg tccaggccaa aacaggatat gaaaacttca tccatctgat catcgctctg   2820
cccgtcgctg tcctgttgat cgtgggaggg ttggtgatta tgctgtacgt cttccataga   2880
aagagaaata acagcaggct ggggaatgga gtgctgtatg cctctgtgaa cccggagtac   2940
ttcagcgctg ctgatgtgta cgttcctgat gagtgggagg tggctcggga gaagatcacc   3000
atgagccggg aacttgggca ggggtcgttt gggatggtct atgaaggagt tgccaagggt   3060
gtggtgaaag atgaacctga aaccagagtg gccattaaaa cagtgaacga ggccgcaagc   3120
atgcgtgaga ggattgagtt tctcaacgaa gcttctgtga tgaaggagtt caattgtcac   3180
catgtggtgc gattgctggg tgtggtgtcc caaggccagc caacactggt catcatggaa   3240
ctgatgacac ggggcgatct caaaagttat ctccggtctc tgaggccaga aatggagaat   3300
aatccagtcc tagcacctcc aagcctgagc aagatgattc agatggccgg agagattgca   3360
gacggcatgg catacctcaa cgccaataag ttcgtccaca gagaccttgc tgcccggaat   3420
tgcatggtag ccgaagattt cacagtcaaa atcggagatt ttggtatgac gcgagatatc   3480
tatgagacag actattaccg gaaaggaggc aaagggctgc tgcccgtgcg ctggatgtct   3540
cctgagtccc tcaaggatgg agtcttcacc acttactcgg acgtctggtc cttcggggtc   3600
gtcctctggg agatcgccac actggccgag cagccctacc agggcttgtc caacgagcaa   3660
gtccttcgct tcgtcatgga gggcggcctt ctggacaagc cagacaactg tcctgacatg   3720
ctgtttgaac tgatgcgcat gtgctggcag tataacccca agatgaggcc ttccttcctg   3780
gagatcatca gcagcatcaa agaggagatg gagcctggct tccgggaggt ctccttctac   3840
tacagcgagg agaacaagct gcccgagccg gaggagctgg acctggagcc agagaacatg   3900
gagagcgtcc ccctggaccc ctcggcctcc tcgtcctccc tgccactgcc cgacagacac   3960
tcaggacaca aggccgagaa cggccccggc cctggggtgc tggtcctccg cgccagcttc   4020
gacgagagac agccttacgc ccacatgaac gggggccgca agaacgagcg ggccttgccg   4080
ctgccccagt cttcgacctg ctga                                          4104
```

<210> SEQ ID NO 92
<211> LENGTH: 726
<212> TYPE: DNA
<213> ORGANISM: Homo sapiens
<300> PUBLICATION INFORMATION:
<302> TITLE: PDGFB
<310> PATENT DOCUMENT NUMBER: NM002608

<400> SEQUENCE: 92
atgaatcgct gctgggcgct cttcctgtct ctctgctgct acctgcgtct ggtcagcgcc 60
gagggggacc ccattcccga ggagctttat gagatgctga gtgaccactc gatccgctcc 120
tttgatgatc tccaacgcct gctgcacgga gaccccggag aggaagatgg ggccgagttg 180
gacctgaaca tgacccgctc ccactctgga ggcgagctgg agagcttggc tcgtggaaga 240
aggagcctgg gttccctgac cattgctgag ccggccatga tcgccgagtg caagacgcgc 300
accgaggtgt tcgagatctc ccggcgcctc atagaccgca ccaacgccaa cttcctggtg 360
tggccgccct gtgtggaggt gcagcgctgc tccggctgct gcaacaaccg caacgtgcag 420
tgccgcccca cccaggtgca gctgcgacct gtccaggtga gaaagatcga gattgtgcgg 480
aagaagccaa tctttaagaa ggccacggtg acgctggaag accacctggc atgcaagtgt 540
gagacagtgg cagctgcacg gcctgtgacc cgaagcccgg ggggttccca ggagcagcga 600
gccaaaacgc cccaaactcg ggtgaccatt cggacggtgc gagtccgccg gccccccaag 660
ggcaagcacc ggaaattcaa gcacacgcat gacaagacgg cactgaagga gacccttgga 720
gcctag 726

<210> SEQ ID NO 93
<211> LENGTH: 1512
<212> TYPE: DNA
<213> ORGANISM: Homo sapiens
<300> PUBLICATION INFORMATION:
<302> TITLE: TGFbetaR1
<310> PATENT DOCUMENT NUMBER: NM004612

<400> SEQUENCE: 93
atggaggcgg cggtcgctgc tccgcgtccc cggctgctcc tcctcgtgct ggcggcggcg 60
gcggcggcgg cggcggcgct gctcccgggg gcgacggcgt tacagtgttt ctgccacctc 120
tgtacaaaag acaattttac ttgtgtgaca gatgggctct gctttgtctc tgtcacagag 180
accacagaca aagttataca caacagcatg tgtatagctg aaattgactt aattcctcga 240
gataggccgt ttgtatgtgc accctcttca aaaactgggt ctgtgactac aacatattgc 300
tgcaatcagg accattgcaa taaaatagaa cttccaacta ctgtaaagtc atcacctggc 360
cttggtcctg tggaactggc agctgtcatt gctggaccag tgtgcttcgt ctgcatctca 420
ctcatgttga tggtctatat ctgccacaac cgcactgtca ttcaccatcg agtgccaaat 480
gaagaggacc cttcattaga tcgccctttt atttcagagg gtactacgtt gaaagactta 540
atttatgata tgacaacgtc aggttctggc tcaggtttac cattgcttgt tcagagaaca 600
attgcgagaa ctattgtgtt acaagaaagc attggcaaag gtcgatttgg agaagtttgg 660
agaggaaagt ggcggggaga agaagttgct gttaagatat tctcctctag agaagaacgt 720
tcgtggttcc gtgaggcaga gatttatcaa actgtaatgt tacgtcatga aaacatcctg 780
ggatttatag cagcagacaa taaagacaat ggtacttgga ctcagctctg gttggtgtca 840
gattatcatg agcatggatc cctttttgat tacttaaaca gatacacagt tactgtggaa 900
ggaatgataa aacttgctct gtccacggcg agcggtcttg cccatcttca catggagatt 960
gttggtaccc aaggaaagcc agccattgct catagagatt tgaaatcaaa gaatatcttg 1020
gtaaagaaga atggaacttg ctgtattgca gacttaggac tggcagtaag acatgattca 1080
gccacagata ccattgatat tgctccaaac cacagagtgg gaacaaaaag gtacatggcc 1140
cctgaagttc tcgatgattc cataaatatg aaacattttg aatccttcaa acgtgctgac 1200
atctatgcaa tgggcttagt attctgggaa attgctcgac gatgttccat tggtggaatt 1260
catgaagatt accaactgcc ttattatgat cttgtacctt ctgacccatc agttgaagaa 1320
atgagaaaag ttgtttgtga acagaagtta aggccaaata tcccaaacag atggcagagc 1380
tgtgaagcct tgagagtaat ggctaaaatt atgagagaat gttggtatgc caatggagca 1440
gctaggctta cagcattgcg gattaagaaa acattatcgc aactcagtca acaggaaggc 1500
atcaaaatgt aa 1512

<210> SEQ ID NO 94
<211> LENGTH: 4044
<212> TYPE: DNA
<213> ORGANISM: Homo sapiens
<300> PUBLICATION INFORMATION:
<302> TITLE: Flk1
<310> PATENT DOCUMENT NUMBER: AF035121

<400> SEQUENCE: 94
atgcagagca aggtgctgct ggccgtcgcc ctgtggctct gcgtggagac ccgggccgcc 60
tctgtgggtt tgcctagtgt ttctcttgat ctgcccaggc tcagcataca aaaagacata 120
cttacaatta aggctaatac aactcttcaa attacttgca ggggacagag ggacttggac 180
tggctttggc ccaataatca gagtggcagt gagcaaaggg tggaggtgac tgagtgcagc 240
gatggcctct tctgtaagac actcacaatt ccaaaagtga tcggaaatga cactggagcc 300
tacaagtgct tctaccggga aactgacttg gcctcggtca tttatgtcta tgttcaagat 360
tacagatctc catttattgc ttctgttagt gaccaacatg gagtcgtgta cattactgag 420
aacaaaaaca aaactgtggt gattccatgt ctcgggtcca tttcaaatct caacgtgtca 480
ctttgtgcaa gatacccaga aaagagattt gttcctgatg gtaacagaat ttcctgggac 540
agcaagaagg gctttactat tcccagctac atgatcagct atgctggcat ggtcttctgt 600
gaagcaaaaa ttaatgatga aagttaccag tctattatgt acatagttgt cgttgtaggg 660
tataggattt atgatgtggt tctgagtccg tctcatggaa ttgaactatc tgttggagaa 720
aagcttgtct taaattgtac agcaagaact gaactaaatg tggggattga cttcaactgg 780
gaataccctt cttcgaagca tcagcataag aaacttgtaa accgagacct aaaaacccag 840
tctgggagtg agatgaagaa atttttgagc accttaacta tagatggtgt aacccggagt 900
gaccaaggat tgtacacctg tgcagcatcc agtgggctga tgaccaagaa gaacagcaca 960
tttgtcaggg tccatgaaaa accttttgtt gcttttggaa gtggcatgga atctctggtg 1020
gaagccacgg tgggggagcg tgtcagaatc cctgcgaagt accttggtta cccaccccca 1080
gaaataaaat ggtataaaaa tggaataccc cttgagtcca atcacacaat taaagcgggg 1140
catgtactga cgattatgga agtgagtgaa agagacacag gaaattacac tgtcatcctt 1200
accaatccca tttcaaagga gaagcagagc catgtggtct ctctggttgt gtatgtccca 1260
ccccagattg gtgagaaatc tctaatctct cctgtggatt cctaccagta cggcaccact 1320
caaacgctga catgtacggt ctatgccatt cctcccccgc atcacatcca ctggtattgg 1380
cagttggagg aagagtgcgc caacgagccc agccaagctg tctcagtgac aaacccatac 1440
ccttgtgaag aatggagaag tgtggaggac ttccagggag gaaataaaat tgaagttaat 1500
aaaaatcaat ttgctctaat tgaaggaaaa aacaaaactg taagtaccct tgttatccaa 1560
gcggcaaatg tgtcagcttt gtacaaatgt gaagcggtca acaaagtcgg gagaggagag 1620
agggtgatct ccttccacgt gaccaggggt cctgaaatta ctttgcaacc tgacatgcag 1680
cccactgagc aggagagcgt gtctttgtgg tgcactgcag acagatctac gtttgagaac 1740

-continued

```
ctcacatggt acaagcttgg cccacagcct ctgccaatcc atgtgggaga gttgcccaca   1800
cctgtttgca agaacttgga tactctttgg aaattgaatg ccaccatgtt ctctaatagc   1860
acaaatgaca ttttgatcat ggagcttaag aatgcatcct tgcaggacca aggagactat   1920
gtctgccttg ctcaagacag gaagaccaag aaaagacatt gcgtggtcag gcagctcaca   1980
gtcctagagc gtgtggcacc cacgatcaca ggaaacctgg agaatcagac gacaagtatt   2040
ggggaaagca tcgaagtctc atgcacggca tctgggaatc cccctccaca gatcatgtgg   2100
tttaaagata atgagaccct tgtagaagac tcaggcattg tattgaagga tgggaaccgg   2160
aacctcacta tccgcagagt gaggaaggag gacgaaggcc tctacacctg ccaggcatgc   2220
agtgttcttg gctgtgcaaa agtggaggca tttttcataa tagaaggtgc ccaggaaaag   2280
acgaacttgg aaatcattat tctagtaggc acggcggtga ttgccatgtt cttctggcta   2340
cttcttgtca tcatcctacg gaccgttaag cgggccaatg gaggggaact gaagacaggc   2400
tacttgtcca tcgtcatgga tccagatgaa ctcccattgg atgaacattg tgaacgactg   2460
ccttatgatg ccagcaaatg ggaattcccc agagaccggc tgaagctagg taagcctctt   2520
ggccgtggtg cctttggcca agtgattgaa gcagatgcct ttggaattga caagacagca   2580
acttgcagga cagtagcagt caaaatgttg aaagaaggag caacacacag tgagcatcga   2640
gctctcatgt ctgaactcaa gatcctcatt catattggtc accatctcaa tgtggtcaac   2700
cttctaggtg cctgtaccaa gccaggaggg ccactcatgg tgattgtgga attctgcaaa   2760
tttggaaacc tgtccactta cctgaggagc aagagaaatg aatttgtccc ctacaagacc   2820
aaaggggcac gattccgtca agggaaagac tacgttggag caatccctgt ggatctgaaa   2880
cggcgcttgg acagcatcac cagtagccag agctcagcca gctctggatt tgtggaggag   2940
aagtccctca gtgatgtaga agaagaggaa gctcctgaag atctgtataa ggacttcctg   3000
accttggagc atctcatctg ttacagcttc caagtggcta agggcatgga gttcttggca   3060
tcgcgaaagt gtatccacag ggacctggcg gcacgaaata tcctcttatc ggagaagaac   3120
gtggttaaaa tctgtgactt tggcttggcc cgggatattt ataaagatcc agattatgtc   3180
agaaaaggag atgctcgcct ccctttgaaa tggatggccc cagaaacaat ttttgacaga   3240
gtgtacacaa tccagagtga cgtctggtct tttggtgttt tgctgtggga aatattttcc   3300
ttaggtgctt ctccatatcc tggggtaaag attgatgaag aattttgtag gcgattgaaa   3360
gaaggaacta gaatgagggc ccctgattat actacaccag aaatgtacca gaccatgctg   3420
gactgctggc acggggagcc cagtcagaga cccacgtttt cagagttggt ggaacatttg   3480
ggaaatctct tgcaagctaa tgctcagcag gatggcaaag actacattgt tcttccgata   3540
tcagagactt tgagcatgga agaggattct ggactctctc tgcctacctc acctgtttcc   3600
tgtatggagg aggaggaagt atgtgacccc aaattccatt atgacaacac agcaggaatc   3660
agtcagtatc tgcagaacag taagcgaaag agccggcctg tgagtgtaaa aacatttgaa   3720
gatatcccgt tagaagaacc agaagtaaaa gtaatcccag atgacaacca gacggacagt   3780
ggtatggttc ttgcctcaga agagctgaaa actttggaag acagaaccaa attatctcca   3840
tcttttggtg gaatggtgcc cagcaaaagc agggagtctg tggcatctga aggctcaaac   3900
cagacaagcg gctaccagtc cggatatcac tccgatgaca cagacaccac cgtgtactcc   3960
agtgaggaag cagaactttt aaagctgata gagattggag tgcaaaccgg tagcacagcc   4020
cagattctcc agcctgactc gggg                                          4044
```

<210> SEQ ID NO 95
<211> LENGTH: 4017
<212> TYPE: DNA
<213> ORGANISM: Homo sapiens
<300> PUBLICATION INFORMATION:
<302> TITLE: Flt1
<310> PATENT DOCUMENT NUMBER: AF063657

<400> SEQUENCE: 95
atggtcagct actgggacac cggggtcctg ctgtgcgcgc tgctcagctg tctgcttctc 60
acaggatcta gttcaggttc aaaattaaaa gatcctgaac tgagtttaaa aggcacccag 120
cacatcatgc aagcaggcca gacactgcat ctccaatgca ggggggaagc agcccataaa 180
tggtctttgc ctgaaatggt gagtaaggaa agcgaaaggc tgagcataac taaatctgcc 240
tgtggaagaa atggcaaaca attctgcagt actttaacct tgaacacagc tcaagcaaac 300
cacactggct tctacagctg caaatatcta gctgtaccta cttcaaagaa gaaggaaaca 360
gaatctgcaa tctatatatt tattagtgat acaggtagac ctttcgtaga gatgtacagt 420
gaaatccccg aaattataca catgactgaa ggaagggagc tcgtcattcc ctgccgggtt 480
acgtcaccta acatcactgt tactttaaaa aagtttccac ttgacacttt gatccctgat 540
ggaaaacgca taatctggga cagtagaaag ggcttcatca tatcaaatgc aacgtacaaa 600
gaaatagggc ttctgacctg tgaagcaaca gtcaatgggc atttgtataa gacaaactat 660
ctcacacatc gacaaaccaa tacaatcata gatgtccaaa taagcacacc acgcccagtc 720
aaattactta gaggccatac tcttgtcctc aattgtactg ctaccactcc cttgaacacg 780
agagttcaaa tgacctggag ttaccctgat gaaaaaaata agagagcttc cgtaaggcga 840
cgaattgacc aaagcaattc ccatgccaac atattctaca gtgttcttac tattgacaaa 900
atgcagaaca aagacaaagg actttatact tgtcgtgtaa ggagtggacc atcattcaaa 960
tctgttaaca cctcagtgca tatatatgat aaagcattca tcactgtgaa acatcgaaaa 1020
cagcaggtgc ttgaaaccgt agctggcaag cggtcttacc ggctctctat gaaagtgaag 1080
gcatttccct cgccggaagt tgtatggtta aaagatgggt tacctgcgac tgagaaatct 1140
gctcgctatt tgactcgtgg ctactcgtta attatcaagg acgtaactga agaggatgca 1200
gggaattata caatcttgct gagcataaaa cagtcaaatg tgtttaaaaa cctcactgcc 1260
actctaattg tcaatgtgaa accccagatt tacgaaaagg ccgtgtcatc gtttccagac 1320
ccggctctct acccactggg cagcagacaa atcctgactt gtaccgcata tggtatccct 1380
caacctacaa tcaagtggtt ctggcacccc tgtaaccata atcattccga agcaaggtgt 1440
gacttttgtt ccaataatga agagtccttt atcctggatg ctgacagcaa catgggaaac 1500
agaattgaga gcatcactca gcgcatggca ataatagaag gaaagaataa gatggctagc 1560
accttggttg tggctgactc tagaatttct ggaatctaca tttgcatagc ttccaataaa 1620
gttgggactg tgggaagaaa cataagcttt tatatcacag atgtgccaaa tgggtttcat 1680
gttaacttgg aaaaaatgcc gacggaagga gaggacctga aactgtcttg cacagttaac 1740
aagttcttat acagagacgt tacttggatt ttactgcgga cagttaataa cagaacaatg 1800
cactacagta ttagcaagca aaaaatggcc atcactaagg agcactccat cactcttaat 1860
cttaccatca tgaatgtttc cctgcaagat tcaggcacct atgcctgcag agccaggaat 1920
gtatacacag gggaagaaat cctccagaag aaagaaatta caatcagaga tcaggaagca 1980
ccatacctcc tgcgaaacct cagtgatcac acagtggcca tcagcagttc caccacttta 2040
gactgtcatg ctaatggtgt ccccgagcct cagatcactt ggtttaaaaa caaccacaaa 2100
atacaacaag agcctggaat tattttagga ccaggaagca gcacgctgtt tattgaaaga 2160
gtcacagaag aggatgaagg tgtctatcac tgcaaagcca ccaaccagaa gggctctgtg 2220
gaaagttcag catacctcac tgttcaagga acctcggaca agtctaatct ggagctgatc 2280
actctaacat gcacctgtgt ggctgcgact ctcttctggc tcctattaac cctctttatc 2340
cgaaaaatga aaaggtcttc ttctgaaata aagactgact acctatcaat tataatggac 2400
ccagatgaag ttcctttgga tgagcagtgt gagcggctcc cttatgatgc cagcaagtgg 2460
gagtttgccc gggagagact taaactgggc aaatcacttg gaagaggggc ttttggaaaa 2520
gtggttcaag catcagcatt tggcattaag aaatcaccta cgtgccggac tgtggctgtg 2580
aaaatgctga aagagggggc cacggccagc gagtacaaag ctctgatgac tgagctaaaa 2640
atcttgaccc acattggcca ccatctgaac gtggttaacc tgctgggagc ctgcaccaag 2700
caaggagggc ctctgatggt gattgttgaa tactgcaaat atggaaatct ctccaactac 2760
ctcaagagca aacgtgactt attttttctc aacaaggatg cagcactaca catggagcct 2820
aagaaagaaa aaatggagcc aggcctggaa caaggcaaga aaccaagact agatagcgtc 2880
accagcagcg aaagctttgc gagctccggc tttcaggaag ataaaagtct gagtgatgtt 2940
gaggaagagg aggattctga cggtttctac aaggagccca tcactatgga agatctgatt 3000
tcttacagtt ttcaagtggc cagaggcatg gagttcctgt cttccagaaa gtgcattcat 3060
cgggacctgg cagcgagaaa cattctttta tctgagaaca acgtggtgaa gatttgtgat 3120
tttggccttg cccgggatat ttataagaac cccgattatg tgagaaaagg agatactcga 3180
cttcctctga aatggatggc tcctgaatct atctttgaca aaatctacag caccaagagc 3240
gacgtgtggt cttacggagt attgctgtgg gaaatcttct ccttaggtgg gtctccatac 3300
ccaggagtac aaatggatga ggacttttgc agtcgcctga gggaaggcat gaggatgaga 3360
gctcctgagt actctactcc tgaaatctat cagatcatgc tggactgctg gcacagagac 3420
ccaaaagaaa ggccaagatt tgcagaactt gtggaaaaac taggtgattt gcttcaagca 3480
aatgtacaac aggatggtaa agactacatc ccaatcaatg ccatactgac aggaaatagt 3540
gggtttacat actcaactcc tgccttctct gaggacttct tcaaggaaag tatttcagct 3600
ccgaagttta attcaggaag ctctgatgat gtcagatatg taaatgcttt caagttcatg 3660
agcctggaaa gaatcaaaac ctttgaagaa cttttaccga atgccacctc catgtttgat 3720
gactaccagg gcgacagcag cactctgttg gcctctccca tgctgaagcg cttcacctgg 3780
actgacagca aacccaaggc ctcgctcaag attgacttga gagtaaccag taaaagtaag 3840
gagtcggggc tgtctgatgt cagcaggccc agtttctgcc attccagctg tgggcacgtc 3900
agcgaaggca agcgcaggtt cacctacgac cacgctgagc tggaaaggaa aatcgcgtgc 3960
tgctccccgc ccccagacta caactcggtg gtcctgtact ccaccccacc catctag 4017

<210> SEQ ID NO 96
<211> LENGTH: 3897
<212> TYPE: DNA
<213> ORGANISM: Homo sapiens
<300> PUBLICATION INFORMATION:
<302> TITLE: Flt4
<310> PATENT DOCUMENT NUMBER: XM003852

<400> SEQUENCE: 96
atgcagcggg gcgccgcgct gtgcctgcga ctgtggctct gcctgggact cctggacggc 60
ctggtgagtg gctactccat gaccccccg accttgaaca tcacggagga gtcacacgtc 120

-continued

```
atcgacaccg gtgacagcct gtccatctcc tgcaggggac agcacccccct cgagtgggct    180
tggccaggag ctcaggaggc gccagccacc ggagacaagg acagcgagga cacgggggtg    240
gtgcgagact gcgagggcac agacgccagg ccctactgca aggtgttgct gctgcacgag    300
gtacatgcca acgacacagg cagctacgtc tgctactaca agtacatcaa ggcacgcatc    360
gagggcacca cggccgccag ctcctacgtg ttcgtgagag actttgagca gccattcatc    420
aacaagcctg acacgctctt ggtcaacagg aaggacgcca tgtgggtgcc ctgtctggtg    480
tccatccccg gcctcaatgt cacgctgcgc tcgcaaagct cggtgctgtg gccagacggg    540
caggaggtgg tgtgggatga ccggcggggc atgctcgtgt ccacgccact gctgcacgat    600
gccctgtacc tgcagtgcga gaccacctgg ggagaccagg acttcctttc caacccccttc    660
ctggtgcaca tcacaggcaa cgagctctat gacatccagc tgttgcccag gaagtcgctg    720
gagctgctgg taggggagaa gctggtcctg aactgcaccg tgtgggctga gtttaactca    780
ggtgtcacct ttgactggga ctacccaggg aagcaggcag agcggggtaa gtgggtgccc    840
gagcgacgct cccagcagac ccacacagaa ctctccagca tcctgaccat ccacaacgtc    900
agccagcacg acctgggctc gtatgtgtgc aaggccaaca acggcatcca gcgatttcgg    960
gagagcaccg aggtcattgt gcatgaaaat cccttcatca gcgtcgagtg gctcaaagga   1020
cccatcctgg aggccacggc aggagacgag ctggtgaagc tgcccgtgaa gctggcagcg   1080
taccccccgc ccgagttcca gtggtacaag gatggaaagg cactgtccgg gcgccacagt   1140
ccacatgccc tggtgctcaa ggaggtgaca gaggccagca caggcaccta caccctcgcc   1200
ctgtggaact ccgctgctgg cctgaggcgc aacatcagcc tggagctggt ggtgaatgtg   1260
ccccccccaga tacatgagaa ggaggcctcc tcccccagca tctactcgcg tcacagccgc   1320
caggccctca cctgcacggc ctacggggtg cccctgcctc tcagcatcca gtggcactgg   1380
cggccctgga caccctgcaa gatgtttgcc cagcgtagtc tccggcggcg gcagcagcaa   1440
gacctcatgc cacagtgccg tgactggagg gcggtgaccg cgcaggatgc cgtgaacccc   1500
atcgagagcc tggacacctg gaccgagttt gtggagggaa agaataagac tgtgagcaag   1560
ctggtgatcc agaatgccaa cgtgtctgcc atgtacaagt gtgtggtctc caacaaggtg   1620
ggccaggatg agcggctcat ctacttctat gtgaccacca tccccgacgg cttcaccatc   1680
gaatccaagc catccgagga gctactagag ggccagccgg tgctcctgag ctgccaagcc   1740
gacagctaca agtacgagca tctgcgctgg taccgcctca acctgtccac gctgcacgat   1800
gcgcacggga acccgcttct gctcgactgc aagaacgtgc atctgttcgc cacccctctg   1860
gccgccagcc tggaggaggt ggcacctggg gcgcgccacg ccacgctcag cctgagtatc   1920
ccccgcgtcg cgcccgagca cgagggccac tatgtgtgcg aagtgcaaga ccggcgcagc   1980
catgacaagc actgccacaa gaagtacctg tcggtgcagg ccctggaagc ccctcggctc   2040
acgcagaact tgaccgacct cctggtgaac gtgagcgact cgctggagat gcagtgcttg   2100
gtggccggag cgcacgcgcc cagcatcgtg tggtacaaag acgagaggct gctggaggaa   2160
aagtctggag tcgacttggc ggactccaac cagaagctga gcatccagcg cgtgcgcgag   2220
gaggatgcgg gacgctatct gtgcagcgtg tgcaacgcca agggctgcgt caactcctcc   2280
gccagcgtgg ccgtggaagg ctccgaggat aagggcagca tggagatcgt gatccttgtc   2340
ggtaccggcg tcatcgctgt cttcttctgg gtcctcctcc tcctcatctt ctgtaacatg   2400
aggaggccgg cccacgcaga catcaagacg ggctacctgt ccatcatcat ggaccccggg   2460
```

-continued gaggtgcctc tggaggagca atgcgaatac ctgtcctacg atgccagcca gtgggaattc 2520
ccccgagagc ggctgcacct ggggagagtg ctcggctacg gcgccttcgg gaaggtggtg 2580
gaagcctccg ctttcggcat ccacaagggc agcagctgtg acaccgtggc cgtgaaaatg 2640
ctgaaagagg gcgccacggc cagcgagcag cgcgcgctga tgtcggagct caagatcctc 2700
attcacatcg gcaaccacct caacgtggtc aacctcctcg ggcgtgcac caagccgcag 2760 ggcccctca tggtgatcgt ggagttctgc aagtacggca acctctccaa cttcctgcgc 2820
gccaagcggg acgccttcag cccctgcgcg gagaagtctc ccgagcagcg cggacgcttc 2880
cgcgccatgg tggagctcgc caggctggat cggaggcggc cggggagcag cgacagggtc 2940
ctcttcgcgc ggttctcgaa gaccgagggc ggagcgaggc gggcttctcc agaccaagaa 3000
gctgaggacc tgtggctgag cccgctgacc atggaagatc ttgtctgcta cagcttccag 3060
gtggccagag ggatggagtt cctggcttcc cgaaagtgca tccacagaga cctggctgct 3120
cggaacattc tgctgtcgga aagcgacgtg gtgaagatct gtgactttgg ccttgcccgg 3180
gacatctaca aagaccccga ctacgtccgc aagggcagtg cccggctgcc cctgaagtgg 3240
atggcccctg aaagcatctt cgacaaggtg tacaccacgc agagtgacgt gtggtccttt 3300
ggggtgcttc tctgggagat cttctctctg ggggcctccc cgtaccctgg ggtgcagatc 3360
aatgaggagt tctgccagcg gctgagagac ggcacaagga tgagggcccc ggagctggcc 3420
actcccgcca tacgccgcat catgctgaac tgctggtccg gagaccccaa ggcgagacct 3480
gcattctcgg agctggtgga gatcctgggg gacctgctcc agggcagggg cctgcaagag 3540
gaagaggagg tctgcatggc cccgcgcagc tctcagagct cagaagaggg cagcttctcg 3600
caggtgtcca ccatggccct acacatcgcc caggctgacg ctgaggacag cccgccaagc 3660
ctgcagcgcc acagcctggc cgccaggtat tacaactggg tgtcctttcc cgggtgcctg 3720
gccagagggg ctgagacccg tggttcctcc aggatgaaga catttgagga attccccatg 3780
accccaacga cctacaaagg ctctgtggac aaccagacag acagtgggat ggtgctggcc 3840
tcggaggagt ttgagcagat agagagcagg catagacaag aaagcggctt caggtag 3897

<210> SEQ ID NO 97
<211> LENGTH: 4071
<212> TYPE: DNA
<213> ORGANISM: Homo sapiens
<300> PUBLICATION INFORMATION:
<302> TITLE: KDR
<310> PATENT DOCUMENT NUMBER: AF063658

<400> SEQUENCE: 97
atggagagca aggtgctgct ggccgtcgcc ctgtggctct gcgtggagac ccgggccgcc 60
tctgtgggtt tgcctagtgt ttctcttgat ctgcccaggc tcagcataca aaaagacata 120
cttacaatta aggctaatac aactcttcaa attacttgca ggggacagag ggacttggac 180
tggctttggc ccaataatca gagtggcagt gagcaaaggg tggaggtgac tgagtgcagc 240
gatggcctct tctgtaagac actcacaatt ccaaaagtga tcggaaatga cactggagcc 300
tacaagtgct tctaccggga aactgacttg gcctcggtca tttatgtcta tgttcaagat 360
tacagatctc catttattgc ttctgttagt gaccaacatg gagtcgtgta cattactgag 420
aacaaaaaca aaactgtggt gattccatgt ctcgggtcca tttcaaatct caacgtgtca 480
ctttgtgcaa gatacccaga aaagagattt gttcctgatg gtaacagaat ttcctgggac 540
agcaagaagg gctttactat tcccagctac atgatcagct atgctggcat ggtcttctgt 600

-continued

```
gaagcaaaaa ttaatgatga aagttaccag tctattatgt acatagttgt cgttgtaggg    660
tataggattt atgatgtggt tctgagtccg tctcatggaa ttgaactatc tgttggagaa    720
aagcttgtct taaattgtac agcaagaact gaactaaatg tggggattga cttcaactgg    780
gaataccctt cttcgaagca tcagcataag aaacttgtaa accgagacct aaaaacccag    840
tctgggagtg agatgaagaa atttttgagc accttaacta tagatggtgt aacccggagt    900
gaccaaggat tgtacacctg tgcagcatcc agtgggctga tgaccaagaa gaacagcaca    960
tttgtcaggg tccatgaaaa accttttgtt gcttttggaa gtggcatgga atctctggtg   1020
gaagccacgg tgggggagcg tgtcagaatc cctgcgaagt accttggtta cccaccccca   1080
gaaataaaat ggtataaaaa tggaataccc cttgagtcca atcacacaat taaagcgggg   1140
catgtactga cgattatgga agtgagtgaa agagacacag gaaattacac tgtcatcctt   1200
accaatccca tttcaaagga gaagcagagc catgtggtct ctctggttgt gtatgtccca   1260
ccccagattg gtgagaaatc tctaatctct cctgtggatt cctaccagta cggcaccact   1320
caaacgctga catgtacggt ctatgccatt cctcccccgc atcacatcca ctggtattgg   1380
cagttggagg aagagtgcgc caacgagccc agccaagctg tctcagtgac aaacccatac   1440
ccttgtgaag aatggagaag tgtggaggac ttccagggag gaaataaaat tgaagttaat   1500
aaaaatcaat ttgctctaat tgaaggaaaa aacaaaactg taagtaccct tgttatccaa   1560
gcggcaaatg tgtcagcttt gtacaaatgt gaagcggtca acaaagtcgg gagaggagag   1620
agggtgatct ccttccacgt gaccaggggt cctgaaatta ctttgcaacc tgacatgcag   1680
cccactgagc aggagagcgt gtctttgtgg tgcactgcag acagatctac gtttgagaac   1740
ctcacatggt acaagcttgg cccacagcct ctgccaatcc atgtgggaga gttgcccaca   1800
cctgtttgca agaacttgga tactctttgg aaattgaatg ccaccatgtt ctctaatagc   1860
acaaatgaca ttttgatcat ggagcttaag aatgcatcct tgcaggacca aggagactat   1920
gtctgccttg ctcaagacag gaagaccaag aaaagacatt gcgtggtcag gcagctcaca   1980
gtcctagagc gtgtggcacc cacgatcaca ggaaacctgg agaatcagac gacaagtatt   2040
ggggaaagca tcgaagtctc atgcacggca tctgggaatc cccctccaca gatcatgtgg   2100
tttaaagata atgagaccct tgtagaagac tcaggcattg tattgaagga tgggaaccgg   2160
aacctcacta tccgcagagt gaggaaggag gacgaaggcc tctacacctg ccaggcatgc   2220
agtgttcttg gctgtgcaaa agtggaggca tttttcataa tagaaggtgc ccaggaaaag   2280
acgaacttgg aaatcattat tctagtaggc acggcggtga ttgccatgtt cttctggcta   2340
cttcttgtca tcatcctacg gaccgttaag cgggccaatg gaggggaact gaagacaggc   2400
tacttgtcca tcgtcatgga tccagatgaa ctcccattgg atgaacattg tgaacgactg   2460
ccttatgatg ccagcaaatg ggaattcccc agagaccggc tgaagctagg taagcctctt   2520
ggccgtggtg cctttggcca agtgattgaa gcagatgcct ttggaattga caagacagca   2580
acttgcagga cagtagcagt caaaatgttg aaagaaggag caacacacag tgagcatcga   2640
gctctcatgt ctgaactcaa gatcctcatt catattggtc accatctcaa tgtggtcaac   2700
cttctaggtg cctgtaccaa gccaggaggg ccactcatgg tgattgtgga attctgcaaa   2760
tttggaaacc tgtccactta cctgaggagc aagagaaatg aatttgtccc ctacaagacc   2820
aaaggggcac gattccgtca agggaaagac tacgttggag caatccctgt ggatctgaaa   2880
cggcgcttgg acagcatcac cagtagccag agctcagcca gctctggatt tgtggaggag   2940
aagtccctca gtgatgtaga agaagaggaa gctcctgaag atctgtataa ggacttcctg   3000
```

-continued

```
accttggagc atctcatctg ttacagcttc caagtggcta agggcatgga gttcttggca   3060
tcgcgaaagt gtatccacag ggacctggcg gcacgaaata tcctcttatc ggagaagaac   3120
gtggttaaaa tctgtgactt tggcttggcc cgggatattt ataaagatcc agattatgtc   3180
agaaaaggag atgctcgcct ccctttgaaa tggatggccc cagaaacaat ttttgacaga   3240
gtgtacacaa tccagagtga cgtctggtct tttggtgttt tgctgtggga aatattttcc   3300
ttaggtgctt ctccatatcc tggggtaaag attgatgaag aattttgtag gcgattgaaa   3360
gaaggaacta gaatgagggc ccctgattat actacaccag aaatgtacca gaccatgctg   3420
gactgctggc acggggagcc cagtcagaga cccacgtttt cagagttggt ggaacatttg   3480
ggaaatctct tgcaagctaa tgctcagcag gatggcaaag actacattgt tcttccgata   3540
tcagagactt tgagcatgga agaggattct ggactctctc tgcctacctc acctgtttcc   3600
tgtatggagg aggaggaagt atgtgacccc aaattccatt atgacaacac agcaggaatc   3660
agtcagtatc tgcagaacag taagcgaaag agccggcctg tgagtgtaaa aacatttgaa   3720
gatatcccgt tagaagaacc agaagtaaaa gtaatcccag atgacaacca gacggacagt   3780
ggtatggttc ttgcctcaga agagctgaaa actttggaag acagaaccaa attatctcca   3840
tcttttggtg gaatggtgcc cagcaaaagc agggagtctg tggcatctga aggctcaaac   3900
cagacaagcg gctaccagtc cggatatcac tccgatgaca cagacaccac cgtgtactcc   3960
agtgaggaag cagaactttt aaagctgata gagattggag tgcaaaccgg tagcacagcc   4020
cagattctcc agcctgactc ggggaccaca ctgagctctc ctcctgttta a            4071
```

```
<210> SEQ ID NO 98
<211> LENGTH: 1410
<212> TYPE: DNA
<213> ORGANISM: Homo sapiens
<300> PUBLICATION INFORMATION:
<302> TITLE: MMP1
<310> PATENT DOCUMENT NUMBER: M13509

<400> SEQUENCE: 98

atgcacagct ttcctccact gctgctgctg ctgttctggg gtgtggtgtc tcacagcttc     60
ccagcgactc tagaaacaca agagcaagat gtggacttag tccagaaata cctggaaaaa    120
tactacaacc tgaagaatga tgggaggcaa gttgaaaagc ggagaaatag tggcccagtg    180
gttgaaaaat tgaagcaaat gcaggaattc tttgggctga aagtgactgg gaaaccagat    240
gctgaaaccc tgaaggtgat gaagcagccc agatgtggag tgcctgatgt ggctcagttt    300
gtcctcactg agggaaaccc tcgctgggag caaacacatc tgaggtacag gattgaaaat    360
tacacgccag atttgccaag agcagatgtg gaccatgcca ttgagaaagc cttccaactc    420
tggagtaatg tcacacctct gacattcacc aaggtctctg agggtcaagc agacatcatg    480
atatcttttg tcaggggaga tcatcgggac aactctcctt ttgatggacc tggaggaaat    540
cttgctcatg cttttcaacc aggcccaggt attggagggg atgctcattt tgatgaagat    600
gaaaggtgga ccaacaattt cagagagtac aacttacatc gtgttgcggc tcatgaactc    660
ggccattctc ttggactctc ccattctact gatatcgggg ctttgatgta ccctagctac    720
accttcagtg gtgatgttca gctagctcag gatgacattg atggcatcca agccatatat    780
ggacgttccc aaaatcctgt ccagcccatc ggcccacaaa ccccaaaagc gtgtgacagt    840
aagctaacct ttgatgctat aactacgatt cggggagaag tgatgttctt taaagacaga    900
ttctacatgc gcacaaatcc cttctacccg gaagttgagc tcaatttcat ttctgttttc    960
```

```
tggccacaac tgccaaatgg gcttgaagct gcttacgaat ttgccgacag agatgaagtc   1020
cggtttttca aagggaataa gtactgggct gttcagggac agaatgtgct acacggatac   1080
cccaaggaca tctacagctc ctttggcttc cctagaactg tgaagcatat cgatgctgct   1140
ctttctgagg aaaacactgg aaaaacctac ttctttgttg ctaacaaata ctggaggtat   1200
gatgaatata aacgatctat ggatccaagt tatcccaaaa tgatagcaca tgactttcct   1260
ggaattggcc acaaagttga tgcagttttc atgaaagatg gatttttcta tttctttcat   1320
ggaacaagac aatacaaatt tgatcctaaa acgaagagaa ttttgactct ccagaaagct   1380
aatagctggt tcaactgcag gaaaaattga                                    1410
```

<210> SEQ ID NO 99
<211> LENGTH: 1743
<212> TYPE: DNA
<213> ORGANISM: Homo sapiens
<300> PUBLICATION INFORMATION:
<302> TITLE: MMP10
<310> PATENT DOCUMENT NUMBER: XM006269

<400> SEQUENCE: 99

```
aaagaaggta agggcagtga gaatgatgca tcttgcattc cttgtgctgt tgtgtctgcc     60
agtctgctct gcctatcctc tgagtggggc agcaaaagag gaggactcca acaaggatct    120
tgcccagcaa tacctagaaa agtactacaa cctcgaaaag gatgtgaaac agtttagaag    180
aaaggacagt aatctcattg ttaaaaaaat ccaaggaatg cagaagttcc ttgggttgga    240
ggtgacaggg aagctagaca ctgacactct ggaggtgatg cgcaagccca ggtgtggagt    300
tcctgacgtt ggtcacttca gctcctttcc tggcatgccg aagtggagga aaacccacct    360
tacatacagg attgtgaatt atacaccaga tttgccaaga gatgctgttg attctgccat    420
tgagaaagct ctgaaagtct gggaagaggt gactccactc acattctcca ggctgtatga    480
aggagaggct gatataatga tctcttttgc agttaaagaa catggagact tttactcttt    540
tgatggccca ggacacagtt tggctcatgc ctacccacct ggacctgggc tttatggaga    600
tattcacttt gatgatgatg aaaaatggac agaagatgca tcaggcacca atttattcct    660
cgttgctgct catgaacttg gccactccct ggggctcttt cactcagcca acactgaagc    720
tttgatgtac ccactctaca actcattcac agagctcgcc cagttccgcc tttcgcaaga    780
tgatgtgaat ggcattcagt ctctctacgg acctcccct gcctctactg aggaacccct    840
ggtgcccaca aaatctgttc cttcgggatc tgagatgcca gccaagtgtg atcctgcttt    900
gtccttcgat gccatcagca ctctgagggg agaatatctg ttctttaaag acagatattt    960
ttggcgaaga tcccactgga accctgaacc tgaatttcat ttgatttctg cattttggcc   1020
ctctcttcca tcatatttgg atgctgcata tgaagttaac agcagggaca ccgtttttat   1080
ttttaaagga aatgagttct gggccatcag aggaaatgag gtacaagcag gttatccaag   1140
aggcatccat accctgggtt ttcctccaac cataaggaaa attgatgcag ctgtttctga   1200
caaggaaaag aagaaaacat acttctttgc agcggacaaa tactggagat ttgatgaaaa   1260
tagccagtcc atggagcaag gcttccctag actaatagct gatgactttc caggagttga   1320
gcctaaggtt gatgctgtat tacaggcatt tggatttttc tacttcttca gtggatcatc   1380
acagtttgag tttgacccca atgccaggat ggtgacacac atattaaaga gtaacagctg   1440
gttacattgc taggcgagat agggggaaga cagatatggg tgtttttaat aaatctaata   1500
attattcatc taatgtatta tgagccaaaa tggttaattt ttcctgcatg ttctgtgact   1560
```

gaagaagatg agccttgcag atatctgcat gtgtcatgaa gaatgtttct ggaattcttc 1620
acttgctttt gaattgcact gaacagaatt aagaaatact catgtgcaat aggtgagaga 1680
atgtattttc atagatgtgt tattacttcc tcaataaaaa gttttatttt gggcctgttc 1740
ctt 1743

<210> SEQ ID NO 100
<211> LENGTH: 1467
<212> TYPE: DNA
<213> ORGANISM: Homo sapiens
<300> PUBLICATION INFORMATION:
<302> TITLE: MMP11
<310> PATENT DOCUMENT NUMBER: XM009873

<400> SEQUENCE: 100
atggctccgg ccgcctggct ccgcagcgcg gccgcgcgcg ccctcctgcc cccgatgctg 60
ctgctgctgc tccagccgcc gccgctgctg gcccgggctc tgccgccgga cgcccaccac 120
ctccatgccg agaggagggg gccacagccc tggcatgcag ccctgcccag tagcccggca 180
cctgcccctg ccacgcagga agccccccgg cctgccagca gcctcaggcc tccccgctgt 240
ggcgtgcccg acccatctga tgggctgagt gcccgcaacc gacagaagag gttcgtgctt 300
tctggcgggc gctgggagaa gacggacctc acctacagga tccttcggtt cccatggcag 360
ttggtgcagg agcaggtgcg gcagacgatg gcagaggccc taaaggtatg gagcgatgtg 420
acgccactca cctttactga ggtgcacgag ggccgtgctg acatcatgat cgacttcgcc 480
aggtactggc atggggacga cctgccgttt gatgggcctg gggcatcct ggcccatgcc 540 ttcttcccca agactcaccg agaaggggat gtccacttcg actatgatga gacctggact 600
atcggggatg accagggcac agacctgctg caggtggcag cccatgaatt tggccacgtg 660
ctggggctgc agcacacaac agcagccaag gccctgatgt ccgccttcta cacctttcgc 720
tacccactga gtctcagccc agatgactgc aggggcgttc aacacctata tggccagccc 780
tggcccactg tcacctccag gaccccagcc ctgggccccc aggctgggat agacaccaat 840
gagattgcac cgctggagcc agacgccccg ccagatgcct gtgaggcctc ctttgacgcg 900
gtctccacca tccgaggcga gctctttttc ttcaaagcgg gctttgtgtg gcgcctccgt 960
gggggccagc tgcagcccgg ctacccagca ttggcctctc gccactggca gggactgccc 1020
agccctgtgg acgctgcctt cgaggatgcc cagggccaca tttggttctt ccaaggtgct 1080
cagtactggg tgtacgacgg tgaaaagcca gtcctgggcc ccgcacccct caccgagctg 1140
ggcctggtga ggttcccggt ccatgctgcc ttggtctggg gtcccgagaa gaacaagatc 1200
tacttcttcc gaggcaggga ctactggcgt ttccacccca gcacccggcg tgtagacagt 1260
cccgtgcccc gcagggccac tgactggaga ggggtgccct ctgagatcga cgctgccttc 1320
caggatgctg atggctatgc ctacttcctg cgcggccgcc tctactggaa gtttgaccct 1380
gtgaaggtga aggctctgga aggcttcccc cgtctcgtgg gtcctgactt ctttggctgt 1440
gccgagcctg ccaacacttt cctctga 1467

<210> SEQ ID NO 101
<211> LENGTH: 1653
<212> TYPE: DNA
<213> ORGANISM: Homo sapiens
<220> FEATURE:
<221> NAME/KEY: misc_feature
<222> LOCATION: (626)..(925)
<223> OTHER INFORMATION: n=A, T, G, C or gap <300> PUBLICATION INFORMATION:
<302> TITLE: MMP12
<310> PATENT DOCUMENT NUMBER: XM006272

<400> SEQUENCE: 101

```
atgaagtttc ttctaatact gctcctgcag gccactgctt ctggagctct tcccctgaac     60

agctctacaa gcctggaaaa aaataatgtg ctatttggtg agagatactt agaaaaattt    120

tatggccttg agataaacaa acttccagtg acaaaaatga aatatagtgg aaacttaatg    180

aaggaaaaaa tccaagaaat gcagcacttc ttgggtctga aagtgaccgg gcaactggac    240

acatctaccc tggagatgat gcacgcacct cgatgtggag tccccgatgt ccatcatttc    300

agggaaatgc caggggggcc cgtatggagg aaacattata tcacctacag aatcaataat    360

tacacacctg acatgaaccg tgaggatgtt gactacgcaa tccggaaagc tttccaagta    420

tggagtaatg ttacccccctt gaaattcagc aagattaaca caggcatggc tgacattttg    480

gtggtttttg cccgtggagc tcatggagac ttccatgctt ttgatggcaa aggtggaatc    540

ctagcccatg cttttggacc tggatctggc attggagggg atgcacattt cgatgaggac    600

gaattctgga ctacacattc aggagnnnnn nnnnnnnnnn nnnnnnnnnn nnnnnnnnnn    660

nnnnnnnnnn nnnnnnnnnn nnnnnnnnnn nnnnnnnnnn nnnnnnnnnn nnnnnnnnnn    720

nnnnnnnnnn nnnnnnnnnn nnnnnnnnnn nnnnnnnnnn nnnnnnnnnn nnnnnnnnnn    780

nnnnnnnnnn nnnnnnnnnn nnnnnnnnnn nnnnnnnnnn nnnnnnnnnn nnnnnnnnnn    840

nnnnnnnnnn nnnnnnnnnn nnnnnnnnnn nnnnnnnnnn nnnnnnnnnn nnnnnnnnnn    900

nnnnnnnnnn nnnnnnnnnn nnnnngagag gatccaaagg ccgtaatgtt ccccacctac    960

aaatatgttg acatcaacac atttcgcctc tctgctgatg acatacgtgg cattcagtcc   1020

ctgtatggag acccaaaaga gaaccaacgc ttgccaaatc ctgacaattc agraccagct   1080

ctctgtgacc ccaatttgag ttttgatgct gtcactaccg tgggaaataa gatctttttc   1140

ttcaaagaca ggttcttctg gctgaaggtt tctgagagac caaagaccag tgttaattta   1200

atttcttcct tatggccaac cttgccatct ggcattgaag ctgcttatga aattgaagcc   1260

agaaatcaag tttttctttt taaagatgac aaatactggt taattagcaa tttaagacca   1320

gagccaaatt atcccaagag catacattct tttggttttc ctaactttgt gaaaaaaatt   1380

gatgcagctg tttttaaccc acgtttttat aggacctact tctttgtaga taaccagtat   1440

tggaggtatg atgaaaggag acagatgatg gaccctggtt atcccaaact gattaccaag   1500

aacttccaag gaatcgggcc taaaattgat gcagtcttct actctaaaaa caaatactac   1560

tatttcttcc aaggatctaa ccaatttgaa tatgacttcc tactccaacg tatcaccaaa   1620

acactgaaaa gcaatagctg gtttggttgt tag                                1653
```

<210> SEQ ID NO 102
<211> LENGTH: 1416
<212> TYPE: DNA
<213> ORGANISM: Homo sapiens

<400> SEQUENCE: 102

```
atgcatccag gggtcctggc tgccttcctc ttcttgagct ggactcattg tcgggccctg     60

ccccttccca gtggtggtga tgaagatgat ttgtctgagg aagacctcca gtttgcagag    120

cgctacctga gatcatacta ccatcctaca aatctcgcgg gaatcctgaa ggagaatgca    180

gcaagctcca tgactgagag gctccgagaa atgcagtctt tcttcggctt agaggtgact    240

ggcaaacttg acgataacac cttagatgtc atgaaaaagc caagatgcgg ggttcctgat    300
```

gtgggtgaat acaatgtttt ccctcgaact cttaaatggt ccaaaatgaa tttaacctac 360
agaattgtga attacacccc tgatatgact cattctgaag tcgaaaaggc attcaaaaaa 420
gccttcaaag tttggtccga tgtaactcct ctgaatttta ccagacttca cgatggcatt 480
gctgacatca tgatctcttt tggaattaag gagcatggcg acttctaccc atttgatggg 540
ccctctggcc tgctggctca tgcttttcct cctgggccaa attatggagg agatgcccat 600
tttgatgatg atgaaacctg gacaagtagt tccaaaggct acaacttgtt tcttgttgct 660
gcgcatgagt tcggccactc cttaggtctt gaccactcca aggaccctgg agcactcatg 720
tttcctatct acacctacac cggcaaaagc cactttatgc ttcctgatga cgatgtacaa 780
gggatccagt ctctctatgg tccaggagat gaagacccca accctaaaca tccaaaaacg 840
ccagacaaat gtgacccttc cttatccctt gatgccatta ccagtctccg aggagaaaca 900
atgatcttta aagacagatt cttctggcgc ctgcatcctc agcaggttga tgcggagctg 960
tttttaacga aatcattttg gccagaactt cccaaccgta ttgatgctgc atatgagcac 1020
ccttctcatg acctcatctt catcttcaga ggtagaaaat tttgggctct taatggttat 1080
gacattctgg aaggttatcc caaaaaaata tctgaactgg gtcttccaaa agaagttaag 1140
aagataagtg cagctgttca ctttgaggat acaggcaaga ctctcctgtt ctcaggaaac 1200
caggtctgga gatatgatga tactaaccat attatggata aagactatcc gagactaata 1260
gaagaagact tcccaggaat tggtgataaa gtagatgctg tctatgagaa aaatggttat 1320
atctattttt tcaacggacc catacagttt gaatacagca tctggagtaa ccgtattgtt 1380
cgcgtcatgc cagcaaattc cattttgtgg tgttaa 1416

<210> SEQ ID NO 103
<211> LENGTH: 1749
<212> TYPE: DNA
<213> ORGANISM: Homo sapiens
<300> PUBLICATION INFORMATION:
<302> TITLE: MMP14
<310> PATENT DOCUMENT NUMBER: NM004995

<400> SEQUENCE: 103
atgtctcccg ccccaagacc cccccgttgt ctcctgctcc ccctgctcac gctcggcacc 60
gcgctcgcct ccctcggctc ggcccaaagc agcagcttca gccccgaagc ctggctacag 120
caatatggct acctgcctcc cggggaccta cgtacccaca cacagcgctc accccagtca 180
ctctcagcgg ccatcgctgc catgcagaag ttttacggct tgcaagtaac aggcaaagct 240
gatgcagaca ccatgaaggc catgaggcgc ccccgatgtg gtgttccaga caagtttggg 300
gctgagatca aggccaatgt tcgaaggaag cgctacgcca tccagggtct caaatggcaa 360
cataatgaaa tcactttctg catccagaat tacaccccca aggtgggcga gtatgccaca 420
tacgaggcca ttcgcaaggc gttccgcgtg tgggagagtg ccacaccact gcgcttccgc 480
gaggtgccct atgcctacat ccgtgagggc catgagaagc aggccgacat catgatcttc 540
tttgccgagg gcttccatgg cgacagcacg cccttcgatg gtgagggcgg cttcctggcc 600
catgcctact tcccaggccc caacattgga ggagacaccc actttgactc tgccgagcct 660
tggactgtca ggaatgagga tctgaatgga aatgacatct tcctggtggc tgtgcacgag 720
ctgggccatg ccctggggct cgagcattcc agtgacccct cggccatcat ggcacccttt 780
taccagtgga tggacacgga gaattttgtg ctgcccgatg atgaccgccg gggcatccag 840
caactttatg ggggtgagtc agggttcccc accaagatgc cccctcaacc caggactacc 900

```
tcccggcctt ctgttcctga taaacccaaa aaccccacct atgggcccaa catctgtgac    960
gggaactttg acaccgtggc catgctccga ggggagatgt ttgtcttcaa ggagcgctgg   1020
ttctggcggg tgaggaataa ccaagtgatg gatggatacc caatgcccat tggccagttc   1080
tggcggggcc tgcctgcgtc catcaacact gcctacgaga ggaaggatgg caaattcgtc   1140
ttcttcaaag gagacaagca ttgggtgttt gatgaggcgt ccctggaacc tggctacccc   1200
aagcacatta aggagctggg ccgagggctg cctaccgaca agattgatgc tgctctcttc   1260
tggatgccca atggaaagac ctacttcttc cgtggaaaca agtactaccg tttcaacgaa   1320
gagctcaggg cagtggatag cgagtacccc aagaacatca aagtctggga agggatccct   1380
gagtctccca gagggtcatt catgggcagc gatgaagtct tcacttactt ctacaagggg   1440
aacaaatact ggaaattcaa caaccagaag ctgaaggtag aaccgggcta ccccaagtca   1500
gccctgaggg actggatggg ctgcccatcg ggaggccggc cggatgaggg gactgaggag   1560
gagacggagg tgatcatcat tgaggtggac gaggagggcg gcggggcggt gagcgcggct   1620
gccgtggtgc tgcccgtgct gctgctgctc ctggtgctgg cggtgggcct tgcagtcttc   1680
ttcttcagac gccatgggac ccccaggcga ctgctctact gccagcgttc cctgctggac   1740
aaggtctga                                                           1749
```

```
<210> SEQ ID NO 104
<211> LENGTH: 2010
<212> TYPE: DNA
<213> ORGANISM: Homo sapiens
<300> PUBLICATION INFORMATION:
<302> TITLE: MMP15
<310> PATENT DOCUMENT NUMBER: NM002428

<400> SEQUENCE: 104
```

```
atgggcagcg acccgagcgc gcccggacgg ccgggctgga cgggcagcct cctcggcgac     60
cgggaggagg cggcgcggcc gcgactgctg ccgctgctcc tggtgcttct gggctgcctg    120
ggccttggcg tagcggccga agacgcggag gtccatgccg agaactggct gcggctttat    180
ggctacctgc ctcagcccag ccgccatatg tccaccatgc gttccgccca gatcttggcc    240
tcggcccttg cagagatgca gcgcttctac gggatcccag tcaccggtgt gctcgacgaa    300
gagaccaagg agtggatgaa gcggccccgc tgtggggtgc cagaccagtt cggggtacga    360
gtgaaagcca acctgcggcg gcgtcggaag cgctacgccc tcaccgggag gaagtggaac    420
aaccaccatc tgacctttag catccagaac tacacggaga agttgggctg gtaccactcg    480
atggaggcgg tgcgcagggc cttccgcgtg tgggagcagg ccacgcccct ggtcttccag    540
gaggtgccct atgaggacat ccggctgcgg cgacagaagg aggccgacat catggtactc    600
tttgcctctg gcttccacgg cgacagctcg ccgtttgatg gcaccggtgg ctttctggcc    660
cacgcctatt tccctggccc cggcctaggc ggggacaccc attttgacgc agatgagccc    720
tggaccttct ccagcactga cctgcatgga aacaacctct tcctggtggc agtgcatgag    780
ctgggccacg cgctggggct ggagcactcc agcaacccca atgccatcat ggcgccgttc    840
taccagtgga aggacgttga caacttcaag ctgcccgagg acgatctccg tggcatccag    900
cagctctacg gtaccccaga cggtcagcca cagcctaccc agcctctccc cactgtgacg    960
ccacggcggc caggccggcc tgaccaccgg ccgccccggc ctccccagcc accaccccca   1020
ggtgggaagc cagagcggcc cccaaagccg ggcccccag tccagccccg agccacagag    1080
cggcccgacc agtatggccc caacatctgc gacggggact ttgacacagt ggccatgctt   1140
```

cgcggggaga tgttcgtgtt caagggccgc tggttctggc gagtccggca caaccgcgtc 1200
ctggacaact atcccatgcc catcgggcac ttctggcgtg gtctgcccgg tgacatcagt 1260
gctgcctacg agcgccaaga cggtcgtttt gtctttttca aggtgaccg ctactggctc 1320 tttcgagaag cgaacctgga gcccggctac ccacagccgc tgaccagcta tggcctgggc 1380
atcccctatg accgcattga cacggccatc tggtgggagc ccacaggcca caccttcttc 1440
ttccaagagg acaggtactg gcgcttcaac gaggagacac agcgtggaga ccctgggtac 1500
cccaagccca tcagtgtctg gcaggggatc cctgcctccc ctaaaggggc cttcctgagc 1560
aatgacgcag cctacaccta cttctacaag ggcaccaaat actggaaatt cgacaatgag 1620
cgcctgcgga tggagcccgg ctaccccaag tccatcctgc gggacttcat gggctgccag 1680
gagcacgtgg agccaggccc ccgatggccc gacgtggccc ggccgccctt caaccccac 1740 gggggtgcag agcccggggc ggacagcgca gagggcgacg tgggggatgg ggatggggac 1800
tttggggccg gggtcaacaa ggacgggggc agccgcgtgg tggtgcagat ggaggaggtg 1860
gcacggacgg tgaacgtggt gatggtgctg gtgccactgc tgctgctgct ctgcgtcctg 1920
ggcctcacct acgcgctggt gcagatgcag cgcaagggtg cgccacgtgt cctgctttac 1980
tgcaagcgct cgctgcagga gtgggtctga 2010

<210> SEQ ID NO 105
<211> LENGTH: 1824
<212> TYPE: DNA
<213> ORGANISM: Homo sapiens
<300> PUBLICATION INFORMATION:
<302> TITLE: MMP16
<310> PATENT DOCUMENT NUMBER: NM005941

<400> SEQUENCE: 105
atgatcttac tcacattcag cactggaaga cggttggatt tcgtgcatca ttcgggggtg 60
tttttcttgc aaaccttgct ttggatttta tgtgctacag tctgcggaac ggagcagtat 120
ttcaatgtgg aggtttggtt acaaaagtac ggctaccttc caccgactga ccccagaatg 180
tcagtgctgc gctctgcaga gaccatgcag tctgccctag ctgccatgca gcagttctat 240
ggcattaaca tgacaggaaa agtggacaga aacacaattg actggatgaa gaagccccga 300
tgcggtgtac ctgaccagac aagaggtagc tccaaatttc atattcgtcg aaagcgatat 360
gcattgacag gacagaaatg gcagcacaag cacatcactt acagtataaa gaacgtaact 420
ccaaaagtag gagaccctga gactcgtaaa gctattcgcc gtgcctttga tgtgtggcag 480
aatgtaactc ctctgacatt tgaagaagtt ccctacagtg aattagaaaa tggcaaacgt 540
gatgtggata taaccattat ttttgcatct ggtttccatg gggacagctc tccctttgat 600
ggagagggag gatttttggc acatgcctac ttccctggac caggaattgg aggagatacc 660
cattttgact cagatgagcc atggacacta ggaaatccta atcatgatgg aaatgactta 720
tttcttgtag cagtccatga actgggacat gctctgggat tggagcattc caatgacccc 780
actgccatca tggctccatt ttaccagtac atggaaacag acaacttcaa actacctaat 840
gatgatttac agggcatcca gaaaatatat ggtccacctg acaagattcc tccacctaca 900
agacctctac cgacagtgcc cccacaccgc tctattcctc cggctgaccc aaggaaaaat 960
gacaggccaa aacctcctcg gcctccaacc ggcagaccct cctatcccgg agccaaaccc 1020
aacatctgtg atgggaactt taacactcta gctattcttc gtcgtgagat gtttgttttc 1080
aaggaccagt ggttttggcg agtgagaaac aacagggtga tggatggata cccaatgcaa 1140
attacttact tctggcgggg cttgcctcct agtatcgatg cagtttatga aaatagcgac 1200
gggaattttg tgttctttaa aggtaacaaa tattgggtgt tcaaggatac aactcttcaa 1260
cctggttacc ctcatgactt gataaccctt ggaagtggaa ttcccctca tggtattgat 1320 tcagccattt ggtgggagga cgtcgggaaa acctatttct tcaagggaga cagatattgg 1380
agatatagtg aagaaatgaa aacaatggac cctggctatc ccaagccaat cacagtctgg 1440
aaagggatcc ctgaatctcc tcagggagca tttgtacaca aagaaaatgg ctttacgtat 1500
ttctacaaag gaaaggagta ttggaaattc aacaaccaga tactcaaggt agaacctgga 1560
catccaagat ccatcctcaa ggattttatg ggctgtgatg gaccaacaga cagagttaaa 1620
gaaggacaca gcccaccaga tgatgtagac attgtcatca aactggacaa cacagccagc 1680
actgtgaaag ccatagctat tgtcattccc tgcatcttgg ccttatgcct ccttgtattg 1740
gtttacactg tgttccagtt caagaggaaa ggaacacccc gccacatact gtactgtaaa 1800
cgctctatgc aagagtgggt gtga 1824

<210> SEQ ID NO 106
<211> LENGTH: 1560
<212> TYPE: DNA
<213> ORGANISM: Homo sapiens
<300> PUBLICATION INFORMATION:
<302> TITLE: MMP17
<310> PATENT DOCUMENT NUMBER: NM004141

<400> SEQUENCE: 106
atgcagcagt ttggtggcct ggaggccacc ggcatcctgg acgaggccac cctggccctg 60
atgaaaaccc cacgctgctc cctgccagac ctccctgtcc tgacccaggc tcgcaggaga 120
cgccaggctc cagcccccac caagtggaac aagaggaacc tgtcgtggag ggtccggacg 180
ttcccacggg actcaccact ggggcacgac acggtgcgtg cactcatgta ctacgccctc 240
aaggtctgga gcgacattgc gcccctgaac ttccacgagg tggcgggcag caccgccgac 300
atccagatcg acttctccaa ggccgaccat aacgacggct accccttcga cggccccggc 360
ggcaccgtgg cccacgcctt cttccccggc caccaccaca ccgccgggga cacccacttt 420
gacgatgacg aggcctggac cttccgctcc tcggatgccc acgggatgga cctgtttgca 480
gtggctgtcc acgagtttgg ccacgccatt gggttaagcc atgtggccgc tgcacactcc 540
atcatgcggc cgtactacca gggcccggtg ggtgacccgc tgcgctacgg gctcccctac 600
gaggacaagg tgcgcgtctg gcagctgtac ggtgtgcggg agtctgtgtc tcccacggcg 660
cagcccgagg agcctcccct gctgccggag cccccagaca accggtccag cgccccgccc 720
aggaaggacg tgccccacag atgcagcact cactttgacg cggtggccca gatccggggt 780
gaagctttct tcttcaaagg caagtacttc tggcggctga cgcgggaccg gcacctggtg 840
tccctgcagc cggcacagat gcaccgcttc tggcggggcc tgccgctgca cctggacagc 900
gtggacgccg tgtacgagcg caccagcgac cacaagatcg tcttctttaa aggagacagg 960
tactgggtgt tcaaggacaa taacgtagag gaaggatacc cgcgccccgt ctccgacttc 1020
agcctcccgc ctggcggcat cgacgctgcc ttctcctggg cccacaatga caggacttat 1080
ttctttaagg accagctgta ctggcgctac gatgaccaca cgaggcacat ggaccccggc 1140
taccccgccc agagcccccct gtggaggggt gtccccagca cgctggacga cgccatgcgc 1200
tggtccgacg gtgcctccta cttcttccgt ggccaggagt actggaaagt gctggatggc 1260
gagctggagg tggcacccgg gtacccacag tccacggccc gggactggct ggtgtgtgga 1320
gactcacagg ccgatggatc tgtggctgcg ggcgtggacg cggcagaggg gccccgcgcc 1380
cctccaggac aacatgacca gagccgctcg gaggacggtt acgaggtctg ctcatgcacc 1440
tctggggcat cctctccccc gggggcccca ggcccactgg tggctgccac catgctgctg 1500
ctgctgccgc cactgtcacc aggcgccctg tggacagcgg cccaggccct gacgctatga 1560

<210> SEQ ID NO 107
<211> LENGTH: 1983
<212> TYPE: DNA
<213> ORGANISM: Homo sapiens
<300> PUBLICATION INFORMATION:
<302> TITLE: MMP2
<310> PATENT DOCUMENT NUMBER: NM004530

<400> SEQUENCE: 107
atggaggcgc taatggcccg gggcgcgctc acgggtcccc tgagggcgct ctgtctcctg 60
ggctgcctgc tgagccacgc cgccgccgcg ccgtcgccca tcatcaagtt ccccggcgat 120
gtcgccccca aaacggacaa agagttggca gtgcaatacc tgaacacctt ctatggctgc 180
cccaaggaga gctgcaacct gtttgtgctg aaggacacac taaagaagat gcagaagttc 240
tttggactgc cccagacagg tgatcttgac cagaatacca tcgagaccat gcggaagcca 300
cgctgcggca acccagatgt ggccaactac aacttcttcc ctcgcaagcc caagtgggac 360
aagaaccaga tcacatacag gatcattggc tacacacctg atctggaccc agagacagtg 420
gatgatgcct ttgctcgtgc cttccaagtc tggagcgatg tgaccccact gcggttttct 480
cgaatccatg atggagaggc agacatcatg atcaactttg gccgctggga gcatggcgat 540
ggatacccct ttgacggtaa ggacggactc ctggctcatg ccttcgcccc aggcactggt 600
gttgggggag actcccattt tgatgacgat gagctatgga ccttgggaga aggccaagtg 660
gtccgtgtga agtatggcaa cgccgatggg gagtactgca agttcccctt cttgttcaat 720
ggcaaggagt acaacagctg cactgatact ggccgcagcg atggcttcct ctggtgctcc 780
accacctaca actttgagaa ggatggcaag tacggcttct gtccccatga agccctgttc 840
accatgggcg gcaacgctga aggacagccc tgcaagtttc cattccgctt ccagggcaca 900
tcctatgaca gctgcaccac tgagggccgc acggatggct accgctggtg cggcaccact 960
gaggactacg accgcgacaa gaagtatggc ttctgccctg agaccgccat gtccactgtt 1020
ggtgggaact cagaaggtgc cccctgtgtc ttccccttca ctttcctggg caacaaatat 1080
gagagctgca ccagcgccgg ccgcagtgac ggaaagatgt ggtgtgcgac cacagccaac 1140
tacgatgacg accgcaagtg gggcttctgc cctgaccaag ggtacagcct gttcctcgtg 1200
gcagcccacg agtttggcca cgccatgggg ctggagcact cccaagaccc tggggccctg 1260
atggcaccca tttacaccta caccaagaac ttccgtctgt cccaggatga catcaagggc 1320
attcaggagc tctatggggc ctctcctgac attgaccttg gcaccggccc cacccccaca 1380
ctgggccctg tcactcctga gatctgcaaa caggacattg tatttgatgg catcgctcag 1440
atccgtggtg agatcttctt cttcaaggac cggttcattt ggcggactgt gacgccacgt 1500
gacaagccca tggggcccct gctggtggcc acattctggc ctgagctccc ggaaaagatt 1560
gatgcggtat acgaggcccc acaggaggag aaggctgtgt tctttgcagg gaatgaatac 1620
tggatctact cagccagcac cctggagcga gggtacccca agccactgac cagcctggga 1680
ctgccccctg atgtccagcg agtggatgcc gcctttaact ggagcaaaaa caagaagaca 1740
tacatctttg ctggagacaa attctggaga tacaatgagg tgaagaagaa aatggatcct 1800
ggctttccca agctcatcgc agatgcctgg aatgccatcc ccgataacct ggatgccgtc 1860
gtggacctgc agggcggcgg tcacagctac ttcttcaagg gtgcctatta cctgaagctg 1920
gagaaccaaa gtctgaagag cgtgaagttt ggaagcatca aatccgactg gctaggctgc 1980
tga 1983

<210> SEQ ID NO 108
<211> LENGTH: 1434
<212> TYPE: DNA
<213> ORGANISM: Homo sapiens
<300> PUBLICATION INFORMATION:
<302> TITLE: MMP2
<310> PATENT DOCUMENT NUMBER: XM006271
<300> PUBLICATION INFORMATION:
<302> TITLE: MMP3
<310> PATENT DOCUMENT NUMBER: XM006271

<400> SEQUENCE: 108
atgaagagtc ttccaatcct actgttgctg tgcgtggcag tttgctcagc ctatccattg 60
gatggagctg caaggggtga ggacaccagc atgaaccttg ttcagaaata tctagaaaac 120
tactacgacc tcgaaaaaga tgtgaaacag tttgttagga gaaaggacag tggtcctgtt 180
gttaaaaaaa tccgagaaat gcagaagttc cttggattgg aggtgacggg gaagctggac 240
tccgacactc tggaggtgat gcgcaagccc aggtgtggag ttcctgacgt tggtcacttc 300
agaacctttc ctggcatccc gaagtggagg aaaacccacc ttacatacag gattgtgaat 360
tatacaccag atttgccaaa agatgctgtt gattctgctg ttgagaaagc tctgaaagtc 420
tgggaagagg tgactccact cacattctcc aggctgtatg aaggagaggc tgatataatg 480
atctcttttg cagttagaga acatggagac ttttaccctt ttgatggacc tggaaatgtt 540
ttggcccatg cctatgcccc tgggccaggg attaatggag atgcccactt tgatgatgat 600
gaacaatgga caaaggatac aacagggacc aatttatttc tcgttgctgc tcatgaaatt 660
ggccactccc tgggtctctt tcactcagcc aacactgaag ctttgatgta cccactctat 720
cactcactca cagacctgac tcggttccgc ctgtctcaag atgatataaa tggcattcag 780
tccctctatg gacctccccc tgactcccct gagacccccc tggtacccac ggaacctgtc 840
cctccagaac ctgggacgcc agccaactgt gatcctgctt tgtcctttga tgctgtcagc 900
actctgaggg gagaaatcct gatctttaaa gacaggcact tttggcgcaa atccctcagg 960
aagcttgaac ctgaattgca tttgatctct tcattttggc catctcttcc ttcaggcgtg 1020
gatgccgcat atgaagttac tagcaaggac ctcgttttca tttttaaagg aaatcaattc 1080
tgggccatca gaggaaatga ggtacgagct ggatacccaa gaggcatcca caccctaggt 1140
ttccctccaa ccgtgaggaa aatcgatgca gccatttctg ataaggaaaa gaacaaaaca 1200
tatttctttg tagaggacaa atactggaga tttgatgaga agagaaattc catggagcca 1260
ggctttccca agcaaatagc tgaagacttt ccagggattg actcaaagat tgatgctgtt 1320
tttgaagaat ttgggttctt ttatttcttt actggatctt cacagttgga gtttgaccca 1380
aatgcaaaga aagtgacaca cactttgaag agtaacagct ggcttaattg ttga 1434

<210> SEQ ID NO 109
<211> LENGTH: 1404
<212> TYPE: DNA
<213> ORGANISM: Homo sapiens
<300> PUBLICATION INFORMATION:
<302> TITLE: MMP8
<310> PATENT DOCUMENT NUMBER: NM002424

<400> SEQUENCE: 109
atgttctccc tgaagacgct tccatttctg ctcttactcc atgtgcagat ttccaaggcc 60
tttcctgtat cttctaaaga gaaaaataca aaaactgttc aggactacct ggaaaagttc 120
taccaattac caagcaacca gtatcagtct acaaggaaga atggcactaa tgtgatcgtt 180
gaaaagctta aagaaatgca gcgatttttt gggttgaatg tgacggggaa gccaaatgag 240
gaaactctgg acatgatgaa aaagcctcgc tgtggagtgc ctgacagtgg tggttttatg 300
ttaaccccag gaaaccccaa gtgggaacgc actaacttga cctacaggat tcgaaactat 360
accccacagc tgtcagaggc tgaggtagaa agagctatca aggatgcctt tgaactctgg 420
agtgttgcat cacctctcat cttcaccagg atctcacagg gagaggcaga tatcaacatt 480
gctttttacc aaagagatca cggtgacaat tctccatttg atggacccaa tggaatcctt 540
gctcatgcct ttcagccagg ccaaggtatt ggaggagatg ctcattttga tgccgaagaa 600
acatggacca acacctccgc aaattacaac ttgtttcttg ttgctgctca tgaatttggc 660
cattctttgg ggctcgctca ctcctctgac cctggtgcct tgatgtatcc caactatgct 720
ttcagggaaa ccagcaacta ctcactccct caagatgaca tcgatggcat tcaggccatc 780
tatggacttt caagcaaccc tatccaacct actggaccaa gcacacccaa accctgtgac 840
cccagtttga catttgatgc tatcaccaca ctccgtggag aaatactttt ctttaaagac 900
aggtacttct ggagaaggca tcctcagcta caaagagtcg aaatgaattt tatttctcta 960
ttctggccat cccttccaac tggtatacag gctgcttatg aagattttga cagagacctc 1020
attttcctat ttaaaggcaa ccaatactgg gctctgagtg gctatgatat tctgcaaggt 1080
tatcccaagg atatatcaaa ctatggcttc cccagcagcg tccaagcaat tgacgcagct 1140
gttttctaca gaagtaaaac atacttcttt gtaaatgacc aattctggag atatgataac 1200
caaagacaat tcatggagcc aggttatccc aaaagcatat caggtgcctt tccaggaata 1260
gagagtaaag ttgatgcagt tttccagcaa gaacatttct tccatgtctt cagtggacca 1320
agatattacg catttgatct tattgctcag agagttacca gagttgcaag aggcaataaa 1380
tggcttaact gtagatatgg ctga 1404

<210> SEQ ID NO 110
<211> LENGTH: 2124
<212> TYPE: DNA
<213> ORGANISM: Homo sapiens
<300> PUBLICATION INFORMATION:
<302> TITLE: MMP9
<310> PATENT DOCUMENT NUMBER: XM009491

<400> SEQUENCE: 110
atgagcctct ggcagcccct ggtcctggtg ctcctggtgc tgggctgctg ctttgctgcc 60
cccagacagc gccagtccac ccttgtgctc ttccctggag acctgagaac caatctcacc 120
gacaggcagc tggcagagga atacctgtac cgctatggtt acactcgggt ggcagagatg 180
cgtggagagt cgaaatctct ggggcctgcg ctgctgcttc tccagaagca actgtccctg 240
cccgagaccg gtgagctgga tagcgccacg ctgaaggcca tgcgaacccc acggtgcggg 300
gtcccagacc tgggcagatt ccaaaccttt gagggcgacc tcaagtggca ccaccacaac 360
atcacctatt ggatccaaaa ctactcggaa gacttgccgc gggcggtgat tgacgacgcc 420
tttgcccgcg ccttcgcact gtggagcgcg gtgacgccgc tcaccttcac tcgcgtgtac 480
agccgggacg cagacatcgt catccagttt ggtgtcgcgg agcacggaga cgggtatccc 540
ttcgacggga aggacgggct cctggcacac gcctttcctc ctggccccgg cattcaggga 600
gacgcccatt tcgacgatga cgagttgtgg tccctgggca agggcgtcgt ggttccaact 660
cggtttggaa acgcagatgg cgcggcctgc cacttcccct tcatcttcga gggccgctcc 720
tactctgcct gcaccaccga cggtcgctcc gacggcttgc cctggtgcag taccacggcc 780
aactacgaca ccgacgaccg gtttggcttc tgccccagcg agagactcta cacccaggac 840
ggcaatgctg atgggaaacc ctgccagttt ccattcatct tccaaggcca atcctactcc 900
gcctgcacca cggacggtcg ctccgacggc taccgctggt gcgccaccac cgccaactac 960
gaccgggaca agctcttcgg cttctgcccg acccgagctg actcgacggt gatgggggc 1020 aactcggcgg gggagctgtg cgtcttcccc ttcactttcc tgggtaagga gtactcgacc 1080
tgtaccagcg agggccgcgg agatgggcgc ctctggtgcg ctaccacctc gaactttgac 1140
agcgacaaga agtggggctt ctgcccggac caaggataca gtttgttcct cgtggcggcg 1200
catgagttcg gccacgcgct gggcttagat cattcctcag tgccggaggc gctcatgtac 1260
cctatgtacc gcttcactga ggggcccccc ttgcataagg acgacgtgaa tggcatccgg 1320
cacctctatg gtcctcgccc tgaacctgag ccacggcctc caaccaccac cacaccgcag 1380
cccacggctc ccccgacggt ctgccccacc ggacccccca ctgtccaccc ctcagagcgc 1440
cccacagctg gccccacagg tccccccctca gctggcccca caggtccccc cactgctggc 1500
ccttctacgg ccactactgt gcctttgagt ccggtggacg atgcctgcaa cgtgaacatc 1560
ttcgacgcca tcgcggagat tgggaaccag ctgtatttgt tcaaggatgg gaagtactgg 1620
cgattctctg agggcagggg gagccggccg cagggcccct tccttatcgc cgacaagtgg 1680
cccgcgctgc cccgcaagct ggactcggtc tttgaggagc ggctctccaa gaagcttttc 1740
ttcttctctg ggcgccaggt gtgggtgtac acaggcgcgt cggtgctggg cccgaggcgt 1800
ctggacaagc tgggcctggg agccgacgtg gcccaggtga ccggggccct ccggagtggc 1860
agggggaaga tgctgctgtt cagcgggcgg cgcctctgga ggttcgacgt gaaggcgcag 1920
atggtggatc cccggagcgc cagcgaggtg gaccggatgt tccccggggt gcctttggac 1980
acgcacgacg tcttccagta ccgagagaaa gcctatttct gccaggaccg cttctactgg 2040
cgcgtgagtt cccggagtga gttgaaccag gtggaccaag tgggctacgt gacctatgac 2100
atcctgcagt gccctgagga ctag 2124

<210> SEQ ID NO 111
<211> LENGTH: 2019
<212> TYPE: DNA
<213> ORGANISM: Homo sapiens
<300> PUBLICATION INFORMATION:
<302> TITLE: PKC alpha
<310> PATENT DOCUMENT NUMBER: NM002737

<400> SEQUENCE: 111
atggctgacg ttttcccggg caacgactcc acggcgtctc aggacgtggc caaccgcttc 60
gcccgcaaag ggcgctgag gcagaagaac gtgcacgagg tgaaggacca caaattcatc 120
gcgcgcttct tcaagcagcc caccttctgc agccactgca ccgacttcat ctgggggttt 180
gggaaacaag gcttccagtg ccaagtttgc tgttttgtgg tccacaagag gtgccatgaa 240
tttgttactt tttcttgtcc gggtgcggat aagggacccg acactgatga ccccaggagc 300
aagcacaagt tcaaaatcca cacttacgga agccccacct tctgcgatca ctgtgggtca 360
ctgctctatg gacttatcca tcaagggatg aaatgtgaca cctgcgatat gaacgttcac 420

```
aagcaatgcg tcatcaatgt ccccagcctc tgcggaatgg atcacactga gaagaggggg    480

cggatttacc taaaggctga ggttgctgat gaaaagctcc atgtcacagt acgagatgca    540

aaaaatctaa tccctatgga tccaaacggg ctttcagatc cttatgtgaa gctgaaactt    600

attcctgatc ccaagaatga aagcaagcaa aaaaccaaaa ccatccgctc cacactaaat    660

ccgcagtgga atgagtcctt tacattcaaa ttgaaacctt cagacaaaga ccgacgactg    720

tctgtagaaa tctgggactg ggatcgaaca acaaggaatg acttcatggg atccctttcc    780

tttggagttt cggagctgat gaagatgccg gccagtggat ggtacaagtt gcttaaccaa    840

gaagaaggtg agtactacaa cgtacccatt ccggaagggg acgaggaagg aaacatggaa    900

ctcaggcaga aattcgagaa agccaaactt ggccctgctg gcaacaaagt catcagtccc    960

tctgaagaca ggaaacaacc ttccaacaac cttgaccgag tgaaactcac ggacttcaat   1020

ttcctcatgg tgttgggaaa ggggagtttt ggaaaggtga tgcttgccga caggaagggc   1080

acagaagaac tgtatgcaat caaaatcctg aagaaggatg tggtgattca ggatgatgac   1140

gtggagtgca ccatggtaga aaagcgagtc ttggccctgc ttgacaaacc cccgttcttg   1200

acgcagctgc actcctgctt ccagacagtg gatcggctgt acttcgtcat ggaatatgtc   1260

aacggtgggg acctcatgta ccacattcag caagtaggaa aatttaagga accacaagca   1320

gtattctatg cggcagagat ttccatcgga ttgttctttc ttcataaaag aggaatcatt   1380

tatagggatc tgaagttaga taacgtcatg ttggattcag aaggacatat caaaattgct   1440

gactttggga tgtgcaagga acacatgatg gatggagtca cgaccaggac cttctgtggg   1500

actccagatt atatcgcccc agagataatc gcttatcagc cgtatggaaa atctgtggac   1560

tggtgggcct atggcgtcct gttgtatgaa atgcttgccg ggcagcctcc atttgatggt   1620

gaagatgaag acgagctatt tcagtctatc atggagcaca acgtttccta tccaaaatcc   1680

ttgtccaagg aggctgtttc tatctgcaaa ggactgatga ccaaacaccc agccaagcgg   1740

ctgggctgtg ggcctgaggg ggagagggac gtgagagagc atgccttctt ccggaggatc   1800

gactgggaaa aactggagaa cagggagatc cagccaccat tcaagcccaa agtgtgtggc   1860

aaaggagcag agaactttga caagttcttc acacgaggac agcccgtctt aacaccacct   1920

gatcagctgg ttattgctaa catagaccag tctgattttg aagggttctc gtatgtcaac   1980

ccccagtttg tgcaccccat cttacagagt gcagtatga                          2019
```

<210> SEQ ID NO 112
<211> LENGTH: 2022
<212> TYPE: DNA
<213> ORGANISM: Homo sapiens
<300> PUBLICATION INFORMATION:
<302> TITLE: PKC beta
<310> PATENT DOCUMENT NUMBER: X07109

<400> SEQUENCE: 112

```
atggctgacc cggctgcggg gccgccgccg agcgagggcg aggagagcac cgtgcgcttc     60

gcccgcaaag gcgccctccg gcagaagaac gtgcatgagg tcaagaacca caaattcacc    120

gcccgcttct tcaagcagcc caccttctgc agccactgca ccgacttcat ctggggcttc    180

gggaagcagg gattccagtg ccaagtttgc tgctttgtgg tgcacaagcg gtgccatgaa    240

tttgtcacat tctcctgccc tggcgctgac aagggtccag cctccgatga cccccgcagc    300

aaacacaagt ttaagatcca cacgtactcc agccccacgt tttgtgacca ctgtgggtca    360

ctgctgtatg gactcatcca ccaggggatg aaatgtgaca cctgcatgat gaatgtgcac    420
```

```
aagcgctgcg tgatgaatgt tcccagcctg tgtggcacgg accacacgga gcgccgcggc    480

cgcatctaca tccaggccca catcgacagg gacgtcctca ttgtcctcgt aagagatgct    540

aaaaaccttg tacctatgga ccccaatggc ctgtcagatc cctacgtaaa actgaaactg    600

attcccgatc ccaaaagtga gagcaaacag aagaccaaaa ccatcaaatg ctccctcaac    660

cctgagtgga atgagacatt tagatttcag ctgaaagaat cggacaaaga cagaagactg    720

tcagtagaga tttgggattg ggatttgacc agcaggaatg acttcatggg atctttgtcc    780

tttgggattt ctgaacttca gaaggccagt gttgatggct ggtttaagtt actgagccag    840

gaggaaggcg agtacttcaa tgtgcctgtg ccaccagaag gaagtgaggc caatgaagaa    900

ctgcggcaga aatttgagag ggccaagatc agtcagggaa ccaaggtccc ggaagaaaag    960

acgaccaaca ctgtctccaa atttgacaac aatggcaaca gagaccggat gaaactgacc   1020

gattttaact tcctaatggt gctggggaaa ggcagctttg gcaaggtcat gctttcagaa   1080

cgaaaaggca cagatgagct ctatgctgtg aagatcctga agaaggacgt tgtgatccaa   1140

gatgatgacg tggagtgcac tatggtggag aagcgggtgt tggccctgcc tgggaagccg   1200

cccttcctga cccagctcca ctcctgcttc cagaccatgg accgcctgta ctttgtgatg   1260

gagtacgtga atgggggcga cctcatgtat cacatccagc aagtcggccg gttcaaggag   1320

ccccatgctg tattttacgc tgcagaaatt gccatcggtc tgttcttctt acagagtaag   1380

ggcatcattt accgtgacct aaaacttgac aacgtgatgc tcgattctga gggacacatc   1440

aagattgccg attttggcat gtgtaaggaa aacatctggg atggggtgac aaccaagaca   1500

ttctgtggca ctccagacta catcgccccc gagataattg cttatcagcc ctatgggaag   1560

tccgtggatt ggtgggcatt tggagtcctg ctgtatgaaa tgttggctgg gcaggcaccc   1620

tttgaagggg aggatgaaga tgaactcttc caatccatca tggaacacaa cgtagcctat   1680

cccaagtcta tgtccaagga agctgtggcc atctgcaaag ggctgatgac caaacaccca   1740

ggcaaacgtc tgggttgtgg acctgaaggc gaacgtgata tcaaagagca tgcatttttc   1800

cggtatattg attgggagaa acttgaacgc aaagagatcc agcccccctta taagccaaaa   1860

gcttgtgggc gaaatgctga aaacttcgac cgatttttca cccgccatcc accagtccta   1920

acacctcccg accaggaagt catcaggaat attgaccaat cagaattcga aggattttcc   1980

tttgttaact ctgaattttt aaaacccgaa gtcaagagct aa                      2022
```

<210> SEQ ID NO 113
<211> LENGTH: 2031
<212> TYPE: DNA
<213> ORGANISM: Homo sapiens
<300> PUBLICATION INFORMATION:
<302> TITLE: PKC delta
<310> PATENT DOCUMENT NUMBER: NM006254

<400> SEQUENCE: 113

```
atggcgccgt tcctgcgcat cgccttcaac tcctatgagc tgggctccct gcaggccgag     60

gacgaggcga accagccctt ctgtgccgtg aagatgaagg aggcgctcag cacagagcgt    120

gggaaaacac tggtgcagaa gaagccgacc atgtatcctg agtggaagtc gacgttcgat    180

gcccacatct atgaggggcg cgtcatccag attgtgctaa tgcgggcagc agaggagcca    240

gtgtctgagg tgaccgtggg tgtgtcggtg ctggccgagc gctgcaagaa gaacaatggc    300

aaggctgagt tctggctgga cctgcagcct caggccaagg tgttgatgtc tgttcagtat    360

ttcctggagg acgtggattg caaacaatct atgcgcagtg aggacgaggc caagttccca    420
```

acgatgaacc gccgcggagc catcaaacag gccaaaatcc actacatcaa gaaccatgag 480
tttatcgcca ccttctttgg gcaacccacc ttctgttctg tgtgcaaaga ctttgtctgg 540
ggcctcaaca agcaaggcta caaatgcagg caatgtaacg ctgccatcca caagaaatgc 600
atcgacaaga tcatcggcag atgcactggc accgcggcca acagccggga cactatattc 660
cagaaagaac gcttcaacat cgacatgccg caccgcttca aggttcacaa ctacatgagc 720
cccaccttct gtgaccactg cggcagcctg ctctggggac tggtgaagca gggattaaag 780
tgtgaagact gcggcatgaa tgtgcaccat aaatgccggg agaaggtggc caacctctgc 840
ggcatcaacc agaagctttt ggctgaggcc ttgaaccaag tcacccagag agcctcccgg 900
agatcagact cagcctcctc agagcctgtt gggatatatc agggtttcga gaagaagacc 960
ggagttgctg gggaggacat gcaagacaac agtgggacct acggcaagat ctgggagggc 1020
agcagcaagt gcaacatcaa caacttcatc ttccacaagg tcctgggcaa aggcagcttc 1080
gggaaggtgc tgcttggaga gctgaagggc agaggagagt actctgccat caaggccctc 1140
aagaaggatg tggtcctgat cgacgacgac gtggagtgca ccatggttga gaagcgggtg 1200
ctgacacttg ccgcagagaa tccctttctc acccacctca tctgcacctt ccagaccaag 1260
gaccacctgt tctttgtgat ggagttcctc aacgggggg acctgatgta ccacatccag 1320
gacaaaggcc gctttgaact ctaccgtgcc acgttttatg ccgctgagat aatgtgtgga 1380
ctgcagtttc tacacagcaa gggcatcatt tacagggacc tcaaactgga caatgtgctg 1440
ttggaccggg atggccacat caagattgcc gactttggga tgtgcaaaga gaacatattc 1500
ggggagagcc gggccagcac cttctgcggc acccctgact atatcgcccc tgagatccta 1560
cagggcctga agtacacatt ctctgtggac tggtggtctt tcggggtcct tctgtacgag 1620
atgctcattg gccagtcccc cttccatggt gatgatgagg atgaactctt cgagtccatc 1680
cgtgtggaca cgccacatta tccccgctgg atcaccaagg agtccaagga catcctggag 1740
aagctctttg aaagggaacc aaccaagagg ctgggaatga cgggaaacat caaaatccac 1800
cccttcttca agaccataaa ctggactctg ctggaaaagc ggaggttgga gccacccttc 1860
aggcccaaag tgaagtcacc cagagactac agtaactttg accaggagtt cctgaacgag 1920
aaggcgcgcc tctcctacag cgacaagaac ctcatcgact ccatggacca gtctgcattc 1980
gctggcttct cctttgtgaa ccccaaattc gagcacctcc tggaagattg a 2031

<210> SEQ ID NO 114
<211> LENGTH: 2049
<212> TYPE: DNA
<213> ORGANISM: Homo sapiens
<300> PUBLICATION INFORMATION:
<302> TITLE: PKC eta
<310> PATENT DOCUMENT NUMBER: NM006255

<400> SEQUENCE: 114
atgtcgtctg gcaccatgaa gttcaatggc tatttgaggg tccgcatcgg tgaggcagtg 60
gggctgcagc ccacccgctg gtccctgcgc cactcgctct tcaagaaggg ccaccagctg 120
ctggacccct atctgacggt gagcgtggac caggtgcgcg tgggccagac cagcaccaag 180
cagaagacca acaaacccac gtacaacgag gagttttgcg ctaacgtcac cgacggcggc 240
cacctcgagt tggccgtctt ccacgagacc cccctgggct acgacttcgt ggccaactgc 300
accctgcagt tccaggagct cgtcggcacg accggcgcct cggacacctt cgagggttgg 360
gtggatctcg agccagaggg gaaagtattt gtggtaataa ccccttaccgg gagtttcact 420

```
gaagctactc tccagagaga ccggatcttc aaacatttta ccaggaagcg ccaaagggct    480

atgcgaaggc gagtccacca gatcaatgga cacaagttca tggccacgta tctgaggcag    540

cccacctact gctctcactg cagggagttt atctggggag tgtttgggaa acagggttat    600

cagtgccaag tgtgcacctg tgtcgtccat aaacgctgcc atcatctaat tgttacagcc    660

tgtacttgcc aaaacaatat taacaaagtg gattcaaaga ttgcagaaca gaggttcggg    720

atcaacatcc cacacaagtt cagcatccac aactacaaag tgccaacatt ctgcgatcac    780

tgtggctcac tgctctgggg aataatgcga caaggacttc agtgtaaaat atgtaaaatg    840

aatgtgcata ttcgatgtca agcgaacgtg gcccctaact gtggggtaaa tgcggtggaa    900

cttgccaaga ccctggcagg gatgggtctc caacccggaa atatttctcc aacctcgaaa    960

ctcgtttcca gatcgaccct aagacgacag ggaaaggaga gcagcaaaga aggaaatggg   1020

attggggtta attcttccaa ccgacttggt atcgacaact ttgagttcat ccgagtgttg   1080

gggaagggga gttttgggaa ggtgatgctt gcaagagtaa aagaaacagg agacctctat   1140

gctgtgaagg tgctgaagaa ggacgtgatt ctgctggatg atgatgtgga atgcaccatg   1200

accgagaaaa ggatcctgtc tctggcccgc aatcacccct tcctcactca gttgttctgc   1260

tgctttcaga cccccgatcg tctgtttttt gtgatggagt ttgtgaatgg gggtgacttg   1320

atgttccaca ttcagaagtc tcgtcgtttt gatgaagcac gagctcgctt ctatgctgca   1380

gaaatcattt cggctctcat gttcctccat gataaaggaa tcatctatag agatctgaaa   1440

ctggacaatg tcctgttgga ccacgagggt cactgtaaac tggcagactt cggaatgtgc   1500

aaggagggga tttgcaatgg tgtcaccacg gccacattct gtggcacgcc agactatatc   1560

gctccagaga tcctccagga aatgctgtac gggcctgcag tagactggtg ggcaatgggc   1620

gtgttgctct atgagatgct ctgtggtcac gcgccttttg aggcagagaa tgaagatgac   1680

ctctttgagg ccatactgaa tgatgaggtg gtctacccta cctggctcca tgaagatgcc   1740

acagggatcc taaaatcttt catgaccaag aaccccacca tgcgcttggg cagcctgact   1800

cagggaggcg agcacgccat cttgagacat ccttttttta aggaaatcga ctgggcccag   1860

ctgaaccatc gccaaataga accgcctttc agacccagaa tcaaatcccg agaagatgtc   1920

agtaattttg accctgactt cataaaggaa gagccagttt taactccaat tgatgaggga   1980

catcttccaa tgattaacca ggatgagttt agaaactttt cctatgtgtc tccagaattg   2040

caaccatag                                                           2049
```

<210> SEQ ID NO 115
<211> LENGTH: 948
<212> TYPE: DNA
<213> ORGANISM: Homo sapiens
<300> PUBLICATION INFORMATION:
<302> TITLE: PKC epsilon
<310> PATENT DOCUMENT NUMBER: XM002370

<400> SEQUENCE: 115

```
atgttggcag aactcaaggg caaagatgaa gtatatgctg tgaaggtctt aaagaaggac     60

gtcatccttc aggatgatga cgtggactgc acaatgacag agaagaggat tttggctctg    120

gcacggaaac acccgtacct tacccaactc tactgctgct tccagaccaa ggaccgcctc    180

tttttcgtca tggaatatgt aaatggtgga gacctcatgt ttcagattca gcgctcccga    240

aaattcgacg agcctcgttc acggttctat gctgcagagg tcacatcggc cctcatgttc    300

ctccaccagc atggagtcat ctacagggat ttgaaactgg acaacatcct tctggatgca    360
```

-continued gaaggtcact gcaagctggc tgacttcggg atgtgcaagg aagggattct gaatggtgtg 420
acgaccacca cgttctgtgg gactcctgac tacatagctc ctgagatcct gcaggagttg 480
gagtatggcc cctccgtgga ctggtgggcc ctgggggtgc tgatgtacga gatgatggct 540
ggacagcctc cctttgaggc cgacaatgag gacgacctat ttgagtccat cctccatgac 600
gacgtgctgt acccagtctg gctcagcaag gaggctgtca gcatcttgaa agctttcatg 660
acgaagaatc cccacaagcg cctgggctgt gtggcatcgc agaatggcga ggacgccatc 720
aagcagcacc cattcttcaa agagattgac tgggtgctcc tggagcagaa gaagatcaag 780
ccacccttca aaccacgcat taaaaccaaa agagacgtca ataattttga ccaagacttt 840
acccgggaag agccggtact cacccttgtg gacgaagcaa ttgtaaagca gatcaaccag 900
gaggaattca aaggtttctc ctactttggt gaagacctga tgccctga 948

<210> SEQ ID NO 116
<211> LENGTH: 1764
<212> TYPE: DNA
<213> ORGANISM: Homo sapiens
<300> PUBLICATION INFORMATION:
<302> TITLE: PKC iota
<310> PATENT DOCUMENT NUMBER: NM002740

<400> SEQUENCE: 116
atgtcccaca cggtcgcagg cggcggcagc ggggaccatt cccaccaggt ccgggtgaaa 60
gcctactacc gcggggatat catgataaca cattttgaac cttccatctc ctttgagggc 120
ctttgcaatg aggttcgaga catgtgttct tttgacaacg aacagctctt caccatgaaa 180
tggatagatg aggaaggaga cccgtgtaca gtatcatctc agttggagtt agaagaagcc 240
tttagacttt atgagctaaa caaggattct gaactcttga ttcatgtgtt cccttgtgta 300
ccagaacgtc ctgggatgcc ttgtccagga gaagataaat ccatctaccg tagaggtgca 360
cgccgctgga gaaagcttta ttgtgccaat ggccacactt tccaagccaa gcgtttcaac 420
aggcgtgctc actgtgccat ctgcacagac cgaatatggg gacttggacg ccaaggatat 480
aagtgcatca actgcaaact cttggttcat aagaagtgcc ataaactcgt cacaattgaa 540
tgtgggcggc attctttgcc acaggaacca gtgatgccca tggatcagtc atccatgcat 600
tctgaccatg cacagacagt aattccatat aatccttcaa gtcatgagag tttggatcaa 660
gttggtgaag aaaaagaggc aatgaacacc agggaaagtg gcaaagcttc atccagtcta 720
ggtcttcagg attttgattt gctccgggta ataggaagag gaagttatgc caaagtactg 780
ttggttcgat taaaaaaaac agatcgtatt tatgcaatga aagttgtgaa aaaagagctt 840
gttaatgatg atgaggatat tgattgggta cagacagaga agcatgtgtt tgagcaggca 900
tccaatcatc ctttccttgt tgggctgcat tcttgctttc agacagaaag cagattgttc 960
tttgttatag agtatgtaaa tggaggagac ctaatgtttc atatgcagcg acaaagaaaa 1020
cttcctgaag aacatgccag attttactct gcagaaatca gtctagcatt aaattatctt 1080
catgagcgag ggataattta tagagatttg aaactggaca atgtattact ggactctgaa 1140
ggccacatta aactcactga ctacggcatg tgtaaggaag gattacggcc aggagataca 1200
accagcactt tctgtggtac tcctaattac attgctcctg aaattttaag aggagaagat 1260
tatggtttca gtgttgactg gtgggctctt ggagtgctca tgtttgagat gatggcagga 1320
aggtctccat ttgatattgt tgggagctcc gataaccctg accagaacac agaggattat 1380
ctcttccaag ttattttgga aaaacaaatt cgcataccac gttctctgtc tgtaaaagct 1440

```
gcaagtgttc tgaagagttt tcttaataag gaccctaagg aacgattggg ttgtcatcct   1500

caaacaggat ttgctgatat tcagggacac ccgttcttcc gaaatgttga ttgggatatg   1560

atggagcaaa aacaggtggt acctcccttt aaaccaaata tttctgggga atttggtttg   1620

gacaactttg attctcagtt tactaatgaa cctgtccagc tcactccaga tgacgatgac   1680

attgtgagga agattgatca gtctgaattt gaaggttttg agtatatcaa tcctcttttg   1740

atgtctgcag aagaatgtgt ctga                                          1764
```

<210> SEQ ID NO 117
<211> LENGTH: 2451
<212> TYPE: DNA
<213> ORGANISM: Homo sapiens
<300> PUBLICATION INFORMATION:
<302> TITLE: PKC mu
<310> PATENT DOCUMENT NUMBER: XM007234

<400> SEQUENCE: 117

```
atgtatgata agatcctgct tttcgccat gaccctacct ctgaaaacat ccttcagctg      60

gtgaaagcgg ccagtgatat ccaggaaggc gatcttattg aagtggtctt gtcagcttcc    120

gccacctttg aagactttca gattcgtccc cacgctctct ttgttcattc atacagagct    180

ccagctttct gtgatcactg tggagaaatg ctgtgggggc tggtacgtca aggtcttaaa    240

tgtgaagggt gtggtctgaa ttaccataag agatgtgcat ttaaaatacc caacaattgc    300

agcggtgtga ggcggagaag gctctcaaac gtttccctca ctggggtcag caccatccgc    360

acatcatctg ctgaactctc tacaagtgcc cctgatgagc cccttctgca aaaatcacca    420

tcagagtcgt ttattggtcg agagaagagg tcaaattctc aatcatacat tggacgacca    480

attcaccttg acaagatttt gatgtctaaa gttaaagtgc cgcacacatt tgtcatccac    540

tcctacaccc ggcccacagt gtgccagtac tgcaagaagc ttctgaaggg gcttttcagg    600

cagggcttgc agtgcaaaga ttgcagattc aactgccata aacgttgtgc accgaaagta    660

ccaaacaact gccttggcga agtgaccatt aatggagatt tgcttagccc tggggcagag    720

tctgatgtgg tcatggaaga agggagtgat gacaatgata gtgaaaggaa cagtgggctc    780

atggatgata tggaagaagc aatggtccaa gatgcagaga tggcaatggc agagtgccag    840

aacgacagtg gcgagatgca agatccagac ccagaccacg aggacgccaa cagaaccatc    900

agtccatcaa caagcaacaa tatcccactc atgagggtag tgcagtctgt caaacacacg    960

aagaggaaaa gcagcacagt catgaaagaa ggatggatgg tccactacac cagcaaggac   1020

acgctgcgga aacggcacta ttggagattg gatagcaaat gtattaccct ctttcagaat   1080

gacacaggaa gcaggtacta caaggaaatt cctttatctg aaattttgtc tctggaacca   1140

gtaaaaactt cagctttaat tcctaatggg gccaatcctc attgtttcga aatcactacg   1200

gcaaatgtag tgtattatgt gggagaaaat gtggtcaatc cttccagccc atcaccaaat   1260

aacagtgttc tcaccagtgg cgttggtgca gatgtggcca ggatgtggga gatagccatc   1320

cagcatgccc ttatgcccgt cattcccaag ggctcctccg tgggtacagg aaccaacttg   1380

cacagagata tctctgtgag tatttcagta tcaaattgcc agattcaaga aaatgtggac   1440

atcagcacag tatatcagat tttcctgat gaagtactgg gttctggaca gtttggaatt    1500

gtttatggag gaaaacatcg taaaacagga agagatgtag ctattaaaat cattgacaaa   1560

ttacgatttc caacaaaaca agaaagccag cttcgtaatg aggttgcaat tctacagaac   1620

cttcatcacc ctggtgttgt aaatttggag tgtatgtttg agacgcctga aagagtgttt   1680
```

gttgttatgg aaaaactcca tggagacatg ctggaaatga tcttgtcaag tgaaaagggc 1740
aggttgccag agcacataac gaagttttta attactcaga tactcgtggc tttgcggcac 1800
cttcatttta aaaatatcgt tcactgtgac ctcaaaccag aaaatgtgtt gctagcctca 1860
gctgatcctt ttcctcaggt gaaactttgt gattttggtt ttgcccggat cattggagag 1920
aagtctttcc ggaggtcagt ggtgggtacc cccgcttacc tggctcctga ggtcctaagg 1980
aacaagggct acaatcgctc tctagacatg tggtctgttg ggtcatcat ctatgtaagc 2040 ctaagcggca cattcccatt taatgaagat gaagacatac acgaccaaat tcagaatgca 2100
gctttcatgt atccaccaaa tccctggaag gaaatatctc atgaagccat tgatcttatc 2160
aacaatttgc tgcaagtaaa aatgagaaag cgctacagtg tggataagac cttgagccac 2220
ccttggctac aggactatca gacctggtta gatttgcgag agctggaatg caaaatcggg 2280
gagcgctaca tcacccatga aagtgatgac ctgaggtggg agaagtatgc aggcgagcag 2340
gggctgcagt accccacaca cctgatcaat ccaagtgcta gccacagtga cactcctgag 2400
actgaagaaa cagaaatgaa agccctcggt gagcgtgtca gcatcctatg a 2451

<210> SEQ ID NO 118
<211> LENGTH: 2673
<212> TYPE: DNA
<213> ORGANISM: Homo sapiens
<300> PUBLICATION INFORMATION:
<302> TITLE: PKC nu
<310> PATENT DOCUMENT NUMBER: NM005813

<400> SEQUENCE: 118
atgtctgcaa ataattcccc tccatcagcc cagaagtctg tattacccac agctattcct 60
gctgtgcttc cagctgcttc tccgtgttca agtcctaaga cgggactctc tgcccgactc 120
tctaatggaa gcttcagtgc accatcactc accaactcca gaggctcagt gcatacagtt 180
tcatttctac tgcaaattgg cctcacacgg gagagtgtta ccattgaagc ccaggaactg 240
tctttatctg ctgtcaagga tcttgtgtgc tccatagttt atcaaaagtt tccagagtgt 300
ggattctttg gcatgtatga caaaattctt ctctttcgcc atgacatgaa ctcagaaaac 360
attttgcagc tgattacctc agcagatgaa atacatgaag gagacctagt ggaagtggtt 420
ctttcagctt tagccacagt agaagacttc cagattcgtc cacatactct ctatgtacat 480
tcttacaaag ctcctacttt ctgtgattac tgtggtgaga tgctgtgggg attggtacgt 540
caaggactga aatgtgaagg ctgtggatta aattaccata aacgatgtgc cttcaagatt 600
ccaaataact gtagtggagt aagaaagaga cgtctgtcaa atgtatcttt accaggaccc 660
ggcctctcag ttccaagacc cctacagcct gaatatgtag cccttcccag tgaagagtca 720
catgtccacc aggaaccaag taagagaatt ccttcttgga gtggtcgccc aatctggatg 780
gaaaagatgg taatgtgcag agtgaaagtt ccacacacat ttgctgttca ctcttacacc 840
cgtcccacga tatgtcagta ctgcaagcgg ttactgaaag gcctctttcg ccaaggaatg 900
cagtgtaaag attgcaaatt caactgccat aaacgctgtg catcaaaagt accaagagac 960
tgccttggag aggttacttt caatggagaa ccttccagtc tgggaacaga tacagatata 1020
ccaatggata ttgacaataa tgacataaat agtgatagta gtcggggttt ggatgacaca 1080
gaagagccat cacccccaga agataagatg ttcttcttgg atccatctga tctcgatgtg 1140
gaaagagatg aagaagccgt taaaacaatc agtccatcaa caagcaataa tattccgcta 1200
atgagggttg tacaatccat caagcacaca aagaggaaga gcagcacaat ggtgaaggaa 1260
gggtggatgg tccattacac cagcagggat aacctgagaa agaggcatta ttggagactt 1320
gacagcaaat gtctaacatt atttcagaat gaatctggat caaagtatta taaggaaatt 1380
ccactttcag aaattctccg catatcttca ccacgagatt tcacaaacat ttcacaaggc 1440
agcaatccac actgttttga aatcattact gatactatgg tatacttcgt tggtgagaac 1500
aatggggaca gctctcataa tcctgttctt gctgccactg gagttggact tgatgtagca 1560
cagagctggg aaaaagcaat tcgccaagcc ctcatgcctg ttactcctca agcaagtgtt 1620
tgcacttctc cagggcaagg gaaagatcac aaagatttgt ctacaagtat ctctgtatct 1680
aattgtcaga ttcaggagaa tgtggatatc agtactgttt accagatctt tgcagatgag 1740
gtgcttggtt caggccagtt tggcatcgtt tatggaggaa aacatagaaa gactgggagg 1800
gatgtggcta ttaaagtaat tgataagatg agattcccca caaaacaaga aagtcaactc 1860
cgtaatgaag tggctatttt acagaatttg caccatcctg ggattgtaaa cctggaatgt 1920
atgtttgaaa ccccagaacg agtctttgta gtaatggaaa agctgcatgg agatatgttg 1980
gaaatgattc tatccagtga gaaaagtcgg cttccagaac gaattactaa attcatggtc 2040
acacagatac ttgttgcttt gaggaatctg cattttaaga atattgtgca ctgtgattta 2100
aagccagaaa atgtgctgct tgcatcagca gagccatttc ctcaggtgaa gctgtgtgac 2160
tttggatttg cacgcatcat tggtgaaaag tcattcagga gatctgtggt aggaactcca 2220
gcatacttag cccctgaagt tctccggagc aaaggttaca accgttccct agatatgtgg 2280
tcagtgggag ttatcatcta tgtgagcctc agtggcacat ttccttttaa tgaggatgaa 2340
gatataaatg accaaatcca aaatgctgca tttatgtacc caccaaatcc atggagagaa 2400
atttctggtg aagcaattga tctgataaac aatctgcttc aagtgaagat gagaaaacgt 2460
tacagtgttg acaaatctct tagtcatccc tggctacagg actatcagac ttggcttgac 2520
cttagagaat ttgaaactcg cattggagaa cgttacatta cacatgaaag tgatgatgct 2580
cgctgggaaa tacatgcata cacacataac cttgtatacc caaagcactt cattatggct 2640
cctaatccag atgatatgga agaagatcct taa 2673

<210> SEQ ID NO 119
<211> LENGTH: 2121
<212> TYPE: DNA
<213> ORGANISM: Homo sapiens
<300> PUBLICATION INFORMATION:
<302> TITLE: PKC tau
<310> PATENT DOCUMENT NUMBER: NM006257

<400> SEQUENCE: 119
atgtcgccat ttcttcggat tggcttgtcc aactttgact gcgggtcctg ccagtcttgt 60
cagggcgagg ctgttaaccc ttactgtgct gtgctcgtca aagagtatgt cgaatcagag 120
aacgggcaga tgtatatcca gaaaaagcct accatgtacc caccctggga cagcactttt 180
gatgcccata tcaacaaggg aagagtcatg cagatcattg tgaaaggcaa aaacgtggac 240
ctcatctctg aaaccaccgt ggagctctac tcgctggctg agaggtgcag gaagaacaac 300
gggaagacag aaatatggtt agagctgaaa cctcaaggcc gaatgctaat gaatgcaaga 360
tactttctgg aaatgagtga cacaaaggac atgaatgaat ttgagacgga aggcttcttt 420
gctttgcatc agcgccgggg tgccatcaag caggcaaagg tccaccacgt caagtgccac 480
gagttcactg ccaccttctt cccacagccc acattttgct ctgtctgcca cgagtttgtc 540
tggggcctga acaaacaggg ctaccagtgc cgacaatgca atgcagcaat tcacaagaag 600

```
tgtattgata aagttatagc aaagtgcaca ggatcagcta tcaatagccg agaaaccatg    660

ttccacaagg agagattcaa aattgacatg ccacacagat ttaaagtcta caattacaag    720

agcccgacct tctgtgaaca ctgtgggacc ctgctgtggg gactggcacg gcaaggactc    780

aagtgtgatg catgtggcat gaatgtgcat catagatgcc agacaaaggt ggccaacctt    840

tgtggcataa accagaagct aatggctgaa gcgctggcca tgattgagag cactcaacag    900

gctcgctgct taagagatac tgaacagatc ttcagagaag gtccggttga aattggtctc    960

ccatgctcca tcaaaaatga agcaaggccg ccatgtttac cgacaccggg aaaaagagag   1020

cctcagggca tttcctggga gtctccgttg gatgaggtgg ataaaatgtg ccatcttcca   1080

gaacctgaac tgaacaaaga aagaccatct ctgcagatta aactaaaaat tgaggatttt   1140

atcttgcaca aaatgttggg gaaaggaagt tttggcaagg tcttcctggc agaattcaag   1200

aaaaccaatc aatttttcgc aataaaggcc ttaaagaaag atgtggtctt gatggacgat   1260

gatgttgagt gcacgatggt agagaagaga gttctttcct tggcctggga gcatccgttt   1320

ctgacgcaca tgttttgtac attccagacc aaggaaaacc tctttttgt gatggagtac    1380

ctcaacggag gggacttaat gtaccacatc caaagctgcc acaagttcga cctttccaga   1440

gcgacgtttt atgctgctga aatcattctt ggtctgcagt tccttcattc caaaggaata   1500

gtctacaggg acctgaagct agataacatc ctgttagaca aagatggaca tatcaagatc   1560

gcggattttg gaatgtgcaa ggagaacatg ttaggagatg ccaagacgaa taccttctgt   1620

gggacacctg actacatcgc cccagagatc ttgctgggtc agaaatacaa ccactctgtg   1680

gactggtggt ccttcggggt tctcctttat gaaatgctga ttggtcagtc gcctttccac   1740

gggcaggatg aggaggagct cttccactcc atccgcatgg acaatccctt ttacccacgg   1800

tggctggaga aggaagcaaa ggaccttctg gtgaagctct tcgtgcgaga acctgagaag   1860

aggctgggcg tgaggggaga catccgccag caccctttgt ttcgggagat caactgggag   1920

gaacttgaac ggaaggagat tgacccaccg ttccggccga aagtgaaatc accatttgac   1980

tgcagcaatt tcgacaaaga attcttaaac gagaagcccc ggctgtcatt tgccgacaga   2040

gcactgatca acagcatgga ccagaatatg ttcaggaact ttccttcat gaaccccggg    2100

atggagcggc tgatatcctg a                                             2121
```

<210> SEQ ID NO 120
<211> LENGTH: 1779
<212> TYPE: DNA
<213> ORGANISM: Homo sapiens
<300> PUBLICATION INFORMATION:
<302> TITLE: PKC zeta
<310> PATENT DOCUMENT NUMBER: NM2744

<400> SEQUENCE: 120

```
atgcccagca ggaccgaccc caagatggaa gggagcggcg gccgcgtccg cctcaaggcg     60

cattacgggg gggacatctt catcaccagc gtggacgccg ccacgacctt cgaggagctc    120

tgtgaggaag tgagagacat gtgtcgtctg caccagcagc acccgctcac cctcaagtgg    180

gtggacagcg aaggtgaccc ttgcacggtg tcctcccaga tggagctgga agaggctttc    240

cgcctggccc gtcagtgcag ggatgaaggc ctcatcattc atgttttccc gagcacccct    300

gagcagcctg gcctgccatg tccgggagaa gacaaatcta tctaccgccg gggagccaga    360

agatggagga agctgtaccg tgccaacggc cacctcttcc aagccaagcg ctttaacagg    420

agagcgtact gcggtcagtg cagcgagagg atatggggcc tcgcgaggca aggctacagg    480
```

tgcatcaact gcaaactgct ggtccataag cgctgccacg gcctcgtccc gctgacctgc 540
aggaagcata tggattctgt catgccttcc caagagcctc cagtagacga caagaacgag 600
gacgccgacc ttccttccga ggagacagat ggaattgctt acatttcctc atcccggaag 660
catgacagca ttaaagacga ctcggaggac cttaagccag ttatcgatgg gatggatgga 720
atcaaaatct ctcaggggct tggctgcag gactttgacc taatcagagt catcgggcgc 780
gggagctacg ccaaggttct cctggtgcgg ttgaagaaga atgaccaaat ttacgccatg 840
aaagtggtga agaaagagct ggtgcatgat gacgaggata ttgactgggt acagacagag 900
aagcacgtgt ttgagcaggc atccagcaac cccttcctgg tcggattaca ctcctgcttc 960
cagacgacaa gtcggttgtt cctggtcatt gagtacgtca acggcgggga cctgatgttc 1020
cacatgcaga ggcagaggaa gctccctgag gagcacgcca ggttctacgc ggccgagatc 1080
tgcatcgccc tcaacttcct gcacgagagg gggatcatct acagggacct gaagctggac 1140
aacgtcctcc tggatgcgga cgggcacatc aagctcacag actacggcat gtgcaaggaa 1200
ggcctgggcc ctggtgacac aacgagcact ttctgcggaa ccccgaatta catcgccccc 1260
gaaatcctgc ggggagagga gtacgggttc agcgtggact ggtgggcgct gggagtcctc 1320
atgtttgaga tgatggccgg gcgctccccg ttcgacatca tcaccgacaa cccggacatg 1380
aacacagagg actacctttt ccaagtgatc ctggagaagc ccatccggat cccccggttc 1440
ctgtccgtca aagcctccca tgttttaaaa ggatttttaa ataaggaccc caaagagagg 1500
ctcggctgcc ggccacagac tggattttct gacatcaagt cccacgcgtt cttccgcagc 1560
atagactggg acttgctgga gaagaagcag gcgctccctc cattccagcc acagatcaca 1620
gacgactacg gtctggacaa ctttgacaca cagttcacca gcgagcccgt gcagctgacc 1680
ccagacgatg aggatgccat aaagaggatc gaccagtcag agttcgaagg ctttgagtat 1740
atcaacccat tattgctgtc caccgaggag tcggtgtga 1779

<210> SEQ ID NO 121
<211> LENGTH: 576
<212> TYPE: DNA
<213> ORGANISM: Homo sapiens
<300> PUBLICATION INFORMATION:
<302> TITLE: VEGF
<310> PATENT DOCUMENT NUMBER: NM003376

<400> SEQUENCE: 121
atgaactttc tgctgtcttg ggtgcattgg agccttgcct tgctgctcta cctccaccat 60
gccaagtggt cccaggctgc acccatggca gaaggaggag ggcagaatca tcacgaagtg 120
gtgaagttca tggatgtcta tcagcgcagc tactgccatc caatcgagac cctggtggac 180
atcttccagg agtaccctga tgagatcgag tacatcttca agccatcctg tgtgcccctg 240
atgcgatgcg ggggctgctg caatgacgag ggcctggagt gtgtgcccac tgaggagtcc 300
aacatcacca tgcagattat gcggatcaaa cctcaccaag gccagcacat aggagagatg 360
agcttcctac agcacaacaa atgtgaatgc agaccaaaga aagatagagc aagacaagaa 420
aatccctgtg ggccttgctc agagcggaga aagcatttgt ttgtacaaga tccgcagacg 480
tgtaaatgtt cctgcaaaaa cacagactcg cgttgcaagg cgaggcagct tgagttaaac 540
gaacgtactt gcagatgtga caagccgagg cggtga 576

<210> SEQ ID NO 122
<211> LENGTH: 624

<212> TYPE: DNA
<213> ORGANISM: Homo sapiens
<300> PUBLICATION INFORMATION:
<302> TITLE: VEGF B
<310> PATENT DOCUMENT NUMBER: NM003377

<400> SEQUENCE: 122
atgagccctc tgctccgccg cctgctgctc gccgcactcc tgcagctggc cccgcccag 60 gcccctgtct cccagcctga tgcccctggc caccagagga aagtggtgtc atggatagat 120
gtgtatactc gcgctacctg ccagccccgg gaggtggtgg tgcccttgac tgtggagctc 180
atgggcaccg tggccaaaca gctggtgccc agctgcgtga ctgtgcagcg ctgtggtggc 240
tgctgccctg acgatggcct ggagtgtgtg cccactgggc agcaccaagt ccggatgcag 300
atcctcatga tccggtaccc gagcagtcag ctgggggaga tgtccctgga agaacacagc 360
cagtgtgaat gcagacctaa aaaaaaggac agtgctgtga agccagacag ggctgccact 420
ccccaccacc gtccccagcc ccgttctgtt ccgggctggg actctgcccc cggagcaccc 480
tccccagctg acatcaccca tcccactcca gccccaggcc cctctgccca cgctgcaccc 540
agcaccacca gcgccctgac cccggacct gccgccgccg ctgccgacgc cgcagcttcc 600
tccgttgcca agggcggggc ttag 624

<210> SEQ ID NO 123
<211> LENGTH: 1260
<212> TYPE: DNA
<213> ORGANISM: Homo sapiens
<300> PUBLICATION INFORMATION:
<302> TITLE: VEGF C
<310> PATENT DOCUMENT NUMBER: NM005429

<400> SEQUENCE: 123
atgcacttgc tgggcttctt ctctgtggcg tgttctctgc tcgccgctgc gctgctcccg 60
ggtcctcgcg aggcgcccgc cgccgccgcc gccttcgagt ccggactcga cctctcggac 120
gcggagcccg acgcgggcga ggccacggct tatgcaagca aagatctgga ggagcagtta 180
cggtctgtgt ccagtgtaga tgaactcatg actgtactct acccagaata ttggaaaatg 240
tacaagtgtc agctaaggaa aggaggctgg caacataaca gagaacaggc caacctcaac 300
tcaaggacag aagagactat aaaatttgct gcagcacatt ataatacaga gatcttgaaa 360
agtattgata atgagtggag aaagactcaa tgcatgccac gggaggtgtg tatagatgtg 420
gggaaggagt ttggagtcgc gacaaacacc ttctttaaac ctccatgtgt gtccgtctac 480
agatgtgggg gttgctgcaa tagtgagggg ctgcagtgca tgaacaccag cacgagctac 540
ctcagcaaga cgttatttga aattacagtg cctctctctc aaggccccaa accagtaaca 600
atcagttttg ccaatcacac ttcctgccga tgcatgtcta aactggatgt ttacagacaa 660
gttcattcca ttattagacg ttccctgcca gcaacactac cacagtgtca ggcagcgaac 720
aagacctgcc ccaccaatta catgtggaat aatcacatct gcagatgcct ggctcaggaa 780
gattttatgt tttcctcgga tgctggagat gactcaacag atggattcca tgacatctgt 840
ggaccaaaca aggagctgga tgaagagacc tgtcagtgtg tctgcagagc ggggcttcgg 900
cctgccagct gtggacccca caaagaacta gacagaaact catgccagtg tgtctgtaaa 960
aacaaactct tccccagcca atgtggggcc aaccgagaat ttgatgaaaa cacatgccag 1020
tgtgtatgta aaagaacctg ccccagaaat caacccctaa atcctggaaa atgtgcctgt 1080
gaatgtacag aaagtccaca gaaatgcttg ttaaaaggaa agaagttcca ccaccaaaca 1140
tgcagctgtt acagacggcc atgtacgaac cgccagaagg cttgtgagcc aggattttca 1200
tatagtgaag aagtgtgtcg ttgtgtccct tcatattgga aaagaccaca aatgagctaa 1260

<210> SEQ ID NO 124
<211> LENGTH: 1074
<212> TYPE: DNA
<213> ORGANISM: Homo sapiens
<300> PUBLICATION INFORMATION:
<302> TITLE: VEGF D
<310> PATENT DOCUMENT NUMBER: AJ000185

<400> SEQUENCE: 124
atattcaaaa tgtacagaga gtgggtagtg gtgaatgttt tcatgatgtt gtacgtccag 60
ctggtgcagg gctccagtaa tgaacatgga ccagtgaagc gatcatctca gtccacattg 120
gaacgatctg aacagcagat cagggctgct tctagtttgg aggaactact tcgaattact 180
cactctgagg actggaagct gtggagatgc aggctgaggc tcaaaagttt taccagtatg 240
gactctcgct cagcatccca tcggtccact aggtttgcgg caactttcta tgacattgaa 300
acactaaaag ttatagatga agaatggcaa agaactcagt gcagccctag agaaacgtgc 360
gtggaggtgg ccagtgagct ggggaagagt accaacacat tcttcaagcc cccttgtgtg 420
aacgtgttcc gatgtggtgg ctgttgcaat gaagagagcc ttatctgtat gaacaccagc 480
acctcgtaca tttccaaaca gctctttgag atatcagtgc ctttgacatc agtacctgaa 540
ttagtgcctg ttaaagttgc caatcataca ggttgtaagt gcttgccaac agccccccgc 600
catccatact caattatcag aagatccatc cagatccctg aagaagatcg ctgttcccat 660
tccaagaaac tctgtcctat tgacatgcta tgggatagca acaaatgtaa atgtgttttg 720
caggaggaaa atccacttgc tggaacagaa gaccactctc atctccagga accagctctc 780
tgtgggccac acatgatgtt tgacgaagat cgttgcgagt gtgtctgtaa aacaccatgt 840
cccaaagatc taatccagca ccccaaaaac tgcagttgct ttgagtgcaa agaaagtctg 900
gagacctgct gccagaagca caagctattt cacccagaca cctgcagctg tgaggacaga 960
tgcccctttc ataccagacc atgtgcaagt ggcaaaacag catgtgcaaa gcattgccgc 1020
tttccaaagg agaaaagggc tgcccagggg ccccacagcc gaaagaatcc ttga 1074

<210> SEQ ID NO 125
<211> LENGTH: 1314
<212> TYPE: DNA
<213> ORGANISM: Homo sapiens
<300> PUBLICATION INFORMATION:
<302> TITLE: E2F
<310> PATENT DOCUMENT NUMBER: M96577

<400> SEQUENCE: 125
atggccttgg ccggggcccc tgcgggcggc ccatgcgcgc cggcgctgga ggccctgctc 60
ggggccggcg cgctgcggct gctcgactcc tcgcagatcg tcatcatctc cgccgcgcag 120
gacgccagcg ccccgccggc tcccaccggc cccgcggcgc ccgccgccgg cccctgcgac 180
cctgacctgc tgctcttcgc cacaccgcag gcgccccggc ccacacccag tgcgccgcgg 240
cccgcgctcg gccgcccgcc ggtgaagcgg aggctggacc tggaaactga ccatcagtac 300
ctggccgaga gcagtgggcc agctcggggc agaggccgcc atccaggaaa aggtgtgaaa 360
tccccggggg agaagtcacg ctatgagacc tcactgaatc tgaccaccaa gcgcttcctg 420
gagctgctga gccactcggc tgacggtgtc gtcgacctga actgggctgc cgaggtgctg 480
aaggtgcaga agcggcgcat ctatgacatc accaacgtcc ttgagggcat ccagctcatt 540
gccaagaagt ccaagaacca catccagtgg ctgggcagcc acaccacagt gggcgtcggc 600
ggacggcttg aggggttgac ccaggacctc cgacagctgc aggagagcga gcagcagctg 660
gaccacctga tgaatatctg tactacgcag ctgcgcctgc tctccgagga cactgacagc 720
cagcgcctgg cctacgtgac gtgtcaggac cttcgtagca ttgcagaccc tgcagagcag 780
atggttatgg tgatcaaagc ccctcctgag acccagctcc aagccgtgga ctcttcggag 840
aactttcaga tctcccttaa gagcaaacaa ggcccgatcg atgttttcct gtgccctgag 900
gagaccgtag gtgggatcag ccctgggaag accccatccc aggaggtcac ttctgaggag 960
gagaacaggg ccactgactc tgccaccata gtgtcaccac caccatcatc tccccccctca 1020 tccctcacca cagatcccag ccagtctcta ctcagcctgg agcaagaacc gctgttgtcc 1080
cggatgggca gcctgcgggc tcccgtggac gaggaccgcc tgtccccgct ggtggcggcc 1140
gactcgctcc tggagcatgt gcgggaggac ttctccggcc tcctccctga ggagttcatc 1200
agcctttccc caccccacga ggccctcgac taccacttcg gcctcgagga gggcgagggc 1260
atcagagacc tcttcgactg tgactttggg gacctcaccc ccctggattt ctga 1314

<210> SEQ ID NO 126
<211> LENGTH: 166
<212> TYPE: DNA
<213> ORGANISM: Human papillomavirus
<300> PUBLICATION INFORMATION:
<302> TITLE: EBER-1
<310> PATENT DOCUMENT NUMBER: Jo2078

<400> SEQUENCE: 126
ggacctacgc tgccctagag gttttgctag ggaggagacg tgtgtggctg tagccacccg 60
tcccgggtac aagtcccggg tggtgaggac ggtgtctgtg gttgtcttcc cagactctgc 120
tttctgccgt cttcggtcaa gtaccagctg gtggtccgca tgtttt 166

<210> SEQ ID NO 127
<211> LENGTH: 172
<212> TYPE: DNA
<213> ORGANISM: Hepatitis C virus
<300> PUBLICATION INFORMATION:
<302> TITLE: EBER-2
<310> PATENT DOCUMENT NUMBER: J02078

<400> SEQUENCE: 127
ggacagccgt tgccctagtg gtttcggaca caccgccaac gctcagtgcg gtgctaccga 60
cccgaggtca agtcccgggg gaggagaaga gaggcttccc gcctagagca tttgcaagtc 120
aggattctct aatccctctg ggagaagggt attcggcttg tccgctattt tt 172

<210> SEQ ID NO 128
<211> LENGTH: 651
<212> TYPE: DNA
<213> ORGANISM: Hepatitis C virus
<300> PUBLICATION INFORMATION:
<302> TITLE: NS2
<310> PATENT DOCUMENT NUMBER: AJ238799

<400> SEQUENCE: 128
atggaccggg agatggcagc atcgtgcgga ggcgcggttt tcgtaggtct gatactcttg 60
accttgtcac cgcactataa gctgttcctc gctaggctca tatggtggtt acaatatttt 120
atcaccaggg ccgaggcaca cttgcaagtg tggatccccc ccctcaacgt tcgggggggc 180
cgcgatgccg tcatcctcct cacgtgcgcg atccacccag agctaatctt taccatcacc 240

-continued

```
aaaatcttgc tcgccatact cggtccactc atggtgctcc aggctggtat aaccaaagtg    300

ccgtacttcg tgcgcgcaca cgggctcatt cgtgcatgca tgctggtgcg gaaggttgct    360

gggggtcatt atgtccaaat ggctctcatg aagttggccg cactgacagg tacgtacgtt    420

tatgaccatc tcaccccact gcgggactgg gcccacgcgg gcctacgaga ccttgcggtg    480

gcagttgagc ccgtcgtctt ctctgatatg gagaccaagg ttatcacctg gggggcagac    540

accgcggcgt gtggggacat catcttgggc ctgcccgtct ccgcccgcag gggggaggag    600

atacatctgg gaccggcaga cagccttgaa gggcaggggt ggcgactcct c             651
```

<210> SEQ ID NO 129
<211> LENGTH: 161
<212> TYPE: DNA
<213> ORGANISM: Hepatitis C virus
<300> PUBLICATION INFORMATION:
<302> TITLE: NS4A
<310> PATENT DOCUMENT NUMBER: AJ238799

<400> SEQUENCE: 129

```
gcacctgggt gctggtaggc ggagtcctag cagctctggc cgcgtattgc ctgacaacag     60

gcagcgtggt cattgtgggc aggatcatct tgtccggaaa gccggccatc attcccgaca    120

gggaagtcct ttaccgggag ttcgatgaga tggaagagtg c                        161
```

<210> SEQ ID NO 130
<211> LENGTH: 783
<212> TYPE: DNA
<213> ORGANISM: Hepatitis C virus
<300> PUBLICATION INFORMATION:
<302> TITLE: NS4B
<310> PATENT DOCUMENT NUMBER: AJ238799

<400> SEQUENCE: 130

```
gcctcacacc tcccttacat cgaacaggga atgcagctcg ccgaacaatt caaacagaag     60

gcaatcgggt tgctgcaaac agccaccaag caagcggagg ctgctgctcc cgtggtggaa    120

tccaagtggc ggaccctcga agccttctgg gcgaagcata tgtggaattt catcagcggg    180

atacaatatt tagcaggctt gtccactctg cctggcaacc ccgcgatagc atcactgatg    240

gcattcacag cctctatcac cagcccgctc accacccaac ataccctcct gtttaacatc    300

ctgggggggat gggtggccgc ccaacttgct cctcccagcg ctgcttctgc tttcgtaggc    360

gccggcatcg ctggagcggc tgttggcagc ataggccttg ggaaggtgct tgtggatatt    420

ttggcaggtt atggagcagg ggtggcaggc gcgctcgtgg cctttaaggt catgagcggc    480

gagatgccct ccaccgagga cctggttaac ctactccctg ctatcctctc ccctggcgcc    540

ctagtcgtcg gggtcgtgtg cgcagcgata ctgcgtcggc acgtgggccc aggggagggg    600

gctgtgcagt ggatgaaccg gctgatagcg ttcgcttcgc ggggtaacca cgtctccccc    660

acgcactatg tgcctgagag cgacgctgca gcacgtgtca ctcagatcct ctctagtctt    720

accatcactc agctgctgaa gaggcttcac cagtggatca acgaggactg ctccacgcca    780

tgc                                                                  783
```

<210> SEQ ID NO 131
<211> LENGTH: 1341
<212> TYPE: DNA
<213> ORGANISM: Hepatitis C virus
<300> PUBLICATION INFORMATION:
<302> TITLE: NS5A
<310> PATENT DOCUMENT NUMBER: AJ238799

<400> SEQUENCE: 131
tccggctcgt ggctaagaga tgtttgggat tggatatgca cggtgttgac tgatttcaag 60
acctggctcc agtccaagct cctgccgcga ttgccgggag tccccttctt ctcatgtcaa 120
cgtgggtaca agggagtctg gcggggcgac ggcatcatgc aaaccacctg cccatgtgga 180
gcacagatca ccggacatgt gaaaaacggt tccatgagga tcgtggggcc taggacctgt 240
agtaacacgt ggcatggaac attccccatt aacgcgtaca ccacgggccc ctgcacgccc 300
tccccggcgc caaattattc tagggcgctg tggcgggtgg ctgctgagga gtacgtggag 360
gttacgcggg tgggggattt ccactacgtg acgggcatga ccactgacaa cgtaaagtgc 420
ccgtgtcagg ttccggcccc cgaattcttc acagaagtgg atggggtgcg gttgcacagg 480
tacgctccag cgtgcaaacc cctcctacgg gaggaggtca cattcctggt cgggctcaat 540
caatacctgg ttgggtcaca gctcccatgc gagcccgaac cggacgtagc agtgctcact 600
tccatgctca ccgacccctc ccacattacg gcggagacgg ctaagcgtag gctggccagg 660
ggatctcccc cctccttggc cagctcatca gctagccagc tgtctgcgcc ttccttgaag 720
gcaacatgca ctacccgtca tgactccccg gacgctgacc tcatcgaggc caacctcctg 780
tggcggcagg agatgggcgg gaacatcacc cgcgtggagt cagaaaataa ggtagtaatt 840
ttggactctt tcgagccgct ccaagcggag gaggatgaga gggaagtatc cgttccggcg 900
gagatcctgc ggaggtccag gaaattccct cgagcgatgc ccatatgggc acgcccggat 960
tacaaccctc cactgttaga gtcctggaag gacccggact acgtccctcc agtggtacac 1020
gggtgtccat tgccgcctgc caaggcccct ccgataccac ctccacggag gaagaggacg 1080
gttgtcctgt cagaatctac cgtgtcttct gccttggcgg agctcgccac aaagaccttc 1140
ggcagctccg aatcgtcggc cgtcgacagc ggcacggcaa cggcctctcc tgaccagccc 1200
tccgacgacg gcgacgcggg atccgacgtt gagtcgtact cctccatgcc cccccttgag 1260
ggggagccgg gggatcccga tctcagcgac gggtcttggt ctaccgtaag cgaggaggct 1320
agtgaggacg tcgtctgctg c 1341

<210> SEQ ID NO 132
<211> LENGTH: 1772
<212> TYPE: DNA
<213> ORGANISM: Hepatitis C virus
<300> PUBLICATION INFORMATION:
<302> TITLE: NS5B
<310> PATENT DOCUMENT NUMBER: AJ238799

<400> SEQUENCE: 132
tcgatgtcct acacatggac aggcgccctg atcacgccat gcgctgcgga ggaaaccaag 60
ctgcccatca atgcactgag caactctttg ctccgtcacc acaacttggt ctatgctaca 120
acatctcgca gcgcaagcct gcggcagaag aaggtcacct ttgacagact gcaggtcctg 180
gacgaccact accgggacgt gctcaaggag atgaaggcga aggcgtccac agttaaggct 240
aaacttctat ccgtggagga agcctgtaag ctgacgcccc cacattcggc cagatctaaa 300
tttggctatg gggcaaagga cgtccggaac ctatccagca aggccgttaa ccacatccgc 360
tccgtgtgga aggacttgct ggaagacact gagacaccaa ttgacaccac catcatggca 420
aaaaatgagg ttttctgcgt ccaaccagag aaggggggcc gcaagccagc tcgccttatc 480
gtattcccag atttgggggt tcgtgtgtgc gagaaaatgg ccctttacga tgtggtctcc 540
accctccctc aggccgtgat gggctcttca tacggattcc aatactctcc tggacagcgg 600
gtcgagttcc tggtgaatgc ctggaaagcg aagaaatgcc ctatgggctt cgcatatgac 660
acccgctgtt ttgactcaac ggtcactgag aatgacatcc gtgttgagga gtcaatctac 720
caatgttgtg acttggcccc cgaagccaga caggccataa ggtcgctcac agagcggctt 780
tacatcgggg gcccccctgac taattctaaa gggcagaact gcggctatcg ccggtgccgc 840
gcgagcggtg tactgacgac cagctgcggt aataccctca catgttactt gaaggccgct 900
gcggcctgtc gagctgcgaa gctccaggac tgcacgatgc tcgtatgcgg agacgacctt 960
gtcgttatct gtgaaagcgc ggggacccaa gaggacgagg cgagcctacg ggccttcacg 1020
gaggctatga ctagatactc tgcccccct ggggacccgc ccaaaccaga atacgacttg 1080
gagttgataa catcatgctc ctccaatgtg tcagtcgcgc acgatgcatc tggcaaaagg 1140
gtgtactatc tcacccgtga ccccaccacc cccctgcgc gggctgcgtg ggagacagct 1200
agacacactc cagtcaattc ctggctaggc aacatcatca tgtatgcgcc caccttgtgg 1260
gcaaggatga tcctgatgac tcatttcttc tccatccttc tagctcagga acaacttgaa 1320
aaagccctag attgtcagat ctacggggcc tgttactcca ttgagccact tgacctacct 1380
cagatcattc aacgactcca tggccttagc gcattttcac tccatagtta ctctccaggt 1440
gagatcaata gggtggcttc atgcctcagg aaacttgggg taccgccctt gcgagtctgg 1500
agacatcggg ccagaagtgt ccgcgctagg ctactgtccc aggggggag ggctgccact 1560 tgtggcaagt acctcttcaa ctgggcagta aggaccaagc tcaaactcac tccaatcccg 1620
gctgcgtccc agttggattt atccagctgg ttcgttgctg gttacagcgg gggagacata 1680
tatcacagcc tgtctcgtgc ccgaccccgc tggttcatgt ggtgcctact cctactttct 1740
gtaggggtag gcatctatct actccccaac cg 1772

<210> SEQ ID NO 133
<211> LENGTH: 1892
<212> TYPE: DNA
<213> ORGANISM: Hepatitis C virus
<300> PUBLICATION INFORMATION:
<302> TITLE: NS3
<310> PATENT DOCUMENT NUMBER: AJ238799

<400> SEQUENCE: 133
cgcctattac ggcctactcc caacagacgc gaggcctact tggctgcatc atcactagcc 60
tcacaggccg ggacaggaac caggtcgagg gggaggtcca agtggtctcc accgcaacac 120
aatctttcct ggcgacctgc gtcaatggcg tgtgttggac tgtctatcat ggtgccggct 180
caaagaccct tgccggccca aagggcccaa tcacccaaat gtacaccaat gtggaccagg 240
acctcgtcgg ctggcaagcg ccccccgggg cgcgttcctt gacaccatgc acctgcggca 300
gctcggacct ttacttggtc acgaggcatg ccgatgtcat tccggtgcgc cggcggggcg 360
acagcagggg gagcctactc tcccccaggc ccgtctccta cttgaagggc tcttcgggcg 420
gtccactgct ctgcccctcg gggcacgctg tgggcatctt tcgggctgcc gtgtgcaccc 480
gaggggttgc gaaggcggtg gactttgtac ccgtcgagtc tatggaaacc actatgcggt 540
ccccggtctt cacggacaac tcgtcccctc cggccgtacc gcagacattc caggtggccc 600
atctacacgc ccctactggt agcggcaaga gcactaaggt gccggctgcg tatgcagccc 660
aagggtataa ggtgcttgtc ctgaacccgt ccgtcgccgc caccctaggt ttcggggcgt 720
atatgtctaa ggcacatggt atcgacccta acatcagaac cggggtaagg accatcacca 780
cgggtgcccc catcacgtac tccacctatg gcaagtttct tgccgacggt ggttgctctg 840

```
ggggcgccta tgacatcata atatgtgatg agtgccactc aactgactcg accactatcc    900

tgggcatcgg cacagtcctg gaccaagcgg agacggctgg agcgcgactc gtcgtgctcg    960

ccaccgctac gcctccggga tcggtcaccg tgccacatcc aaacatcgag gaggtggctc   1020

tgtccagcac tggagaaatc cccttttatg gcaaagccat ccccatcgag accatcaagg   1080

gggggaggca cctcattttc tgccattcca agaagaaatg tgatgagctc gccgcgaagc   1140

tgtccggcct cggactcaat gctgtagcat attaccgggg ccttgatgta tccgtcatac   1200

caactagcgg agacgtcatt gtcgtagcaa cggacgctct aatgacgggc tttaccggcg   1260

atttcgactc agtgatcgac tgcaatacat gtgtcaccca gacagtcgac ttcagcctgg   1320

acccgacctt caccattgag acgacgaccg tgccacaaga cgcggtgtca cgctcgcagc   1380

ggcgaggcag gactggtagg ggcaggatgg gcatttacag gtttgtgact ccaggagaac   1440

ggccctcggg catgttcgat tcctcggttc tgtgcgagtg ctatgacgcg ggctgtgctt   1500

ggtacgagct cacgcccgcc gagacctcag ttaggttgcg ggcttaccta aacacaccag   1560

ggttgcccgt ctgccaggac catctggagt tctgggagag cgtctttaca ggcctcaccc   1620

acatagacgc ccatttcttg tcccagacta agcaggcagg agacaacttc ccctacctgg   1680

tagcatacca ggctacggtg tgcgccaggg ctcaggctcc acctccatcg tgggaccaaa   1740

tgtggaagtg tctcatacgg ctaaagccta cgctgcacgg gccaacgccc ctgctgtata   1800

ggctgggagc cgttcaaaac gaggttacta ccacacaccc cataaccaaa tacatcatgg   1860

catgcatgtc ggctgacctg gaggtcgtca cg                                 1892
```

<210> SEQ ID NO 134
<211> LENGTH: 822
<212> TYPE: DNA
<213> ORGANISM: Homo sapiens
<300> PUBLICATION INFORMATION:
<302> TITLE: stmn cell factor
<310> PATENT DOCUMENT NUMBER: M59964

<400> SEQUENCE: 134

```
atgaagaaga cacaaacttg gattctcact tgcatttatc ttcagctgct cctatttaat     60

cctctcgtca aaactgaagg gatctgcagg aatcgtgtga ctaataatgt aaaagacgtc    120

actaaattgg tggcaaatct tccaaaagac tacatgataa ccctcaaata tgtccccggg    180

atggatgttt tgccaagtca ttgttggata agcgagatgg tagtacaatt gtcagacagc    240

ttgactgatc ttctggacaa gttttcaaat atttctgaag gcttgagtaa ttattccatc    300

atagacaaac ttgtgaatat agtcgatgac cttgtggagt gcgtcaaaga aaactcatct    360

aaggatctaa aaaaatcatt caagagccca gaacccaggc tctttactcc tgaagaattc    420

tttagaattt ttaatagatc cattgatgcc ttcaaggact ttgtagtggc atctgaaact    480

agtgattgtg tggtttcttc aacattaagt cctgagaaag attccagagt cagtgtcaca    540

aaaccattta tgttaccccc tgttgcagcc agctccctta ggaatgacag cagtagcagt    600

aataggaagg ccaaaaatcc ccctggagac tccagcctac actgggcagc catggcattg    660

ccagcattgt tttctcttat aattggcttt gcttttggag ccttatactg gaagaagaga    720

cagccaagtc ttacaagggc agttgaaaat atacaaatta atgaagagga taatgagata    780

agtatgttgc aagagaaaga gagagagttt caagaagtgt aa                       822
```

<210> SEQ ID NO 135
<211> LENGTH: 483

<212> TYPE: DNA
<213> ORGANISM: Homo sapiens
<300> PUBLICATION INFORMATION:
<302> TITLE: TGFalpha
<310> PATENT DOCUMENT NUMBER: AF123238

<400> SEQUENCE: 135
atggtcccct cggctggaca gctcgccctg ttcgctctgg gtattgtgtt ggctgcgtgc 60
caggccttgg agaacagcac gtccccgctg agtgcagacc cgcccgtggc tgcagcagtg 120
gtgtcccatt ttaatgactg cccagattcc cacactcagt tctgcttcca tggaacctgc 180
aggtttttgg tgcaggagga caagccagca tgtgtctgcc attctgggta cgttggtgca 240
cgctgtgagc atgcggacct cctggccgtg gtggctgcca gccagaagaa gcaggccatc 300
accgccttgg tggtggtctc catcgtggcc ctggctgtcc ttatcatcac atgtgtgctg 360
atacactgct gccaggtccg aaaacactgt gagtggtgcc gggccctcat ctgccggcac 420
gagaagccca gcgccctcct gaagggaaga accgcttgct gccactcaga aacagtggtc 480
tga 483

<210> SEQ ID NO 136
<211> LENGTH: 1071
<212> TYPE: DNA
<213> ORGANISM: Homo sapiens
<300> PUBLICATION INFORMATION:
<302> TITLE: GD3 synthase
<310> PATENT DOCUMENT NUMBER: NM003034

<400> SEQUENCE: 136
atgagcccct gcgggcgggc ccggcgacaa acgtccagag ggcccatggc tgtactggcg 60
tggaagttcc cgcggacccg gctgcccatg ggagccagtg ccctctgtgt cgtggtcctc 120
tgttggctct acatcttccc cgtctaccgg ctgcccaacg agaaagagat cgtgcagggg 180
gtgctgcaac agggcacggc gtggaggagg aaccagaccg cggccagagc gttcaggaaa 240
caaatggaag actgctgcga ccctgcccat ctctttgcta tgactaaaat gaattcccct 300
atggggaaga gcatgtggta tgacggggag tttttatact cattcaccat tgacaattca 360
acttactctc tcttcccaca ggcaacccca ttccagctgc cattgaagaa atgcgcggtg 420
gtgggaaatg gtgggattct gaagaagagt ggctgtggcc gtcaaataga tgaagcaaat 480
tttgtcatgc gatgcaatct ccctcctttg tcaagtgaat acactaagga tgttggatcc 540
aaaagtcagt tagtgacagc taatcccagc ataattcggc aaaggtttca gaaccttctg 600
tggtccagaa agacatttgt ggacaacatg aaaatctata accacagtta catctacatg 660
cctgcctttt ctatgaagac aggaacagag ccatctttga gggtttatta tacactgtca 720
gatgttggtg ccaatcaaac agtgctgttt gccaacccca actttctgcg tagcattgga 780
aagttctgga aaagtagagg aatccatgcc aagcgcctgt ccacaggact tttctggtg 840 agcgcagctc tgggtctctg tgaagaggtg gccatctatg gcttctggcc cttctctgtg 900
aatatgcatg agcagcccat cagccaccac tactatgaca acgtcttacc cttttctggc 960
ttccatgcca tgcccgagga atttctccaa ctctggtatc ttcataaaat cggtgcactg 1020
agaatgcagc tggacccatg tgaagatacc tcactccagc ccacttccta g 1071

<210> SEQ ID NO 137
<211> LENGTH: 744
<212> TYPE: DNA
<213> ORGANISM: Homo sapiens
<300> PUBLICATION INFORMATION:

<302> TITLE: FGF14
<310> PATENT DOCUMENT NUMBER: NM004115

<400> SEQUENCE: 137
atggccgcgg ccatcgctag cggcttgatc cgccagaagc ggcaggcgcg ggagcagcac 60
tgggaccggc cgtctgccag caggaggcgg agcagcccca gcaagaaccg cgggctctgc 120
aacggcaacc tggtggatat cttctccaaa gtgcgcatct tcggcctcaa gaagcgcagg 180
ttgcggcgcc aagatcccca gctcaagggt atagtgacca ggttatattg caggcaaggc 240
tactacttgc aaatgcaccc cgatggagct ctcgatggaa ccaaggatga cagcactaat 300
tctacactct tcaacctcat accagtggga ctacgtgttg ttgccatcca gggagtgaaa 360
acagggttgt atatagccat gaatggagaa ggttacctct acccatcaga actttttacc 420
cctgaatgca agtttaaaga atctgttttt gaaaattatt atgtaatcta ctcatccatg 480
ttgtacagac aacaggaatc tggtagagcc tggtttttgg gattaaataa ggaagggcaa 540
gctatgaaag ggaacagagt aaagaaaacc aaaccagcag ctcattttct acccaagcca 600
ttggaagttg ccatgtaccg agaaccatct ttgcatgatg ttggggaaac ggtcccgaag 660
cctggggtga cgccaagtaa aagcacaagt gcgtctgcaa taatgaatgg aggcaaacca 720
gtcaacaaga gtaagacaac atag 744

<210> SEQ ID NO 138
<211> LENGTH: 1503
<212> TYPE: DNA
<213> ORGANISM: Human immunodeficiency virus
<300> PUBLICATION INFORMATION:
<302> TITLE: gag (HIV)
<310> PATENT DOCUMENT NUMBER: NC001802

<400> SEQUENCE: 138
atgggtgcga gagcgtcagt attaagcggg ggagaattag atcgatggga aaaaattcgg 60
ttaaggccag ggggaaagaa aaaatataaa ttaaaacata tagtatgggc aagcagggag 120
ctagaacgat tcgcagttaa tcctggcctg ttagaaacat cagaaggctg tagacaaata 180
ctgggacagc tacaaccatc ccttcagaca ggatcagaag aacttagatc attatataat 240
acagtagcaa ccctctattg tgtgcatcaa aggatagaga taaaagacac caaggaagct 300
ttagacaaga tagaggaaga gcaaaacaaa agtaagaaaa aagcacagca agcagcagct 360
gacacaggac acagcaatca ggtcagccaa aattacccta tagtgcagaa catccagggg 420
caaatggtac atcaggccat atcacctaga actttaaatg catgggtaaa agtagtagaa 480
gagaaggctt tcagcccaga agtgataccc atgttttcag cattatcaga aggagccacc 540
ccacaagatt taaacaccat gctaaacaca gtgggggggac atcaagcagc catgcaaatg 600
ttaaaagaga ccatcaatga ggaagctgca gaatgggata gagtgcatcc agtgcatgca 660
gggcctattg caccaggcca gatgagagaa ccaaggggaa gtgacatagc aggaactact 720
agtacccttc aggaacaaat aggatggatg acaaataatc cacctatccc agtaggagaa 780
atttataaaa gatggataat cctgggatta aataaaatag taagaatgta tagccctacc 840
agcattctgg acataagaca aggaccaaag gaacccttta gagactatgt agaccggttc 900
tataaaactc taagagccga gcaagcttca caggaggtaa aaaattggat gacagaaacc 960
ttgttggtcc aaaatgcgaa cccagattgt aagactattt taaaagcatt gggaccagcg 1020
gctacactag aagaaatgat gacagcatgt cagggagtag gaggacccgg ccataaggca 1080
agagttttgg ctgaagcaat gagccaagta acaaattcag ctaccataat gatgcagaga 1140

-continued ggcaatttta ggaaccaaag aaagattgtt aagtgtttca attgtggcaa agaagggcac 1200
acagccagaa attgcagggc ccctaggaaa aagggctgtt ggaaatgtgg aaaggaagga 1260
caccaaatga aagattgtac tgagagacag gctaattttt tagggaagat ctggccttcc 1320
tacaagggaa ggccagggaa ttttcttcag agcagaccag agccaacagc cccaccagaa 1380
gagagcttca ggtctggggt agagacaaca actccccctc agaagcagga gccgatagac 1440
aaggaactgt atcctttaac ttccctcagg tcactctttg gcaacgaccc ctcgtcacaa 1500
taa 1503

<210> SEQ ID NO 139
<211> LENGTH: 1101
<212> TYPE: DNA
<213> ORGANISM: Human immunodeficiency virus
<300> PUBLICATION INFORMATION:
<302> TITLE: TARBP2
<310> PATENT DOCUMENT NUMBER: NM004178

<400> SEQUENCE: 139
atgagtgaag aggagcaagg ctccggcact accacgggct gcgggctgcc tagtatagag 60
caaatgctgg ccgccaaccc aggcaagacc ccgatcagcc ttctgcagga gtatgggacc 120
agaataggga agacgcctgt gtacgacctt ctcaaagccg agggccaagc ccaccagcct 180
aatttcacct tccgggtcac cgttggcgac accagctgca ctggtcaggg ccccagcaag 240
aaggcagcca agcacaaggc agctgaggtg gccctcaaac acctcaaagg ggggagcatg 300
ctggagccgg ccctggagga cagcagttct ttttctcccc tagactcttc actgcctgag 360
gacattccgg tttttactgc tgcagcagct gctaccccag ttccatctgt agtcctaacc 420
aggagccccc ccatggaact gcagcccccct gtctcccctc agcagtctga gtgcaacccc 480
gttggtgctc tgcaggagct ggtggtgcag aaaggctggc ggttgccgga gtacacagtg 540
acccaggagt ctgggccagc ccaccgcaaa gaattcacca tgacctgtcg agtggagcgt 600
ttcattgaga ttgggagtgg cacttccaaa aaattggcaa agcggaatgc ggcggccaaa 660
atgctgcttc gagtgcacac ggtgcctctg gatgcccggg atggcaatga ggtggagcct 720
gatgatgacc acttctccat tggtgtgggc ttccgcctgg atggtcttcg aaaccggggc 780
ccaggttgca cctgggattc tctacgaaat tcagtaggag agaagatcct gtccctccgc 840
agttgctccc tgggctccct gggtgccctg ggccctgcct gctgccgtgt cctcagtgag 900
ctctctgagg agcaggcctt tcacgtcagc tacctggata ttgaggagct gagcctgagt 960
ggactctgcc agtgcctggt ggaactgtcc acccagccgg ccactgtgtg tcatggctct 1020
gcaaccacca gggaggcagc ccgtggtgag gctgcccgcc gtgccctgca gtacctcaag 1080
atcatggcag gcagcaagtg a 1101

<210> SEQ ID NO 140
<211> LENGTH: 219
<212> TYPE: DNA
<213> ORGANISM: Human immunodeficiency virus
<300> PUBLICATION INFORMATION:
<302> TITLE: TAT (HIV)
<310> PATENT DOCUMENT NUMBER: U44023

<400> SEQUENCE: 140
atggagccag tagatcctag cctagagccc tggaagcatc caggaagtca gcctaagact 60
gcttgtacca cttgctattg taaagagtgt tgctttcatt gccaagtttg tttcataaca 120

```
aaaggcttag gcatctccta tggcaggaag aagcggagac agcgacgaag aactcctcaa    180

ggtcatcaga ctaatcaagt ttctctatca aagcagtaa                           219


<210> SEQ ID NO 141
<211> LENGTH: 22
<212> TYPE: RNA
<213> ORGANISM: Synthetic sequence
<220> FEATURE:
<223> OTHER INFORMATION: Description of the synthetic sequence: sense
      strand (R1A) of a dsRNA that is homologous to an MDR1 sequence

<400> SEQUENCE: 141

ccaucucgaa aagaaguuaa ga                                              22


<210> SEQ ID NO 142
<211> LENGTH: 24
<212> TYPE: RNA
<213> ORGANISM: Synthetic sequence
<220> FEATURE:
<223> OTHER INFORMATION: Description of the synthetic sequence:
      antisense strand (R1B) of a dsRNA, that it
      complementary to an MDR1 sequence

<400> SEQUENCE: 142

ucuuaacuuc uuuucgagau gggu                                            24


<210> SEQ ID NO 143
<211> LENGTH: 22
<212> TYPE: RNA
<213> ORGANISM: Synthetic sequence
<220> FEATURE:
<223> OTHER INFORMATION: Description of the synthetic sequence: sense
      strand (R2A) of a dsRNA that is homologous to an MDR1 sequence

<400> SEQUENCE: 143

uauagguucc aggcuugcug ua                                              22


<210> SEQ ID NO 144
<211> LENGTH: 22
<212> TYPE: RNA
<213> ORGANISM: Synthetic sequence
<220> FEATURE:
<223> OTHER INFORMATION: Description of the synthetic sequence: sense
      strand (R3A) of a dsRNA that is homologous to an MDR1 sequence

<400> SEQUENCE: 144

ccagagaagg ccgcaccugc au                                              22


<210> SEQ ID NO 145
<211> LENGTH: 24
<212> TYPE: RNA
<213> ORGANISM: Synthetic sequence
<220> FEATURE:
<223> OTHER INFORMATION: Description of the synthetic sequence:
      antisense strand (R3B) of a dsRNA, that it
      complementary to an MDR1 sequence

<400> SEQUENCE: 145

augcaggugc ggccuucucu ggcu                                            24


<210> SEQ ID NO 146
<211> LENGTH: 21
<212> TYPE: RNA
<213> ORGANISM: Synthetic sequence
<220> FEATURE:
<223> OTHER INFORMATION: Description of the synthetic sequence: sense
      strand (R4A) of a dsRNA that is homologous to an MDR1 sequence
```

<400> SEQUENCE: 146
ccaucucgaa aagaaguuaa g 21

<210> SEQ ID NO 147
<211> LENGTH: 21
<212> TYPE: RNA
<213> ORGANISM: Synthetic sequence
<220> FEATURE:
<223> OTHER INFORMATION: Description of the synthetic sequence: antisense strand (R4B) of a dsRNA, that it complementary to an MDR1 sequence

<400> SEQUENCE: 147
uaacuucuuu ucgagauggg u 21

<210> SEQ ID NO 148
<211> LENGTH: 22
<212> TYPE: RNA
<213> ORGANISM: Synthetic sequence
<220> FEATURE:
<223> OTHER INFORMATION: Description of the synthetic sequence: sense strand (S1A) of a dsRNA, that is homologous to the YFP- and GFP sequence, respectively

<400> SEQUENCE: 148
ccacaugaag cagcacgacu uc 22

<210> SEQ ID NO 149
<211> LENGTH: 22
<212> TYPE: RNA
<213> ORGANISM: Synthetic sequence
<220> FEATURE:
<223> OTHER INFORMATION: Description of the synthetic sequence: antisense strand(S1B) of a dsRNA that is complementary to the YFP- and GFP sequence, respectively

<400> SEQUENCE: 149
gaagucgugc ugcuucaugu gg 22

<210> SEQ ID NO 150
<211> LENGTH: 21
<212> TYPE: RNA
<213> ORGANISM: Synthetic sequence
<220> FEATURE:
<223> OTHER INFORMATION: Description of the synthetic sequence: antisense strand(S7A) of a dsRNA that is homologous to the YFP- and GFP sequence, respectively

<400> SEQUENCE: 150
ccacaugaag cagcacgacu u 21

<210> SEQ ID NO 151
<211> LENGTH: 21
<212> TYPE: RNA
<213> ORGANISM: Synthetic sequence
<220> FEATURE:
<223> OTHER INFORMATION: Description of the synthetic sequence: antisense strand(S7B) of a dsRNA, that is complementary to the YFP- and GFP sequence, respectively

<400> SEQUENCE: 151
gucgugcugc uucauguggu c 21

<210> SEQ ID NO 152
<211> LENGTH: 24
<212> TYPE: RNA

```
<213> ORGANISM: Synthetic sequence
<220> FEATURE:
<223> OTHER INFORMATION: Description of the synthetic sequence:
      antisense strand(R2B) of a dsRNA that is
      complementary to the MDR-1 sequence

<400> SEQUENCE: 152

uacagcaagc cuggaaccua uagc                                          24


<210> SEQ ID NO 153
<211> LENGTH: 22
<212> TYPE: RNA
<213> ORGANISM: Synthetic sequence
<220> FEATURE:
<223> OTHER INFORMATION: Description of the synthetic sequence: sense
      strand (K1A) of a dsRNA that is homologous to the 5'-UTR of
      the neomycin sequence

<400> SEQUENCE: 153

acaggaugag gaucguuucg ca                                            22


<210> SEQ ID NO 154
<211> LENGTH: 22
<212> TYPE: RNA
<213> ORGANISM: Synthetic sequence
<220> FEATURE:
<223> OTHER INFORMATION: Description of the synthetic sequence:
      antisense strand(K1B) of a dsRNA that is
      complementary to the 5'-UTR of the neomycin sequence

<400> SEQUENCE: 154

ugcgaaacga uccucauccu gu                                            22


<210> SEQ ID NO 155
<211> LENGTH: 21
<212> TYPE: RNA
<213> ORGANISM: Synthetic sequence
<220> FEATURE:
<223> OTHER INFORMATION: Description of the synthetic sequence: sense
      strand (K3A) of a dsRNA that is homologous to the 5'-UTR of the
      neomycin sequence

<400> SEQUENCE: 155

gaugaggauc guuucgcaug a                                             21


<210> SEQ ID NO 156
<211> LENGTH: 21
<212> TYPE: RNA
<213> ORGANISM: Synthetic sequence
<220> FEATURE:
<223> OTHER INFORMATION: Description of the synthetic sequence:
      antisense strand(K3B) of a dsRNA that
      complementary to the 5'-UTR of the neomycin sequence

<400> SEQUENCE: 156

augcgaaacg auccucaucc u                                             21


<210> SEQ ID NO 157
<211> LENGTH: 24
<212> TYPE: RNA
<213> ORGANISM: Synthetic sequence
<220> FEATURE:
<223> OTHER INFORMATION: Description of the synthetic sequence: sense
      strand (K2A) of a dsRNA that is homologous to the 5'-UTR of the
      neomycin sequence

<400> SEQUENCE: 157

acaggaugag gaucguuucg caug                                          24
```

<210> SEQ ID NO 158
<211> LENGTH: 24
<212> TYPE: RNA
<213> ORGANISM: Synthetic sequence
<220> FEATURE:
<223> OTHER INFORMATION: Description of the synthetic sequence: antisense strand(K2B) of a dsRNA that is complementary to the 5'-UTR of the neomycin sequence

<400> SEQUENCE: 158
ugcgaaacga uccucauccu gucu 24

<210> SEQ ID NO 159
<211> LENGTH: 24
<212> TYPE: RNA
<213> ORGANISM: Synthetic sequence
<220> FEATURE:
<223> OTHER INFORMATION: Description of the synthetic sequence: antisense strand(S4B) of a dsRNA that is complementary to the YFP- and GFP sequence, respectively

<400> SEQUENCE: 159
gaagucgugc ugcuucaugu gguc 24

<210> SEQ ID NO 160
<211> LENGTH: 24
<212> TYPE: RNA
<213> ORGANISM: Synthetic sequence
<220> FEATURE:
<223> OTHER INFORMATION: Description of the synthetic sequence: sense strand (PKC1 A) of a dsRNA that is homologous to the proteinkinase C sequence

<400> SEQUENCE: 160
cuucuccgcc ucacaccgcu gcaa 24

<210> SEQ ID NO 161
<211> LENGTH: 22
<212> TYPE: RNA
<213> ORGANISM: Synthetic sequence
<220> FEATURE:
<223> OTHER INFORMATION: Description of the synthetic sequence: antisense strand(PKC2 B) of a dsRNA that is complementary to the proteinkinase C sequence

<400> SEQUENCE: 161
gcagcggugu gaggcggaga ag 22

<210> SEQ ID NO 162
<211> LENGTH: 21
<212> TYPE: RNA
<213> ORGANISM: Synthetic sequence
<220> FEATURE:
<223> OTHER INFORMATION: Description of the synthetic sequence: antisense strand(S12B) of a dsRNA that is complementary to the YFP- and GFP sequence, respectively

<400> SEQUENCE: 162
aagucgugcu gcuucaugug g 21

<210> SEQ ID NO 163
<211> LENGTH: 23
<212> TYPE: RNA
<213> ORGANISM: Synthetic sequence
<220> FEATURE:
<223> OTHER INFORMATION: Description of the synthetic sequence: antisense strand(S11B) of a dsRNA that is complementary to the YFP- and GFP sequence, respectively

<400> SEQUENCE: 163
aagucgugcu gcuucaugug guc 23

<210> SEQ ID NO 164
<211> LENGTH: 20
<212> TYPE: RNA
<213> ORGANISM: Synthetic sequence
<220> FEATURE:
<223> OTHER INFORMATION: Description of the synthetic sequence: sense strand (S13A) of a dsRNA that is homologous to the YFP- and GFP sequence, respectively

<400> SEQUENCE: 164
ccacaugaag cagcacgacu 20

<210> SEQ ID NO 165
<211> LENGTH: 22
<212> TYPE: RNA
<213> ORGANISM: Synthetic sequence
<220> FEATURE:
<223> OTHER INFORMATION: Description of the synthetic sequence: antisense strand(S13B) of a dsRNA that is complementary to the YFP- and GFP sequence, respectively

<400> SEQUENCE: 165
agucgugcug cuucaugugg uc 22

<210> SEQ ID NO 166
<211> LENGTH: 20
<212> TYPE: RNA
<213> ORGANISM: Synthetic sequence
<220> FEATURE:
<223> OTHER INFORMATION: Description of the synthetic sequence: antisense strand(S14B) of a dsRNA that is complementary to the YFP- and GFP sequence, respectively

<400> SEQUENCE: 166
agucgugcug cuucaugugg 20

<210> SEQ ID NO 167
<211> LENGTH: 24
<212> TYPE: RNA
<213> ORGANISM: Synthetic sequence
<220> FEATURE:
<223> OTHER INFORMATION: Description of the synthetic sequence: sense strand (S4A) of a dsRNA that is homologous to the YFP- and GFP sequence, respectively

<400> SEQUENCE: 167
ccacaugaag cagcacgacu ucuu 24

<210> SEQ ID NO 168
<211> LENGTH: 21
<212> TYPE: RNA
<213> ORGANISM: Synthetic sequence
<220> FEATURE:
<223> OTHER INFORMATION: Description of the synthetic sequence: sense strand (ES-7A) of a dsRNA that is homologous to the human EGFR sequence

```
<400> SEQUENCE: 168

aacaccgcag caugucaaga u                                              21


<210> SEQ ID NO 169
<211> LENGTH: 21
<212> TYPE: RNA
<213> ORGANISM: Synthetic sequence
<220> FEATURE:
<223> OTHER INFORMATION: Description of the synthetic sequence:
      antisense strand(ES-7B) of a dsRNA that is
      complementary to the human EGFR sequence

<400> SEQUENCE: 169

cuugacaugc ugcgguguuu u                                              21


<210> SEQ ID NO 170
<211> LENGTH: 22
<212> TYPE: RNA
<213> ORGANISM: Synthetic sequence
<220> FEATURE:
<223> OTHER INFORMATION: Description of the synthetic sequence: sense
      strand (ES-8A) of a dsRNA that is homologous to the human
      EGFR sequence

<400> SEQUENCE: 170

aaguuaaaau ucccgucgcu au                                             22


<210> SEQ ID NO 171
<211> LENGTH: 22
<212> TYPE: RNA
<213> ORGANISM: Synthetic sequence
<220> FEATURE:
<223> OTHER INFORMATION: Description of the synthetic sequence:
      antisense strand(ES-8B) of a dsRNA that is
      complementary to the human EGFR sequence

<400> SEQUENCE: 171

ugauagcgac gggaauuuua ac                                             22


<210> SEQ ID NO 172
<211> LENGTH: 22
<212> TYPE: RNA
<213> ORGANISM: Synthetic sequence
<220> FEATURE:
<223> OTHER INFORMATION: Description of the synthetic sequence: sense
      strand (ES-2A) of a dsRNA that is homologous to the human
      EGFR sequence

<400> SEQUENCE: 172

agugugaucc aagcuguccc aa                                             22


<210> SEQ ID NO 173
<211> LENGTH: 24
<212> TYPE: RNA
<213> ORGANISM: Synthetic sequence
<220> FEATURE:
<223> OTHER INFORMATION: Description of the synthetic sequence:
      antisense strand(ES-5B) of a dsRNA that is
      complementary to the human EGFR sequence

<400> SEQUENCE: 173

uugggacagc uuggaucaca cuuu                                           24
```

We claim:

1. A double-stranded ribonucleic acid (dsRNA) for inhibiting the expression of a target gene in a cell, comprising a complementary RNA strand and a sense RNA strand, wherein the sense RNA strand comprises a nucleotide sequence which is substantially identical to the corresponding part of the target gene, wherein the complementary RNA strand comprises a complementary nucleotide sequence which is complementary to an mRNA transcript formed during expression of the target gene, wherein the complementary strand specifically hybridizes with the mRNA transcript, wherein the complementary RNA strand comprises a 3'-end and a 5'-end, wherein the 3'-end has a nucleotide overhang of 2 to 4 nucleotides and wherein the dsRNA at the 5'-end of the complementary RNA strand is blunt, and wherein the dsRNA is 20 to 49 base pairs in length.

2. The dsRNA of claim 1, wherein the nucleotide overhang is 2 nucleotides in length.

3. The dsRNA of claim 1, wherein the nucleotides of the nucleotide overhang are replaced with nucleoside thiophosphates.

4. The dsRNA of claim 1, wherein at least one of the complementary RNA strand and the sense RNA strand is 21 nucleotides in length.

5. The dsRNA of claim 1, wherein at least one of the complementary RNA strand and the sense RNA strand is 22 nucleotides in length.

6. The dsRNA of claim 1, wherein at least one of the complementary RNA strand and the sense RNA strand is 24 nucleotides in length.

7. A method of inhibiting the expression of the target gene in the cell, the method comprising:

(a) introducing into the cell the double-stranded ribonucleic acid (dsRNA) of claim 1 for inhibiting the expression of the target gene in the cell; and (b) maintaining the cell produced in step (a) for a time sufficient to obtain degradation of the mRNA transcript of the target gene, thereby inhibiting expression of the target gene in the cell.

8. The method of claim 7, wherein the nucleotide overhang is 2 nucleotides in length.

9. The method of claim 8, wherein the nucleotides of the nucleotide overhang are replaced with nucleoside thiophosphates.

10. The method of claim 7, wherein at least one of the complementary RNA strand and the sense RNA strand is 21 nucleotides in length.

11. The method of claim 7, wherein at least one of the complementary RNA strand and the sense RNA strand is 22 nucleotides in length.

12. The method of claim 7, wherein at least one of the complementary RNA strand and the sense RNA strand is 24 nucleotides in length.

13. The method of claim 7, wherein the target gene comprises EGFR.

14. The method of claim 7, wherein the target gene comprises MDR1.

15. The method of claim 7, wherein the target gene comprises MDR1 or EGFR.

* * * * *